US006815575B1

(12) United States Patent
Kazemi-Esfarjani et al.

(10) Patent No.: US 6,815,575 B1
(45) Date of Patent: Nov. 9, 2004

(54) ANIMAL MODEL OF POLYGLUTAMINE TOXICITY, METHODS OF USE, AND MODULATORS OF POLYGLUTAMINE TOXICITY

(75) Inventors: Parsa Kazemi-Esfarjani, Williamsville, NY (US); Seymour Benzer, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 406 days.

(21) Appl. No.: 09/639,207

(22) Filed: Aug. 14, 2000

Related U.S. Application Data

(60) Provisional application No. 60/148,934, filed on Aug. 12, 1999, provisional application No. 60/148,933, filed on Aug. 12, 1999, provisional application No. 60/177,047, filed on Jan. 18, 2000, and provisional application No. 60/205,720, filed on May 19, 2000.

(51) Int. Cl.[7] ...................... A01K 67/033; A01K 67/00; G01N 33/00

(52) U.S. Cl. ................................. 800/13; 800/3; 800/9

(58) Field of Search .................................. 800/3, 9, 13

(56) References Cited

PUBLICATIONS

Tsubota et al., P–element–induced control mutations at the r gene of drosophila melanogaster, 1985, Molecular and Cellular Biology, pp. 2567–2574.*

Kazemi–Esfarjani et al., Genetic suppression of polyglutamine toxicity in drosophila, 2000, Science, vol. 287, pp. 1837–1840.*

Warrick et al., Expanded polyglutamine protein forms nuclear inclusions and causes neural degeneration in drosophila, 1998, Cell, vol. 93, pp. 939–949.*

Rorth, A modular misexpression screen in drosophila detecting tissue–specific phenotypes, 1996, Proc. Natl. Acad. Sci. USA, vol. 93, pp. 12418–12422.*

Paulson et al., Intranuclear inclusions of expanded polyglutamine protein in spinocerebellar ataxia type 3, 1997, Neuron, vol. 19, pp. 333–344.*

Atkinson et al., Genetic transformation of non–drosophilid insects by transposable elements, 1999, Ann. Entomol. Soc. Am, vol. 92, pp. 930–936.*

Sequence paper.*

John M. Warrick et al., *Cell,* 93:939–949 (1998).

George R. Jackson et al., *Neuron,* 21:633–642 (1998).

Bergmann et al., "The *Drosophila Gene hid* is a direct molecular target of ras–dependent survival signaling," Cell, vol. 95, pp. 331–341, Oct. 30, 1998.

Loukeris et al., "Gene transfer into the Medfly, *Ceratitis capitata,* with a *Drosophila hydei* Transposable Element," Science, vol. 270, pp. 2002–2005, Dec. 22, 1995.

Perez et al., "Recruitment and the role of nuclear localization in polyglutamine–mediated aggregation," J. Cell Biol., vol. 143, No. 6, pp. 1457–1470, Dec. 14, 1998.

Rubin et al., "Genetic transformation of Drosophila with transposable element vectors," Science, vol. 218, pp. 348–353, Oct. 22, 1982.

* cited by examiner

*Primary Examiner*—Anne-Marie Falk
*Assistant Examiner*—Daniel M. Sullivan
(74) *Attorney, Agent, or Firm*—Fish & Richardson P.C.

(57) ABSTRACT

The present invention is based on an in vivo animal model that mimics human cellular and tissue degenerative disorders. The animal model exhibits cellular toxicity in response to expanded polyglutamine repeat sequences. The animal model is therefore useful for identifying genes or other compounds that modulate cellular and tissue degeneration and cell survival, for example, in neural, muscle, mesoderm, kidney and other tissues associated with frontotemporal dementia, prion diseases, polyglutamine disorders and protein aggregation disorders, Genes that suppress degeneration identified using the animal model include HDJ1, TPR2 and MLF. These genes, and their human homologues, functional fragments and probes are therefore useful in treating such disorders and for diagnostic purposes. Accordingly, methods for identifying nucleic acids and other compounds that modulate frontotemporal dementia, prion diseases, polyglutamine disorders and protein aggregation disorders is therefore provided. Pharmaceutical compositions comprising HDJ1, TPR2 and, MLF genes, and subsequences encoding functional polypeptides are also provided, as they are useful in treating such degenerative disorders.

15 Claims, 68 Drawing Sheets

20CAGHA

CTGCAGGCCAGCGTCCTGATAAGTGAATTCGCCGCCACCATGGAG
GCCCACCGTCAACCCCCCAGCAGCAGCAACAGCAGCAGCAACAGCA
ACAGCAGCAGCAACAACAGCAGCAGCAACAGACTAGTCGTACGTAT
CCCTATGACGTGCCCGACTATGCGTAG

127CAGHA

CTGCAGGCCAGCGTCCTGATAAGTGAATTCGCCGCCACCATGGAG
GCCCACCGTCAACCCCCCAGCAGCAGCAACAGCAGCAGCAACAGCA
ACAGCAGCAGCAACAACAGCAGCAGCAACAGCAACAGCAGCAGCAA
CAACAGCAGCAGCAACAGCAACAGCAGCAGCAACAGCAGCAGCAAC
AGCAACAGCAGCAGCAACAACAGCAGCAGCAACAGCAACAGCAGCA
GCAACAACAGCAACAACAACAGCAACAGCAGCAGCAACAGCAGCAG
CAACAGCAACAGCAGCAGCAACAACAGCAGCAGCAACAGCAACAGC
AGCAGCAACAACAGCAGCAGCAACAGCAACAGCAGCAGCAACAGCA
GCAGCAACAGCAACAGCAGCAGCAACAACAGCAGCTGCAACAGCAA
CAGCAGCAGCAACAACAGCAGCAGCAACAGACTAGTCGTACGTATC
CCTATGACGTGCCCGACTATGCGTAG

*FIG. 1A*

20QHA

MGGPPSTPQ$_{20}$TSRTYPYDVPDYA

127QHA

MGGPPSTPQ$_{127}$TSRTYPYDVPDYA

*FIG. 1B*

Generation of P-element insertion and screening for modifiers

M P[Δ2-3]/P[Δ2-3] X F EP55/EP55

↓

M EP55/Y;;P[Δ2-3]/+ X F w/w

↓

M w/Y;pEP/+;+ or w/Y;+;pEP/+ X F w;GMR/CyO;127Q/127Q

↓

Progeny screened for eye phenotype

Isolation of the new P-element insertion (pEP=suppressor or enhancer)

M (GMR;127Q)/pEP X F (CyO;TM3)/Xa

↓

M GMR/CyO;pEP/TM3 X F w1118

↓

M GMR;TM3 or CyO;pEP X F w;GMR/CyO;127Q/127Q to test

X F (CyO;TM3)/Xa to establish line

↓

M +/CyO;pEP/TM3 X F +/CyO;pEP/TM3

↓ pEP/TM3 or pEP/pEP established lines

*FIG. 3*

FIGURE 9A dTPR2 Protein 508 amino acids
MDDEVIEISDSEREETSSNSEMDVEITTEQPTIDVKAEQIVPKDAATIAEEKKKLG
NDQYKAQNYQNALKLYTDAISLCPDSAAYYGNRAACYMMLLNYNSALTDARH
AIRIDPGFEKAYVRVAKCCLALGDIIGTEQAVKMVNELNSLSTAVAAEQTAAQK
LRQLEATIQANYDTKSYRNVVFYLDSALKLAPACLKYRLLKAECLAFLGRCDEA
LDIAVSVMKLDTTSADAIYVRGLCLYYTDNLDKGILHFERALTLDPDHYKSKQM
RSKCKQLKEMKENGNMLFKSGRYREAHVIYTDALKIDEHNKDINSKLLYNRALV
NTRIGNLREAVADCNRVLELNSQYLKALLLRARCYNDLEKFEESVADYETALQL
EKTPEIKRMLREAKFALKKSKRKDYYKILGIGRNASDDEIKKAYRKKALVHHPD
RHANSSAEERKEEELKFKEVGEAYAILSDAHKKSRYDSGQDIEEQEQADFDPNQ
MFRTFFQFNGGGRNNSSFNFEF

FIGURE 9B dTPR2 cDNA 2239 base pairs
GGCACGAGCCACTACTTCGCATGGCACGCTTTTTCCGTGTGCTCGGTTCGTT
CGGCCATACAAAACACAAAATTCAAGTTTAAAAACTAAATAGGCAACTAAAA
GGGAAGCCGCAGCGAATAAAGTGATTTGCTGAAAGAGACGTAAGAAAGTTA
ATCGCATCGAAGGCACCAGAAATCGGGGATTTCTAACACGGCGCGCGTGCGA
CGTACATACATACGCAAGCGCACACACACACGAACAATTACTTGCCATTGAC
GCAAAAGCGAAAAAGCAGTGGAATAAAGGGGAATTGACAAATAACAACGTT
TTGCAAGCACTGGACTCTGGTCGCTGGTGTTCTTTCATTTTGTAATTGCCACG
CATGGACGACGAAGTAATTGAAATTAGCGACAGCGAACGCGAAGAAACCTC
ATCGAACTCCGAAATGGATGTGGAAATAACGACAGAACAGCCAACCATCGAT
GTCAAAGCAGAGCAAATTGTGCCCAAGGACGCGGCAACCATTGCCGAGGAG
AAGAAGAAACTGGGCAACGACCAATACAAGGCGCAGAACTATCAGAATGCA
CTCAAGCTCTACACGGATGCCATATCGCTGTGTCCGGACTCGGCGGCATACTA
TGGCAATCGGGCCGCCTGCTACATGATGCTGCTCAACTATAATAGCGCCCTG
ACCGACGCCCGACACGCCATACGCATCGATCCGGGCTTCGAGAAGGCCTACG
TCCGTGTGGCCAAGTGCTGTCTGGCCCTGGGCGACATTATTGGCACCGAACA
GGCCGTCAAAATGGTCAACGAGCTGAATTCGCTTAGCACGGCTGTTGCTGCC
GAACAGACGGCGGCGCAAAAGTTGCGCCAATTGGAGGCCACCATTCAGGCG
AACTACGATACGAAATCCTATCGCAATGTGGTCTTCTATTTGGATAGTGCCTT
GAAATTGGCGCCCGCCTGTTTGAAATATCGTCTACTCAAGGCTGAGTGCCTTG
CATTTTTGGGGCGATGTGATGAGGCCTTGGACATTGCGGTCAGTGTAATGAA
ACTGGATACCACATCGGCGGATGCGATATACGTGAGAGGTCTGTGCCTGTAC
TACACGGACAACCTGGACAAGGGAATTCTTCATTTCGAGCGCGCCCTGACCC
TCGACCCGGACCACTACAAGTCCAAGCAGATGCGCAGCAAATGCAAGCAGCT
CAAGGAGATGAAGGAGAACGGCAATATGCTATTCAAGTCGGGTCGGTATCGC
GAGGCACACGTTATCTACACGGACGCCCTGAAGATCGATGAACACAACAAGG
ATATCAATTCGAAATTGCTTTACAATCGGGCTTTGGTCAACACGCGTATTGGC
AATTTGCGAGAGGCCGTGGCCGATTGCAATCGAGTGCTGGAGCTGAATAGTC
AGTATCTGAAGGCTCTGTTGCTGCGAGCGCGCTGCTACAATGATCTGGAGAA
GTTCGAGGAGTCGGTGGCGGACTATGAGACGGCGCTGCAGCTGGAGAAGAC
GCCGGAGATTAAGCGAATGCTGCGCGAGGCCAAGTTTGCGTTGAAGAAGTCG
AAGCGAAAGGACTACTACAAGATCCTGGGCATTGGACGCAATGCGTCCGACG
ACGAGATCAAGAAGGCGTATCGCAAAAAGGCGCTGGTACATCATCCGGATCG

FIGURE 9B (Continued)

```
ACACGCAAACAGCAGTGCCGAGGAGCGCAAGGAGGAGGAGCTCAAGTTCAA
GGAGGTGGGCGAGGCGTACGCCATACTGTCGGATGCTCACAAGAAGTCGCGC
TACGACAGCGGCCAGGATATCGAGGAGCAGGAGCAAGCCGACTTCGATCCG
AATCAAATGTTCCGCACATTCTTCCAATTCAACGGCGGTGGCCGGAATAATTC
ATCGTTCAACTTTGAGTTCTAGGATCCCAACGAGTGTTGTTCACCACCACAGA
GAAGAAGACCATCTCAATCCCATACTTTCTGCCTCATCCGAAACCAACATAC
AGCAGCGCACAAATTTTGAACTCTTTTACATATTTCTTTTCCAAAAAGCAAGA
AAATACCACATTTTGATTATGTTAACGAATGAATATATGCCAAGTTATTTGAA
AAAATATTCTAAATCAAAATAATGCAACTAAATTCCAGTGTAAGTTCACATT
TTTAAATGTTCTTTCTTGGATTTTTTTTTCGGCAACATTAATAAATCATGGGAG
ATTTGTGTTAAATAAACAGAAATATACATATAAAAAAAAAAAAAAAAAAAAA
```

FIGURE 10A dMLF Protein 273 amino acids
MSLFGALMGDFDDDLGLMNNHMNHTMNAMNMQMRSMNRLMNSFMPDPFMQ
VSPFDQGFQQNALMERPQMPAMPAMGLFGMPMMPNFNRLLNADIGGNSGASF
CQSTVMTMSSGPDGRPQIYQASTSTKTGPGGVRETRRTVQDSRTGVKKMAIGHH
IGERAHIIEKEQDMRSGQLEERQEFINLEEGEAEQFDREFTSRASRGAVQSRHHAG
GMQAIMPARPAAHTSTLTIEPVEDDDDDDDCVIQEQQPVRSSAGRHYSSAPTAP
QNRYNY

FIGURE 10B dMLF cDNA 1753 base pairs
GGCACGAGGAAAATATTCGTGAAAATTCTGCATACGGAAAGAAGAAAATTC
GAGCAACAGAAAGCCAACACAATCCACAAAAATGTCTTTATTCGGAGCGTTG
ATGGGTGATTTCGACGACGATCTCGGCCTTATGAACAACCACATGAACCACA
CTATGAACGCGATGAACATGCAGATGCGCTCGATGAATCGCCTGATGAACAG
CTTTATGCCCGATCCCTTCATGCAGGTCTCGCCCTTTGACCAGGGATTCCAGC
AGAACGCTCTCATGGAGCGTCCGCAGATGCCGGCCATGCCAGCCATGGGCCT
CTTCGGCATGCCCATGATGCCAAACTTTAATCGCCTGTTGAACGCTGATATTG
GTGGCAATTCAGGCGCATCCTTCTGCCAGAGCACCGTGATGACCATGTCATC
GGGTCCCGATGGGCGTCCTCAGATCTACCAGGCCAGCACTAGTACCAAAACA
GGACCGGGAGGCGTTCGTGAGACCCGCAGGACGGTGCAGGACTCGCGCACT
GGGGTGAAGAAGATGGCCATTGGTCATCACATCGGCGAGCGGGCACACATTA
TTGAGAAAGAGCAGGACATGCGCTCAGGACAACTGGAGGAGCGCCAGGAGT
TCATTAATCTGGAGGAGGGAGAAGCCGAGCAGTTTGACAGGGAGTTTACATC
GCGCGCTAGTCGCGGAGCGGTGCAGTCAAGACATCATGCTGGTGGCATGCAG
GCCATCATGCCCGCCCGTCCAGCGGCACACACCTCGACGTTGACCATTGAGC
CAGTGGAGGACGACGACGACGATGATGATGACTGTGTAATCCAGGAGCAGC
AACCGGTTCGCTCCTCCGCGGGCCGCCATTATTCCAGTGCGCCAACGGCACC
GCAGAACAGATATAATTACTAAATCTAAAGTCAATACAGTATATTTTACTAA
CTATCCGATAAAACAGAAACAGAATTGCATACTATAAATTTCTGCTAATTAC
ATTCCCAACTGCGTTCAAACGAAACGAATATCGAATCGAAATCATAGAATGC
ACAGAGCAGCATACATCCACATCCCTATGCCGCCAATCCGAGGCGCCAACAA
CGTGCCGTAAAACATTTTCACACGGAGGACGAAGCGGCCAGCTCCTACAAGG
CGGTCAAGCGCGGCAAGAAGAAGTAGTAGAAACGTGATCATCTGTATGCCAA
CATCTTCCGCATCGCACACTCAAAAACACTAGGAAGCAAAGCGTTGGGTTCT
GTTCCATAGCAGGAAAACCAATTCAAATATTTTTTAACAAACACAATTCTTTA
CCAGTTCTGTCTTATCCTGCGTGAGTCGACCAGAATGCAACACTAAAAAATGT
ACAACTTCAAGATGCTATTGATGTGCACGCAGGATACAGAACAACTTGCTTA
AATTTACTTAAAACAAATGTGACTATTCAACGCCGAAATCATTACAACACAC
ACTCTCAGACCTAATCGAAAAATTCAATGAAAGTAATGGAATATATATGAAA
TCGTAATTATAAGTTTGAATTATTTGATTAATTCTCAAGTTTTTAGATTTTGTT
AGCCACTAAGCTTTAAATTATGGATGCCAGTTAGCGTGCAAATGAACACAAT
TGATTTGAAGGCTCCGAACGATAGAAAACAACAATTACCAATTCCCCAAATA
CATGTAATTCGTAAGGCCTAAGTAAATGTTAACGTGAATTTAATTAAATGGTA
ATTACATTATAATAGTAAAAAAAAAAAAAAAAAA ClustalW Formatted Alignments

FIGURE 11A (Continued)

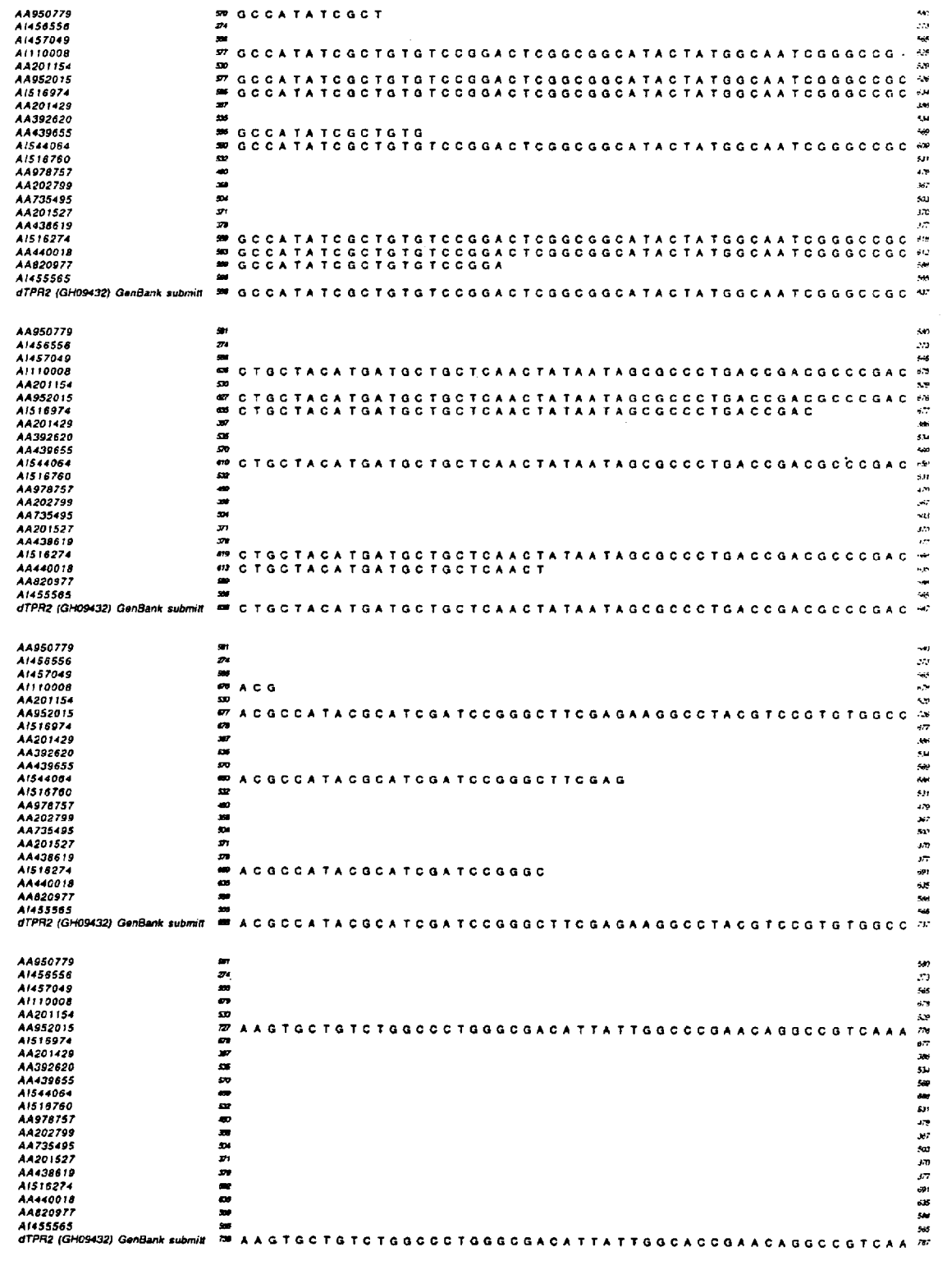

| Sequence | Start | Alignment | End |
|---|---|---|---|
| AA950779 | 570 | GCCATATCGCT | 580 |
| AI456556 | 274 | | 273 |
| AI457049 | 586 | | 585 |
| AI110008 | 577 | GCCATATCGCTGTGTCCGGACTCGGCGGCATACTATGGCAATCGGGCCG- | 625 |
| AA201154 | 530 | | 529 |
| AA952015 | 577 | GCCATATCGCTGTGTCCGGACTCGGCGGCATACTATGGCAATCGGGCCGC | 626 |
| AI516974 | 586 | GCCATATCGCTGTGTCCGGACTCGGCGGCATACTATGGCAATCGGGCCGC | 634 |
| AA201429 | 387 | | 386 |
| AA392620 | 535 | | 534 |
| AA439655 | 556 | GCCATATCGCTGTG | 569 |
| AI544064 | 560 | GCCATATCGCTGTGTCCGGACTCGGCGGCATACTATGGCAATCGGGCCGC | 609 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 569 | GCCATATCGCTGTGTCCGGACTCGGCGGCATACTATGGCAATCGGGCCGC | 618 |
| AA440018 | 563 | GCCATATCGCTGTGTCCGGACTCGGCGGCATACTATGGCAATCGGGCCGC | 612 |
| AA820977 | 570 | GCCATATCGCTGTGTCCGGA | 589 |
| AI455565 | 566 | | 565 |
| dTPR2 (GH09432) GenBank submitt | 588 | GCCATATCGCTGTGTCCGGACTCGGCGGCATACTATGGCAATCGGGCCGC | 637 |

| Sequence | Start | Alignment | End |
|---|---|---|---|
| AA950779 | 581 | | 580 |
| AI456556 | 274 | | 273 |
| AI457049 | 586 | | 585 |
| AI110008 | 626 | CTGCTACATGATGCTGCTCAACTATAATAGCGCCCTGACCGACGCCCGAC | 675 |
| AA201154 | 530 | | 529 |
| AA952015 | 627 | CTGCTACATGATGCTGCTCAACTATAATAGCGCCCTGACCGACGCCCGAC | 676 |
| AI516974 | 635 | CTGCTACATGATGCTGCTCAACTATAATAGCGCCCTGACCGAC | 677 |
| AA201429 | 387 | | 386 |
| AA392620 | 535 | | 534 |
| AA439655 | 570 | | 569 |
| AI544064 | 610 | CTGCTACATGATGCTGCTCAACTATAATAGCGCCCTGACCGACGCCCGAC | 659 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 619 | CTGCTACATGATGCTGCTCAACTATAATAGCGCCCTGACCGACGCCCGAC | 668 |
| AA440018 | 613 | CTGCTACATGATGCTGCTCAACT | 635 |
| AA820977 | 590 | | 589 |
| AI455565 | 566 | | 565 |
| dTPR2 (GH09432) GenBank submitt | 638 | CTGCTACATGATGCTGCTCAACTATAATAGCGCCCTGACCGACGCCCGAC | 687 |

| Sequence | Start | Alignment | End |
|---|---|---|---|
| AA950779 | 581 | | 580 |
| AI456556 | 274 | | 273 |
| AI457049 | 586 | | 585 |
| AI110008 | 676 | ACG | 678 |
| AA201154 | 530 | | 529 |
| AA952015 | 677 | ACGCCATACGCATCGATCCGGGCTTCGAGAAGGCCTACGTCCGTGTGGCC | 726 |
| AI516974 | 678 | | 677 |
| AA201429 | 387 | | 386 |
| AA392620 | 535 | | 534 |
| AA439655 | 570 | | 569 |
| AI544064 | 660 | ACGCCATACGCATCGATCCGGGCTTCGAG | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 669 | ACGCCATACGCATCGATCCGGGC | 691 |
| AA440018 | 636 | | 635 |
| AA820977 | 590 | | 589 |
| AI455565 | 566 | | 565 |
| dTPR2 (GH09432) GenBank submitt | 688 | ACGCCATACGCATCGATCCGGGCTTCGAGAAGGCCTACGTCCGTGTGGCC | 737 |

| Sequence | Start | Alignment | End |
|---|---|---|---|
| AA950779 | 581 | | 580 |
| AI456556 | 274 | | 273 |
| AI457049 | 586 | | 585 |
| AI110008 | 679 | | 678 |
| AA201154 | 530 | | 529 |
| AA952015 | 727 | AAGTGCTGTCTGGCCCTGGGCGACATTATTGGCCCGAACAGGCCGTCAAA | 776 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 590 | | 589 |
| AI455565 | 566 | | 565 |
| dTPR2 (GH09432) GenBank submitt | 738 | AAGTGCTGTCTGGCCCTGGGCGACATTATTGGCACCGAACAGGCCGTCAA | 787 |

FIGURE 11A (Continued)

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 777 | A T G G T T | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 788 | A A T G G T C A A C G A G C T G A A T T C G C T T A G C A C G G C T G T T G C T G C C G A A C A G A | 837 |

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 838 | C G G C G G C G C A A A A G T T G C G C C A A T T G G A G G C C A C C A T T C A G G C G A A C T A C | 887 |

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 888 | G A T A C G A A A T C C T A T C G C A A T G T G G T C T T C T A T T T G G A T A G T G C C T T G A A | 937 |

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 938 | A T T G G C G C C C G C C T G T T T G A A A T A T C G T C T A C T C A A G G C T G A G T G C C T T G | 987 |

FIGURE 11A (Continued)

| | | | |
|---|---|---|---|
| AA950779 | 581 | | 580 |
| AI456556 | 274 | | 273 |
| AI457049 | 586 | | 585 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 586 | | 585 |
| dTPR2 (GH09432) GenBank submitt | 988 | C A T T T T T G G G G C G A T G T G A T G A G G C C T T G G A C A T T G C G G T C A G T G T A A T G | 1037 |

| | | | |
|---|---|---|---|
| AA950779 | 581 | | 580 |
| AI456556 | 274 | | 273 |
| AI457049 | 586 | | 585 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 586 | | 585 |
| dTPR2 (GH09432) GenBank submitt | 1038 | A A A C T G G A T A C C A C A T C G G C G G A T G C G A T A T A C G T G A G A G G T C T G T G C C T | 1087 |

| | | | |
|---|---|---|---|
| AA950779 | 581 | | 580 |
| AI456556 | 274 | | 273 |
| AI457049 | 586 | | 585 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 586 | | 585 |
| dTPR2 (GH09432) GenBank submitt | 1088 | G T A C T A C A C G G A C A A C C T G G A C A A G G G A A T T C T T C A T T T C G A G C G C G C C C | 1137 |

| | | | |
|---|---|---|---|
| AA950779 | 581 | | 580 |
| AI456556 | 274 | | 273 |
| AI457049 | 586 | | 585 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 586 | | 585 |
| dTPR2 (GH09432) GenBank submitt | 1138 | T G A C C C T C G A C C C G G A C C A C T A C A A G T C C A A G C A G A T G C G C A G C A A A T G C | 1187 |

FIGURE 11A (Continued)

| | | | |
|---|---|---|---|
| AA950779 | 581 | | 580 |
| AI456556 | 274 | | 273 |
| AI457049 | 586 | | 585 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 1188 | A A G C A G C T C A A G G A G A T G A A G G A G A A C G G C A A T A T G C T A T T C A A G T C G G G | 1237 |

| | | | |
|---|---|---|---|
| AA950779 | 581 | | 580 |
| AI456556 | 274 | | 273 |
| AI457049 | 586 | | 585 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 1238 | T C G G T A T C G C G A G G C A C A C G T T A T C T A C A C G G A C G C C C T G A A G A T C G A T G | 1287 |

| | | | |
|---|---|---|---|
| AA950779 | 581 | | 580 |
| AI456556 | 274 | | 273 |
| AI457049 | 586 | | 585 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 1288 | A A C A C A A C A A G G A T A T C A A T T C G A A A T T G C T T T A C A A T C G G G C T T T G G T C | 1337 |

| | | | |
|---|---|---|---|
| AA950779 | 581 | | 580 |
| AI456556 | 274 | | 273 |
| AI457049 | 586 | | 585 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 1338 | A A C A C G C G T A T T G G C A A T T T G C G A G A G G C C G T G G C C G A T T G C A A T C G A G T | 1387 |

FIGURE 11A (Continued)

| | | | |
|---|---|---|---|
| AA950779 | 581 | | 580 |
| AI456556 | 274 | | 273 |
| AI457049 | 547 | | 546 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 1388 | G C T G G A G C T G A A T A G T C A G T A T C T G A A G G C T C T G T T G C T G C G A G C G C G C T | 1437 |

| | | | |
|---|---|---|---|
| AA950779 | 581 | | 580 |
| AI456556 | 274 | | 273 |
| AI457049 | 547 | | 546 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 1438 | G C T A C A A T G A T C T G G A G A A G T T C G A G G A G T C G G T G G C G G A C T A T G A G A C G | 1487 |

| | | | |
|---|---|---|---|
| AA950779 | 581 | | 580 |
| AI456556 | 274 | | 273 |
| AI457049 | 547 | | 546 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 1488 | G C G C T G C A G C T G G A G A A G A C G C C G G A G A T T A A G C G A A T G C T G C G C G A G G C | 1537 |

| | | | |
|---|---|---|---|
| AA950779 | 581 | | 580 |
| AI456556 | 274 | | 273 |
| AI457049 | 547 | | 546 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submitt | 1538 | C A A G T T T G C G T T G A A G A A G T C G A A G C G A A A G G A C T A C T A C A A G A T C C T G G | 1587 |

FIGURE 11A (Continued)

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 590 | | 589 |
| AI455565 | 566 | | 565 |
| dTPR2 (GH09432) GenBank submitt | 1588 | G C A T T G G A C G C A A T G C G T C C G A C G A C G A G A T C A A G A A G G C G T A T C G C A A A | 1637 |

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 590 | | 589 |
| AI455565 | 566 | | 565 |
| dTPR2 (GH09432) GenBank submitt | 1638 | A A G G C G C T G G T A C A T C A T C C G G A T C G A C A C G C A A A C A G C A G T G C C G A G G A | 1687 |

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 590 | | 589 |
| AI455565 | 566 | | 565 |
| dTPR2 (GH09432) GenBank submitt | 1688 | G C G C A A G G A G G A G G A G C T C A A G T T C A A G G A G G T G G G C G A G G C G T A C G C C A | 1737 |

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 590 | | 589 |
| AI455565 | 566 | | 565 |
| dTPR2 (GH09432) GenBank submitt | 1738 | T A C T G T C G G A T G C T C A C A A G A A G T C G C G C T A C G A C A G C G G C C A G G A T A T C | 1787 |

FIGURE 11A (Continued)

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 586 | | 585 |
| dTPR2 (GH09432) GenBank submitt | 1788 | G A G G A G C A G G A G C A A G C C G A C T T C G A T C C G A A T C A A A T G T T C C G C A C A T T | 1837 |

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 586 | | 585 |
| dTPR2 (GH09432) GenBank submitt | 1838 | C T T C C A A T T C A A C G G C G G T G G C C G G A A T A A T T C A T C G T T C A A C T T T G A G T | 1887 |

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 586 | | 585 |
| dTPR2 (GH09432) GenBank submitt | 1888 | T C T A G G A T C C C A A C G A G T G T T G T T C A C C A C C A C A G A G A A G A A G A C C A T C T | 1937 |

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 388 | | 387 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 586 | | 585 |
| dTPR2 (GH09432) GenBank submitt | 1938 | C A A T C C C A T A C T T T C T G C C T C A T C C G A A A C C A A C A T A C A G C A G C G C A C A A | 1987 |

FIGURE 11A (Continued)

| | | | |
|---|---|---|---|
| AA950779 | 561 | | 560 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submit | 1988 | A T T T T G A A C T C T T T T A C A T A T T T C T T T T C C A A A A A G C A A G A A A A T A C C A C | 2037 |

| | | | |
|---|---|---|---|
| AA950779 | 561 | | 560 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submit | 2038 | A T T T T G A T T A T G T T A A C G A A T G A A T A T A T G C C A A G T T A T T T G A A A A A A T A | 2087 |

| | | | |
|---|---|---|---|
| AA950779 | 561 | | 560 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submit | 2088 | T T C T A A A T C A A A A T A A T G C A A C T A A A T T T C C A G T G T A A G T T C A C A T T T T T | 2137 |

| | | | |
|---|---|---|---|
| AA950779 | 561 | | 560 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 689 | | 688 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 692 | | 691 |
| AA440018 | 636 | | 635 |
| AA820977 | 589 | | 588 |
| AI455565 | 566 | | 565 |
| dTPR2 (GH09432) GenBank submit | 2138 | A A A T G T T C T T T C T T G G A T T T T T T T T T C G G C A A C A T T A A T A A A T C A T G G G A | 2187 |

FIGURE 11A (Continued)

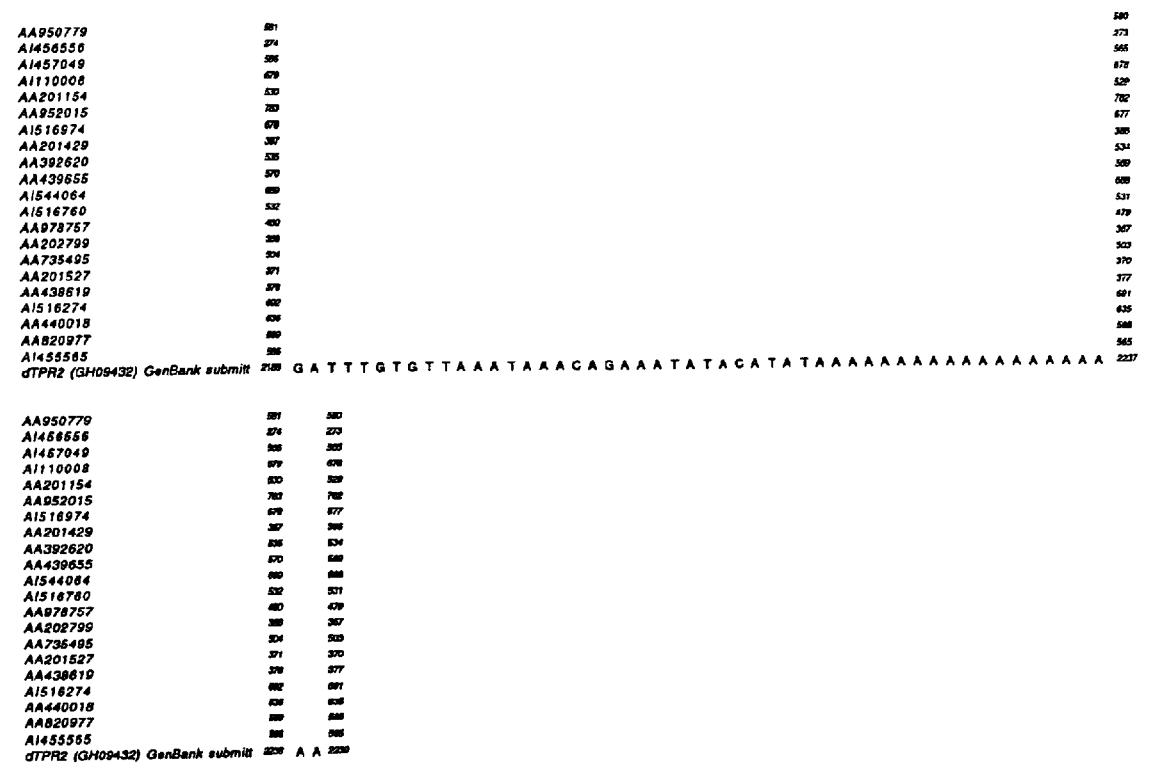

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 669 | | 668 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 602 | | 601 |
| AA440018 | 636 | | 635 |
| AA820977 | 589 | | 588 |
| AI455565 | 566 | | 565 |
| dTPR2 (GH09432) GenBank submitt | 2188 | G A T T T G T G T T A A A T A A A C A G A A A T A T A C A T A T A A A A A A A A A A A A A A A A A | 2237 |

| | | | |
|---|---|---|---|
| AA950779 | 581 | | 580 |
| AI456556 | 274 | | 273 |
| AI457049 | 566 | | 565 |
| AI110008 | 679 | | 678 |
| AA201154 | 530 | | 529 |
| AA952015 | 783 | | 782 |
| AI516974 | 678 | | 677 |
| AA201429 | 387 | | 386 |
| AA392620 | 535 | | 534 |
| AA439655 | 570 | | 569 |
| AI544064 | 669 | | 668 |
| AI516760 | 532 | | 531 |
| AA978757 | 480 | | 479 |
| AA202799 | 368 | | 367 |
| AA735495 | 504 | | 503 |
| AA201527 | 371 | | 370 |
| AA438619 | 378 | | 377 |
| AI516274 | 602 | | 601 |
| AA440018 | 636 | | 635 |
| AA820977 | 589 | | 588 |
| AI455565 | 566 | | 565 |
| dTPR2 (GH09432) GenBank submitt | 2238 | A A | 2239 |

ClustalW Formatted Alignments

FIGURE 11B (Continued)

| | | | |
|---|---|---|---|
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 741 | T G C T G T C T G G C C C T G G G C G A C A T T A T T G G C A C C G A A C A G G C C G T C A A A A T | 790 |
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 791 | G G T C A A C G A G C T G A A T T C G C T T A G C A C G G C T G T T G C T G C C G A A C A G A C G G | 840 |
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 841 | C G G C G C A A A A G T T G C G C C A A T T G G A G G C C A C C A T T C A G G C G A A C T A C G A T | 890 |
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 891 | A C G A A A T C C T A T C G C A A T G T G G T C T T C T A T T T G G A T A G T G C C T T G A A A T T | 940 |

FIGURE 11B (Continued)

| | | | |
|---|---|---|---|
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 941 | G G C G C C C G C C T G T T T G A A A T A T C G T C T A C T C A A G G C T G A G T G C C T T G C A T | 990 |

| | | | |
|---|---|---|---|
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 991 | T T T T G G G G C G A T G T G A T G A G G C C T T G G A C A T T G C G G T C A G T G T A A T G A A A | 1040 |

| | | | |
|---|---|---|---|
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1041 | C T G G A T A C C A C A T C G G C G G A T G C G A T A T A C G T G A G A G G T C T G T G C C T G T A | 1090 |

| | | | |
|---|---|---|---|
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1091 | C T A C A C G G A C A A C C T G G A C A A G G G A A T T C T T C A T T T C G A G C G C G C C C T G A | 1140 |

FIGURE 11B (Continued)

```
AI456052              590                                                                                                    58?
AA391402              654                                                                                                    65?
AI514849              632                                                                                                    631
AI519786              552                                                                                                    5??
AI546378              542                                                                                                    5??
AA438290              561                                                                                                    51?
AA820520              618                                                                                                    68?
AA941597              523                                                                                                    55?
AI455870              551                                                                                                    54?
AA950277              547                                                                                                    48?
AA941028              488                                                                                                    248
AA951077              247                                                                                                    17?
AA951083              171                                                                                                    511
AA949900              512                                                                                                    68?
AA541065              700                                                                                                    5??
AA441093              597
dTPR2 (GH09432) GenBank submitt 1141 C C C T C G A C C C G G A C C A C T A C A A G T C C A A G C A G A T G C G C A G C A A A T G C A A G 1190

AI456052              590                                                                                                    58?
AA391402              654                                                                                                    65?
AI514849              632                                                                                                    631
AI519786              552                                                                                                    5??
AI546378              542                                                                                                    5??
AA438290              561                                                                                                    61?
AA820520              618                                                                                                    68?
AA941597              583                                                                                                    58?
AI455870              551                                                                                                    5??
AA950277              547                                                                                                    48?
AA941028              488                                                                                                    248
AA951077              247                                                                                                    17?
AA951083              171                                                                                                    511
AA949900              512                                                                                                    68?
AA541065              700                                                                                                    5??
AA441093              597
dTPR2 (GH09432) GenBank submitt 1191 C A G C T C A A G G A G A T G A A G G A G A A C G G C A A T A T G C T A T T C A A G T C G G G T C G 1240

AI456052              590                                                                                                    58?
AA391402              654                                                                                                    65?
AI514849              632                                                                                                    631
AI519786              552                                                                                                    5??
AI546378              542                                                                                                    5??
AA438290              561                                                                                                    58?
AA820520              618                                                                                                    61?
AA941597              580                                                                                                    55?
AI455870              551                                                                                                    5??
AA950277              547                                                                                                    48?
AA941028              488                                                                                                    248
AA951077              247                                                                                                    17?
AA951083              171                                                                                                    511
AA949900              512                                                                                                    68?
AA541065              700                                                                                                    5??
AA441093              597
dTPR2 (GH09432) GenBank submitt 1241 G T A T C G C G A G G C A C A C G T T A T C T A C A C G G A C G C C C T G A A G A T C G A T G A A C 1290

AI456052              590                                                                                                    58?
AA391402              654                                                                                                    65?
AI514849              632                                                                                                    631
AI519786              552                                                                                                    5??
AI546378              542                                                                                                    5??
AA438290              561                                                                                                    61?
AA820520              618                                                                                                    68?
AA941597              580                                                                                                    55?
AI455870              551                                                                                                    5??
AA950277              547                                                                                                    48?
AA941028              488                                                                                                    248
AA951077              247                                                                                                    17?
AA951083              171                                                                                                    511
AA949900              512                                                                                                    68?
AA541065              700                                                                                                    5??
AA441093              597
dTPR2 (GH09432) GenBank submitt 1291 A C A A C A A G G A T A T C A A T T C G A A A T T G C T T T A C A A T C G G G C T T T G G T C A A C 1340
```

FIGURE 11B (Continued)

| | | | |
|---|---|---|---|
| AI456052 | 590 | | 589 |
| AA391402 | 654 | | 653 |
| AI514849 | 632 | | 631 |
| AI519786 | 582 | | 581 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1341 | A C G C G T A T T G G C A A T T T G C G A G A G G C C G T G G C C G A T T G C A A T C G A G T G C T | 1390 |

| | | | |
|---|---|---|---|
| AI456052 | 590 | | 589 |
| AA391402 | 654 | | 653 |
| AI514849 | 632 | | 631 |
| AI519786 | 582 | | 581 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1391 | G G A G C T G A A T A G T C A G T A T C T G A A G G C T C T G T T G C T G C G A G C G C G C T G C T | 1440 |

| | | | |
|---|---|---|---|
| AI456052 | 590 | | 589 |
| AA391402 | 654 | | 653 |
| AI514849 | 632 | | 631 |
| AI519786 | 582 | | 581 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1441 | A C A A T G A T C T G G A G A A G T T C G A G G A G T C G G T G G C G G A C T A T G A G A C G G C G | 1490 |

| | | | |
|---|---|---|---|
| AI456052 | 590 | | 589 |
| AA391402 | 654 | | 653 |
| AI514849 | 632 | | 631 |
| AI519786 | 582 | | 581 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1491 | C T G C A G C T G G A G A A G A C G C C G G A G A T T A A G C G A A T G C T G C G C G A G G C C A A | 1540 |

FIGURE 11B (Continued)

| | | | |
|---|---|---|---|
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1541 | G T T T G C G T T G A A G A A G T C G A A G C G A A A G G A C T A C T A C A A G A T C C T G G G C A | 1590 |

| | | | |
|---|---|---|---|
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1591 | T T G G A C G C A A T G C G T C C G A C G A C G A G A T C A A G A A G G C G T A T C G C A A A A A G | 1640 |

| | | | |
|---|---|---|---|
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1641 | G C G C T G G T A C A T C A T C C G G A T C G A C A C G C A A A C A G C A G T G C C G A G G A G C G | 1690 |

| | | | |
|---|---|---|---|
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 581 | | 580 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1691 | C A A G G A G G A G G A G C T C A A G T T C A A G G A G G T G G G C G A G G C G T A C G C C A T A C | 1740 |

FIGURE 11B (Continued)

```
AI456052                                 500                                                                                    58:
AA391402                                 654                                                                                    65!
AI514849                                 632                                                                                    63!
AI519786                                 552                                                                                    58!
AI546378                                 542                                                                                    5!!
AA438290                                 561                                                                                    61!
AA820520                                 618                                                                                    54!
AA941597                                 583                                                                                    56!
AI455870                                 551                                                                                    5.!
AA950277                                 547                                                                                    48!
AA941028                                 488                                                                                    24!
AA951077                                 247                                                                                    170
AA951083                                 171                                                                                    511
AA949900                                 512                                                                                    66!
AA541065                                 700                                                                                    56!
AA441093                                 597
dTPR2 (GH09432) GenBank submitt         1741  T G T C G G A T G C T C A C A A G A A G T C G C G C T A C G A C A G C G G C C A G G A T A T C G A G  1790

AI456052                                 500                                                                                    58!
AA391402                                 654                                                                                    65!
AI514849                                 632                                                                                    63!
AI519786                                 552                                                                                    56!
AI546378                                 542                                                                                    57!
AA438290                                 561                                                                                    61!
AA820520                                 618                                                                                    59!
AA941597                                 583                                                                                    56!
AI455870                                 551                                                                                    5.!
AA950277                                 547                                                                                    48!
AA941028                                 488                                                                                    24!
AA951077                                 247                                                                                    170
AA951083                                 171                                                                                    511
AA949900                                 512                                                                                    66!
AA541065                                 700                                                                                    56!
AA441093                                 597
dTPR2 (GH09432) GenBank submitt         1791  G A G C A G G A G C A A G C C G A C T T C G A T C C G A A T C A A A T G T T C C G C A C A T T C T T  1840

AI456052                                 500                                                                                    58!
AA391402                                 654                                                                                    65!
AI514849                                 632                                                                                    63!
AI519786                                 552                                                                                    56!
AI546378                                 542                                                                                    58!
AA438290                                 561                                                                                    61!
AA820520                                 618                                                                                    56!
AA941597                                 583                                                                                    55!
AI455870                                 551                                                                                    5.!
AA950277                                 547                                                                                    48!
AA941028                                 488                                                                                    24!
AA951077                                 247                                                                                    170
AA951083                                 171                                                                                    511
AA949900                                 512                                                                                    66!
AA541065                                 700                                                                                    56!
AA441093                                 597
dTPR2 (GH09432) GenBank submitt         1841  C C A A T T C A A C G G C G G T G G C C G G A A T A A T T C A T C G T T C A A C T T T G A G T T C T  1890

AI456052                                 500                                                                                    58!
AA391402                                 654                                                                                    63!
AI514849                                 632                                                                                    56!
AI519786                                 552                                                                                    56!
AI546378                                 542                                                                                    56!
AA438290                                 561                                                                                    61!
AA820520                                 618                                                                                    56!
AA941597                                 583                                                                                    55!
AI455870                                 551                                                                                    5.!
AA950277                                 547                                                                                    48!
AA941028                                 488                                                                                    24!
AA951077                                 247                                                                                    177
AA951083                                 171                                                                                    511
AA949900                                 512                                                                                    66!
AA541065                                 700                                                                                    56!
AA441093                                 597
dTPR2 (GH09432) GenBank submitt         1891  A G G A T C C C A A C G A G T G T T G T T C A C C A C C A C A G A G A A G A A G A C C A T C T C A A  1940
```

FIGURE 11B (Continued)

| | | | |
|---|---|---|---|
| AI456052 | 590 | | 589 |
| AA391402 | 654 | | 653 |
| AI514849 | 632 | | 631 |
| AI519786 | 582 | | 581 |
| AI546378 | 542 | | 541 |
| AA438290 | 561 | | 560 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1941 | T C C C A T A C T T T C T G C C T C A T C C G A A A C C A A C A T A C A G C A G C G C A C A A A T T | 1990 |

| | | | |
|---|---|---|---|
| AI456052 | 590 | | 589 |
| AA391402 | 654 | | 653 |
| AI514849 | 632 | | 631 |
| AI519786 | 582 | | 581 |
| AI546378 | 542 | | 541 |
| AA438290 | 561 | | 560 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 1991 | T T G A A C T C T T T T A C A T A T T T C T T T T C C A A A A A G C A A G A A A A T A C C A C A T T | 2040 |

| | | | |
|---|---|---|---|
| AI456052 | 590 | | 589 |
| AA391402 | 654 | | 653 |
| AI514849 | 632 | | 631 |
| AI519786 | 582 | | 581 |
| AI546378 | 542 | | 541 |
| AA438290 | 561 | | 560 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 2041 | T T G A T T A T G T T A A C G A A T G A A T A T A T G C C A A G T T A T T T G A A A A A A T A T T C | 2090 |

| | | | |
|---|---|---|---|
| AI456052 | 590 | | 589 |
| AA391402 | 654 | | 653 |
| AI514849 | 632 | | 631 |
| AI519786 | 582 | | 581 |
| AI546378 | 542 | | 541 |
| AA438290 | 561 | | 560 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 2091 | T A A A T C A A A A T A A T G C A A C T A A A T T T C C A G T G T A A G T T C A C A T T T T T A A A | 2140 |

FIGURE 11B (Continued)

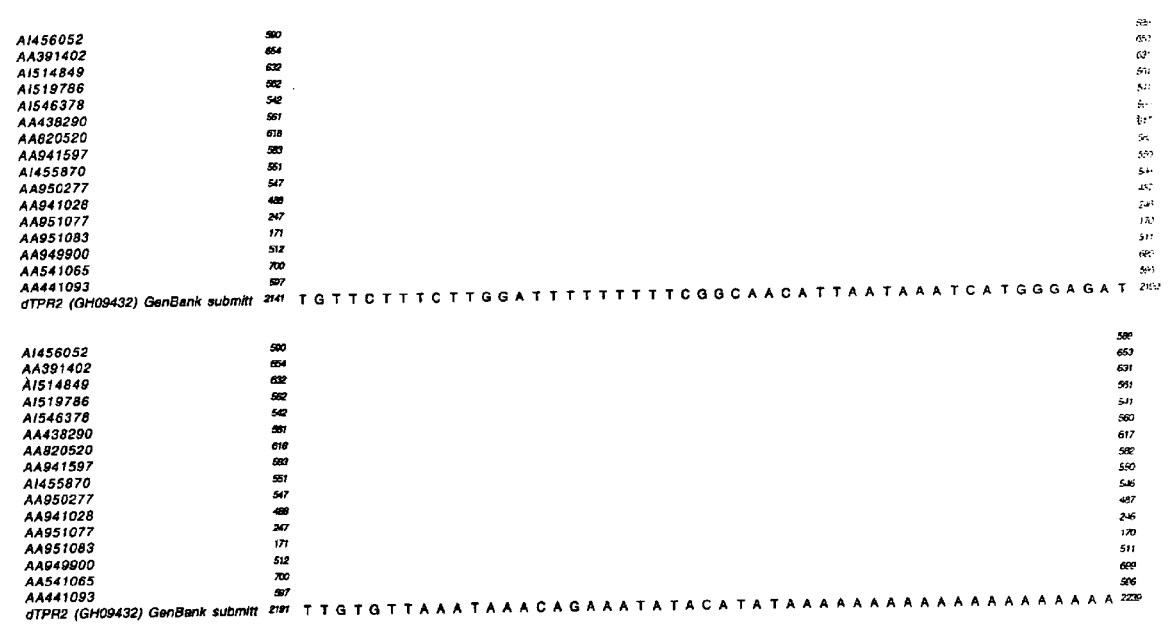

| | | | |
|---|---|---|---|
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 561 | | 560 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 2141 | T G T T C T T T C T T G G A T T T T T T T T T C G G C A A C A T T A A T A A A T C A T G G G A G A T | 2190 |

| | | | |
|---|---|---|---|
| AI456052 | 590 | | 589 |
| AA391402 | 654 | | 653 |
| AI514849 | 632 | | 631 |
| AI519786 | 562 | | 561 |
| AI546378 | 542 | | 541 |
| AA438290 | 561 | | 560 |
| AA820520 | 618 | | 617 |
| AA941597 | 583 | | 582 |
| AI455870 | 551 | | 550 |
| AA950277 | 547 | | 546 |
| AA941028 | 488 | | 487 |
| AA951077 | 247 | | 246 |
| AA951083 | 171 | | 170 |
| AA949900 | 512 | | 511 |
| AA541065 | 700 | | 699 |
| AA441093 | 597 | | 596 |
| dTPR2 (GH09432) GenBank submitt | 2191 | T T G T G T T A A A T A A A C A G A A A T A T A C A T A T A A A A A A A A A A A A A A A A A A A A | 2239 |

ClustalW Formatted Alignments

FIGURE 12 (Continued)

| | | | |
|---|---|---|---|
| AA950937 | 668 | | 667 |
| AI113626 | 564 | | 563 |
| AA978719 | 748 | A C G A C G A C G A T G A T G C | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmif cDNA only | 792 | A C G A C G A C G A T G A T G A T G A C T G T G T A A T C C A G G A G C A G C A A C C G G T T C G C | 841 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmif cDNA only | 842 | T C C T C C G C G G G C C G C C A T T A T T C C A G T G C G C C A A C G G C A C C G C A G A A C A G | 891 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmif cDNA only | 892 | A T A T A A T T A C T A A A T C T A A A G T C A A T A C A G T A T A T T T T A C T A A C T A T C C G | 941 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmif cDNA only | 942 | A T A A A A C A G A A A C A G A A T T G C A T A C T A T A A A T T T C T G C T A A T T A C A T T C C | 991 |
| AA264488 | 687 | | 686 |

FIGURE 12 (Continued)

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 992 | C A A C T G C G T T C A A A C G A A A C G A A T A T C G A A T C G A A A T C A T A G A A T G C A C A | 1041 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1042 | G A G C A G C A T A C A T C C A C A T C C C T A T G C C G C C A A T C C G A G G C G C C A A C A A C | 1091 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1092 | G T G C C G T A A A A C A T T T T C A C A C G G A G G A C G A A G C G G C C A G C T C C T A C A A G | 1141 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1142 | G C G G T C A A G C G C G G C A A G A A G A A G T A G T A G A A A C G T G A T C A T C T G T A T G C | 1191 |
| AA264488 | 687 | | 686 |

FIGURE 12 (Continued)

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1192 | C A A C A T C T T C C G C A T C G C A C A C T C A A A A A C A C T A G G A A G C A A A G C G T T G G | 1241 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1242 | G T T C T G T T C C A T A G C A G G A A A A C C A A T T C A A A T A T T T T T T A A C A A A C A C A | 1291 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1292 | A T T C T T T A C C A G T T C T G T C T T A T C C T G C G T G A G T C G A C C A G A A T G C A A C A | 1341 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1342 | C T A A A A A A T G T A C A A C T T C A A G A T G C T A T T G A T G T G C A C G C A G G A T A C A G | 1391 |
| AA264488 | 687 | | 686 |

FIGURE 12 (Continued)

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1392 | A A C A A C T T G C T T A A A T T T A C T T A A A A C A A A T G T G A C T A T T C A A C G C C G A A | 1441 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1442 | A T C A T T A C A A C A C A C A C T C T C A G A C C T A A T C G A A A A A T T C A A T G A A A G T A | 1491 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1492 | A T G G A A T A T A T A T G A A A T C G T A A T T A T A A G T T T G A A T T A T T T G A T T A A T T | 1541 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1542 | C T C A A G T T T T T A G A T T T T G T T A G C C A C T A A G C T T T A A A T T A T G G A T G C C A | 1591 |
| AA264488 | 687 | | 686 |

FIGURE 12 (Continued)

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1592 | G T T A G C G T G C A A A T G A A C A C A A T T G A T T T G A A G G C T C C G A A C G A T A G A A A | 1641 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1642 | A C A A C A A T T A C C A A T T C C C C A A A T A C A T G T A A T T C G T A A G G C C T A A G T A A | 1691 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1692 | A T G T T A A C G T G A A T T T A A T T A A A T G G T A A T T A C A T T A T A A T A G T A A A A A A | 1741 |
| AA264488 | 687 | | 686 |

| | | | |
|---|---|---|---|
| AA950937 | 668 | | 667 |
| AI113626 | 564 | | 563 |
| AA978719 | 764 | | 763 |
| AI260802 | 709 | | 708 |
| AI541593 | 600 | | 599 |
| AI541599 | 609 | | 608 |
| AA695052 | 586 | | 585 |
| AI107772 | 592 | | 591 |
| AI113621 | 658 | | 657 |
| AI515548 | 718 | | 717 |
| AI532198 | 498 | | 497 |
| AI389024 | 686 | | 685 |
| AA391063 | 541 | | 540 |
| AA940727 | 682 | | 681 |
| AA802232 | 676 | | 675 |
| AI531980 | 628 | | 627 |
| dmlf cDNA only | 1742 | A A A A A A A A A A A A | 1753 |
| AA264488 | 687 | | 686 |

FIGURE 13A hTPR2 Protein 484 amino acids
MAATEPELLDDQEAKREAETFKEQGNAYYAKKDYNEAYNYYTKAIDMCPKNA
SYYGNRAATLMMLGRFREALGDAQQSVRLDDSFVRGHLREGKCHLSLGNAMA
ACRSFQRALELDHKNAQAQQEFKNANAVMEYEKIAETDFEKRDFRKVVFCMDR
ALEFAPACHRFKILKAECLAMLGRYPEAQSVASDILRMDSTNADALYVRGLCLY
YEDCIEKAVQFFVQALRMAPDHEKACIACRNAKALKAKKEDGNKAFKEGNYKL
AYELYTEALGIDPNNIKTNAKLYCNRGTVNSKLRKLDDAIEDCTNAVKLDDTYI
KAYLRRAQCYMDTEQYEEAVRDYEKVYQTEKTKEHKQLLKNAQLELKKSKRK
DYYKILGVDKNASEDEIKKAYRKRALMHHPDRHSGASAEVQKEEEKKFKEVGE
AFTILSDPKKKTRYDSGQDLDEEGMNMGDFDPNNIFKAFFGGPGGFSFEASGPGN
FFFQFG

FIGURE 13B hTPR2 cDNA 1756 base pairs
CGGCTGCCGCGGAGTGCGATGTGGTAATGGCGGCGACCGAGCCGGAGCTGCT
CGACGACCAAGAGGCGAAGAGGGAAGCAGAGACTTTCAAGGAACAAGGAAA
TGCATACTATGCCAAGAAAGATTACAATGAAGCTTATAATTATTATACAAAA
GCCATAGATATGTGTCCTAAAAATGCTAGCTATTATGGTAATCGAGCAGCCA
CCTTGATGATGCTTGGAAGGTTCCGGGAAGCTCTTGGAGATGCACAACAGTC
AGTGAGGTTGGATGACAGTTTTGTCCGGGGACATCTACGAGAGGGCAAGTGC
CACCTCTCTCTGGGGAATGCCATGGCAGCATGTCGCAGCTTCCAGAGAGCCC
TAGAACTGGATCATAAAAATGCTCAGGCACAACAAGAGTTCAAGAATGCTAA
TGCAGTCATGGAATATGAGAAAATAGCAGAAACAGATTTTGAGAAGCGAGA
TTTTCGGAAGGTTGTTTTCTGCATGGACCGTGCCCTAGAATTTGCCCCTGCCT
GCCATCGCTTCAAAATCCTCAAGGCAGAATGTTTAGCAATGCTGGGTCGTTAT
CCGGAAGCACAGTCTGTGGCTAGTGACATTCTACGAATGGATTCCACCAATG
CAGATGCTCTGTATGTACGAGGTCTTTGCCTTTATTACGAAGATTGTATTGAG
AAGGCAGTTCAGTTTTTCGTACAGGCTCTCAGGATGGCTCCTGACCACGAGA
AGGCCTGCATTGCCTGCAGAAATGCCAAAGCACTCAAAGCAAAGAAAGAAG
ATGGGAATAAAGCATTTAAGGAAGGAAATTACAAACTAGCATATGAACTGTA
CACAGAAGCCCTGGGGATAGACCCCAACAATATAAAAACAAATGCTAAACTC
TACTGTAATCGGGGTACGGTTAATTCCAAGCTTAGGAAACTAGATGATGCAA
TAGAAGACTGCACAAATGCAGTGAAGCTTGATGACACTTACATAAAAGCCTA
CTTGAGAAGAGCTCAGTGTTACATGGACACAGAACAGTATGAAGAAGCAGTA
CGAGACTATGAAAAAGTATACCAGACAGAGAAAACAAAAGAACACAAACAG
CTCCTAAAAAATGCGCAGCTGGAACTGAAGAAGAGTAAGAGGAAAGATTAC
TACAAGATTCTAGGAGTGGACAAGAATGCCTCTGAGGACGAGATCAAGAAA
GCTTATCGGAAACGGGCCTTGATGCACCATCCAGATCGGCATAGTGGAGCCA
GTGCTGAGGTTCAGAAGGAGGAGGAGAAGAAGTTCAAGGAAGTTGGAGAGG
CCTTTACTATCCTCTCTGATCCCAAGAAAAAGACTCGCTATGACAGTGGACAG
GACCTAGATGAGGAGGGCATGAATATGGGTGATTTTGATCCAAACAATATCT
TCAAGGCATTCTTTGGCGGTCCTGGCGGCTTCAGCTTTGAAGCATCTGGTCCA
GGGAATTTCTTTTTTCAATTTGGCTAATGAAGGGCAACCACCCAGAACCCAG
AAAATGCAGATTCACTCAGTTTAATCTTGAATGTGGAAACAGTTCACCTCCTC
CCTTCATCACGTCTCCGTGTGCTTAGAGCAGTTTCGTTTTCTCAGTTGGATGCC
CTGTGTCTCTGTGAGTGGGGTGGAGCAAAGGGAACCAATGCCGAAGACCGAG
GGCAGGGGAGGGAGGCGGGGGTGGACAGGGAGGCAGCTTGTGAATTTTTGT
TTTACTGTTTAACTTTATTAAAAAAGAAAAAAAAAAAAAA

FIGURE 14 A hMLF Protein 268 amino acids
MFRMLNSSFEDDPFFSESILAHRENMRQMIRSFSEPFGRDLLSISDGRGRAHNRRG
HNDGEDSLTHTDVSSFQTMDQMVSNMRNYMQKLERNFGQLSVDPNGHSFCSSS
VMTYSKIGDEPPKVFQASTQTRRAPGGIKETRKAMRDSDSGLEKMAIGHHIHDR
AHVIKKSKNKKTGDEEVNQEFINMNESDAHAFDEEWQSEVLKYKPGRHNLGNT
RMRSVGHENPGSRELKRREKPQQSPAIEHGRRSNVLGDKLHIKGSSVKSNKK

FIGURE 14B hMLF cDNA 1116 base pairs
GTTATGTGTTCCCGTCCGTACTGGAGGCTAGCTCTTGTCGCGGCCGCGGCGAG
TTAACATCGTTTTTCCAATCTGTCCGCGGCTGCCGCCACCCAAGACAGAGCCA
GAATGTTCAGGATGCTGAACAGCAGTTTTGAGGATGACCCCTTCTTCTCTGAG
TCCATTCTTGCACACCGAGAAAATATGCGACAGATGATAAGAAGTTTTTCTG
AACCCTTTGGAAGAGACTTGCTCAGTATCTCTGATGGTAGAGGGAGAGCTCA
TAATCGTAGAGGACATAATGATGGTGAAGATTCTTTGACTCATACAGATGTC
AGCTCTTTCCAGACCATGGACCAAATGGTGTCAAATATGAGAAACTATATGC
AGAAATTAGAAAGAAACTTCGGTCAACTTTCAGTGGATCCAAATGGACATTC
ATTTTGTTCTTCCTCAGTTATGACTTATTCCAAAATAGGAGATGAACCGCCAA
AGGTTTTTCAGGCCTCAACTCAAACTCGTCGAGCTCCAGGAGGAATAAAGGA
AACCAGGAAAGCAATGAGAGATTCTGACAGTGGACTAGAAAAAATGGCTAT
TGGTCATCATATCCATGACCGAGCTCATGTCATTAAAAAGTCAAAGAACAAG
AAGACTGGAGATGAAGAGGTCAACCAGGAGTTCATCAATATGAATGAAAGC
GATGCTCATGCTTTTGATGAGGAGTGGCAAAGTGAGGTTTTGAAGTACAAAC
CAGGACGACACAATCTAGGAAACACTAGAATGAGAAGTGTTGGCCATGAGA
ATCCTGGCTCCCGAGAACTTAAAAGAAGGGAGAAACCTCAACAAAGTCCAGC
CATTGAACATGGAAGGAGATCAAATGTTTTGGGGGACAAACTCCACATCAAA
GGCTCATCTGTGAAAAGCAACAAAAAATAAATAGCCATGCATTTGATTTGTT
TAGTTTTGATTGTTTTAACAGTTAGTAATGGTGCTGGGTAATAAGCATAAGAC
CAATCTCTTGCTGTTAAATCAGTTCTGTCCTTGGCAACTTTCTTCTGATATCTG
AATGTTCATGAAGGTCCTAGCTTTATATTGTCCCTCTTTTAGGAATAAAATTTT
GATTTTCAACAAAAAAAA

FIGURE 16 dHDJ1 5' region, 24333 base pairs
TTACGGTTTATTTACTATTACTCTAGTTAATCAAATAAACTGTATAATTCCTGG
CTTGTACAATAATTTTGCTAACACGCCGATGCGTTCGATCTTTTTTTTACCGC
TCTCCGTCGTATTCATCATGGTACATATTACATCCAACATACTTTATTTTTTT
GGGTTATTAACATTGGCAATATCGCTGCTCGCCGCCGTTCGGTTATGCTCTAT
AAATAAAAGGGGGGCGCCGCTAAAATTATAATAAAATTTTCATGGGTCCTAA
ATCTAGTCTCGAAATCTATGTACAAAGTTTGCTTGCATGCTGGTTAGGCATAG
GTTCTTAACGTATTATTGGGTTGCTTTATTTCCATTCTGCGCAGTTGTGCAGCC
TGTTTAGTGTTTGCCTTTACGGGGTTAACATTTTTTAAAAATGAAACATTAGA
GCGGTAACCTTGTTGTCTGATTATTGGCGTCATTAAAGCGGTATCGCCAGCAC
GCGATTGATGCAAGGATACCGATTCAATGAAATAAAAACGAATTCAGCCAAA
CACAATCTTTCATTTCTTTTTTTTTATCGTACTTAATGATAGCCTTAGTTTCTA
ATGGGACTGTGTGCTTCGGTGAAGGTTGGGGATGATTTTGGGAGGCAACAAT
TATGTTCTAGCTTATAGCTTACAGTCCTACGCCTACTCCTATTTCTAATATGTT
CATCATCAGCAGTTAAAAAACGTTTACAAAACTCATGCGAAATTGAAATCCA
ATAACAAATGCACACGCCGCAGTCGCATCGGCGTCATCTCTTTCTCCTGACCC
TCGCCTATCCGCATCCAGTTAGGTTTGCTGCTGCTGCTGCGCCGACGGTTGTC
GCCGACTGAAGCCACCGCCGGCGGACAGATGTCGTTGCAGGGCTCGCTGCTG
CTGGAACTTGGCGCTGCCTGGTCCTCCGAAGCGGTTGAACTTGAACTTGTTGC
GCTGCTGGAAGTTCTGGCGATAGTTCTGATTGTAGAATCGCGGAAATCCTCCA
CCTCCGCCGTTCTTGTTCCAGCGCTTCTGGCCCTCGTACTCCTGGAATGGATT
GTACCCGGGCGTGCTGTTGCTGGCATTGTTTCCCTTAGCCGAACCGGACTTCA
CCTTCCGCTGACGTCCACGATCCATCTCGTTCTCTTCGTCGTCGTCGATGTCCC
GCTGCCGCTGCTCACGCGCATCCACCAGTAGCTACGGAAAACAGAATATCAA
GCATTAGGCTAGAGTTCGGACCTTGTGAATGGGGAGGCTTGGCTGGCTGGCT
GACGCATGCGCTAGTTAATGGAGCTTATGCAGATGAGTACGGTCGCTCGCGA
ACAAGCACTGGGAATATGCACATTGTATTCGAAATGGGTGAGTGGCTTACGG
TTCACGGTTCACTGTAACAGGTTATCAGGCAAAACGGTAACGGCACAACGGT
TGAATTTATGGCGTATCAGGCGGTTGAAATGAAAGAAACAACGTGCCGGCCA
GCAGTCAAATCATAAGCTTCATTGCACGGGAAAACGGATGCGGAGTCATCGG
GTGAATTACCTAGGCTCCGGTGCAGTCACTCTCTCCCGCAATGACTTTTGCAA
CTCTCTCTACACTTTTCACGCTCGCTGAACGGAGGACGCGTTGTGGTGACCGC
CCGGTTGGGAACGGATACCAGCAACGCAGCCATCACAGACTATTCGGGGTAA
TCGTATTATTTGTATTTGTTTTGTGTGGTATGTGCTTAGTGGGGAAAAAGAAG
AAGCGTCGCCTCTGCCGCCGACGCTTCTACCTCCTACCGGCCGTCCGTGAGAC
GATCCGGATCGGGTGCGTCAGCGGTCGTGTCTGTTACCGCCACTGCAATTACG
ACCACATCTTTACTGTCACTGCCACTAGTCACTGCCGCGTCGACTGCAACCGA
GCCCTCGACGATATCGCTGCCTTCCACACTGCCGTGACCAGCTATCCGTTTCG
CACAAACCAACTCAAAAGTCTAAATGAATGGGGATAATGTGGAAACAAATG
CAAATTACAAACAAGTTCGTTTAGTAAATCAACTCAATCGAATTGCATTTTAT
GCAACAGCTAAGCGAACGACATAGAAAACAAAAAAGAAGACCAAAGAGCCA
GTTAAATAATAAAGAATTAGTTAAACCCGCAAAAAGAGAACCAATTTATGTA
CATTTTCATCGTATTAAGCCCGCAACTTGTTATTTTTGAAGCACAGACCCAAA
GAAAGTGTTAACCATGCATAGATTTAGTATCTACGTTAGTGACATGGTCACA
AGGGATAGATAAGCGCTTCAAGGTGAATGCCTCTCTAAACTCACCTCCTTTTC

FIGURE 16 (Continued)

GAGCTCCGCGGGCTTGCCATTCCAACTGAGCACGGGGGAGCCGTATCCACGA
TACGATTGCTTCAGCAGCTCATTGATGGTGCTCCCATTCGAGGTGGCATTGCT
CTGGTAGCCATTGCCCACCCTTGGCTGCTGGTGCGACTTGAGCGCACTGCCGT
TGAGCAACTTTTGGCGCTTGGCGCCTGGCGTTGCGGGCGAGTCCGTGGAGGG
CTTGCTACTCGAGAAGGGATTGCGATGGTTCTTGTTCGGCGTCGGAATTTTCA
CCGGCGATCCCTCCACCACCACGACGTCAACATCATCTTCGATGGCATCGAC
CTCATCGTTACGCGTAACTTTCCAGATACCCGTTTTCGATTTGATGACCGCTG
GCGAGGGTGGCGTCTTTGGCGATGGTGGTGCTTTGCTTTGAGACTGTGATTGC
TTCTGTGGGTGCCAGCCATTCGTTAGCTGAATGCTGGGCTCCTCCTCATCGTC
GTCCTCATCACTGTCTGCGGACTTTTTTAGGCTCTTGAATATCTCGTCTATGGC
ATCAGTCTTTTGTTTGCTGTTGTTAACGTGAACCGATGACGAGGCTGAGCCGT
TGGTGTGGCTGCCATTGGTCTTACTGTGACCATTGGTCTGGCCAGACTCTTGG
TCCGACTCGCTAGAATCCTCCCCACTTGGACGCTTGCGGGGATTCGGTAGAG
GCGCCTCCTCCTCCTCAGATGCTGATTCGTAGGGCACAAGACTTTTCAGTGGC
GTTTTGACGGGAGTCTTTACTTGAATCTTTACAGGAGACTTTGCCTTAGGCTC
CGTATGATTCTCCGTCATATTGGGCATGCTCGGTAGCTGGGCTGTCGTTGGTC
TGGGCTTCATCTCATCCTCGATGTCTTCATCATCCGAGGAAATTGGCAGATAT
TGTTGCTGGTTTATTGATTTATGGTTGCTGCTGCTGTTGCTGCTTGGGGAGGA
ACTTTTGTTACCATTTGCAGTGGGAGCTGAAGTAGCTTCGCCTTTAGCGTGAG
CGCCAACCAGTGGAGGCTTCGCAGTGTCCTGAAACTTTCCGGTACCCAGCTG
GAGTCCGTTCTGTGGACTTTGCTGGTTTTGTTGCTTGAACTGGATGGCGGTTTT
CTGGGCATTTCCATTAGTGTAACCGTTTGCTCCACCCGCCGGCAGTTGAGGAC
CAATGAAACGCGTTGGTGAAGGCGAAGACACAGTCGCCGCCGGCACTGGCGT
TGTGCTGTGTCCGTTGGTCAAACGCACTCCATTGGGCCTGTTGGCCGCCGGAC
TGGCAGCCTGTGAGAGGTCCAGTTCGAAAAACATTATATAGGCATTTGTGTT
GCACACACTGTGCATTGCGATTGGCCGCACGTAGCTGTCGTCGAAGTTGTAA
AAGCTGCCCGTATCCGTGGAGCCAATGGCCGTGTAGTGACCGCAGTGCTGGG
ACGCCCCCAAGTGAGTGACCATCGACACCAGGCGATAGGTGAGCGGTTGAGC
CTGAGCTGCTTGTGAACGGGCTGCGTATTTGCTCAAATCTATGCGTGACTTGA
AGGAAATCTGCTTGGTCAGTTTGTTGCCGATCATGGAGAATCGCTTCAGCTGT
ATACAAAGCGTGATTGGGGCACGCTCCAAAGAGAATTGCTTTGTGGCAGATA
CCTGCAAGCGATACGTTTAAATAAAATGAACTACAGAACAAAGGTCACAAAG
ACCTACCTTCTTCTTGCATCCCTCGCACTTGTAGCCCATATCCTCTAGCCGTTC
GCGAGAAAAGTGTCCCTCGAAAGCATCCTCCAAGGAGTCTGCCTTGCGGATG
TCGAGCAACAGATCCTGGAAGTGCTGAAACGTAATGGACACATGGTTGCAGC
TCAGACAGCGCACCTCGCTGCGCAGATAGCCGCCAAAGATCTGTCCCAGCGG
CGTGGTCTCCTTAACCAACTGATCCAGCTCTTTGTAGTTACGAAACCGCATCA
AATACGCCCGCTCCATGGCCTCGACCAGGAAGCGCAGGAACTCGTGCGCATC
CTCTTGGCGACCAACGACCATGTGTTTGCAGATCTGCTTTAGCTTCGAGTAGA
TGAGGAAGGGTCTGACGGCCGACTGATTGCTTTGGGTGGCCAAAAGTGTTTT
GGTCATGGCGCAAATGATGCAACCGCTGCCAGGTTCGGCCACATTGCAGTCA
GCCAGATGCGCCTGCTCCGAAACGAGCCAATTGGCCAGGGCGGGTATGTGCA
GGAGCGCCTGAAGCGTTGAGTTGAGGTAGCAGGTGTTGCCCACATTGATCAT
GCCCGTGCCCACCTGCCATTTGCGCTCCGACTGCTTCCAGCCAATGCGTATGT
TCTCCCGCGGATAGAGGACCCTCTTCGGCTTGGGCAGCTCATTGGGATTGCTT
GTCGGATGCTGATGATTGTGGTGGTTGATGTGGTGCGACTGATTGTTCGGGTG

FIGURE 16 (Continued)

CTCCGCTTGCTTGCGGGCGCCGTTATTGTCTGCAAAGGTAAAGAGGACGGTA
GACAGTTTAAGCACGTGCCACAGGAGAAGGCAGCAGGGAGACAGGAACAGC
TTGTAGAGCAGCCACAGGGCGAACCCGTCCACCATTATCACAGTCATAATGC
ATTTATTGGAAGAATTCCCTTCTGCAGATTAAGTCACTTGATCCGCGCTGCTA
TGAAATATAAATAAAACGAGCAGTGCTCGCTGTGGAAACTGCTGACACACAA
TCGCGCTTCCATCACCTGTTCGCAGTGTTGGAAAGGGTACACATTTGTTGTAC
CTAGGCACCGGACTGTGCAGCATTAAGATAGCTATTCTATTGAACAAAGAAA
CTTGAACACAAAGTATACGCCGAAAAAAATTTCCAGTACTAGATTTTGAAAT
ACAATTCTTTGAACATCGTTACAGAATGTGATATCACCAGATTTTATCTGAAA
ATATTTTCACAGCATCGTAATTTCATATGTACCCTGAATATGTATCTTGCAGTT
TTGTTTGGGAAAGTGTACCAATCGAGGTACTTATCCTGGTACACATATCTCAG
ATATTACCCAGCACTATTGTATCTTTGATAACAGCTAGCGTGTGAGCGGGATG
GCGACTGGCAGAAGAAGAAATTTAAACTGATAACAGCAAGCGAATGAGAGG
GATGGCGAGTGGTGAAGCAGTCCAAGTGTCTGCTGCCGACGAATACAGTGGT
CTCGTTCTGGCGTAGGGGGTTGGGGCGGCAGTGTTGCCAACTGAATTTTTGGC
GCGACCTAACAGTGGTTGTTGTAGGCCCAATGCTCCCCCCTTTTATTGTCTTT
GTAACTGTGTTCGAGGCATTGACCAGGCCAAAAAAAAGAAAAGAAAAGAAA
AGTCGAAACATCGTGTAACAGCTCCTGGTGCTGAGCTTTGTGTCCACTTCCTG
CTCTGTGTGAATCACTTCTGCGAGTCTGGCCTTTGTTTGTGCTCTTTTTATCAC
GCAAAAGCAGATTGCGGCGCATTTACCGCATCTAAAAAAATAAAGCAAAGCC
AATAAAAGCACCGCTGGGGCTGGCCATGTGCGGGGGAAAGAGACGGAACTA
CGGAGGGGAGCCCTCGTGCTTTTTGTCTTTTTTTCCTTCTTTCATTTGCCGCTG
GAAATACAGCACGTTTTTTTCCGCCACAACTTCTGTGAATCAGAAGTTTGGAA
GAGGCGGCTCTGTTGTTGCTGCTGCTGCTGTCACTTTTCCAGCTTACTCTTTAC
GGCGTTGTACTTGTTTTGCTTTTTCCGCGTATTCCTTTGCATTCTGTTTACACG
TACACCACCCAAAAACGCCGTCACACACGGACACACACGCACGCACTCACAT
ACAGAAGCGCCTAAAAAGTACAGGTATGCTGCGCTGCCGACGTCGACTGCAC
TGCCGACAAAATGCAGGCGGAGCAATAAAAAAAATATGTTTGCGGAAAAAC
ATCACACGTGATTTGTGGAGGGATATTCCCAAAAGATTTGGCAAAAACAAAC
GGGACGATACATAAATACATTTAAGTATATATACATCTTATATATATAATATG
AAGATATAGCACATGGAAAATTGCGCAAAAATTGCCACACAAAGAAGAAAC
ACAGACGAAGGCGCAGACGGAAAAAGCCACTTTTGCAAGCAACTTTTGGATT
TTACATTTTGTTGTATCTTTACACAGTGTACTCACCATGTCCATTTGCGCCCAC
AAGTTTGCCTGTATTGTTTTTGCCACTAAAGCCATTGATGGCGCCTGGATTTC
CCGGCTTGATGACAATATATTTGGACTTGAGGTTCTCCAGCACCGATTCGTGG
TAGTTGGGCACCTCCTCGTATTCGATTTTGGCCATCAGGATGCGTTTGGCATT
GGCCACGATGTGATTTTGCAGGCTGCCGTTGGTGTCCTCGCCGCTCTTGGCCT
GGTCAGTCGACGAGCCGGCGGAGGAGTTGCCGCCAAGGGATTCGCGCAGCG
CTGCGTTGACGACATTCGCCGTTTCGCATACGGCCATCGAAACGGGCATGGC
GATGCTCCGGCTGGGGATTTGCGGTGGAATTTTGAACGGGTGTGAGGGGCGT
GGTGTGGCGTGTGTTGGTGGTTTTCGCCACCCAGTTAGCTAATGCACATGGGC
GTGCGATCCAAAGCAGATACTAGAGATCCTTCTGCACAGCCCACACGTCCTT
CAAAACTCTCCTACTGCTCTACGCTCACTTTTCTCCTCGCCCCTCTCTCGAACA
CTTCTTGTTTCACACACCGACTGCGACACCGACACACGCACACTAACGCACTC
GGGAGCACTCTTCTTTTTCTGGCTTTTTCGCGCTGCGATCTCGATCTGTTGGCC
TACTGAGCATTACGATTAAGAAACGTTCGCTCACAAATTGATCTGTTTCAATT

FIGURE 16 (Continued)

TCGTGCGCGGCCAGGCATTTTAGAACGAAAAGTCTGCTTTCGAAAATAATGG
CAATTCCTTCCCTCGTGTTTCTTCCGACTGCGGATTCTCTTTTCGCTTCATTTTC
GTCATTTGGGGATGCCAACTCGCGAGTGGCCAAGTGACGCGATAGGCCTCTC
GAAATGTCCTAAAGCATTTCACGATATTTACAAAAATGTATTTCGATGTTTTC
TTAACAATAAAAAATTGGTTTAAATTTAATAAGACATTTGTTACCTTGAATAT
GTAAGCAATATCTTATTGAAAGGCTTGCAGCGACATTTTTTATTTATGCCTAC
TATTCAAGTTATAAATTTAATTTTTATAACGGTATTTTTACACCTTATCAGCAC
ATATCGATAAGTGTGATTGGGAACGACAACCCATCGGCACAATGTTGATGCA
ATTGTTGAGCTAGCCTTCATAATTAGTCGCAATCAATCGAGCAGAATGGCTTC
ATCCACAGGTCTCCTGGTGGTGTCCAACATCAAGCACCTTGGCAAATCCCTGC
GAGCCATCGAGAAGTACGTGAATTCACTGTACATCCACCTAAATGTGGCGGG
GTCAACGTCCACGACGTCACCAGTTCCACCGCCTCCGGTTTGGGGTCGTCTAA
TCTCGCAGCTGTACGCCAACAGCAGCAGCTATGTGGGCAAGCAGTTGGACCT
TCGCGTCCTTGTCTCTCCCCTACGACCAGGTGCCAATGGATCCCTGAAGTTGC
GCCAGCCCGTCGACCTAATCTTCTCGGATGCACATCATCCGGAGCTGTGCGAC
AGGCTTCGCGCGGATCTTAACATCAGCAAGCCAACAATCTTCCTGGATGACT
CGGTCATCTCGGATTTAAGTGCCCAGCAGGATGACACCCAGCCGCCTAAGGT
GTATCCCTCGGTTGTCCTGGGCGGAACATTCGATCGCATCCATCTGGGACACA
AGATATTCCTCACCCAGGCTGTACTGCGCACCTGCAAGCGTTTGGTTGTGGGC
GTAACCACCTCCGCCATGACGAAGGGTAAGACGGGCATGAATTGGCAAAATA
AAACGCTTATCTTAACGACCATTCTTATCGCTGTCTGCAGGAAAGACGCTGCC
GGACTTGATTTTGCCCGTGGAAGAGCGCATCGCCCGGCTAAGGGAGTTCCTG
GTGGACATAGATGATACGCTGCAGTACGAAATTGTGCCCATCGATGATCCCT
TTGGTCCCACGCAAGTGGATCCTGACCTGGACATGATTGTGGTCAGTGCGGA
GACGTTGCGAGGAGGGCAGAAGGTCAACGAGGTACGCTCCGCTAAGCAACT
GCGCGAGCTGGAGATCTTTGTGATTGACATTGTTGAAAGCAACGTGCATGAT
GGCATCCACGAGACCAAGGTCAGCTCGAGTAACACACGCATCGATCTGCTGG
GAACCCGCTGGAGAAGGCCGGAGCCACGACCACAGCTCCCGCCGCGCCCTTA
CATTATTGGACTCACTGGCGGCATCGCATCTGGCAAGAGCAAGATGGGCGAG
AGATTGGCCAACATGGGCGCCCACGTGATCGACTGCGATAAGGTGGCGCACG
ATGTTTACGAACCTGGTCAGTTGTGCTACACCCGAATTGTGCAGCACTTCGGA
CAGGGTATTGTTTCAGACGATGGTCGCATCGATCGGTCCAAGCTGGGACCCTT
GGTGTTTGCCGATCCCAAGCAGTTGCAAGCACTCAACGGCATTGTCTGGCCG
GAACTTATTGCGGAGGTTAACAGGCGGCTGGATGCACTGCGTTCCCAGGCGG
ACGTGCCGCGTGTGGTGGTCCTGGAGGCAGCGGTGCTGCTGCGAGCGGGCTG
GGAGACCAATTGCCATGAGGTGTGGTCCATGATTGTGCCACCGGATGAGGCT
GTGCGGCGGATTATTGAGCGCAACAAGTTGAGCGAAGTGGAGGCCCAAAAG
CGACTGGCCAGTCAGGTGCCCAATTCTGAGATCGTGGCCAAGTCGCATGTGA
TATTCAGTTCGCAATGGGATCACGAATTCACCCAGAAACAGGCGGAGCGTGC
GTGGAAAATGCTTACCAAGGAACTGGACTCTTACCAGAGCAGCCTTTAACCC
GATGGATATTTAGATTATCTTGTTGATCCTTATTTTGTATGATTTTTTATGCAT
TTGTTGTATATTGTTTAGTTGTAAGTCCAAAGTTGAAAAGAAATGCTGGGACG
TCATTGGGGAAAAACGCTGAAAATTTCAATGGAACCTTAGTGGCTCTCGCCC
TTCTTGCCAGCCACTCGCTTGAAGTCGTTCATCTTGGTGGTCATGATGGGGGA
ACCGATGAAGCCGATATAATCAATCTGCGTCACATCGCCACCTGACTGATTGT
TCTTCACGAAGATTTGGATGTTTTGCACATTCTGGAACTTGACGTAGCGCAGA

FIGURE 16 (Continued)

TTCACGGGCACTCCACTCTCCAGCTCCTTCTGAGCCAGGCTGCAAAATGGATT
GAACAGTGAGAAGAGCTAAGCAGCCATAGAGAAGGCAATAGCTACCTTAGA
TCCTGCACACTGTTCATGGACTCGGCCATGTCAAAGTCAATCGTGCGGGGCTG
GTTAATGAACAGCTTCACATCCTTGGGACCCAGGTGCGAAGGTGCCTTGAAC
TTCAAAGAGTGGATCTTCACAGCCTGATTAAAGGTGATGGACAGGATGAGCT
GCTCATCGCAATCGGACTGCAGGTAGCCACCGGCGGAGGCCAGGGCGTGCTT
TAAGTTGTGGTCATCAGCTTCGTTGAGGCACTCGCACTCCTGCTTCGAAATAA
ATGTATTCAGTTCCATCTGTAAGAAGGATTAGGGATTATTTTGGAACATTTC
CAAATACTGCACTATATTACCAATCCCTGCCCGTAATCCTCGCCCCCCTCCTC
GCCACCGGATGTACCGATGTGCTCCTGGATCTTGGCCTCGAGCCCATTGACGT
CCGCACCCTGGACGCGATCGATCTTGGTCCTGTTCCTGTAGAAGATGAATGTT
GGCATGGCCGAAACGCCCTGTCCAGCAGCCGTGTCCTGGCACTTGTCCACAT
CCACTTTCAGGAAGATGGCCTTTGGGTACTTTGTTGGAAACGTCTCGAAGATG
GGCGCAATCCGCTTGCAGGGACCACACCACGAAGCTGTGAAGTCCACCACAA
CCAATTGAATGCCCGCTTGGGCCAACTCCGCCTGGAAGTGGGACTCGTCGTT
GATCACGCGCACGGACATGGTGATAGGATTAGGTTTCTATTAATTGAGCTTTT
GTTTCGGCAGCCGAATTGGATTTAAGCAAGTAAATGTTATTATTAACGTTCAA
TGCAAATTTTTTTTGTTAAAGATGACTTGTAATATGCATTTAGTCCAAATTCGT
GCTAAGAAAAATACCGAATGCGGTATTCCACAAGCGGTCACACTGTGATGGT
ATCGATATTTCGAGCTCTTTGACTTCCTATTTTTAGAGGGACCATTTATGTGTA
ATAGAAAAAAACCGAAACTTAATATTTAAACTTTTATTGAAATATTAGTGGA
TTACAATATGTAAAACTATGAAATATTCTCATTTGATATAGCTCAAAGTGTTA
TTTAAAATTCATTCAGTGTTTACGACTAGCAATCTACGCTTTCACGCTCATCTT
AAGCTTACCGCCCATTTGCCAGGGTTGTCAAGGCGAATGAGCGGTCCCACCA
TACACGCCACTGGAACTTTCGATACCTGCGCTGCGCCTGGCCACACGTTCATT
ACCTCGTGGTGTTTCAGTCGGTCGCATTTTCATTAAGTCGCCATTTTAAAATT
ATTAGAGTCAAGTACAATGGCAGATGTGGAAAAGGAGCCCGAGAAGACCAT
CGCCGAGGATTTGGTGGTGACCAAGTATAAGTTGGCCGGCGAAATCGTCAAC
AGTGAGTATTCCTTGGCCGGAAACAGCGAACGCTGGCCGATTCCTGGAGTCG
CTGCTACGTGGCGCTTACACAATGCACCGAATGCCGCTTTCCCTTGTGCGCCA
CGCGTTGGTTAATCTGCCTATTTCTGGACTCTGTCTGCTCGTTTAATTTTAGAA
ACCCTCAAGGCGGTAATTGGACTCTGCGTGGTTGATGCCTCCGTCCGGGAGA
TCTGCACCCAGGGCGACAATCAGCTCACCGAGGAGACCGGCAAAGTAAGTG
GTGGCCACCTGGCGGTCATTCGCGCCAATTTCATGTCCAATGATTAAGACTTA
CACCTTTGAGGGTTTCCCGATGGCGAGCCATGTGCTGTGCGGGCTGGGGATC
ACCTCGTGGTCGCCAGGCGCACGCGGGGACTCCAATGCTCCACGTGCCCGGC
TTGTGTGCTCTCCAAAAGGTCCCGAGGATTTACAGATTATGAGATCTGAGGA
CACACCGCGCACTATCATTGATATATAGTACAACGAACAAGCAATCTAATGC
TTTTATCGATCTTTCACAAACAGGTATACAAAAAGGAGAAAGACCTGAAGAA
GGGCATTGCCTTTCCCACCTGTCTGTCCGTCAACAACTGTGTCTGCCACTTCT
CGCCAGCCAAAAACGATGCTGACTACACGTTAAAGGCCGGTGATGTGGTCAA
AATGTAAGTTGAACCTCCTATTCCACATATACCGCCACTAAATACGTAACATT
TCTTTTCTACAGCGATCTGGGTGCCCACATTGATGGTTTCATTGCCGTGGCCG
CTCACACAATTGTGGTAGGCGCTGCTGCGGATCAGAAGATCAGTGGTCGCCA
GGCCGATGTCATCCTCGCCGCCTACTGGGCTGTCCAGGCTGCCTTACGTCTGC
TCAAGTCCGGCGCCAATGTGAGTCCTCCCTTACTTCTAGGTAATCCTCCGTTA

FIGURE 16 (Continued)

ATCCCTGCAAGAAACGGATTGTCTGCCGCGATTCTCCAGCGACTGAACATCTC
AACACTTGCAAAGATCAGCTGTGGCAGCTGGTAATTGCCCTGGCCTATTATTC
AGGACTGGAGGCTTCTTGTCAGTTGTCCACAAGGTTATTTCTTCTGCAGGCAA
CGGATTGACTGCGCTCAAACTCTGACACAGATCAGCTCAACACCTGCGGATA
GAAACTGTGTCAATTTCGTGAACTGAACAAGTTCATTCCATAGAAGTGTTCGG
TCTTTAAATTTGTCCACATCTCCAGTTTATAGATATGTCGGAATTGTAATCTGC
AGGCAACGGATTGTCTGCTGCCTTAACTCGTGGCTCAGCACAGCTCAACGTCT
GCAGAGATCAACAGTGTCGATTTCGTGAACTGAACAAGTTTAGATACTTGAA
ATGTTCGGTCTTTAAAGTTGTCCACAATCGCAATGATAATGCCGATCAGTTAT
TGTTATTTTGCGTTATCTATAGTATACTATGATATTTGATTAAGATTAGTCAAA
GGGAATTGGAATGTTTTCTTTATCTCTGCTTTGAACTATTTCCATTTTATTTCA
TACTTAATATTTATGTTTCAATTCTGTATCCTTACAGAACTACTCCCTCACCGA
TGCAGTGCAACAAATCAGCGAGTCGTATAAGTGCAAGCCCATTGAGGGCATG
CTCAGTCACGAGCTGAAGCAGTTCAAAATTGACGGCGAGAAGACGATCATAC
AGAACCCCAGCGAGGCGCAGCGCAAGGAGCATGAGAAGTGCACCTTCGAAA
CGTACGAGGTGTATGCCATCGATGTTATCGTCAGTACCGGCGAAGGAGTGGT
TAGTAATCCATCAATAGACACTACATCTCCACTAATTTGTTCGATGATTAAAA
ACACGCGCTTGAGGCTGACTTTGCTGGAATGCGGTGTTTGTTGCGAGAGTGA
CTTGTTTGCTCGGCGTTTTTTTATACTAAAATGCGGCACGTGCAGACACCAAG
TTCCGGCTGGCTGTTGTCCGAAGATTGCAAGATTATGAGATCTGAGAACGCC
AAATTTAAGCTGGATCCTGGATCATCGCAGCCAGAGCATTATTGCTAACATTA
TTCGTATTCGTTGCAGGGACGCGAAAAGGACACCAAGGTCTCAATTTACAAG
AAGTCTGAGGAGAACTACATGCTCAAGATGAAGGCGTCCCGTGCTCTGCTGG
CAGAGGTGAAAACCAAGTACGGAAACATGCCATTCAACATCCGCAGCTTCGA
GGAGGAGACCAAGGCCCGCATGGGAGTTGTTGAGTGCGTCGGCCACAAGAT
GATTGAGCCCTTCCAAGTGCTGTACGAGAAGCCATGTAAGTGTGATGCATAT
TATTATTAATCCTATTCCCTATTATGCGAGTTGGCAGAACTTAATTCCGGACC
TGGTACACCTTCGGGTGCTAAGTGCGGCCAGACATTTTGCCAGAACAAATTC
CAGGCATTGTCGTCTTCAGCAGTTGCCTCAGTGTGGCCTCTGTCTGAACATGG
CACTGTCACAATCGTATCCAATCTATTAACCTGTTTTCTTATACTTATTAAAGT
TAATTTAGAGACTAAACTAGTTTGAGCAACCTTTATAAAGTTCGAATTTTAGC
CGGAAGTAATAGCAAAGTTAAACAATCCTTTTCCTTATCTTGCATTACAGCCG
AGATTGTGGCGCAGTTTAAGCACACGGTTCTGCTCATGCCTAACGGCGTCAA
CTTGGTCACCGGCATCCCATTCGAGGCGGAGAACTATGTGAGCGAGTACAGT
GTTGCGCAGGAGGAGCTCAAGGTAAGCTGCAACAATTTCCTTGTATTCACGA
TGCGTACTCAATGAAATCTCAACTTTTTGCAGACTCTGCTCGCGCAGCCTTTG
GGTCCTGTGAAGGGCAAGGGTAAGGGCAAGAAGGCAACAGCTGGGGCGGCG
ACAAAGGTGGAAACGGCGCCGGCCGTGGAGACCAAGGCATAGACCAGCCCG
CTGATGATGATCCGCACCGCCAAGCCATCAACGGAAACACAATGTGAACAAT
TGCGCTGCCCAACGCTGCGCTCCACAGATTTTTACTATCGAATTCGTTGCGTA
TTAGAGGACCCTTTTGACAACAGAACAGGACAGAAGAGAAGACGGCAACAA
TTTGAGGATACATTTCCCCAGAAATCCTCCATCCATCAACAAGGCGGGCGGT
CGGTCGGTCCCGCGCCAACTTTACCTCTTTATTTCCTTTACTATAAGCTGCCTT
CGTTTATCGGTCTGTTCAACATCATCGCAACGAAAAAGCAAAGCAAGAACTG
TCATCAAATTGTAACAATTTTAACGCTAAATGATCTTAAAATATAATTCAAGT
GAAACGTTATTAACGCTGCGTAGTAGGTATTAAATAAAATTAACATTTTCTAT

FIGURE 16 (Continued)

AAAACAGCCGATAAATGCCAAACGATTTTCATTTATTTACTTTCCGCTGGCG
CCCAATTTTAATTCGATTTCGATACGCTTCTCATTCTAATAAATGCACTTGCG
AGTTGTGTTTATTTTATACGTTTAATTTAGTTTTGATGTTCACATTCACATTAT
ACAATTTGTAATTTAGATTTCTTGCCTTTTGTTATTTTAAATTTTACAGTCTCA
TCTTTGAACTCTTGTATTACGAAAGTTGCAAGAATAACTTCGTTATGTTAAAC
GTCACTTAGTGCTGTGCTCACTTGGCCACCCCAGTTGTCCATCCCAGATCCAA
TCCCAACAAGACCAGACCAATTCGATGCCGTATACGGCGACTTTGCCCAACT
CGCTGACCTCTTCCCTTGCGTCAAACAAAATAAAGAACAACAAAAAACGCAA
TTGCTGCGGATGAAGTATAGAAAACACGAGCAGCACTTGCAGACGACAAAG
ATATGTGGCCGGTGATCAAAAGAGGATCTGGGATTTAATGGTCTGCCGTCGC
TTACATACATGGTTTGGTGTACTTTTTTTTTTTTGTTATGATCGCCGCGACTG
TTTTCTACTCGCCAGACTAATTATTGACATGCACGTCCATCGGTGCGGAGGCG
GTCACGTTGCTCGACTTCTCCGGAGAGTCCAGGTAAATCTTCAAGGCACGTTC
CCGGCGCTGCGCATACCGCGTGGTGGACACGCAGCCCACCCGATCCAGTCGT
GCCTTCTCCCTGGCGTTCATCAGGCGTCGCTCCTCCAGCGTCAGCTCTCGCGC
AGGTACCGTCCTATCTCTGTTGAATTCATTGGTTAGTCTAGGAACTGAACTGC
CACTTGCTCCACGCTTACTTGTACAGGTAGATGTTTCCTGTCTGTGTGCTATTA
AGCGGATATTTGTCCAGGGTGGTGGGCACGGAGTACCAACTGCTGGACTCGT
TAACACTTAACGCTGATATGCTTGTGCAGGGGAAGTTGCTGTTCAACTGCAG
AGAAGACCAATTAGATCAATATACACAGTAGAACGCAATTTTACGAACCTTC
ATATAGCTCAGTTTGTCTATTGGGATGTCGCTGATCTGTGATAATGAAAGTCT
GATTTCGCTGTCCTCTGCAGAAGATACGAGTTCGATTTACTGCTTACAGGGCA
ATATACAGATTTAACTTACGGTCCAAAGTGATTTCTTGGAACTTTCCAAACTC
CAGTTTAGCCGGACACCACCGTCTTACAAATAAAGTCAGAGAATCGTCCTTG
GGCTGCGGGTCCACTTCCTCCTCGCACTCTTGCACAATGAACTGAAATGGTGT
GATATAAAATCCAAGTTAAGTTTTTTTCTCATCACAGAGACAGGGGAACCCA
CCTCCGCTGCGATGCTGGAGCGCATGTCGCAGTAGAGCGTTTCATCGTCGGA
CAGAATTTTGATGGGAATACGTCCGCCCTTCAGCCAGATGCGACAGTTTTGCA
CAGACAGTGTGGCGTACTTGGCGTCTATGCGATGCAGCTTGGCCACCAGTTCC
TTCTTGGCCTGCTCCGCCGTGGTGTTGGCATTGTAGACCCACTCGCATACGCA
AGGCAGTTTGGACGTCTCGTTATCAATGTCCGCCAGTCGCAGGAAGTGAATC
TTGGCCTTGAACTCGTCCGGCTCCAGCGTCTTACCCAACTCCACCGTCAGTGT
TTCGCCTTCTATGAGATGTACCAACGAGTTGTTCTGGTTGTTCGACAGATTAT
TATCGTGTTTCCGCTGCAGTTTAAAGTGGGCGGCGGGCACTTGGATCAGCTGC
TCGATGTGTTTCTTAAAGGCCCCCATTCGCATGTGTGTGCCCACCAGCAGCTT
ATAGGCACGCGTGGGCTTACGCAGCTGAGCCTCTTCGTCGGACTGGTGACCA
GAACTGGAACCGGTGCCAACCACATCCACGCACTCGACCTTTGTGGCGTAGA
AGAAGTGGTTGGTGCTGGTGGGCAGGAGCAGCGGATCCACCACATCGGCCGC
CGCATAACTGCCGTTTCCATTGCAGTAGGCATGAACGCGCATCATGGCATCGT
GTGAGGCTGCTTCGTCCTCCGGACTAGACAGCTGCGGCGAGTGACTGGTGGA
ACTGACTTGGCTGTCGCCTCCACCGCGATGTGCCATGTTGTCCGTCTCCACCA
GAGTTCGGTCTCCGTCGCTCAGACTACTGTCCTCCGAGTTGGACTCGTGGCCG
TGGCTGGGACTGGGTTGTGACATGGGTTCCACTAGATCTCGCTTGTAGCGCCT
CCAATCGTAGTCGTTGCTGGATGACATGTGACCAGGTGCCACGCCATTCATCA
TTGCAGCATCCACAACATCACCCCCGCTGGCGCACTGAAAGGACAGCCAAAA
ATTAACCTTAGTTATAAACCCAACAGCTGTATAACCTACCTCGACTGACTCAA

FIGURE 16 (Continued)

CGGTGGGCACACCGAGCATCTCAAGGGTCGCGGCATCCGTGTTGGGTACGTT
CAAGTAGAAGTATGTTATGGACTTAAACTGGGTGTTGGCCATGTTCTGGAGA
TGTTGCAGGGCCTCCGGCGTCGGATGCGGATCGTAGGACACGAAAGCCTTCG
GCACCGTGGCGCGCACCGTGGCGAGTAGGAACTGCTGCTCGCTAATGTGCAA
ACGGAGGGCGATCGAGCGGCGAAGGACGTCGCTGGCTTCCCGCTCCCGCGCT
GCTGAGTAAACCAGGAAGGGACCGTCCATCGCCATGGTCGATAGATCTACCT
TAAACACATACCAAGTAATGCCGTTCGGCGGATAGACCTCAAACTCTTGGTC
CTCGGCCCGGTACTCCAGCAGGAAGTCGAGACTGTAGTTCTGCGCCGCGCGC
AGTTCGGTCAAAGCTGGGTCTGTGCAACTCTCCAGGGACTGAATAATCGTGT
CCATCGAGGAGTTGTAAGCCACCAAACGACAGCGGGAAAGCGGCGCGAATT
GTTCCACATTCAACATCTCATAGGCCGACATGAGGACCAAGTTGATGTTGAA
ACTCTGCGATACGTACACTCTGGTAATCTTCATCTTCTTCAGGGAGGGATTAT
AGAAGTAGACGCGCGGCTTGTACAAATCCGGAAGAGCCAAGTCCGTAACCGT
GATATGCCTGCCCAGGCGGGACACGCGCGTCTCCTCCTCCGAGTGCAGCTTTG
GTAGCAGCGTTTTGATGTGCTCAGGAAAGTCGGCCACCTTGGCGACTAGCTC
GTTTCTTTTGGCATCCACCTGCCGGTACATCAACATGTATGCATTGGTGCTGG
AGGTGTAGGCACTGGAGTAGTAGCTCCCGTTGGGTCCGCCAAACGAACGTTG
GATGTCCTCTTGGGTGATCTATGGATAGATAGTCGTTCAATATTTTCTCAAGT
TATGAATGTGTTGCGAAAACCTACACTAGTCACGTTCTGATCGTTAAAACAG
AACCACTCGTTGTTGTCGAAGTCCTTAATATAAGCATAGTAGTGTCCGCCCGA
AGCGCTGCCTGAATGAATCATGATGGCGAACAGTTCGTAGAGATACGGACCG
GATCCTTGCTTGGCGCTCTTGCTGGTGCTGCTGCTCATGTCGATGCCTTCATCC
TCGTCGTTCAGATCGTTTTCGTGCTGACTAGAGCTCGCTGTGGTCACCACGCC
GCTGCTCAAATTATCGTCCTCCATGGCGGATCCACTATCCGCCGTGCTGCAAT
CGTCCACGGTGCCGTTGAGCTGAGAGTTTTGCTCACCGCTGTTTCCACTTCGG
TTAATGAACGTGTTCAGGTTGAGCGTCTGAGGGAAGGTCACTCTGAAATAGA
GGGCGAGCATGGAATTAAATGCTTATGGATTATGGCAAAGAGACTAACCTGT
CGTTTAATTTGATGCGGTGCATGGTCTGGTAGTCAAAGTCAAAGCGTTTAAGG
TGCAGCGTGAGGATGTAGGGAAAGGACTTAAAGTGCAGTCCCTTGTGGGCGT
CGCATTTTTTCTTGCACTTCTCGCACAGATACTGGTTATTGCCATCGAGTGTTT
CGGGCTGAACGAAGGCACGCAGAGCTTCCTCGATGCTGCCGTATGCGGAGCT
GCTTCCAAAGGGCCTCACAGGGAGCGGGATATCTAGAAAGGTGTCCTCGCGC
GTCTTCTCGGTATTGCACTCCAAACACTTGACATAATCATTCATCTTGCCCTC
GTACAGATTAGAGATGAGATTTGCCTGCTTAGTGTTCTTGAATTTGTGCTCCA
GAGCGTCGAACATAACTCGGCACAGTTCCTGGATATCGTGCTGCTGCCATGC
CTCCGTCGAGTCCCACCCAAAGCTGCGAGTCAGGTCTGTGGTTTCTACCGCCG
CTTTGGGCGAGGTCTGCAAGTTGAGGAAGAGCTTTTGCAGTTGGTATGGTAT
GTTCTTGGCCTCGTTGTCATTGTCGAACTCCCAGCGGTACAGAGCATTTCTGA
ACTCGGGTGTCATAAAGAGTGCCTGCAGCAAGCTGTTTAGATAGCAGGTCAT
GGCTTGGTTGACCAAACCAACATATCCCCTGGGACCCAAGCTCGCCTGCCTTG
CCTCTGCCTCAGTTTCTGTGGTGGCCGAGGACACGAAGTCCGCACCCGTTGTG
TTGACTCTCTGCCATGCTCGCAACTCATCGCCTCCATACTTGCGACGATAGAA
GTTTGACAGAGCCGGGTACGTACCATCGTCTGTTCCAATTGTGGATGGGTCTG
TCACTCCGGTCACACCCTCGACGTCCGAGTCACCGGTCGGAGCTCCGTAATC
GTATCCAGGTCCCAGCATTGTCGGACTAGCAGATGCTCCGAGTGCCAGGTCG
TCATCCGACAATTGTTCAGCATCTGAGATGAAAAGATCTGAAGGAGCATCGT

FIGURE 16 (Continued)

CCACCGGTGAGATTAGGTTTCTACCTTGTGGATACAGCTGCAGTTGCTCAGAG
AGCTGTTGCTTGCTCAGGGTGTCTACTGGTTCGCAGTCCAACTCTTTGATGGG
TGATGACGGCTTGATTGGACTCAGCAACTCTAAAGTCGGCTTAGAAGTGACC
TTGGCCGTTTTCTTGGCCACAGGACTCTCCGAAGAAGTGTTTTTAGAGTTTAT
CTCTGTAGACAGCTCGGGACATTCTTCAGGGCTAGCCCTGGGAGCTTTTTCCG
AACCGGGCTTGGAGATCTTTGCTGCAGTCGTCTTGATCTTGGAAGTCTTTTCG
GGACTTGATTCCGAACTGATGCTGGTCTTAGCCAAAGAGTCCTCACTCGTCGT
CTTGGCCTTGCTTGGAGAGGAAGATCCCGAAGCTGGCTTCTTTTTCGTTTTCT
CACCAACTACGCGTTTCTTCTTCTCGCCGGTGGCAGGACTCTTGGCCTTCTCG
CCGTCCGACTTCATAACCTTTTTGACTACCACTCTTTTAATGGGTAACTCAAA
GCGTTTGGTCACGTCACCATCCCAACTGCCGGAGGGCAGCAGGATCAAGTGA
TTCTTCAGCTGGGGCTCAAAACCAGCCACTTCGTACATCAGCTGAGATTCCAG
GGCATTCAGATTGACCTAAAGTAAAGGGGAATTCAATTAGCGGTTTATTAGA
ACCTCAAGATGTGCAGATATTTTTACCAGATCCTTGTTATCGTGTGGCTGCAG
CAACAGCTCGAACTTTTCGTACGAGAACTGCGTGCCAATAAGGTCAATCACG
CGTTTCACCGTGAAGTGGGAGCGGACCACTACGTTGATCTTCTTTTGCTCCGA
GCCGGGTGTCTGGTCAAAGACCGAGACGGTGCACTGCTCGCTCTCCTTGTCCG
TCATGTCCAGCCCGCGGAATAATCAAGTGATGGTGGAGAAAACCCTGCAAAA
AGATTGTAGGCGAAACGTTGGCTTTACTTATGAATTTTGTCTGGAGTTTTCTTT
TTATTTTTTTTATTTCTTTATTTTAGAATTAAAAAGGTGACACGACACCTTTG
ACGTTTTCGGCGGGGCCAAGTTCCTGGACATGACGATGCTTCTTGGCCCATAG
TAAATAAGGAAGAGATGCCCAGCCCCAAATTACTGCGAAATCTTCTTGTTTTC
GACCCCATTCGCGAATAAAGCGGCAGAAACCAAGAAGATTCCGTCCCACCTC
CCGCAGCCGCAGATATTGACGTGCTCCGGGTTTGCTTTTCGCGCCTTATTTGT
ACGGGCCAGCACCAGTTGCCGTATACATATATATATATATATATAGATAGAT
ATACACATATAGCACGTACACCCAATCGAGCATCGACTGCCCCCCGAAATCG
ACGTCGTGACTAACGCGCAGGGGAATTTCGTAAACAACCGGCCATCAGAGTT
GCCTCCGGAGGATGCTACGGGAATTATTATTTGCCTCCAATGGACTACCAAC
GTCATCATCATCATCATGACCATAGCTATCACCATCGGGCGTACCGAATGCAT
AAATTTCAGTGCAAATGTCGCTCCATGTTTCAGCTGGCTTCCTTTGTGGCTCC
CCGCAAGACTCTGTAACGGAAGTGGTGGCTATTATACGAACGAATATCTGGC
GCCTTCAATTCGGCAGTGCGCATATTGCAAGTGGACGGTGGACATATCCATA
TGTACAAATTAATACTTATCGGACATCAGCGTGAACACTGCGAATTATTCTAG
AAACATTTGTAGAATTCGAAAGATTTAAGGAAAGCAGATGCTGAATATTAGG
CGAAAAGCGATTGAACTACTCTATAATATGCAGTCAAAAATATCATCGATTC
GCCTGTCAATTAATTGTATCTAAAATTATACTTTTCGAATGTCTATTTTGGCAA
TAATCTTTAGTGATTCGTACTGCTCAGCATTTAATTGAGTGTCGCAAGCAATT
GGGGCCGGGGTATTTGCAATGTTTTTCCAATTCTCTGCACCGAAATAACCACA
AAAAAGACAGCCAGTCAGCCAAGATATTTTGGGTCTCCTCCGAATGGAGGAT
GCACATCCACGATGTGCGATGTGAATGCGCTGCAATTGGGCGTTCAAACACA
TGTTGGATGGTCCAAACACAAACCGCATTGCCCGGCAAGGGAGCGAGTGAGA
TGGGGATCCAAAAATGCTAATACACGTCGGCCAGCACAAAATCAAAATAAG
AAACCCATGCTGCTAAAAATAAAAACTGGCGGCGGCGACACAACGACACAT
CGGAGCGGTCGGAAAAAGCACACAGGCGAGTGGAGGAGCAAGATATAAGAC
AGCTTTGGGAGCGTCTTGAATACGCGTATATCTGGCTATTTGTGAATGCGAAG
GTTTTTGAGAAATTCAGAGAAGCGCACAGACTGTTCGAATACGTCTATCCTAT

FIGURE 16 (Continued)

ACATCAGAATGGTCAGGCACTTTCAACACATTGGCCCCATCCATCCCACTCAA
TATTTACATGATGACGATGATCTTTTGGTCAATGTTTGTGTTGGTCGGGTATT
ACAGAAACCGATATCGCGAGTTATCTATGCCATATACACGATCCAATGGGGG
GACGGCGGGAGGGGCAACAGTCATGCTCGCATATATTTGTGCTATTTTTGAA
CTATTTCGGTACTGCGAAATCTATGTGATCTACAAAAACCATGAGATGTCTGA
GATATGACTGCTGAGTGCCGGAAATTGTAGGATTCTCGATTCCCGATCATATA
ATGCATTCTCGAACAGAAAATCTCCATTACGAAATGCTTTCTATTCTTAGGCG
TCGCACAACTTTAATTGGAGCTTCCAATGTTGTGTGAATAAGTGTGTATATAT
CCGTGGTCTATATATGCAACGGATTTTGGTGAGTTTTACCGTCTGTGTCGGAA
CTGAGTGTGCCGAAATCTTTCCGAACTAGAAGACCGCACCGTCAACGCACGG
CATAGTTCACGCGTGTACTGGCCGCTTAGGATGCCGATGCCGATTCCGATTGC
GATCCGAAGATACACCACCCGATCTGGCGCCCGATCTTTGGCGAAGCGAGCT
ACGTGTTAAGTTCTCGGCGTGATGTACTATAACAATGAGAAACAGTTTACTTA
TCTGGCTTACACTTCAATAGGAAAACAATACTTTTATATAGCTTCTATAACTT
CGGGGTGCGATAAGAACATGAATACAGATACACGGATTGCAACAGTACCCA
AGCCACTTGTTTTAAACAAATAACAGGATAATGGGGAGTAATGTAAGCTATT
GACTGGGTTACAATCAGGGGTCTGATAACAATCAAACATTGTCCAGTTGCCTT
TTGCGAATATCAATGACCACTCACGAGTTGCAACTGATAACGATTATCGCCG
CACAATGCAGTGGGTGGGTATTTCACTGGGGGGAACTTTTGGGTCCCTAGAA
CCCAGACGGATTACTCAATGAATATAGGCGATATGTTTGGGTTTACAGCGAA
AGTGCTATTAATGTCGACCGTATGCTCTCTTCGATGTGCCAGCTCTCTATTTGC
GGGAATGAATGACTATTTTTATGGGTCTGCCGTCGCTGCTACAATGCTGCATT
GCTGCAGTGGGACATCCTTTGAACAGGCGCCATGCCAAAGGATATTCTTTGT
GGAAGGGGGGGGGGGGGCAAGGGTTAAGGGTCACATTCGTTTGCGCAATAC
TTCCAGCGATGGGGCGGTGAACGGTGGGCGGGGCGATCGGTCAAGGCTTCGA
CTGTGGAACGTGACACGCATATGTCGGCCGGAGTTTGGCCCAAAAAGTGGCC
CCAATGGTTGTCCTTCGCGCTGGCAATTAGTCCCTAGCAAGGCGCGTCCATAT
TTTGCAAAAATTCGTGGGGCGCCTTGTTTTCTTCTCTCTGTATGTGTGCATGTG
TGTGTACCTCCGTCTCACTCACCTCAAGTGTGTGTGTGTGTATGAAAATACTG
CGGTATACGGCTGCGTTTGTGTGTGAGTGTGGGTTTCGGCTCTACTCTCCCGA
TGATCCTGCTCCTCCGGTCCTAATCCCGGCCTGCTCGGCTGCTCCTGCGTCCT
GACTGCGCTAGAAATTCGCTTAAAACGAGCCTCGACGGGTCATTTTTACAATT
GTTTTTTGTTGTTCCGTTCGGCTGTTTTACCAGACGTGCTCGTTCCGGTGTGAC
TGCCCGCCGCTGACTGTAAAATACTAAACGCATTGCAGCTGTGGCAATGCCC
AAGTCTTGGTCTTACGGTCACACTGGCAAAGTTTAAAAATTTATTTATTTCAA
CTTTCAGTTACTTTTCGTTGGCTTGAATATTACACTAAGAATTCAATTTGACAC
TTGCAATTTATACATTGTATATTATAATATATTATATGTATTATATTTTATATC
ATATAAAGATATTTATATCTATTGATCTTTTGATTATAAGCTCTTTGGTTGAAC
AATATAAGTGCAACTTTCTCCATCACCTTCCTATCTTTTTACAATATGCTTACC
TCGTCAATACGTTTTTTCTATTTCAAATATTTCAATATTTCAAAGAAATATTTT
GTTTATTTTTCTGTGTGTTTTTAAGCAATCTGACCCCTGTAGAAGAATCCCTTA
TAATATTAACAAATGTATCCTCAAAATAGATCGATCTCTATCTTCGCAGACTT
ACACGAAACATTCCAGAACCGATAGTTTTATGCGATATATGAGATTTAAGGA
GTACTTTCCGCATTTCGCCATCACAGTCACGCTTTCCTTGGCATTTGCAATCA
AATAAGCGCTAATAATAATCGTAAAAGCATAAGAAGCATATAAAGAAGAGT
CACCGCCAAAAGCATGCACAAATATATATAAATGGGGAGCGATTTAAAAACA

FIGURE 16 (Continued)

GTGCACTGTGTTTAAAACATCGACAGCTATCGGTTAGCATATCGATATTGACA
TTCGCAGTCAAACGTTTTCGAGATACAACCCTAAAATCCGAGAAGCATCCAG
AAATTTCGACGTAGACGAGGGCGAACCTATAAAATGAGGTTGACGCACGAAT
CCCGCTCATTATTAAACAAAATTTTGAAGAGAAAGAAACTCTGAAGTAGGGT
GTGTTTTTAGTGCGCAAGCCACATTTGGTGGATAAAG

FIGURE 17 dTPR2 5' region, 13015 base pairs
AGACAAAGACAGCGCTGACTTCAGTCGACTTTCGTATTCATTGTTAAATGACA
TGCAAATGTACGAATGACATGGCATTCGCCAAAGGGTTTTGAAAGGGGGGCC
AGATCCAAAGGGCAGGTCTCAGGGAAATGTTTCCAGGCTAATTGTGGGTTTT
ACGCCCTGTACTTCTCCAAATGATCAAGTACGTCATTTAATGGAAGCCACTGA
CAATTGGAATCGTAAATTATACAGCACAAACTAGATTTGTTTGAGTGCTCTCA
ATGTAGGCTAATATTAGATTTCTGCGCTGAATTAAAATTATTGTAATACGTAT
TATAATGCATTTGTACCCAAATTTGACAGACTTAAGCAGTTCTCTAACATAAT
TGGCATCATTGGCAAAGAGAAATAATATTAAATTGGCAGCATTGCCAGAAAA
AACTCTTCTCCTAAATTTTGCTTGATTGAATGTTGTAGTTGAGAATGTTGTAA
AATAGTGTTAGTATTGTAACACACGACATTTTTCAAATATTTAAATGAAAATC
ACATGGTAATTAGCAATTTTGGGTGGCCTTCTTTCCTCCCCAAGCCAAAGCCA
TATAATTTCAGCCAGCTACTTGCGATTTCCCCCATGACCAACAACAACAGCCC
CATATGTGCAGTGCATTAATGCAGATTTCTTGGCAATTGTTTTTGCATACTTTG
TTTTTTCCTCACTCACTTCAATTTCAATTGGCGTGCTAATAACTCATTTAGTTC
GCAACAAAAAAACAAAAAACGAACAGCGGGCCACAAAAAATGTAGCTACAA
ACATGGCACACCAACAATGGATTGGATGGCTAACCAAGATCGCCCCCACTTC
CCTTTCCATCAATTGCGAATATATCGCATCTCATGATGCTGAGAGAATACTCG
TACTCAACTATGCCGACTTTATATGAACACTGTGTGCAGTTTTGTTTTAGGCTT
TGTAATTATTATAAAAATAAATTGAACTATTGTTGCCTCATTTAGATTGAACA
GTGAGGCAGCCACAATGTTGCTTTTGTTATTCGGATACACTCAATTAAGCTGA
ATTTGCAAAATGCAAATGGCCCGTATGAAACTCACACCTCGAAAATCATAGA
CTCGAATTATTTTAGAAATTTAATATAATTATATTTTGTTTTCTTCTTTTTTTTT
GGTTTGGTTTTTTTTTTTTTTTTGTTTTTTGTTTCCTTGCAACACTTTTCCGCCTC
TCATTTTGACAGCCCGAGGAGTTCGGTTGGTTCAGTTGATCTCTTGATTGTCA
GTCAGTCATTTGTGATTAGACATTCGACAGTCGCCGCTATTGTTGGATGGCAT
AAATTATAGTCTGTCTCAACAACAAAGCGCTGCATATGAAATCCACATAATA
AATCAATGTGCTGTCGTAATTTGTGTTAAGTTATTTGTAATCAATTTGAATTCT
CGCCGTACCTCCCCACCCCCCTCGGTTGGTGAGATTTATGGGAATATTTTATT
CATTTTGCTATTTTGGTTAAATGGCTTTTTGGGGTTTTCCCGAATATAAGTTTA
AAATTAACGCGGCAATAGGCTTAAGATCATGTAATATTATATATTGCCCGTA
AACAAATGCTTTCTACTTTCATTATCATGAGTGTTTTAAAACTCCACGACTGC
TCTAAACTTTAATCTTTAAATATTTTTGTACCCTTTGAAGAACTAACCACTTAG
CAAATCCCTCCTATTATTTCCTCAAACTCTTGCACTTATCGAACTCGCTTCCTT
TCCCCGCCATCTTCACTCGAACAAATTTAACAACAAATTAAACTGAAATGCA
GTCAAATCAATCGCTGACTTTTCAATTCGTTTTCCTTCTTTTTCGGCCCAACA
TTTTCCACTTGGCCCGAGCGTTTTGCATAGTCCATGGCTTCGATTGGATCGGC
TCGGATCGGTTGGTAAGTCTTCGGCGGAGTATGGCTTTAGTCCAATTTAGTGG
AAAGGTGTGCCCACCAGCTCGGTCACAACACGTTGCTGTGGCTCATTGGAGT
TTCGCCTTTGCCTCGCTGGCTTTTGAGCCGTTTGGTCGGTGCCGCTTAAACGC
CGTTTTAGCCAAGTTAGGTGAAAAATGCCAAGGGAGTGAGGAGTGGAGACC
GAACTGTCAACTGTGATCAAAATCAATTGTTTGCCATTTGCCAAACCAAATTG
ACTGAGCCAAGTCAGTGCGAGTCACACAAAAATGCTGACAAAATTATACCAT
AACCCATGAAATGTCAGTGTCAATAATTTTTGTAATTATGAGAGCATTGAGCT
TGAGTACATAAAAAAAAAGTTATATATTTAAAAAAATCATTATTTTAGTTGGC

FIGURE 17 (Continued)

TGCCATTGGAGAAGCCCCCAAAAAAGGCAAACAAATATAATAAAAAATTATT
GCAACGTAAGTTTGATTTGAACAAAAGGCGTATACAATTGGATGAGCTCAA
GAGTGTTTTAGAGTGAAAATGTGAGGATCATTGTTCGCAACCAACTAACAGA
GGTTCGTCTCTAACATTTTTCAAAAAAATTACATAACTTTTAAATTTGATTTCA
GTTTATTTGTAAGTGAGAAGCCTATTTTCTAACCATAAATTCTGCACGTTAAG
AGTATTTCCTTTCATATCGTATCTACAAAAATCAATCCAACACACCTGTTTCA
TCTACCGTTAACACCGTTAAGCCCCGCCCCATTTTCTTATCGAAAATATAGCC
CTTTTTCACGCTCTATTTATAGCATTCACATTCTTTCTTTTTTTTGCACTTTTT
AGCTGGCATATCCTTTCGACTTCCGCCATTCGAGGCTCGCCCAATTTCCGTTT
CGAGTTTAATTAATTTAATAAACAAATTCTTTTCGCTCTAAAAACTCTCAAGT
GTATCGATACGATGCGTTTCTTTTTTTCCTTCGTTAAATAAATAATAACCAAA
AAAAAAAAAAAACCAAAAAGTAGGAGGAGAAAAGTTATTGCCATAGTTTTTT
ATTATACTTGTGTGTTTACCTTTCTGGTGGCTTGATCGATAGGCATCTGCAATT
AAAAAGAGAAGAAGAAGAGACAAGTGAGGCAAAATTGTTAAACGTTTTGTG
TAAGCTTTAATACGAAAAACAAGTACTGCAACATAACGGAAGGAAACACGG
CTTAAATTCGGGGCACAAATGCTGAAAGGGAAGTTTTTCATTGACGGGTTCG
TTCTGACGGACTTGCATTTTGGCGGGCAAGCGGGTGTGAAAATGCACACGCC
CCGAGAACCCCCCCTTTCCACCCCCCCTGGACCCCTTTATCCAGCCCACTGGCC
AAAAACAATTTGTAATTATCCACAGAGAGCGCTGCCTTCAGCGGTTTCGCATT
TCCCCTTTCGCTCGCTCTCCCAACTTGTTTCAATTTAGCGCAAAACTTTTTCAA
CCTAATAATAGGTTTAACCGCATTTTTAACCGTTCCTCATGTTCGGTCCGGTTC
GGTTTTCAAAACCGGGAATCGTACTTAGACTGGGTCTCCTTATTTCTGTTCTG
GCTCTCTGTACAACTTTTCATTGAGAAAAATGTAACTAGTTTTTCATAGCAAC
GGAATACAATTTAATCCAATAATCCAATAGTTTAATCCAATACAAATGATATT
ACTACCATTTCTATTTTCGTTAATTTCGATTTGACTTATTTGGCTGGATTTACT
TTTCAAAATATATGTTATCAATAAGACACAAACCTTACTTTTCTAGCTATTAA
CATAGTTTAAAAAAAAAAAAAAACTAATAAAAATTACGTGAATCTAAATTTT
TAAACCCGATATCCAAGAAGATCTCAATTTTTGCCTGTGTACTCAGTTCTCTG
AACAAAGCGCATGTGCACTTTGGAGCACACTCCATACATGTGGCTCAGCCCT
TTTCCATAATTAACTAGATGGTTTTCCATCGACTTCATTGTGGTCAGCGGCCA
GTTCAACCCGTTCTTCACTGCAACCGAGAACTGTAAACACAAAAACCCCAGG
ACTCTACATTGGCTTAAAAAAATAAGAACAGAACAGAACCAAAACCAAAAA
AAGAAGGGATATTGAAATACAAGGTTGTAATCGTTTCGACTGTTGATGTCTC
AATGCATGGGCAGTTCAGTTAGTAAATGTTTTTCAAAATCTTTCAGGCAGGAG
ATGTTTAAATATCCATGAAATATTTGGATCTCCTGGGGATCAATCGGAATATT
AGCCTTTAATTGTGTTGATCTTTTAAGCCTTTTTGTATCTAATCTAAGCCATTC
GATCTAATCACAATTTATAAATATCTGCATATTTCTGTATAAGTCTGCATCAT
TTGACGTAACTCTTTAAGTCTTTTGGCTTAAGTTGCAACTATAAGGAAGTATT
TATTTTAGAGACACAAATATTTCAGTCGCCTTCATTTGAACAAATCGGCGAAA
ATTGGCTAGCTCGCCAAACTTTCTGTAACCAAGGACAATGGTTTTATTTTAAA
CCATTAAAAACTTTAGACCCACTAGCTCCTAGATCCCCCTCAAAAGATTTAAA
AAAAAAAAACACGATACCCATTTCTACTGAACTTCGTTTTTGCTTGTCGTTTT
TTCCACTCGAACGGAAATGAGCTGACAGCGCACCGCACACGTCGATTGCAGA
AAAACATCGGATAAAACAGGAGGAAAAGTTGTGCAAGGTGGAAAACTGTTT
TACCAACTATTGTTAGAGGCGTTCAAAAGAATTACGCAGCTTTCGGTTAGTTA
GCAAGGGGTCACCGGGGAGCGTTACGTTTGCATTGCGTATTTCCGCTAAATGT

FIGURE 17 (Continued)

CATCGGAAAAGGCAAACGGCGAAATGCGAAACGAAAGTTTTTGATTGCCCG
TGTTAATCGATATCGATGCACAAACTATTTGCATTGCAACCGTTGCAAGAATA
TGCAAGAAGTTGGGGGCGGCCGCGGCAGGGGGTGGAAGTTGAGTGCGTAAG
TTGGCTAAAGCGGAAACAGGAAATGAGAAAATTTTGCAGAGCAAACCCCGA
ACTGGAAATGCAACTAACTGGGCACATGCACTTTGCGAAATCATTGGATAGC
GTTAAGAAATTTATTTTAAAATTGTAACTAACATTTAATCGTATTCAAAAGCA
ATTAAATCCCAATCCAATTCTTATATAAAATCCTTACAAGATTATTCTATTTA
CTGTAAATCTAAGCAAAAACTCCCTTTGCAAAATATTCGCCTGCACAGCACA
GATCAGTGAAATAATCAAATGAAGTCTTGAAATAACGAAAAACCCCCAATTG
CGTGTGGAACTGCCCCCAATGCTTTTGCTTCGGTTTCGTACCTGGCCGTGGTG
CAGTCCCTGTAGAGGATGTCGAAGTCCTTGCAGCAGAGCAACTTGCAGCGAT
TGACGCCCGGCTGGATGGCGCCCAAGCCGCGTAATATGCGCACCTGTTCCAC
ATTGCAGACGAGCGGTACGATGTCAAGGCGCTTTAGTTTGGTATAAACCGTA
TGCAGACCGCCGACCAAGTGCTTCAGGAAGAGCTCGAAGGCCTGCGGCAGGC
AGAGCATCGTTTCGTTGCTAATTATGAATGCGGCGACCTTCTGACCCCGGTAC
TCCACCAGCTTGCACTCATTGGCACTGGGATCCGAGGTGGAGATCGGCGGCG
GTGAGTTGTACGACCTTGGCGGCACATGGTGATGGGCGGCGGCCATCAGTTC
CAAGGGGGAGGCATGGTGCATCATCTGCAGGGAGTTGAGGAGCCCCAGCGA
ATGGGGCGGCAGTCCATGGGGCATTCTGGGCGGTAGGCCCGTCGGCAGTCCG
TTGCCCGATGGCATTCCATGTGGCGGGGGGCTGAGCTGATGGTGTTGCTGCTG
CTGCTGTTGCTGCTGCTGTTGTTGCTGCTGTTGCTGCATCTGCTGCATCATGGA
GTGGTTGAGGGAGCTCACCGGACTGACGGCACTGGGATGGCGACTTGGTGAA
CTGGCCGGTGAGCAACTGGATCCTCGTCCTGTGTGCGAGCTCCGTCCATTTGG
ACGATCCTCGTTGGCTCCACGCGAACTGTTGCTACCGTCGCGTCCATTGTGCT
GCTGCTGTTGCTGCTGGGCTGCTGCGGCTGCCGCTGCTGCGGCTGCCTGCTGC
TGCTGCTGGTGATGCATCAACATGGCGGTGGTGTTCATATTGCCCGCGGCTCT
TTCAATACCACTATTAATATTGTTATTTATTGCGCCCGCTTTATTGTTGTTATT
TTCACTCTGTTCACTTGTCACAGAATCCATACTTCATCATGGCCGACACTTTTG
TTTATTTACTTTTTAATCGATTCGTTAATTTGACGTTTTTTCTATCGTGACAAA
AATTTGACACAAAGTAAGGGAGAAATAGAAAATAGATGGTGAGAGGAAGAT
AAATAATTAATGAACTCTTAATTCATTTTTAATTATTTATTAGGCTTCTATATG
CAAATTCTAAGTGAGCGTGTCTCGTATATTCCTATCCGCTTATTATTGGCTTTA
CATTTTTAATACTTCTGTAAGTTTTATAACATCAAATTTAAATGCAGACCTTC
AAAAAATTTACAAACGATTTAGGATTTGTATTAGGCTCAGCTATGCTCCTATT
TATTAAAATCTATTTTTGAGCCAGTTTAGTTAGTTATATGGTAGCTACAAGTT
TATATTGCTAAATATTTTTTGTAAATTAATATCCTAACAAACATTTTACTTACA
AAGAAATATAGAGAACTAACAGAAAATAGAAAAGTTTCCTTTCAGACATTTA
AAGTCCGATTATCTTCTAATACCCCCCATAAATAATCCTTTATCAACAGAACT
ATTGCTTTGCAAACTTTGCTTTAATTAAGTTTTGGGAAAAACAAGGCAATGAA
GCTAATTTGGATCCTTACTGCCAATTTGCATAAATATACCTATTGTCAGCTTT
ATTTGAATAATTCGATATAGAACATAGATTTACCTTTAAGGAGGTCTAAAAGT
AATTTATAAACTCAACATCACTGACACAAGACACTCGCGCACTTTGCTTTTTG
AATTTCGCTGTGAAATATATACTCTGAATATTTCAAGTTATTTATTCCGATTGC
CCGCTTGTGTTAATCGAGTTCGAATAACCGTTTTCGTACTGGAATTTTGGAAA
CCGGAGCTGTGTCCGTTTTCGAGTACCGTACCGACGGATTGTCACTCAGAGAT
TGAGAGATGGCAGCTACTCCGCTGCGACGGCGACGGTGGCGTCGCTGCCTCT

FIGURE 17 (Continued)

GCTTCTTCGCCTTCGACTGGTTCCTCTTCCCCCTCTCGTTCGGAGAAATCAAC
GAAACGAATTGCATTCGAATGGGAATCGACTGAGAGCGAGACGGCGCGAGG
CGACGACTGCGAGTGAGCGAGTGAGCGGGCGCTAACGAGTGCTATTTTTTA
GCCCACCCACACACACGTACGTACGTACGTACACACGAAGCGCTACCGTTAT
GTACTGAGAGAAATGCGCGCGCAAAAGTTTTATTGCATTACCTTCTCTTGCGA
ATGACAAATTCGTAATGAAAGGCGAGTTTCAATTCGATTCCTTTCGGATTTTC
GTGGCAGCGACGCCGGCAGCGCGGTCGGCCGAGACGAGTGTGCTTGTATGTG
TGTGTCTGTGCCTGTGAGAGCGAGCTGGTGTATCTGTATCTGCGATTGTGCAA
AACCAGAATACGAATACGAGTACGAATACGAATGTCTGTTGCCCGTCCACGT
CTCGCATTACACCAATACCAGGCCAAAAAGGGGAGTGGTATGTGCGATTGAT
CGGTGTGTTTGCATCTGTGTATATTTCTGTGTGCAACCCCGAAAATACAATGA
CAAACGTAATCGCTCTCTCTCTCTTGCATTCGTTTTATTTATTTTTTCAATTCGT
TTGTGCGTGTTGTGTTCTTCAAATCCTCCCGCTCTCTCTCTTTGGAAAAAAAA
ACGTTTTTCATTTCAATTTCATTTCGTTTCAGTCTGAGCCCTCTCTCTCACACC
ATCTCGCCATCTCTGTCGCACGCTCAGGTGGGCTGCAACCAATAAACACGAG
CGAGCGAGAAAGCAGCATATTTGCATAGCCAGTCGTACATGTTTGCGCTCTC
GCTCGCCCCCATGGGCGACGCCTTATATAAACAAATGACAATTGTTTTGGCAT
TTTGTGTTGCAAAGTAAATTATAATAAATGCATTGCCAGAGAAGAAAAGTAA
AAAAAAATAGCTTTACTTCGAGTTTGCGCAGCTGTCTTTGACAAAAAGCATTT
TAATTTCAATTAAAAGTAAATGACAAACTTTCAACGAATTATACTTTTCGGGG
CAGTGTTGCTATCTCTTTCCGTCCCAAGCTTTGATTTTTTTTGTCAACCGTTTT
CCGTTTCCCATTCGTTTCCATTCGAGTCCCGTTTATTTGTATTTCTTTTTGTGTT
GCTGATTCGGAGGAGAGCAGCACTATGGCAGGGCATCTTTCTTCCACTTACA
CATATTGCGATAATGGGGTTTTTTTTCGCCTGAGGGGCGTTCGTTTTTCGGGTT
CTTATAAATAGCATTGCTTATAAATTCTGGCATCGCACCTTTGCCACCTCTAT
ATGTTTATGTACAATGTATCTGAGAGCTCGGTCATTTTTCTATTATTTGTCTTC
GTTTCGCCTTCTGCGATTCTTCTCCATAACGATTGCCATTCCGTCGCCGAACC
AATCGCATTCCGTTCTCTCCATTTGAGAGTTCCATGTACATATTTCTTTCTATA
TGGGAATGGAATACGTCTTTATGTATTGTGTTTGCACATGACGTATGAATTTT
TCTTGTTCGTTTCGTTTGGGGCTTTTCTTTTGTGGATTTCCTCACCCACTGTCTT
TTAGGTGACAGCAACCATTTAATATTAAATTGATTGCAAATGTGGATTTCCAA
CAGCTTTTAGAAAATATTTTCGGGCTTTAAAGAAGAATTTAAAACACAATAA
TTATTGTAATGTAAATATTTTATTTTTACATCGGTTTGTTTCATTAAAAAATAG
TTATAAGATTATATTAGATATGAAAATTAATATGTAACGCTACTTTTTTTCTA
AACTGTGACATTTTAGGCTATTTTTTCTTTTACCATTTCCTTATGTCATATGAA
TTTCATTTAATTATGACATATACATGAATCGCTGGCTTTAAATTCGAATAAGT
ACATTAAATTTACCAAAAATGACATGCAGAATTAAAAAGTATTCATTCAAAC
AAATTTGTTTTCCCCCCATAAATGGACAACAAAAAGGTACTGCCTCTATCATC
CAAGTGTCAAAATATGTCATAGCAACCAACTATCGTCAGTAAGAAATGAGTT
CTACAACATGCAACTTTTTCATGGTGTCGCAACTGTGGGCGGGAAGTTTGATT
TTTCGCAACAAACAGCTCGCTTTGAACTCTGGTTTTTCTCTTTAATAAATGCA
ACTGATCTAACTATTAAGTAAAATTGTATTTTTTATTAACCACAAGCAAGCGC
AAAGATGAGTTTATATTCTAAAAAAAAGGAGGGTGATTAATTTCTATTAGTTT
GGATTACAAATTTGGACTAGGAGTCAATTTGAAAGTCGTTATATCAATAATA
CTTCTGGACTTTGAAGCGACAGTTACTGTTCCATAACTTCGGATTATCAGCTT
TGCCTTCACCACATATATAGAGTATTCTCTGGATGTGTCGAGATTTGTATTTTT

FIGURE 17 (Continued)

AAACGACGACTGGATGGCAAAAGTTCAGTGCGCTCGCAGCTATTATGTGGAT
TATCTGCCTCTTGCTGGTGCCCCTTGTGGCGGCCAGTTCCAATACAAGACTTC
TAAATGGCATCCTAAGTCATGTGGACAAGGAAGCCAATCCCTGTGAGAACTA
CTACAACCACGCCTGCGGCCAGTACAACATGCGTCACATCGACGACACCTTC
TTCGACATTATACAAATGCTGGATCACCAGGTTAACCAGAACTTGGTGAAAC
TAATGGACGAGCTGGAAATGAGTTCTCAATTGCCGGACTTTAATGTATCTAGT
GTAGATGGCAAGGTCCTTCGTTACTACCTTAGTTGTCGTGGAGCGCCGCGGA
ATATGGATAGTTTAAGCCAGTATCTGAAAGTGATTTCCCCCGGCGAAGGACT
CACATGGCCTCAATTCATTCCGGACGGTAGTTCTTGGCCCCAGGAGAATTTCA
AATGGCTCAAGGCACTGGCTCATCTGCATCGCTACGGTCTAACTAACGTGTTT
TTTAACCTTGAAGTCGTGTCAAACCCACGAAATGCCAGCGAGTACATGGTAG
AATTAAATACACCCACTTTTGGAGAAGAATCTCAACTGCCGAACAGTTTTATT
GAAATTCTATCCGTTCTCTATATCATAAAGGTTCCTTCCAGTGAAATCATTAC
TCTGGCGCGAAAAATGCGAACGCTTGAATTGTTGCTTAAAACGATGATCAAT
CCGATCGACACACTGAATAATAGATACATTAGTATCCGCGATTTTCAGATGG
AAACCGGTCACAACTGGCAGCGTTTCTTTGAGATTTTAATAGGCTCCAGCGCA
GCCCCAGAACTCCAAGTGTTGGTGCGCAATTTTAGGTACTTTACCGCCCTTAA
GGAACTAATGGACAAACAGGATGCTCGGCTGGTGGCCAGCTACATAATGACC
CGATTTGCAATATTTCTATTGGATGAAACCATGGGTGGCAGAGAATCCACGG
AGTGTGTGTCACAGGTGCGCCGCAACATGAATTTGGCTGCAAACATGCTCTA
TAAGGAACGATTTTTCGAAGACTCCACTTTCAGTGCCAATATCCTGGAAATTA
AGGACATTTTCGAGAAACTACGCCATCAGTTTCTGCTGCAAGTCGATCAAAA
TCATCTAGAGTTGACTGCTTTGCAGATGAAATTTTTCGTTCGAAAGGCAGAGG
CAATTGAGATCAACGTTGTGAATCTTCCAAAAACCGATGATCTTCGCCATTTC
ATCGGCCAGTACTACCAAGACTTGCAGTTTCCCACTGGCGAGCTGGATTACC
ATCAGGAGCACCTCAAGGTGCTGCAGTTTCGCACCCAAAAGATGTTGGCCCA
ATCCAGCAAAGGGCACTCAGAGGAGCAGAATATTTTGACTTACAGGAGCCAA
GCGGCGCCATTGCCTCCACCTCGTACTATGTGATGCGCCCCAATGTGATTATT
GTCCCCCTTGGGCTACTGCAAGAGCCATTCTTTCAGCTGGAAAGCGAAGATG
TCTTCAAATACAGCCTGATGGGATATATTATGGCACATCACTTGATAAGCGCC
TTTGCCACCGAGGGCATTACAATTGGCAGCGATGGAAACGATCAATCATTTA
GATCGCATCGTTTCGAAGAAGCAGTCAGTTGCTTGTCACGCAATTCAGAGAA
CATCGATGAAAGCATGGGCGATATTGCTGGTTTAGAACTGGCCTATTTTACTT
ATGCTAAGATGGCCAAGAATCGAAACCGTTTGGATTTCACCCATTTGCCACC
GGAGCAGATATTCTTCCTAAATGTTGGCCAGTTCTTCTGCGGCAATAGCGATA
TGTTGGTTCAGTACAAGGAAGATCAAGTGCGTTTACAGCGAGCTATTGAAGG
GTTTGAGCCATTTGACAAGGCTTTTGGGTGCTACCGCAATAAGCCTAAGCAC
GAGAAGTGTCGTTTATAGTGAATACCTTGTACATATGCTTAGAAATACATATT
TTTTGATAACAATAATACAAGACAATCGTGTTAAATTATAAAAGTGTTACAAT
CACATCCATTCTGTTCTTTTAAAATTAGTTTTAAACTAACAATAGTCAATAGG
CTAAGATAGTTAAATGATCATCATTCGAATAAACAACGTTCAAGATTGACTCT
TCAATGTCATGCACCTGCAAGATTACCATTTATTATAAATTAAAAAAACACAC
AAAGTTATACGTGTGTTACTTACATGCATTACATTCGGGCCTGGCCATCCACT
TAATATACTGAGATGTAGCGGTCTTTGATTTGCGGGATCTCTTATGGATTTTA
GAACATTGTTAACTTTGCTGACAAAGTAAATTCAACTTTTAACGACTTGTGGT
GTGTGCGGCCCGATGAAATGTCTTAAAATACAAATTAAATACAATTCAAATA

FIGURE 17 (Continued)

TAATTCAGACGTCAAAAGGTTTAAAGTTAAAATATATTTTACCTTTTAGTGTT
ATTTATACGTATGAGCCTTGAAAACACAGTTGAATATCAAACGGATTTTTGTT
ACCAACAGATTCCAACAGATTCTCCAACTTTCGTTTTTTGATTGCCTATTCACT
CGAAGATCTATTTCCAGTACTATGATCCTCCATAGTAGAGTCAGCTCAGGATC
TTGTGATAATCCGCAAGCAATTCGACAAAGAATTCGTCGGCCAGAACAAAAT
TTATTAAATCATTGTAGTCATTCTCAGGATCTCTCTTAACTGGCAATCCGTAA
TAACGTATTTCATTATCTCCAAAATACAGTCGGAATTCAGATTAAATTTGCCG
TTTCCGTCCTTTTTTATAAATATACATACAAATATACTAAGCAATAGACTGAA
ATGAATTCTAGAATTTGAGGAAACTAATTATGTACCTTTATGAATACTTTTCC
TTACTTGTACTAATCAAACTAATTTTTAACAGATTTTTCATGCCGAATGATTA
CAATCTTATTTGGATGATTTGATAGAGCTTAGGAATAATGGTTTTAATTTTGG
ATTAAAGAGTTGCGATTAAGAAACGAAGATATTATCTAGTTTTTGAAGAACA
CAGGGTACTTTAAATTTCGCACGCGGAACGTCAAAACAAGAAGAAGTTTTCA
TCAACACTGAATTTCCGCTTGGTAATCAGCTGATAAGCGTGCTCACGATAGCC
GAGTTCACATCCAACAGATGTTTCCCTTAGCAGGGTTTCAGACCCAAATGATG
ATTTATCTTATTTTGATTAAGCTCCAACACGCATTGCTTTGCATAATTCAGGTA
TTATTAGGCTGCTTAATATACAATCCACTTATATTGTTGTGTCCATGAGGAAC
ATCGACACGTGAGGATAAAAATATTTATTTATCGATATATTTTTACTCTTGAG
CCTTTTGCACACCCCTAGTTGTGTTCCA

FIGURE 18 dMLF 5' region, 8374 base pairs
GCCTGATTGTTTTCCACTTTGCAGCAGAGGAGCCGGGAAGGAGCGGTAGAGG
CGCACCCAGTGTATCCGGCAAAGGCAAGTCACCCCAGGTGCGTTCCATGCCC
AGCTCTCCGCTGCCTCAGCGATCCGCTACGCCGACGCGGCTGATGAGCCAAC
GTGTCCGTGAGGCGGCCGAGCGTCTTGCCCAACAGCACACGGTGGCCAGTGC
TCAGCGGCATTTGGGCAATGGGAGAGGCACTGGCACTGGCAATGGAAATGGC
AATAGCAATAGTAATGGCAATGGTAATGGGAACACCGCGGAGACGAATCGC
GAATCACGCGCGCGACGTCTCATCAACCGATTCAATAGCGAAACGCAGCATA
TCACGTCCTAGTTTAAGTCGGTTAAATGCCGACGAGCATAACTTTATTACAGA
TAAAGCAGATATAGCATTGTTTAAGTAAAAAATATATATATATACCCCAGAG
AAACTTTACGAAACACTCGAATATGAATGCGACTGCGGATCAGCATCCCACC
CACCCACACACACACGTCTACCCACTCACAGTAGGATATATGTATGTATGTCT
GCATTCAAGCGGATGCACTCCCTCCGTTCAGAGGGAACTGTACTTAGGCTAG
AGGAAGCTAAGTGTTTAAATTATTGTATCGATTTATATACATATTTACCATAC
TAATTAAAGTTAATGTAACGAAAACGCAGGATCAGTAATCTTATTTAGTTCA
ATGGTAATCAATGTGCGATTAGCGGATGATCGCGCTCCTTGAGTCGCACCCA
CAGTCCGCCGGAGGCTCTCAGCGTAATCCGGAAGGTGGCCGCAATGGTTGTC
TTTCCGGTTACAGGAAGCAGCTGGTAGCTACGCAGCAGGCGCGACACTATGG
TCTTGATCTCCATGATGGCGAATCGATTGCCAATGCAATATCTCGGTCCAGCG
CTGAAGGGTAAAAAGGCGTAGGGATGACGGTTCTCGGAGTTCTCGGGCGAAA
ATCGCTCCGGCTGGAACTTTTCCGGATCGGGATAAATGTGGGCAAGACGATG
GGTGGCATAGGGGCAAATGAAAACGTTGCTGCCGGCGGGCAATGTGTGCTTT
GCCAGGCGAACCTCTTCGCCCAGTTTACGAGCAATAAGCGGGACACTGGGAT
ACAGACGCAGTGCCTCCTTGATGCACATCTCCATGTAACGCATCTCGTGCAGA
TCCGTCATCGTGGGAGCTCTATTACTGTCCTCGAATATGGTCGCCAGCTCCAG
GACACAGCGATCCTGGCACTCGGGATTCTGTGTCAGCAGAAAGAGAGTGAAA
GCCACGGCGGCACCCACCGAATCCTGGCCAGCCAGCATAAAGGTACAGGCCT
CGTTGACGATATCCTCCTCGGTGAAGTCCCGATTGCTCTCGGAGATCTCGATC
ATGTGGTCGAGCAGACACTTTCGCTCGCTATTGCCATTATTATTGTTCTGGAT
TTGGCGACGTCTCTGGATCATTTTGCGTGTGAAGTCATTGAGGCGCTTCTTCT
GGTTAAGCTCATCGTTGGCCATCTTGGTCCAGTGGTAGATCCCGTCCAGCAGC
AGCCAGGGTTGCGTAAACCGCGCGGGCATCATGATCTTGCCCTGGCGGAACG
GCGAGTCCTCCATCATGGCCACATCCTGACCTCTTTTCTTGATCGGCACACCC
AAAACGGCCTCTGCAAGTCGTTCAGGGATTAAGTGAGAAATTATAGCTTGCT
AATCCCCTAGAGACTCACCATTTAGTATGTCCAGTACACAGTTGTTCACGTAC
TTGGCAATATTTATCTCCGTTCCCACGGCTTCGGCATCCAGATTCTCGTACAA
CGATTGCGAGGCATCCACAAAGGTGTCGATGAACTTCTCCAGCAGATTGTGA
TGAAACGCTGGCTGGATGAGCCGTCGATGATTGCTCCACTTGGAACCACTGC
TGGTTATCAGCCCATCACCCAGGAAATTGTGCATCAGTCGGTAGAAGAAGAC
CTTGTTGGTGTGCTTCTTCGAGGAGAGTATCACCTGCAGATCCTCCGGCTCCA
GGACAGCAAAGAAGGGAAAGAGCAGCACCCAGATCCGCACCAGAGATCCAT
ATAGATCGAAGGCCTTGCCGGCACATCTGCGCATCACTGTGAAATGGGATTC
AATTTAACTTAAAAGGTATCTTTCACGAAAAGGTTTCTTCAAGGATCTTACAG

FIGURE 18 (Continued)

TCCTTATCCGTGACCAGCATGCAGTTGCCCAGAAATGGCAGCGATGGCGGAC
CCGTGAGTCTCAGCGAGAGGAGAACCGATCTCAAGTACGTGTTCAGGGTGGC
GTAGAATGTGTAGATGCTCAGGCTGATCACCAGGAGGATCAGAATGGAGCAT
AGCTCCAAATTGGTGGTGCGCTCCAGCTGTGGGGGCGAAAGCAAACGTAAAT
GCATTGGGTCAAGTCGCGTGGATAATTGCCCGCTTAGGTCAATATTTGGTTTG
CTATCGAGAACGCCGAGCTCTTGAACGCACTTCATCAGCTACGCACTGCGCTC
ACTGGAGTCTAATTAACTGAGGAATCTTGGAGCACTTAGGCATTCGAACTTG
GATGCGAGCACTTGCCCTTGCCGCGTGTCGCAAGTTTTCGGCAAACACACGTT
ATCGTAATCGCAACGAAAGTATAAGTTATGTATCTAACTGCGGTGTGAATTG
CTTGGGCCAACATGGCGTATGGGCGATGCTATAAGTACGTGTGTGTGTATCC
ATAAGATCGATTAAAGCACCACACCGTTCATGTGTACGTGTTGCTTTGCTTTG
GTTTTTTTTCTTTATTTTTGGGCCATTCGCGTCGATGTTTCGTGGTGCAACAG
GTTACACGATGAGCACAAAACATGACAAATGATGATGATCACCGGACAAAA
ATCCAGGGACAGCCTTTTGTTGCCCACACTTCCCACACCTGTCGTCGCCCCAC
ACCCTTGCACCACTAACCCCCCCCCCCCCCCCAAAAAAAAACCCCTTTGTTTG
GTTCTGGACGAGAGTGAGAGCCCCAACACCATTAGCCAAATGCGATTGGTTT
CAGGGCCAAGTGAAACCACCGGTTGGTTAACTGACTCAGATCTCAATGATTA
ATTTATTACGGACAAGGAATCGGCAAACGATCGCAGTTGGTCATCATAAAGT
TTATCCAAAAATCTAGGTGGCATTCCATTTAGTGGGAACTTCTTACCATCAGT
TCGTAGTAAGCTAAGTTAAAGAGTAAAATAATAGGCGCTTTTAATCCTCCTCA
GCCACCTCATCCTCGTAGCCCTCGGGCAGGGCATTCACCTCGGCATTGTGAAA
CAAACTGCGATTGCCATCTCCCCATGGGAATCGTTTGGTCCGCCGCCTCAGGT
ACTCGTACTTGGCGAACGGCTCCCGCTCCACGTGCTTGTGTCCGGTGAAGGCG
TTTGCGGCGCACAGGACGATGGCCGGTAGGGCCAGCAGGAAGGTGACACGC
TTCCACAGACCAGCGGTATTGGCGGGCATATTGCCCATAAGCCGGATATCAA
AGATCGGCATGTATCTGCACAATAACTCGACTTATTCTGATGCCTGGCTGGAT
GGCTAAGCTAGCTTGAATTTGAATACTACGTACTGTAGCGATTTGAATCTGAT
CCGTAACACCCACGCCTGCTGCCCGAAACTATTGTCGCAATTAGGAACTCTCA
AGGGGATCCGAGCCAGCGCCACAAGGTCCAACAACCCGCGTATCTTTGTTTA
ATCAGCCCAATATTTGACCAGAAACCGCTGAAGCGTCCAGAAGGCTTGCGCT
CCGCTCCAAGCGGCTACTTCTATTTTTTTCCTCTTCATCGAATATTTCTTTCTT
AGTTTCGAATGCTTCTTTTTTTTTTGGGCACGGCATATCCATCCCCATCCAGG
CTGCGAGGTGTGCAGAACCCGCGCCGTGTTTGCTCGCCAATTGGCACCTGGC
CACTAATAGATATACATCATGATTATTTCCCACTAATTCCATAAGTTATCATA
ATGGTCTTCCTAAACGAGAGGCTGCTTGTCGAGGCACTAAGACCGCCCAAAA
TCTAACGATCCATTGAGATTGCGGTTAAAAATGATTCAAATGCAAGCGAAGT
TACTAAAATTTGTGAGAGTATATCTAGTTGAAAACTTGAACTTGAAAATGTG
GTTTTCATAAAATTATCCAAATTGATGGGTGTGAATTAAAATTAAATTAAAAA
CTTGCACTTGAATACTCAAAATTCATTGCTCAATTCATTGATAGATAAATGAT
GATTAAATAATAAGTTATAAACCTAGATCATTTCACTTTAGTATTGGTAATGA
AATTTAGGTTTATATATCCTCACTCTTCTTAAAGTAATGTAAATATTTGTTATC
CTTTAGGAAATACACCTTATTAAAATAATTATTTTAAATTCTATTAAAATTCTT
TTAAAAAACAGAAACGTAATAGCCACCATTTTACATTTTACTTAAACGTTTTT
CCTTTTCTTTTTTAAACTTTAGCTGTGAGTAATCCTTTTTATTCATAACGAATT
GCGTTTAAATATTTTTATATTTTCTTCACTCACCACTTTTTCCACAAACATTTT
AGTCACGTATTTGTATTCCCTTGATATAGTCAATATATTTTGTTTTTATCTTTA

FIGURE 18 (Continued)

ATAGCTTCACACAAAAGTCCTTGCCACAAGCACTGTCCAAATCCACACATAC
ACCAAGTTAGTTAGCTCCACTTCGATTTGGGATATATCCGTATTGTGATCTTA
TTGGCCAGAGTCACATCCGGCGACTGATGAGCTACGAGTGCGGGACCTCCGC
CGGTTAGCGTCTATTTATAACCGATTTGGCCCGATCAAGCTCGGCTTGAACGC
CGCCGAAAATGATGTACGTGCTAGCTAAGTCGTTGGAGTCCCCGGATACCCG
AATCCCCGTATCACCGAATCACCAAATCGCCGAGTCGCCGCGTATCCGCTAG
ATGCCCGAGTGTATCGAGTATAGGTAGTAATTGCCAACTAGTCGGCACTCGA
AGTGCTAAGTAGCTAGAAGTGGATATGGTGCTGGATGCTGGATGCCCCTGCC
AAGTGGCATGGCAATCAATTATCCGTTTGGTGCTTGTTTGATGTATCCCTCCT
CCGCCACCGCCCACGCTATCCACCTCCTCCATGGAATGGCAGACCCTTTGGGT
TGCCAGTGGCACTCAACGATCTGAGCGGTGGGAACGAGGGGGAAGTCAGCT
AGAAATCTTCAGACGCGTGCCAGTGGATCGAACTTTGAGCGGATATTCAAAT
GGCGCAGACGGACCTCTTCACGTTGTTGATTACATCAATCATTTATGTTTACA
GTGTAGTCGTCGGATCTTTGCACATTCACATACTGTTGCTTTTAACGTCATCAT
AAATTCTACAAAATATATTCGGGATTTATTTCCGCGAAATTTTAACCTTTGCT
AATCTTCAATTGTTTACTGAACACAAACGAATTACGTTTCTTATTCATTCATTC
ATCATTCAGTATTCCTAGATGTGTTTAGTCAGTTAAGATCGTTTGAGTTATAG
GTTTAGAAATCTTGGAAATTCAATAGCGCATTGGTTACTGATTAAGAGTTATT
ATCAGTAAGAATATTATTAGTAATTATTATTATGCCAATCAGACCGATTAGAC
TACCACTTCTTGTACTTTTGCTGCGAGTTCTCGTGCACCACCGATTAATATGGT
AAATAAATCTCAGCCTGCTTTTCCAACACCACTTATCTGAAGACACGATTCCA
TGGAGCACATGGAGATTGAGATTACAGCCATCGACTAGACGCCTTCGTCATT
CGGGACGATTAAAGTTCAGTGGCAAATGAAATAGAGTCGATCGATGACTCAA
CGGATCGCTTTGCTGATAATCCCCATTTGTGTTCTCCTTAGCTGGCCAGTTGA
CTTTTTGGTCAGTTGACTTTCTGGCCAGTTGGCTTTCTGGCCATTTGGGTCTTT
AGAAGACCACCGCCCAGTTTATAATGGATATAAAACGAATTGAGCTGCAAGT
CGTATAAACTTTACGATATCATAGCAGAAGTTTATGAAAATCCAAAATACCA
ATCATGGATGATCGCTAAATTCGCCATTTTGGTGATAAGTGATAAGCTGGCTA
CTCCAGCCCTATATAAGAGACCTAAATCGAACCACACTTTAAGTTTAACCATG
TCGCTACGTTTGGGTTTGTTTCTTTTGGCTGCACTTGGTGTGGTAATTCTCACG
GATTCCGCCTCCATAAGCACCCACATTGTTGGTGGCGATCAGGCGGACATCG
CTGACTTTCCGTACCAGGTGTCCGTTCGCCTGGAGACCTACATGCTGCTCCAC
ATCTGCGGTGGTAGCATCTATGCACCACGGGTCGTCATCACCGCCGCCCACTG
CATCAAGGGACGCTATGCCTCGTACATCCGGATCGTGGCTGGTCAGAACTCG
ATTGCCGATCTGGAGGAGCAGGGTGTTAAGGTCAGCAAACTGATCCCCCATG
CCGGCTACAATAAGAAAACGTATGTGAATGATATCGGTTTGATCATCACTCG
CGAGCCATTGGAGTACTCAGCCCTGGTGCAACCCATTGCTGTGGCCCTGGAG
GCACCGCCGTCGGGTGCCCAGGCCGTTGTAAGTGGTTGGGGCAAGCGGGCTG
AAGATGATGAAGCTCTGCCCGCCATGCTGCGCGCCGTTGAGCTGCAGATCAT
CGAGAAGAGCACCTGCGGTGCCCAGTATCTGACCAAGGACTACACGGTGACC
GATGAGATGCTCTGCGCCGGCTATCTGGAGGGCGGCAAGGACACCTGCAACG
GCGATTCCGGTGGACCCTTGGCCGTGGACGGAGTCCTGGTGGGTGTGGTGTC
CTGGGGCGTGGGTTGCGGCAGGGAAGGATTCCCGGGTGTCTACACCAGCGTC
AATTCCCATATCGATTGGATCGAAGAGCAGGCGGAGGCGTATCTCTAAAAAT
GTGGATAGCTTCACAAGCACAACGCGAACAAATAAATCGAACAAATTATTAT
TTTACCACAATAATAAATATGAAATGAGCATTTAGAAAACATGGTTTATAAT

FIGURE 18 (Continued)

ATATTTACAAATTAATATACGGTGTTTAACTCTTCATTTCAACTGGTTTTCCTA
ATCAAAAACCTTTTTTATCTGACCATTACATTGGAATCTATAAGCCATTCTCG
ACGATTTATATAAAAATAAAATTATTACCCAATTGGCATAGGTGAAGGCAAT
TTATCTTGAGGAAGGGAAAAAGTACAATGTAACTAACCATAAATTTTATACT
TTACAAAATCGTTTGATTGCATCATTTTAGAATAACTCAATGCAGAAATTAAA
ATTATAAAATATGTAAATGTGGCTTGAAGTATCATTATTATTTATTTGTGACA
TTTATATTTGACTTGATGCAATCAAATAATATCCACAATATTAGAAATTTACC
GTTTGCAGATAGTTTAACGTATTCGAGTAAGATTACATTTGTTTAAATCTTAA
AAATTTAAAATAATTAGGAAGATTTTGTTTTTAAATATTAACGGCTTCTGGTA
TTTTTTAGAGCTAGTATATACTTTCGTGGTAGACGTCGCTGGTATTTAAGCCA
GTAAGATTCAGCCACACTGACAAAGAAAATATTCGTGAAAATTCTGCATACG
GAAAGAAGAAAATTCGAGCAACAGAAAGCCAACACAATCCACAAAAATGTC
TTTATTCGGAGCGTTGATGGGTGATTTCGACGACGATCTCGGCCTTATGAAGT
AAGTACCAAATGGCGCAAAAAAAAACTAAATAAATGCGGCTCGCCCCGCAG
AAGCCCCATATATTTCCATACGTGTGCAGCTAACGAAGCCCTCTTGGGGCGTG
GAAAAACAGCCAAATAATCGCAAAACAAGGTGTAAATCATTAATTGGCCCAT
AGGCACACAATTAGGCCAATTAAACATATTTACGTGCCCAAAAATTAGCAAT
AAATAGCGTGCCAAAATTAACAGTAACCATCGGAGTGTGCGTGTGTGTGTGT
GCGCAGCATGCGTGAAGTGAAGACGTAATAATCGATAATTTGAATCGAGCGA
CCGCAGGGAAATGGAATTGGGGAAAATGCACTAGCAGGCGTTATTTCAAAGG
TTTCGCCCTGTCACTGGGACTTTTGATAAGGCCCAACCGCAAAGTGACCCATG
TAAAGGCAGGCTATCAGACCCTATTTTATGTATATACGTAGGCTACGCTGCCT
TTATCACTATACTGCGATATTTGGCCACAAGTCATTTAGTTTGGCTTTGTTTAA
AACTTAATTTCGGCTCAGTTTAAAATGAAACAAAAACGTAAAAGCAAATCAA
ACCGTTCACAAATGGAGCTCCAGTAACTCGCACATCAGTCAAGTATCACTAA
GTTACTCATCTTTCGTTTGCAG

ANIMAL MODEL OF POLYGLUTAMINE TOXICITY, METHODS OF USE, AND MODULATORS OF POLYGLUTAMINE TOXICITY

CROSS-REFERENCE TO RELATED APPLICATIONS

This application claims priority to provisional application serial Nos. 60/148,934, filed Aug. 12, 1999; 60/148,933, filed Aug. 12, 1999; 60/177,047, filed Jan. 18, 2000; and 60/205,720, filed May 19, 2000.

STATEMENT AS TO FEDERALLY SPONSORED RESEARCH

This invention was made with Government support under Grant Nos. AG 12289, awarded by the National Institutes of Health, and MCB-9408718, awarded by the National Science Foundation. The Government has certain rights in this invention.

TECHNICAL FIELD

This invention relates to an animal model that exhibits polyglutamine toxicity, and more particularly to methods for identifying genes that modulate polyglutamine toxicity using Drosophila.

BACKGROUND

Expansion of polyCAG tracts is associated with human hereditary neurodegenerative disorders and neuronal toxicity (Kaytor et al., *J Bio. Chem.*, 274:37507–37510 (1999)). Huntington's disease and several other hereditary neurodegenerative disorders are characterized by expansion of a polyglutamine sequence (LaSpada et al., *Nature*, 352:77–79 (1991); Koide et al., *Nat. Genet.*, 6:9–13 (1994); Kawaguchi et al., *Nat. Genet.*, 8:221–228 (1994); Orr et al., *Nat. Genet.*, 4:221–226 (1993); Sanpei et al., *Nat. Genet.*, 14:277–284 (1996); and Zhuchenko et al., *Nat. Genet.*, 15:62–69 (1997)). The expanded polyCAG tracts encode abnormally long polyglutamine sequences within specific proteins promoting their nuclear and/or cytoplasmic aggregation. The protein aggregation is believed to contribute to cellular toxicity including cell death or apoptosis (Trottier et al., Nature, 378:403–406 (1995); Davies et al., Cell, 90:537–548 (1997); and DiFiglia et al., Science, 277:1990–1993 (1997)).

The mechanism of toxicity and cell death by expanded polyglutamines is not yet fully understood. Peptides containing expanded polyglutamine tracts are prone to forming cytoplasmic (CIs) and/or nuclear inclusions (NIs). Two variables appear as major determinants of the aggregation propensity, subcellular localization or toxicity of polyglutamine-containing peptides. The relative length of the polyglutamine tract determines the aggregation propensity and cytotoxicity; the longer it is, the more likely it is to form inclusions and cause cell death. The overall size of the peptide determines subcellular localization as well as aggregation propensity and cytotoxicity; shorter, truncated gene products with expanded repeats are more likely to form inclusions, and these inclusions are more likely to be in the nucleus than in the cytoplasm. These inclusions occasionally recruit their full-length counterpart.

Perinuclear inclusions produced by truncated huntingtin peptides recruit endogenous huntingtin in transfected human kidney epithelial 293Tcells (HEK 293T). Cotransfection of truncated ataxin-3 (SCA3 gene product) with its full-length counterpart, containing either a normal or an expanded polyglutamine tract, resulted in the recruitment of either of the two full-length proteins into perinuclear inclusions formed by the truncated ataxin-3. However, this type of recruitment was not observed in HD brains. In another set of experiments, huntingtin was recruited to neuritic plaques, neurofibrillary tangles and dystrophic neurites in Alzheimer's disease, and to Pick bodies found in Pick disease. Heteromerous aggregates were also formed between co-expressed ataxin-1, with normal or expanded polyglutamine, and ataxin-3 with an expanded polyglutamine repeat in transfected HEK 293T.

Experiments in mouse striatal cell culture and transgenic mice suggested that nuclear localization was necessary for the pathogenic effects. On the other hand, experiments in a human embryonic kidney cell line suggested that polyglutamine can be equally cytotoxic in the cytoplasm or the nucleus. Furthermore, in cultured mouse clonal striatal cells or in SCA1 transgenic mice, aggregation of polyglutamines appeared to be neither sufficient nor necessary for pathogenesis. When NI formation was suppressed in neurons transfected with mutant huntingtin, cell death increased.

The molecular components of the pathways involved in neuronal degeneration and protein aggregation have been investigated. These include: components of protein folding (Cummings et al., *Nat Genet*, 19:148–154 (1998); Wyttenbach et al., *Proc. Natl. Acad Sci. USA*, 97:2898–2903 (2000); and Kobayashi et al., *J. Biol. Chem.*, 275:8772–8778 (2000)), protein degradation (Chai et al., Hum. *Mol. Genet.*, 8:673–682 (1999)), gene expression (Boutell et al., *Hum. Mol. Genet.*, 8:1647–1655 (1999); Kazantsev et at, *Proc. Natl. Acad. Sci. USA*, 96:11404–11409 (1999); and Li et al., *J. Neurosci.*, 19:5159–5172 (1999)), and programmed cell death (Portera et al., *J. Neurosci.*, 3775–3787 (1995); Wellington et al., *J Biol. Chem.*, 273:9158–9167 (1998); and Ona et al., *Nature*, 399:263–267 (1999)), as well as interacting proteins (Kaichman et al., *Nat, Genet*, 16:44–53 (1997); Sittler. et al., Mol. Cell, 2:427–436 (1998); Waragai et al., *Hum. Mol Genet.*, 8:977–987 (1999)), neurotransmitters, and their receptors (Cha et al., *Proc. Natl. Acad. Sci. USA*, 95:6480–6485 (1998); Chen et a., *J. Neurosci.*, 72:1890–1898 (1999); and Reynolds et al., *J. Neurochem.*, 72:1773–1776 (1999)). A Drosophila model has recapitulated abnormal protein aggregation and neuronal toxicity associated with polyglutamine disorders, and a candidate heat shock gene has been shown to have a suppressing effect (Warrick et a., *Cell*, 93:939–949 (1998); Jackson et al., *Neuron*, 21:633–642 (1998); Marsh et al., *Hum. Mol Genet.*, 9:13–25 (2000); and Kazemi-Esfarjani, *Science*, 287:1837–1840 (2000)). The present invention is based upon an alternative animal model that mimics polyglutamine and/or protein folding abnormalities observed in humans.

SUMMARY

The present invention relates to an animal model useful for identifying molecules that modulate expression or activity of proteins involved in polyglutamine toxicity, neuronal and other degenerative disorders, cancer and other proliferative disorders in humans. This animal model is also useful for identifying molecules that modulate disorders associated with undesirable or aberrant protein folding, aggregation, degradation or aberrant transport. Such molecules include genes and other compounds that modulate protein aggregation or folding and associated disorders, including polyglutamine toxicity and polyglutamine related disorders.

A genetic screen using a Drosophila animal model of the invention identified in vivo genetic modulators of polyglutamine toxicity. Three Drosophila genes, heat shock protein 40/HDJ1 (dHDJ1), tetratricopeptide repeat protein 2 (dTPR2) and myeloid leukemia factor 1 (dMLF), were capable of decreasing polyglutamine toxicity in affected flies. Thus, the Drosophila genes or their mammalian homologues and other compounds identified using an in vivo animal model of the invention can be used as therapeutics in treating polyglutamine toxicity and associated disorders in humans. A method of the invention, and the genes and compounds identified, are also applicable for the identification and treatment of disorders associated with other diseases that result from or are associated with intracellular or extracellular protein misfolding/aggregation. Particular examples include Alzheimer's disease, Parkinson's disease, Creutzfeldt-Jacob's disease (CJD), bovine spongiform encephalopathy, Huntington's disease (HD), Machado-Joseph disease (MJD), Spinocerebellar ataxias (SCA), dentatorubropallidoluysian atophy (DRPLA), Kennedy's disease, stroke and head trauma. In addition, as the human homologues of dTPR2 and DMLF (TPR2 and MLF, respectively) are associated with tumorigenesis (neurofibromatosis 1) and leukemias (myelodysplastic syndrome and acute myeloid leukemias), respectively, these genes, and the flies carrying dTPR2 and dMLF P-element insertions or their transgenic versions, will be helpful in identifying cancer therapeutics.

In accordance with the present invention, there are provided methods of screening for genes or compounds that modulate polyglutamine toxicity. In one embodiment, a method of the invention includes providing a first animal expressing a polyglutamine sequence, wherein the sequence produces polyglutamine toxicity in the animal; breeding the first animal to a second animal, wherein the second animal has a marker sequence inserted into its germline, thereby producing progeny; screening the progeny for increased or decreased polyglutamine toxicity relative to the first animal thereby identifying a progeny having increased or decreased polyglutamine toxicity; and identifying one or more genes adjacent to or having an insertion of the marker sequence that confers increased or decreased polyglutamine toxicity in the progeny having increased or decreased polyglutamine toxicity. In another embodiment, a method further includes identifying a mammalian homologue (e.g., human homologue) of the gene.

Methods of screening that are included employ first and second animal invertebrates. In one embodiment, a method includes invertebrates of the genus Drosophila (e.g., *Drosophila melanogaster*).

In one embodiment, a marker used in the methods and animals of the invention includes a P element sequence. In another embodiment, the marker sequence comprises a polynucleotide sequence that disrupts or alters expression of one or more genes near the sequence. In yet another embodiment, a marker sequence includes an expression control element conferring expression of the one or more genes near the marker. In one aspect, the expression control element increases expression. In another aspect, the expression control element decreases expression.

Methods of the invention include screening methods in which a plurality of second animals having markers located at different positions within their genome are screened. Thus, in one embodiment, a second animal is selected from a group of two or more animals having markers inserted into different locations of its genomic DNA. In another embodiment, the second animal is selected from a group of 10 to 100, 100 to 500, or 500 or more of the animals. In yet another embodiment, the second animal is selected from a library of animals having markers inserted at random locations of their genomic DNA. In still another embodiment, each of the second animals is generated by random P-element insertions into the genome. In one aspect, a library of animals is generated by random P element insertion.

Polyglutamine sequences of the methods and transgenic animals of the invention include, for example, sequences having between about 35 to 50 glutamine residues, between about 50 to 100 glutamine residues, between about 100 to 150 glutamine residues and having about 150 or more glutamine residues. The sequences can be encoded by a plurality of CAGs, CAAs or a combination thereof. Expression of the plurality of CAGs, CAAs or combination thereof can be conferred by a constitutive, regulatable or tissue specific expression control element. In one embodiment, the regulatable element comprises an inducible or repressible element. In another embodiment, the regulatable element comprises a GAL4 responsive sequence. In yet another embodiment, the tissue specific element confers neural, retinal, muscle or mesoderm cell expression.

Polyglutamine sequences can additionally include other molecular entities. In one embodiment, a polyglutamine sequence further includes a tag. In one aspect, a tag comprises an epitope tag. In another aspect, a tag comprises a hemagglutinin sequence.

Animals of the invention include progeny animals produced by the screening methods of the invention that employ animals. In one embodiment, a progeny animal exhibits decreased polyglutamine toxicity relative to a parent that exhibits polyglutamine toxicity. In another embodiment, a progeny animal exhibits increased polyglutamine toxicity relative to a parent that exhibits polyglutamine toxicity.

Animals of the invention further include transgenic animals including a transgene containing a plurality of CAGs and at least one CAA sequence encoding a polyglutamine repeat sequence. In one embodiment, a transgenic animal is an invertebrate. In another embodiment, a transgenic animal is of the genus Drosophila (e.g., *Drosophila melanogaster*).

Transgenic animals of the invention including a transgene containing a plurality of CAGs and at least one CAA sequence encoding a polyglutamine repeat sequence can have any number of CAGs and CAAs in any ratio encoding the repeat sequence. In one embodiment, the number of GAGs to GAAs is in ratio of between about 1:1 and 2:1. In another embodiment, the number of GAGs to GAAs is in ratio of between about 2:1 and 5:1. In yet another embodiment, the number of GAGs to GAAs is in ratio of between about 5:1 and 10:1. In still another embodiment, the number of GAGs to GAAs is in ratio of between about 10:1 and 50:1.

Thus, a transgenic animal of the invention including a transgene containing a plurality of CAGs and at least one CAA sequence encoding a polyglutamine repeat sequence can express a polyglutamine repeat sequence of any length. In one embodiment, the polyglutamine sequence is between about 5 and 20 amino acids in length. In another embodiment, the polyglutamine sequence is between about 20 and 50 amino acids in length. In yet another embodiment, the polyglutamine sequence is between about 50 and 100 amino acids in length. In additional embodiments, the polyglutamine sequence is between about 100 and 200 amino acids in length, between about 100 and 500 amino acids in length and between about 50 and 200 amino acids in length. In various aspects, a polyglutamine sequence further includes a tag (e.g., epitope, hemagluttinin, etc.).

In other embodiments, expression of the polyglutamine sequence in the transgenic animals of the invention is conferred by a constitutive, regulatable or tissue specific expression control element. In one aspect, a tissue specific expression control element confers neural, retinal, muscle or mesoderm cell expression. In another aspect, a tissue specific expression control element comprises an Appl or rhodopsin 1 promoter or GLASS transcription factor element.

Transgenic animals of the invention further include animals having a polyglutamine sequence of sufficient length to produce toxicity in one or more cells, tissue or organs of the animal. In one embodiment, toxicity is produced in a neuron cell or brain. In another embodiment, toxicity is produced in a retinal cell or eye. In additional embodiments, toxicity is produced in muscle and mesoderm. Such animals can further include a gene that increases or decreases polyglutamine toxicity produced in the cell, tissue or organ. In one embodiment, such an animal includes a marker sequence inserted into its genomic DNA, wherein the marker is located adjacent to a gene or inserted into a gene whose expression or activity increases or decreases polyglutamine toxicity in the animal. In one aspect, the marker sequence is near or inserted into a gene containing a J domain. In another aspect, the marker sequence is near or inserted into HDJ1. In yet another aspect, the marker sequence is near or inserted into TPR2. In still another aspect, the marker sequence is near or inserted into MLF gene.

Thus, methods for identifying a compound or transactivating factor that modulates polyglutamine toxicity in an animal also are provided. In one embodiment, a method includes contacting an animal that exhibits polyglutamine toxicity with a test compound; and determining whether the test compound increases or decreases polyglutamine toxicity in the animal. Increased or decreased polyglutamine toxicity identifies the test compound as a compound that modulates polyglutamine toxicity. The compound may be present in the animal's food or drink or administered to a tissue or organ of the animal (directly or indirectly).

In addition, methods of producing a transgenic animal characterized by polyglutamine toxicity are provided. In one embodiment, a method includes transforming an animal embryo or egg with a transgene comprising a plurality of CAA and CAG sequences encoding a polyglutamine sequence having sufficient length to produce polyglutamine toxicity in the animal produced from the embryo or egg; and selecting an animal that exhibits polyglutamine toxicity in one or more cells or tissues. Polyglutamine sequences need only be of a length (or sequence where other non-glutamine residues are present) to produce toxicity in one or more cells, tissue or organs of the animal. Animal produced by these methods include transgenic animals of the invention.

Compositions including isolated polynucleotides and polypeptides are also provided. In one embodiment, a polypeptide or a polynucleotide encodes a polypeptide that decreases polyglutamine toxicity. In one embodiment, a polynucleotide sequence has about 65% or more identity to a Drosophila TPR2 (dTPR2) sequence set forth as SEQ. ID NO:2, with the proviso that the sequence is distinct from the EST sequences set forth in FIG. 11. In another embodiment, a polynucleotide sequence has about 65% or more identity to a Drosophila MLF (dMLF) sequence set forth as SEQ. ID NO:4, with the proviso that the sequence is distinct from the EST sequences set forth in FIG. 12. Functional subsequences of TPR2 and MLF that decrease polyglutamine toxicity also are provided.

Invention polynucleotides can be operatively linked to an expression control element. In one embodiment, an expression control element confers expression in a cell, organ or tissue that has or is at risk of having polyglutamine toxicity. In one aspect, an expression control element confers expression in neuron, eye, muscle or mesoderm. In additional aspects, an expression control element is an Appl or rhodopsin 1 promoter or GLASS transcription factor element.

Further provided are isolated polynucleotide sequences that to invention Drosophila TPR2 (dTPR2) set forth as SEQ. ID NO:2, and dMLF set forth as SEQ. ID NO:4, sequences. In one embodiment, a sequence hybridizes to a Drosophila TPR2 (dTPR2) sequence set forth as SEQ. ID NO:2 under moderately stringent or highly stringent conditions, with the proviso that the sequence is distinct from the EST sequences set forth in FIG. 11. In another embodiment, a sequence hybridizes to a Drosophila MLF (dMLF) set forth as SEQ. ID NO:4 under moderately stringent or highly stringent conditions, with the proviso that the sequence is distinct from the EST sequences set forth in FIG. 12.

Such polynucleotide sequences can be of any length, and include, inter alia, polynucleotide having 20 or more contiguous nucleotides, polynucleotide having 30 or more contiguous nucleotides, polynucleotide having 40 or more contiguous nucleotides, polynucleotide having 50 or more contiguous nucleotides, etc.

Such sequences further include sequences that encode polypeptides, including functional polypeptides as described herein. In one embodiment, a sequence encodes a subsequence of TPR2 that decreases polyglutamine toxicity. In another embodiment, a sequence encodes a subsequence of MLF that decreases polyglutamine toxicity. Expression of such sequences can be conferred by an expression control element, for tissue specific expression, for example. Polypeptides encoded by such sequences also are provided.

Compositions of the invention further include mammalian (e.g., human) homologues of the genes that modulate polyglutamine toxicity in an animal as described herein operatively linked to an expression control element in a pharmaceutically acceptable carrier. In one embodiment, a composition includes a polynucleotide sequence encoding a human MLF polypeptide operatively linked to an expression control element in a pharmaceutically acceptable carrier. In another embodiment, a composition includes a polynucleotide sequence encoding a human TPR2 polypeptide operatively linked to an expression control element in a pharmaceutically acceptable carrier. In additional embodiments, expression control elements confer expression of the mammalian (e.g., human) homologue in a cell, tissue or organ of a subject, having or at risk of having polyglutamine toxicity or a polyglutamine related disorder, as described herein.

Methods of identifying compounds or trans-activating protein factors that modulate expression or activity of a target dHDJ1, dTPR and dMLF also are provided. In one embodiment, a target gene is screened by transforming host cells with a promoter or regulatory region of the target gene operatively linked to a reporter construct. In various aspects, a promoter or regulatory region of the target gene includes a sequence set forth in any of SEQ ID NO:s:9, 10 or 11. Candidate target gene promoters and regulatory regions also include promoter or regulatory regions of mammalian (e.g., human) homologues of dHDJ1, dTPR2 and dMLF.

In another embodiment, a method includes incubating components containing HDJ1, TPR2 and MLF polypeptide or subsequence thereof, or a cell or animal expressing HDJ1, TPR2 and MLF polypeptide or subsequence thereof, and a test compound, under conditions sufficient to allow the components to interact. The effect of the test compound on HDJ1, TPR2 and MLF polypeptide activity (e.g., polyglutamine toxicity) or expression is then determined.

In yet another embodiment, transactivating factors are identified using the polynucleotides of the invention in vitro or in a cell-based assay. A method includes contacting a promoter or regulatory region of a target gene of HDJ1, TPR2 or MLF (e.g., a sequence set forth in any of SEQ ID NO:s:9, 10 or 11) with a candidate factor and determining whether the factor bins to the promoter or regulatory region. The invention methods therefore include in vitro, cell-based and in vivo methods to screen for effector compounds, transacting factors or binding proteins. Such methods are useful for identifying transactivating factors or other compounds that modulate HDJ1, TPR2 or MLF expression and are therefore applicable in methods of identifying treatments as well as the treatment methods described herein.

Methods of increasing survival of a cell having or at risk of having polyglutamine toxicity are also provided. In one embodiment, a method includes contacting the cell with an amount of TPR2 or MLF polypeptide sequence, or a polynucleotide sequence encoding TPR2 or MLF polypeptide, to increase survival of the cell. Such methods include in vitro, ex vivo and in vivo, and where the cell is a neural, retinal, muscle or mesoderm cell.

Methods of decreasing apoptosis of a cell also are provided. In one embodiment, a method includes contacting the cell with an amount of TPR2 or MLF polypeptide sequence or a polynucleotide sequence encoding TPR2 or MLF polypeptide to decrease apoptosis of the cell. Such methods include in vitro, ex vivo and in vivo, and where the cell is a neural, retinal, muscle or mesoderm cell.

Methods of decreasing polyglutamine toxicity in a cell having or at risk of having also are provided. In one embodiment, a method includes contacting the cell with an amount of J domain containing polypeptide, TPR2 or MLF polypeptide sequence, or a polynucleotide sequence encoding the J domain containing polypeptide, TPR2 or MLF polypeptide sequence to decrease polyglutamine toxicity in the cell. The toxicity may be decreased by decreasing cell death or apoptosis. The toxicity may be decreased by decreasing protein aggregation, increasing transport or folding, etc.

Such in vitro, ex vivo and in vivo methods include where the cell is a neural, retinal, muscle or mesoderm cell. Thus, methods of decreasing polyglutamine toxicity in a tissue or organ of a subject having or at risk polyglutamine toxicity also are provided. In one embodiment, a method includes contacting the cell, tissue or organ with an amount of a J domain containing polypeptide, a TPR2 or MLF polypeptide sequence, or a polynucleotide sequence encoding the J domain containing polypeptide, TPR2 or MLF polypeptide, to decrease polyglutamine toxicity in the cell, tissue or organ of the subject. In various aspects, the tissue is brain, eye, muscle or mesoderm.

Methods of decreasing the severity of a frontotemporal dementia, prion disease, polyglutamine disorder or protein aggregation disorder in a subject having or at risk of a frontotemporal dementia, prion disease, polyglutamine disorder or protein aggregation disorder are provided. In one embodiment, a method includes administering to the subject an amount of J domain containing polypeptide, a TPR2 or MLF polypeptide sequence, or a polynucleotide sequence encoding the J domain containing polypeptide, TPR2 or MLF polypeptide, to decease the severity of the frontotemporal dementia, prion disease, polyglutamine disorder or protein aggregation disorder in the subject.

Methods of treatment include prophylactic administration. Disorders treatable include neurological and muscle disorders and disorders that impair long term or short term memory or coordination of the subject. Disorders treatable also include disorders characterized by the presence of protein aggregates, amyloid plaques, degeneration or atrophy in an affected tissue or organ.

Particular disorders treatable by the methods of the invention include Alzheimer's disease, Parkinson's disease, Creutzfeldt-Jacob's disease (CJD), bovine spongiform encephalopathy, Huntington's disease (HD), Machado-Joseph disease (MJD), Spinocerebellar ataxias (SCA), dentatorubropallidoluysian atophy (DRPLA), Kennedy's disease, stroke and head trauma. The severity is decreased by decreasing cell death or apoptosis, increasing cell survival, decreasing protein aggregation, increasing protein folding, transport, etc. Severity is also decreased by slowing the progression or reversing one or more symptoms of the disorder (e.g., decreasing memory loss, improving memory, decreasing loss of coordination, improving coordination).

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 is a diagram showing the (A) polynucleotide and (B) encoded polypeptide sequences containing polyglutamine tracts of 20 and 127 amino acids and a hemaglutinin tag with the amino acid residues flanking the polyglutamine repeats. Underlining indicates the coding region of the polynucleotide sequence and italics indicates the Kozak sequence.

FIG. 3 is a schematic diagram showing a genetic scheme for generating P-element mutants, screening for modulators of polyglutamine toxicity by crossing a fly that exhibits polyglutamine toxicity with the P-element mutants and isolating a modulatory P-element insertion on chromosome 3. EP55 (virgin females): source of transposable P-element; P[Δ2–3]: source of transposase; F: female; M: male; CyO: balancer chromosome 2; TM3: balancer chromosome 3. Xa: translocation (2;3) Xa (Chromosome 4 is omitted).

FIG. 9 shows an (A) amino acid and (B) nucleic acid sequence encoding Drosophila TPR2 (dTPR2), set forth as SEQ ID NO:1 and SEQ ID NO:2, respectively.

FIG. 10 shows an (A) amino acid and (B) nucleic acid sequence encoding Drosophila MLF (dMLF), set forth as SEQ ID NO:3 and SEQ ID NO:4, respectively.

FIG. 13 shows an (A) amino acid and (B) nucleic acid sequence encoding human TPR2, set forth as SEQ ID NO:5 and SEQ ID NO:6, respectively.

FIG. 14 shows an (A) amino acid and (B) nucleic acid sequence encoding human MLF, set forth as SEQ ID NO:7 and SEQ ID NO:8, respectively.

FIG. 16 shows a polynucleotide sequence located 5' of a nucleic acid sequence encoding dHDJ1, set forth as SEQ ID NO:9.

FIG. 17 shows a polynucleotide sequence located 5' of a nucleic acid sequence encoding dTPR2, set forth as SEQ ID NO: 10.

FIG. 18 shows a polynucleotide sequence located 5' of a nucleic acid sequence encoding dMLF, set forth as SEQ ID NO: 11.

DETAILED DESCRIPTION OF THE INVENTION

Figure 2:
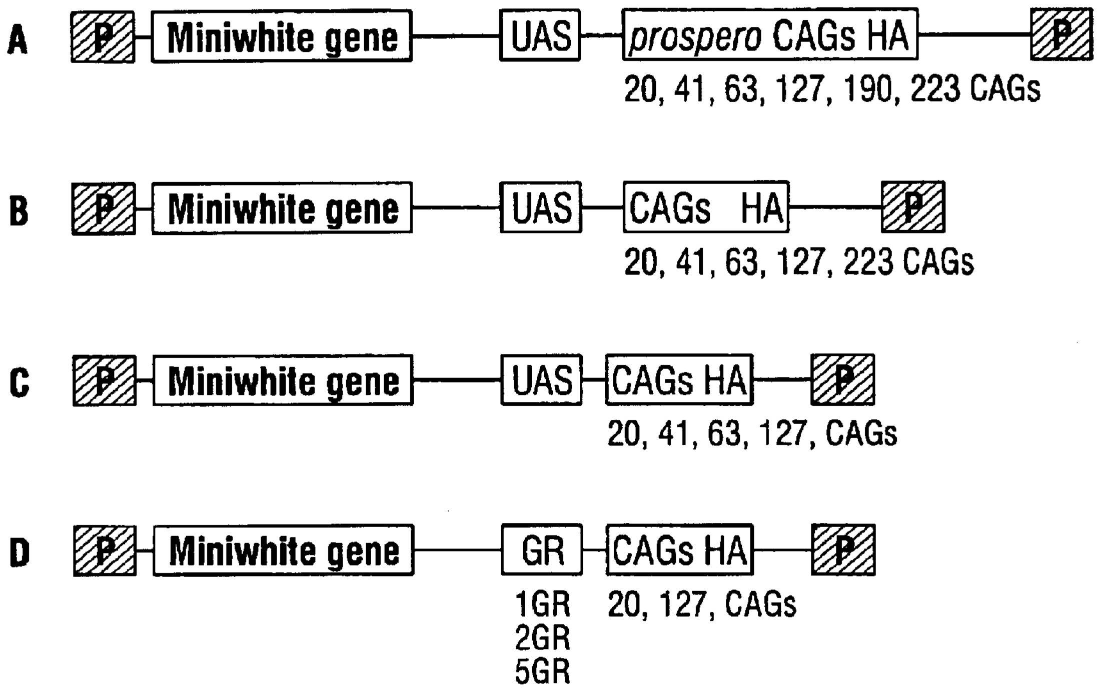
FIG. 2 is a diagram showing P-element expression constructs encoding variously sized hemagglutinin (HA)-tagged polyglutamine sequences. (A) contains the full length prospero gene linked to the indicated HA-tagged polyglutamine encoding sequences located towards the 3' end; (B) contains a partial cDNA sequence encoding 422 amino acids of the C-terminus of prospero linked to variously sized HA-tagged polyglutamine encoding sequences; (C) contains variously sized HA-tagged polyglutamine encoding sequences; (D) contains variously sized HA-tagged polyglutamine encoding sequences driven by one, two or five eye-specific GLASS response elements (1GR, 2GR and 5GR). Polyglutamine tract sizes are denoted as 20, 41, 63, 127, 190 and 223 CAGs. UAS indicates the position of the upstream activating sequence that is responsive to the yeast GAL4 transcription factor. Miniwhite gene produces red pigmentation in the eye.

The present invention provides an in vivo animal model that mimics the cellular degeneration observed in human neurological disorders. A genetic screen in Drosophila that exhibits toxicity in response to expression of expanded polyglutamine sequences was used to identify genes that modulate polyglutamine toxicity. Using the model, lines that contained either suppressors or enhancers of toxicity were produced. Of the suppressors, three genes were identified that decrease polyglutamine toxicity; a Drosophila homologue of human HDJ1 (DHDJ1), a Drosophila homologue of human TPR2 (dTPR2); and a Drosophila homologue of human myeloid leukemia factor 1 (dMLF). Expression of each of these cDNAs in the animal model ameliorates the toxicity conferred by expanded polyglutamine repeat sequences both in the eye and in neurological tissues. The in vivo animal model system is therefore useful in discovering genes and other compounds with therapeutic applications in polyglutamine disorders, frontotemporal dementia, prion diseases and protein aggregation disorders. Particular therapeutic applications include, for example, treating Alzheimer's disease, Parkinson's disease, Creutzfeldt-Jacob's disease (CJD), bovine spongiform encephalopathy, Huntington's disease (HD), Machado-Joseph disease (MJD), Spinocerebellar ataxias (SCA), dentatorubropallidoluysian atophy (DRPLA), Kennedy's disease, stroke and head trauma.

Thus, in accordance with the present invention, there are provided methods for screening for genes and other compounds that modulate polyglutamine toxicity. In one embodiment, a method of the invention includes providing a first animal expressing a polyglutamine sequence that produces polyglutamine toxicity in the animal; breeding the first animal to a second animal, wherein the second animal has a marker sequence inserted into its germline, thereby producing progeny; screening the progeny for increased or decreased polyglutamine toxicity relative to the first animal thereby identifying a progeny having increased or decreased polyglutamine toxicity; and identifying one or more genes adjacent to the marker sequence or having an insertion of the marker sequence that confers increased or decreased polyglutamine toxicity in the progeny. In another embodiment, a method of the invention further includes identifying a mammalian homologue (e.g., human) of the gene that confers increased or decreased polyglutamine toxicity. Identification of such homologues can be performed by comparison to sequence databases (Genbank, Swiss-prot, EMBL, etc.), including the complete human sequence database (Celera Genomics, Inc., Rockville, Md.). Alternatively, library screening of cDNA, genomic or expression libraries can be performed using libraries available in the art.

As used herein, the term "animal" refers to a multicellular organism that reproduces sexually and that exhibits one or more characteristics of polyglutamine toxicity when a polyglutamine repeat sequence of sufficient length is expressed in a cell or tissue of the organism. As such sequences produce polyglutamine toxicity in a wide variety of animals, including human and non-human mammals (e.g., bovine, murine, porcine, ungulates, etc.), many different types of non-human animals are applicable in the screening methods of the invention. In one embodiment, the animal comprises an invertebrate. Preferred invertebrate animals are insects, such as flies, e.g., of the genus Drosophila. In another embodiment, the animal comprises *Caenorhabditis elegans*. The exemplified animal is of the species *Drosophila melanogaster*.

As used herein, the term "modulate," means an increase, decrease or alteration of the term modified. For example, the term modulate can be used in various contexts to refer to a morphological or structural condition of a cell or tissue, a physiological condition of an organism, or an activity, a function, activity or expression of a polypeptide, gene or signaling pathway. Thus, where the term "modulate" is used to modify the term "polyglutamine toxicity," this means that the toxicity is either increased (worsens) or decreases (improves). Detecting increased or decreased polyglutamine toxicity can be determined as set forth herein using an in vivo animal model. For example, improvement in cell and tissue morphology or structure, eye pigmentation or aberrant behavior, animal survival or development, or decreased protein aggregates, of the Drosophila animal model, indicates decreased polyglutamine toxicity whereas a worsening of one or more of these parameters indicates increased polyglutamine toxicity.

The polyglutamine sequences will typically contain consecutive glutamine residues ($Q_n$). Polyglutamine sequences that produce toxicity in a cell or tissue will have a sufficient number of glutamine residues to produce toxicity. Such toxic sequences typically are at least about 30 glutamine residues or greater in length, although they may be less in particularly sensitive animals, cells or tissues, or where a non-polyglutamine sequence that enhances toxicity of the polyglutamine sequence is also included. Toxic sequences, for example, can be between about 30 and 40, 40 and 50, 50 and 60, 60 and 70, 70 and 80, 80 and 90, 90 and 100, 100 and 110, 110 and 120, 120 and 130, 130 and 140, 140 and 150, etc. Such sequences will likely be between about 50 and 75, 75 and 100, 100 and 125, 100 and 150, or greater (150 and 200, 200 and 250, 250 and 300, 300 and 500, etc.). Non-toxic sequences, which are useful as a control or to detect increased sensitivity to polyglutamine toxicity, will typically be shorter, for example, between about 5 and 10, 10 and 20, 20 and 30, 5 and 20 amino acids in length, or greater, where such sequences may not be toxic in certain tissues, even though they may be toxic in others. The glutamine residues in the repeat sequences need not be consecutive. For example, the glutamines can have one or more non-glutamine residues interspersed within the glutamine repeat (e.g., $Q_nX_nQ_n$, where X is a non-glutamine residue, and n is any integer between 1 and 150). For toxic sequences, such interspersing non-glutamine residues may or may not have an affect on toxicity. Accordingly, toxic polyglutamine sequences that have non-glutamine residues are also included in the polyglutamine repeat sequences described herein. The effect of non-glutamine residues on toxicity can be determined using in vitro, cell based assays or in vivo toxicity assays described herein or known in the art (e.g., in vivo animal assays that detect cell/tissue degeneration, death or apoptosis, behavioral abnormalities, altered development or viability, or protein aggregate formation; in vitro assays that detect protein aggregation or misfolding; and cell based assays that detect aggregates in nucleus or in the cytoplasm, or extracellular aggregates such as plaques, etc.).

Polyglutamine repeat sequences expressed in the animal will be encoded by either a plurality of CAG or CAA codons or a combination of CAGs and CAAs. Where the sequence is encoded by a combination of CAGs and CAAs, the ratio of the number of CAGs to CAAs can be from about 240:1, 210:1, 180:1, 150:1, 120:1, 90:1, 75:1, 60:1, 45:1, 30:1, 15:1, 9:1, 3: 1,1: 1, or less, for example, 1:3, 1:9, 1:15, 1:30, 1:45, 1:60, 1:75, 1:90, 1:120, 1:150, 1:180, 1:210, 1:240, or even less. The presence of one or more CAAs in a plurality of CAGs encoding a polyglutamine repeat sequence decreases the likelihood that sequence truncations will occur. For longer polyglutamine repeat sequences, for example, those greater than about 40, 50, 60, 70, 80, 90, 100, 110, 120 or more glutamine residues, which typically produce polyglutamine toxicity, the effect increases as the length of the sequence increases. Thus, including one or more CAAs within a sequence of CAGs can lead to expression of an encoded polyglutamine sequence that does not become truncated. Accordingly, in the transgenic animals of the invention that include a polyglutamine sequence of sufficient length to produce toxicity, it is likely that at least one CAA will be included with a plurality of CAGs encoding the sequence. The CAAs in the polynucleotide encoding the polyglutamine repeat sequence can be interspersed at regular or irregular intervals within the polynucleotide, for example, a single CAA within a CAG repeat encoding 40–50 amino acids, 30–40 amino acids, 20–30 amino acids, 10–20 amino acids or 5–10 or fewer amino acids. Of course, the sequence can have greater numbers of CAAs than CAGs, if desired.

As used herein, the term "marker" or "marker sequence" means a sequence that is "marked" so as to be identifiable. The presence of the marker in the genome of the organism allows identification of gene(s) that modulate toxicity. Detecting the presence of a polynucleotide marker sequence in the genome of the organism, and genes that modulate toxicity, can be performed by sequence analysis using marker specific primers, for example. Thus, when using a polynucleotide sequence marker, it will typically be distinguishable from endogenous gene sequences so that the marker may be sequenced without interference from endogenous gene sequences.

Where a marker sequence comprises a polynucleotide sequence inserted into the genome of the animal, the inserted sequence may alter expression or activity of one or more genes near the sequence. Where the animal having the marker exhibits a modulation of polyglutamine toxicity, the effect will therefore be due to changes in expression or activity of the gene(s) near or adjacent to the marker sequence, or a gene into which the marker has been inserted.

The latter will typically result in decreased expression of the gene, or an altered or aberrant activity, due to the marker disrupting the sequence of the endogenous gene, such as by insertion into the coding sequence (producing a deleted or "Knocked-out" gene, or a truncated gene product, etc.) or insertion into a 5', 3' or intron regulatory sequence that confers expression of the endogenous gene. An insertion of a marker can also produce a gene product that lacks a portion of the sequence, or contains a foreign sequence encoded by the marker. A marker that is positioned near a gene, but not inserted, likely alters expression levels of the endogenous gene (increasing or decreasing).

Thus, in one embodiment, a marker sequence decreases expression of an endogenous gene. In another embodiment, a marker sequence increases expression of an endogenous gene. In yet another embodiment, a marker sequence alters an activity of an endogenous gene (increases or decreases).

Decreased polyglutamine toxicity will occur when genes that increase polyglutamine toxicity are disrupted or their expression is decreased, or when expression or activity of a suppressor of toxicity is increased. Decreased polyglutamine toxicity will result in improvements in the phenotype associated with toxicity (e.g., a return to a more normal cell morphology or tissue structure, increased eye pigmentation, decreased animal lethality or behavioral abnormalities, normal development, decreased protein aggregation, increased cell survival, decreased apoptosis, increased cell proliferation/differentiation etc.), or a decreased sensitivity to expansion of polyglutamine repeat sequences.

Increased polyglutamine toxicity will occur when genes that decrease polyglutamine toxicity are disrupted or their expression is decreased, or when expression or activity of an enhancer of toxicity is increased. Increased toxicity will result in more pronounced toxicity or a worsening of the phenotype associated with toxicity (e.g., a more pronounced degeneration of cell morphology or loss of characteristic tissue structure, loss of eye pigmentation, increased animal lethality or behavioral abnormalities, increased protein aggregation, decreased cell survival, increased apoptosis, decreased cell proliferation/differentiation, etc.), or an increased sensitivity to shorter polyglutamine sequences. For example, a 20 residue glutamine repeat sequence that is normally non-toxic in the animal may be toxic when the marker sequence decreases or disrupts expression or alters activity of a toxicity suppressor, or increases expression or alters activity of a toxicity enhancer.

As discussed, marker sequences need only be distinguishable from endogenous genes in order to identify one or more nearby genes that modulate polyglutamine toxicity. In one embodiment, a marker comprises a P-element. In another embodiment, the marker further includes an expression control element regulating expression of one or more genes nearby the marker. In one aspect, the expression control element increases expression of one or more of the nearby genes. In another aspect, the expression control element decreases expression of one or more of the nearby genes. In additional aspects, the expression control element is regulatable (inducible or repressible) or tissue specific.

As used herein, the term "expression control element" means an element that influences expression of a nearby or adjacent gene(s) sequence to which it is operatively linked. An expression control element operatively linked to a nucleic acid sequence controls transcription and, as appropriate, translation of the nucleic acid sequence. Thus an expression control element can include one or more promoters, enhancers, transcription terminators, a start codon (e.g., ATG) in front of a protein-encoding gene. "Operatively linked" refers to a juxtaposition wherein the components so described are in a relationship permitting them to function in their intended manner. Expression control elements either increase, decrease or confer regulatable (inducible expression or repression) expression of a nearby or adjacent gene(s). For example, where the animal expresses or is made to express a transcriptional activator that is present in a wide variety of cell types, i.e., it is constitutively expressed, an expression control element that responds to the transcriptional activator can be used to increase expression of the nearby or adjacent gene in the cells in which the activator is present. Where the animal expresses a transcriptional repressor, an expression control element that responds to the transcriptional repressor can be used to decrease expression of the nearby or adjacent gene in the cells in which the activator is present.

Expression control elements also include elements that confer tissue or cell specific expression, such as in eye, neural, muscle or mesoderm. For example, the GLASS sequence, a segment of the rhodopsin 1 regulatory region, confers expression in Drosophila retinal cells. The Appl control element confers expression in neural cells. Other elements that confer tissue or cell specific, including muscle and mesoderm elements, are known or can otherwise be identified using methods known in the art.

Expression control elements that may also be used include those that are normally not present in the organism. For example, the yeast GAL4 responsive expression control element, UAS, is normally not present in animals yet is activated when driven by the yeast GAL4 protein. A GAL4 driven UAS element can be used to express a polyglutamine sequence transgene in response to GAL4 in a transgenic animal or to express a nearby or adjacent gene when included with a marker sequence. A tetracycline response element can be used to confer conditional expression in various tissues. Accordingly, a variety of expression control elements, as well as combinations and/or multiples of such elements, (e.g., UAS and GR, see FIG. 2) can be used for expression of the polyglutamine sequences or to alter expression of a nearby or adjacent gene(s) in the animals that include a marker sequence.

As used herein, the terms "near" "nearby" or "adjacent," when used to describe the position of a marker sequence inserted into the animal's genome in relationship to a gene, means that the marker is close enough to the gene(s) to either affect activity or expression. Typically, a marker that does not include an expression control element, to effect expression or activity, will either be inserted into the coding sequence of the gene or an intron, or 5' or 3' sequence thereby controlling expression of the gene, transcript stability, splicing of the transcript, etc. Such markers will generally be within about 5 Kb or less of the gene, depending on the nature of the genes' regulatory region. Markers that further include expression control elements, such as an enhancer that can act at a distance, up to 50 Kb, can be much farther away from the gene and still affect activity or expression of the gene. More typically, a marker will be within 5 Kb or less of the gene coding sequence (e.g., less than 4 Kb, 3 Kb, 2 Kb, 1 Kb, 0.5 Kb, 250 bp, 100 bp, 50 bp, etc.). The type and number of expression control elements included with the marker will determine the amount of expression control exerted over the gene(s), and the distance from the gene(s) with which it will exert control.

In order to produce progeny having increased or decreased polyglutamine toxicity relative to the first animal that exhibits polyglutamine toxicity, at least one marker sequence will be present in the germline of the second animal. Typically, second animals will each have one or a few marker sequences inserted into the germline so that the gene(s) that confers altered polyglutamine toxicity in progeny will be easier to identify. Nevertheless, multiple marker sequences can be present in a given second animal without departing from the invention. In the case of multiple markers located at different positions within the genome of the second animal, genes near or adjacent to each of the marker (or having insertions of the marker) can be individually tested for activity by individually expressing each of the genes, for example, in a transgenic animal that exhibits polyglutamine toxicity or a cell-based or in vitro assays that reflects one or more aspects of toxicity (e.g., protein aggregation, misfolding aberrant transport, etc.).

The greater the number of second animals that can be screened, each of which differs as to the location of the marker inserted into their genome, the greater the number of candidate modulatory genes that can be screened. Thus, by screening a sufficient number of animals having marker sequences inserted randomly throughout their genome, for example, every gene in the animal can be tested for its modulation of polyglutamine toxicity. Accordingly, a population of second animals, for example, 10 to 100, 100 to 500, 500 or more, e.g., 1000 or more, 5000 or more, or enough animals to encompass the entire number of genes of the animal can be screened. In the present case, 7000 Drosophila having randomly generated P-element insertions were screened for modulators of polyglutamine toxicity identified 30 enhancers and 29 suppressors of polyglutamine toxicity. It is anticipated that approximately 50,000 Drosophila each having a randomly generated P-element insertion would be sufficient to screen the entire Drosophila genome for modulators of polyglutamine toxicity.

Non-Drosophila genes can also be assayed for the ability to modulate polyglutamine toxicity. Drosophila exhibiting polyglutamine toxicity engineered to contain non-Drosophila gene sequences can be used to screen for gene sequences from other organisms hat modulate toxicity. For example, a P-element containing a mammalian (e.g., human) gene can be introduced into Drosophila exhibiting polyglutamine toxicity in order to screen the mammalian (e.g., human) gene for modulatory activity. Conceivably, a library of P-elements containing a library of any non-Drosophila organism genetic elements could be tested in order to directly identify genes of the non-Drosophila organism that modulate polyglutamine toxicity. Thus, a library of P-elements each containing a human gene, individually or as collections, can be introduced into Drosophila exhibiting polyglutamine toxicity in order to directly identify human genes that modulate polyglutamine toxicity. Accordingly, it is specifically intended that the methods of the invention include screening of non-Drosophila genes for their ability to modulate polyglutamine toxicity.

In the screening methods of the invention for identifying genetic elements that modulate polyglutamine toxicity, or polyglutamine related or like disorders, genetically manipulatable animals are preferred. Such animals are useful for introducing marker sequences at different locations within the animals' genome in order to test a variety of genes. An exemplary animal is of the genus Drosophila, in particular, *Drosophila melanogaster*. Marker sequences, in particular, random P-element insertions in the genome were generated in Drosophila as outlined in FIG. 3. The F2 males having colored eyes (indicating the presence of the P-element miniwhite gene as shown in FIG. 2) were selected as they have a stable P-element insertion in their genome. Subsequent crosses between the F2 males and the Drosophila lines exhibiting polyglutamine toxicity produced progeny that exhibited altered polyglutamine toxicity.

As the methods of the invention for screening for genes and other compounds that modulate polyglutamine toxicity produce progeny in which toxicity is modulated in comparison to a parent, the invention further provides progeny animals produced by the methods of the invention. In one embodiment, a progeny exhibits increased polyglutamine toxicity in comparison to a parent. In another embodiment, a progeny exhibits decreased polyglutamine toxicity in comparison to a parent. In still another embodiment, a progeny exhibits altered cell death or survival, apoptosis, proliferation, differentiation, behavior, development or viability, neuron excitability, protein aggregation (intracellular, in nucleus or in cytoplasm, or extracellular), folding, transport or degradation, relative to a parent animal. The progeny that exhibit increased or decreased toxicity, cell death or survival, apoptosis, proliferation, differentiation, altered behavior, neuron excitability, development or viability, protein aggregation (intracellular, in nucleus or in cytoplasm, or extracellular), protein folding, transport or degradation, etc., relative to parent, are useful in further characterizing the molecular aspects of the pathways of polyglutamine toxicity and disorders associated with cell death or survival, apoptosis, proliferation, differentiation, behavior, development or viability abnormality, protein aggregation (intracellular, in nucleus or in cytoplasm, or extracellular), folding, transport or degradation, in general, and the role of particular enhancers and suppressors in disease pathways associated with these characteristics.

In accordance with the present invention, there are also provided transgenic animals comprising one or more transgenes. In one embodiment, a transgenic animal of the invention includes a transgene containing a plurality of CAGs and at least one CAA encoding a polyglutamine repeat sequence. In one aspect, the polyglutamine repeat sequence is of a sufficient length or sequence to produce polyglutamine toxicity in one or more tissue or organs of the transgenic animal. In another embodiment, a transgenic animal includes a marker sequence inserted into its genome, wherein the marker is located adjacent to a gene or inserted into a gene whose expression or activity increases or decreases polyglutamine toxicity in the animal. In one aspect, the marker sequence is near or inserted into a gene containing a J domain. In another aspect, the marker sequence is near or inserted into HDJ1gene. In yet another aspect, the marker sequence is near or inserted into a TPR2 gene. In still another aspect, the marker sequence is near or inserted into a MLF gene.

In yet another embodiment, a transgenic animal of the invention includes a transgene identified by a method of the invention. In one aspect, the transgene comprises HDJ1, TPR2 or MLF, mammalian, human or Drosophila. In another aspect, a transgenic animal of the invention includes a transgene identified by a method of the invention and a transgene encoding a polyglutamine repeat sequence. In various aspects, a transgenic animal is an invertebrate (e.g., *Drosophila melanogaster*).

As discussed, the number of CAGs to CAAs in a polynucleotide encoding a polyglutamine repeat sequence can vary. In one embodiment, the number of CAGs to CAAs is in ratio of between about 1:1 and 2: 1. In another embodiment, the number of CAG's to CAA's is in ratio of between about 2:1 and 5:1. In additional embodiments, the number of CAG's to CAA's is in ratio of between about 5:1 and 10:1, between about 10:1 and 30:1 between about 30:1 and 50:1 and between about 50:1 and 90:1.

The transgenic animals of the invention that include a polyglutamine repeat sequence or a transgene can include any of a variety of expression control elements. In one embodiment, polyglutamine sequence expression is conferred by a constitutive, regulatable or tissue specific expression control element. In another embodiment, transgene expression is conferred by a constitutive, regulatable or tissue specific expression control element.

To target polyglutamine toxicity to particular cells or tissue of the animal, tissue specific expression control elements that confer expression of polyglutamine repeat sequences can be used. In addition to modulating polyglutamine toxicity in the tissues that express the polyglutamine repeat sequences, expression control elements that confer tissue specific expression can be included in a marker sequence to target that particular tissue or to confer expression of a transgene that modulates toxicity or any of the other phenotypes described herein in a target tissue. In one embodiment, the tissue specific expression control element confers expression in a neural, retinal, muscle or mesoderm cell. In one aspect, the tissue specific expression control element comprises an Appl or rhodopsin 1 promoter or GLASS transcription factor element.

Other animals may be used in the invention so long as polyglutamine toxicity can be produced in a cell, tissue or organ of the animal. Such animals may be less genetically manipulatable than Drosophila, but, nevertheless, owing to artificial or natural (e.g., polymorphic) identifiable sequences present in the animal they may be used to identify genetic modulators of polyglutamine toxicity because breeding the animal may produce a progeny having altered polyglutamine toxicity. For identifying non-genetic modulators of toxicity and polyglutamine related disorders, such as drugs or compounds (e.g., small organic molecules that are generally membrane permeable or can be modified or included in a membrane permeable material), the organisms need not be genetically manipulatable as the animal is merely contacted with the drug or compound. Thus, it is contemplated that any non-human animal that exhibits polyglutamine toxicity is applicable for identifying modulators of polyglutamine toxicity.

Thus, in accordance with the present invention, there are also provided methods for identifying a compound that modulates polyglutamine toxicity in an animal. A method of the invention includes contacting an animal that exhibits polyglutamine toxicity with a test compound and determining whether the test compound increases or decreases polyglutamine toxicity in the animal. A test compound that increases or decreases polyglutamine toxicity is identified as a compound that modulates polyglutamine toxicity. In one embodiment, the test compound is present in the animal's food or drink. In another embodiment, the test compound is administered to a tissue or organ of the animal. Compounds which decrease polyglutamine toxicity can be a broad spectrum inhibitor of cell or tissue degeneration, death or apoptosis, for example, and can be useful in various therapies including the therapeutic methods of the invention.

As with the screening methods and genetic elements that modulate polyglutamine toxicity described herein, such screening methods and the compounds identified are useful in identifying therapeutics and for treating polyglutamine toxicity and polyglutamine related disorders. In addition, such compounds are also useful as therapeutics that modulate cell death or survival, apoptosis, proliferation, differentiation, development or viability, behavior, neuron excitability, protein aggregation (intracellular, in nucleus or in cytoplasm, or extracellular), folding, transport or degradation, and diseases associated with these processes.

As used herein, the term "transgenic animal" refers to a non-human animal whose somatic or germ line cells bear genetic information received, directly or indirectly, by genetic manipulation at the subcellular level, such as by nucleic acid microinjection or infection of an egg or embryo with recombinant virus. In the present context, a "transgenic animal" also includes progeny animals produced by mating of such genetically manipulated transgenic animals. Invention transgenic animals can be either heterozygous or homozygous with respect to the transgene, although it is likely that for identifying genetic modulators of polyglutamine toxicity that germline transgenics will be used.

The term "transgenic" also includes any animal whose genome has been altered by in vitro manipulation of the early embryo or fertilized egg or by transgenic technology to induce a gene knockout. The term "gene knockout" as used herein, refers to the disruption of a targeted gene in vivo with a loss of function achieved by any transgenic technology which can produce an animal in which an endogenous gene has been rendered non-functional or "knocked out." The term "transgenic" further includes cells or tissues (i.e., "transgenic cell," "transgenic tissue") obtained from a transgenic animal genetically manipulated as described herein.

As discussed, transgenic animals that contain the marker sequences will generally have the markers integrated into the germline. Such animals having a marker integrated into germ cells have the ability to transfer the marker to progeny offspring. Although it is preferred that the transgene be integrated into the animal's chromosome, the present invention also contemplates the use of extrachromosomally replicating sequences, such as those similar to yeast artificial chromosomes, so long as they can be passed onto progeny.

The transgenic animals as set forth herein include insects. The term "insect" as used herein includes all insect species. The term "insect" further includes an individual insect in any stage of development.

Transgenic animals can be produced by methods known in the art. For transgenic insects, generally the transgene is introduced at an embryonic stage. For example, transgenic insects can be produced by introducing into single cell embryos invention polynucleotides, either naked or contained in an appropriate vector, by microinjection, for example, which can produce insects by P-element mediated germ line transformation (see e.g., Rubin et at., *Science* 218:348–353 (1982)). Totipotent or pluripotent stem cells transformed by microinjection, calcium phosphate mediated precipitation, liposome fusion, retroviral infection or other means are then introduced into the embryo, and the polynucleotides are stably integrated into the genome. A transgenic embryo so transformed then develops into a mature transgenic insect in which the transgene is inherited in normal Mendelian fashion. Additional methods for producing transgenic insects can be found, for example, in O'Brochta et al., *Insect Biochem. Mol. Biol.* 26:739–753 (1996) and in Louleris et al., *Science* 270:2002–2005 (1995).

In a particular embodiment, developing insect embryos are infected with a virus, such as a baculovirus (e.g., Autographa californica AcNPV), containing the desired polynucleotide, and transgenic insects produced from the infected embryo. The virus can be an occluded virus or a nonoccluded virus. A virus can be occluded by coinfection of cells with a helper virus that provides polyhedrin gene function. The skilled artisan will understand how to construct recombinant viruses in which the polynucleotide is inserted into a nonessential region of the baculovirus genome. For example, in the AcNPV genome, nonessential regions include the p10 region (Adan et al., *Virology* 444:782–793 (1982)), the DA26 region (O'Reily et al., *J. Gen. Virol.* 71:1029–1037 (1990)), the ETL region (Crawford et al., *Virology* 62:2773–2781 (1988)), the egt region (O'Reily et al., J Gen. Virol. 64:1321–1328), among others.

Significant homology exists among particular genes of different baculoviruses and therefore, one of skill in the art will understand how to insert an invention polynucleotide into similar nonessential regions of other baculoviruses. Thus, for example, a polynucleotide encoding a polyglutamine repeat sequence, or a genetic modulator of polyglutamine toxicity (e.g., J domain protein or HDJ1, TPR2 or MLF polypeptide) may be placed under control of an AcNPV promoter (e.g., the polyhedrin promoter). Depending on the vector utilized, any of a number of suitable transcription and translation elements, including constitutive, inducible and conditional promoters, enhancers, transcription terminators, etc. may be used in order to transcribe polynucleotides (sense or antisense) or express polypeptides. Alternatively, a transgene containing a nucleic acid sequence disrupting expression of a J domain protein, HDJ1, TPR2 or MLF may not contain a promoter as the nucleic acid sequence need not be transcribed or translated to obtain a transgenic insect having a disrupted gene.

Thus, the invention provides methods for producing transgenic animals characterized by polyglutamine toxicity. A method of the invention includes transforming an animal embryo or egg with a transgene comprising a plurality of CAA and CAG sequences encoding a polyglutamine sequence having sufficient length to produce polyglutamine toxicity in the animal produced from the embryo or egg; and selecting an animal that exhibits polyglutamine toxicity in one or more cells or tissues. Such methods can include introducing into the genome of the insect a nucleic acid construct including a disrupted gene, and obtaining a transgenic insect having a disrupted nucleic acid sequence, such as a gene encoding a J domain protein, HDJ1, TPR2 or MLF.

The invention also provides methods for producing transgenic animals having transgenes that modulate polyglutamine toxicity. In one embodiment, a method of the invention includes transforming an animal embryo or egg from an animal that exhibits polyglutamine toxicity with a transgene comprising a polynucleotide encoding a polyglutamine toxicity modulating polypeptide; and selecting an animal produced from the embryo or egg that exhibits modulated polyglutamine toxicity in one or more cells or tissues.

As the transgenic insects described herein having invention polynucleotides or invention polypeptides may exhibit an altered sensitivity to polyglutamine toxicity or polyglutamine related disorders, such transgenic insects can be useful, for example, as biological tools to elucidate the signaling pathways that these genes participate in. As discussed, animals having modulated polyglutamine toxicity can mate with other animals in order to determine the effect of various genetic combinations on polyglutamine toxicity.

Substantially pure, isolated and recombinant polypeptides that modulate polyglutamine toxicity are provided. In one embodiment, the polypeptide comprises a dTPR2 polypeptide characterized as having a predicted molecular weight of about 58,000 Da (58 kDa). 4TPR2 polypeptide is exemplified by the 508 amino acid sequence set forth in SEQ ID NO:1 (FIG. 9). In another embodiment, the polypeptide comprises a dMLF polypeptide characterized as having a predicted molecular weight of about 30,000 Da (30 kDa). dMLF polypeptide is exemplified by the 273 amino acid sequence set forth in SEQ ID) NO:3 (FIG. 10).

Figure 7:
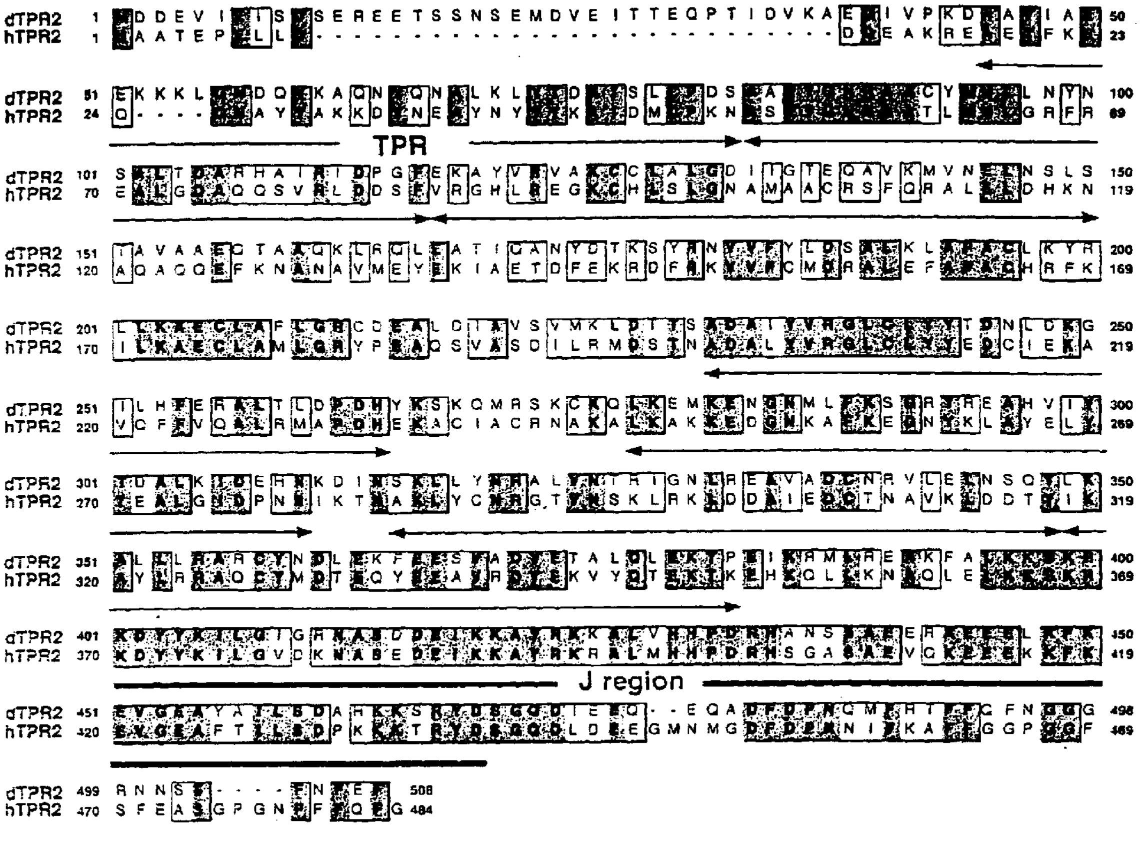
FIG. 7 shows a sequence alignment between Drosophila dTPR2 and the human teratricopeptide repeat protein 2 (hTPR2). Overall amino acid sequence homology is 46% identical and 67% similar, denoted as above. J region homology (bold underlining, from about amino acid 401 to 469) is 74% identical and 93% similar, denoted as above. Arrows indicate the seven tetratricopeptide repeats ($TPR_1$ approximately amino acids 45–82; $TPR_2$ approximately amino acids 83–116; $TPR_3$ approximately amino acids 117–150; $TPR_4$ approximately amino acids 231–264; TPRs approximately amino acids 277–310; $TPR_6$ approximately amino acids 315–348; and $TPR_7$ approximately amino acids 349–382).

Characteristic features of TPR2 include, for example, a J domain located at approximately amino acids 401 to 469, which binds to other proteins having secondary and tertiary structure (FIG. 7). J proteins are implicated in preventing protein aggregation. TPR2 also has multiple tpr domains which are found in proteins involved in protein import, neurogensis, stress response, and chaperone action. Characteristic features of MLF are based on the role of its human counterpart in cell survival and proliferation. In this regard, human MLF is associated with myelodysplastic syndrome (MDS) and acute myeloid leukemia (AML) (Weiss et al., Amer. *J Med Genet*., 89:14–22 (1999). In stable transfections of NIH3T3 mouse fibroblast cells with MLF cDNA, MLF antibody stained the cytoplasm, whereas the NPM-MLF chimeric product was exclusively nuclear and nucleolar (Bergmann et al., *Cell*, 95:331–341 (1998). Neither MLF nor NPM alone had any detectable effect, but NPM-MLF induced apoptosis. The region necessary for apoptotic activity was narrowed down to a 92-amino acid stretch in MLF (FIG. 8) (Bergmann et al., 1998, supra). Therefore, it is likely that the corresponding region of dMLF has a similar role in modulating apoptosis. For example, dMLF may protect against polyglutamine toxicity through its function as a component of cell survival signaling pathway.

As used herein, the terms "peptide," "polypeptide" and "protein" are used interchangeably and refer to two or more amino acids covalently linked by an amide bond or equivalent. The polypeptides of the invention are of any length and include L- and D-isomers, and combinations of L- and D-isomers. The polypeptides can include modifications typically associated with post-translational processing of proteins, for example, cyclization (e.g., disulfide bond), phosphorylation, glycosylation, carboxylation, ubiquitination, myristylation, or lipidation. Polypeptides described herein further include compounds having amino acid structural and functional analogues, for example, peptidomimetics having synthetic or non-natural amino acids or amino acid analogues, so long as the mimetic has one or more functions or activities of a native polypeptide set forth herein. Non-natural and non-amide chemical bonds, and other coupling means can also be included, for example, glutaraldehyde, N-hydoxysuccinimide esters, bifunctional maleimides, or N, N'-dicyclohexylcarbodiimide (DCC). Non-amide bonds can include, for example, ketomethylene aminomethylene, olefin, ether, thioether and the like (see, e.g., Spatola (1983) in *Chemistry and Biochemistry of Amino Acids, Peptides and Proteins*, Vol. 7, pp 267–357, "Peptide and Backbone Modifications," Marcel Decker, N.Y.).

As used herein, the term "isolated," when used as a modifier of polypeptide, means that they are produced by the hand of man and are therefore separated from their native in vivo cellular environment. An "isolated" polypeptide, antibody or polynucleotide can also be "substantially pure" when free of most or all of the materials with which they may normally be associated with in nature. Thus, an isolated compound that also is substantially pure does not include polypeptides or polynucleotides present among millions of other sequences, such as nucleic acids in a genomic or cDNA library, for example. Typically, the purity can be at least about 60% or more by mass. The purity can also be about 70% or 80% or more, and can be greater, for example, 90% or more. Purity can be determined by any appropriate method, including, for example, UV spectroscopy, chromatography (e.g., HPLC, gas phase), gel electrophoresis and sequence analysis (nucleic acid and peptide).

As used herein, the term "recombinant," when used as a modifier of polypeptides, polynucleotides and antibodies, means that the compositions have been manipulated (i.e., engineered) in a fashion that generally does not occur in nature (e.g., in vitro). A particular example of a recombinant polypeptide would be where HDJ1, TPR2 or MLF polypeptide is expressed by a cell transfected with a polynucleotide encoding the polypeptide. A particular example of a recombinant polynucleotide would be where a nucleic acid (e.g., genomic or cDNA) encoding HDJ1, TPR2 or MLF is cloned into a plasmid, with or without 5', 3' or intron regions that the gene is normally contiguous with in the genome of the organism. Another example of a recombinant polynucleotide or polypeptide is a hybrid or fusion sequence, such as a chimeric sequence comprising HDJ1, TPR2 or MLF and a second sequence, such as a heterologous functional domain.

The invention further includes polypeptides having minor modifications of and additions to the amino acid sequence of the HDJ1, TPR2 and MLF polypeptides set forth herein. Such polypeptides have one or more activities or biological functions substantially equivalent to unmodified HDJ1, TPR2 and MLF polypeptide. Such activities include, for example, decreasing polyglutamine toxicity, increasing cell survival, decreasing degeneration, cell death or apoptosis, decreasing protein aggregation, misfolding, plaque formation, improving development, viability, or behavior, etc.

Thus, a "functional polypeptide" or "active polypeptide" refers to a modified polypeptide that possesses a function or biological activity identified through an assay. As described herein, a particular example of a biological activity is the ability to modulate (increase or decrease) polyglutamine toxicity in vivo. Another example of a biological activity is the ability to modulate cell death, apoptosis, survival, degeneration, protein aggregation, transport, folding, degradation, etc. Other examples include the ability to directly or indirectly decrease cellular toxicity associated with protein aggregation, or aberrant or undesirable protein folding, transport or degradation. Thus, functional assays such as cell survival and cell death assays (e.g., apoptosis), development or viability assays, behavioral assays, neuron excitability assays and protein binding, folding, aggregation and transport assays, as well as toxicity in cells or in other organisms can be used to identify polypeptides having one or more functions described herein.

Cell-based assays for assaying toxicity (cell death, apoptosis and protein aggregation) are described, for example, in Hackam et al., *Human Molecular Genetics* 8:25–33 (1999) and Saudou et al., Cell 95:55–66 (1998). Other animal assays include mouse behavior and viability as described, for example, in Reddy et al., *Nature Genetics* 20:198–202 (1998). Bacterial toxicity assays are described, for example, in Onodera et al., FEBS Lett. 399:135–9 (1996). Yeast toxicity assays are described, for example, in Krobitsch and Linquist, *Proc. Natl. Acad Sci. USA* 97:1589–1594 (2000). Toxicity and apoptosis assays in Caenorhabditis elegans are described, for example, in Faber et al., *Proc. Natl. Acad Sci. USA* 96:179–184 (1999).

Additional functions include transcriptional activation (direct or indirect through one or more intermediates), transcriptional repression, the ability to bind or interact with proteins in vitro or in vivo, and the ability to modulate protein folding or transport. Such assays are described further below or are otherwise known in the art. As the proteins affect neural function and neurodegeneration, such biological activities also include behavioral characteristics of the organism. Useful functional assays for characterizing polypeptides and identifying modulators of polyglutamine toxicity therefore also include behavioral assays.

Yet another biological activity of a polypeptide is the ability to bind to an antibody which binds a polypeptide as set forth in SEQ ID NO:1, SEQ ID NO:3, SEQ ID NO:5 or SEQ ID NO:7. Thus, a modified HDJ1, TPR or MLF polypeptide that binds an antibody to which a polypeptide set forth in SEQ ID NO:1, SEQ ID NO:3, SEQ ID NO:5 or SEQ ID NO:7 binds has the requisite biological activity. Antibody binding can be tested using a variety of methods known in the art.

Thus, in another embodiment, the invention provides functional polypeptides or functional subsequences thereof that share at least 65% identity with SEQ ID NO:1, SEQ ID NO:3, SEQ ID NO:5 or SEQ ID NO:7. In other embodiments, the polypeptides have at least 75% identity with SEQ ID NO:1, SEQ ID NO:3, SEQ ID NO:5 or SEQ ID NO:7, more likely at least 85% identity with SEQ ID NO:1, SEQ ID NO:3, SEQ ID NO:5 or SEQ ID NO:7, or 90%, 95%, or more identity with SEQID NO:1, SEQID NO:3, SEQID NO:5 or SEQ ID NO:7. The polypeptides of the invention may have one or more of the functions or biological activities described herein.

The invention also provides functional subsequences of HDJ1, TPR2 or MLF polypeptides. As used herein, the term "functional subsequence" refers to a polypeptide fragment that retains at least one function or biological activity characteristic of a full length counterpart polypeptide as described herein. Functional subsequences can therefore vary in size from a polypeptide as small as an epitope capable of binding an antibody molecule (i.e., about five amino acids) up to the entire length of a HDJ1, TPR2 or MLF polypeptide. Functional HDJ1, TPR2 or MLF subsequences are at least ten amino acid residues in length; more likely, 20 or more amino acid residues in length; and most likely, at least 30, 40, 50 or more amino acid residues in length, e.g., 60, 75, 80, 90, 100, 125, 150, 200, 250, or more.

Particular examples of functional subsequences contain one or more domains that are likely to be important for in vivo activity. By inference from the structure of tetratricopeptide proteins, for example, for TPR2, a functional subsequence may include a J domain or one or more of the tetratricopeptide domains, e.g., $TPR_1$ approximately amino acids 45–82; $TPR_2$ approximately amino acids 83–116; $TPR_3$ approximately amino acids 117–150; $TPR_4$ approximately amino acids 231–264; $TPR_5$ approximately amino acids 277–310; $TPR_6$ approximately amino acids 315–348; and $TPR_7$ approximately amino acids 349–382of SEQ ID NO: 1. The 90 amino acid region of MLF that modulates apoptosis is another example of a particular domain likely to have function.

Functional polypeptides include, for example, conservative substitutions of the amino acid sequences set forth in SEQ ID NO:1, SEQ ID NO:3, SEQ ID NO:5 or SEQ ID NO:7. As used herein, the term "conservative substitution" denotes the replacement of an amino acid residue by another, chemically or biologically similar residue. Examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. The term "conservative substitution" also includes the use of a substituted amino acid in place of an unsubstituted parent amino acid.

Functional polypeptides further include "chemical derivatives," in which one or more of the amino acids therein has a side chain chemically altered or derivatized. Such derivatized polypeptides include, for example, amino acids in which free amino groups form amine hydrochlorides, p-toluene sulfonyl groups, carobenzoxy groups; the free carboxy groups form salts, methyl and ethyl esters; free hydroxl groups that form O-acyl or O-alkyl derivatives as well as naturally occurring amino acid derivatives, for example, 4-hydroxyproline, for proline, 5-hydroxylysine for lysine, homoserine for serine, ornithine for lysine etc. Also included are amino acid derivatives that can alter covalent bonding, for example, the disulfide linkage that forms between two cysteine residues that produces a cyclized polypeptide.

The polypeptide modifications may be deliberate, as by site-directed (e.g., PCR based) or random mutagenesis (e.g., EMS) or may be spontaneous or naturally occurring. For example, naturally occurring allelic variants can occur by alternative RNA splicing, polymorphisms, or spontaneous mutations of a nucleic acid encoding HDJ1, TPR2 or MLF polypeptide. Further, deletion of one or more amino acids can also result in a modification of the structure of the resultant polypeptide without significantly altering a biological activity. Deletion can lead to the development of a smaller active molecule that could have broader utility. For example, it may be possible to remove amino or carboxy terminal or internal amino acids not required for activity. Alternatively, additions to the sequence may provide an additional or increased functionality.

Invention functional polypeptides and subsequences of HDJ1, TPR2 and MLF include all modifications, amino acid substitutions, additions, deletions, insertions and derivatives set forth herein in respect to full length polypeptides, provided that the subsequence so modified retains at least one function or biological activity of HDJ1, TPR2 or MLF polypeptide. Thus, functional polypeptides and subsequences of HDJ1, TPR2 and MLF can have an amino acid sequence that varies from an amino acid sequence set forth in SEQ ID NO: 1, SEQ ID NO:3, SEQ ID NO:5 or SEQ ID NO:7.

Modified polypeptides are included as long as the modified or otherwise altered polypeptide possesses at least one function or biological activity as described herein (e.g., modulates polyglutamine toxicity, cell degeneration, survival, death, apoptosis, development or viability, behavior, or protein aggregation, folding, transport, degradation, etc.) that is detectable using such a functional assay. Thus, to identify functional polypeptides and subsequences one skilled in the art need only test for the requisite function. For example, recombinant modifying the candidate polypeptide (e.g., HDJ1, TPR2 and MLF) by deletion, insertion, or mutation of selected regions and testing whether the modified polypeptide maintains its ability to decrease polyglutamine toxicity. Recombinant modification methods are well established and include, for example, producing successively smaller fragments of the polypeptide by nuclease deletion of a polynucleotide encoding the polypeptide, site-directed mutagenesis of the polynucleotide (using polymerase chain reaction, for example), randomly generated mutations of the polynucleotide, etc.

Loss of toxicity suppressing activity indicates that the modified sequences are important for decreasing toxicity whereas an absence of an effect indicates that the sequences may be modified. A modified polypeptide, such as TPR2 or MLF that retains a function of decreasing polyglutamine toxicity when expressed in Drosophila can be assayed for cell death and survival activity, if desired. For example, synthesized or recombinant produced polypeptides can be introduced into cells in culture to determine their ability to protect against polyglutamine toxicity or apoptosis. In vitro and in vivo assays to measure protein aggregation, transport, folding and degradation as described herein and also known in the art are applicable in testing function of modified polypeptide. In addition to functional assays described herein for identifying functional polypeptides and subsequences, functional polypeptides and subsequences can be identified as having significant sequence homology, in particular, to other proteins or domains whose function has been characterized, for example, the J domain, the tpr domains, the apoptosis modulating domain of MLF, etc.

HDJ1, TPR2 and MLF polypeptides and functional subsequences can be obtained using standard techniques for protein purification, for example, by chromatography (e.g., ion-exchange, size-exclusion, reverse-phase, immunoaffinity etc.). Other protein purification methods known in the art additionally can be used (see e.g., Deutscher et al., Guide to *Protein Purification: Methods in Enzvmology*, Vol. 182, Academic Press, 1990). Alternatively, HDJ1, TPR2 and ML polypeptides and subsequences can be obtained using recombinant expression methods as described herein or otherwise known in the art. For example, polynucleotide encoding the protein can be produced, inserted into a vector and transformed into host cells using well known techniques described herein and further known in the art (Sambrook et al., *Molecular Cloning: A Laboratory Manual*, Cold Spring Harbor Laboratory, N.Y., 1989). Following transformation, protein may be isolated and purified in accordance with conventional methods. For example, lysate prepared from an expression host (e.g., bacteria) can be purified using HPLC, size-exclusion chromatography, gel electrophoresis, affinity chromatography, or other purification technique. HDJ1, TPR2 and MLF polypeptides and subsequences also can be obtained by chemical synthesis using a peptide synthesizer (e.g., Applied Biosystems, Inc., Foster City, Calif.; Model 430A or the like).

The invention also provides isolated polynucleotides encoding polypeptides. In one embodiment, an isolated polynucleotide sequence has about 65% or more identity to a Drosophila TPR2 (dTPR2) sequence set forth as SEQ. ID NO:2, with the proviso that the sequence is distinct from the EST sequences set forth in FIG. 11. In one aspect, the polynucleotide encodes a polypeptide that has a function or biological activity, for example, decreases polyglutamine toxicity. In another aspect, the polynucleotide encodes a subsequence of TPR2 that decreases polyglutamine toxicity. In additional aspects, the polynucleotide encodes a polypeptide that decreases cell death or apoptosis, increases cell survival, proliferation or differentiation, improves development, viability, or behavior, modulates neuron excitability, or decreases protein aggregation (intracellular or extracellular), misfolding, degradation, or aberrant or deficient transport. In yet other aspects, the polynucleotide is operatively linked to an expression control element.

In another embodiment, an isolated polynucleotide sequence has about 65% or more identity to a Drosophila MLF (dMLF) sequence set forth as SEQ. ID NO:4, with the proviso that the sequence is distinct from the EST sequences set forth in FIG. 12. In one aspect, the polynucleotide encodes a polypeptide that has a function or biological activity, for example, decreases polyglutamine toxicity. In another aspect, the polynucleotide encodes a subsequence of MLF that decreases polyglutamine toxicity. In additional aspects, the polynucleotide encodes a polypeptide that decreases cell death or apoptosis, aberrant development or behavior, increases cell survival, proliferation, differentiation, or viability, or decreases protein aggregation (intracellular or extracellular), misfolding, degradation, or aberrant or deficient transport. In yet other aspects, the polynucleotide is operatively linked to an expression control element.

The TPR2 gene corresponds to a cDNA of 2239 nucleotides. The MLF gene corresponds to a cDNA of 1753 nucleotides. Specifically disclosed herein are nucleic acid sequences for Drosophila TPR2 and MLF (SEQ ID NO:2 and SEQ ID NO:4, respectively; FIGS. 9 and 10).

As used herein, the terms "polynucleotide" and "nucleic acid" are used interchangeably to refer to all forms of nucleic acid, oligonucleotides, primers, and probes, including deoxyribonucleic acid (DNA) and ribonucleic acid (RNA). Polynucleotides include genomic DNA, cDNA and antisense DNA, and spliced or unspliced mRNA, rRNA tRNA and antisense RNA (e.g., RNAi). Polynucleotides include naturally occurring, synthetic, and intentionally altered or modified polynucleotides as well as analogues and derivatives. Alterations can result in increased stability due to resistance to nuclease digestion, for example. Polynucleotides can be double, single or triplex, linear or circular, and can be of any length.

The polynucleotides of the invention include sequences that are degenerate as a result of the genetic code. There are 20 natural amino acids, most of which are specified by more than one codon. Degenerate sequences may not selectively hybridize to other invention nucleic acids; however, they are nonetheless included as they encode invention HDJ1, TPR2 and MLF polypeptides and functional subsequences thereof. Thus, in another embodiment, degenerate nucleotide sequences that encode HDJ1, TPR2 and MLF polypeptides set forth in SEQ ID NO:1, SEQ ID NO:3, SEQ ID NO:5 and SEQ ID NO:7, and functional subsequences thereof, are provided.

The polynucleotide sequences for HDJ1, TPR2 and MLF include complementary sequences (e.g., antisense to all or a part of SEQ ID NO:2, SEQ ID NO:4, SEQ ID NO:6 and SEQ ID NO:8). Antisense polynucleotides, to decrease activity or expression of HDJ1, TPR2 and MLF, for example, do not require expression control elements to function in vivo. However, antisense may be encoded by a nucleic acid and such a nucleic acid may be operatively linked to an expression control element for sustained or increased expression of the encoded antisense in cells or in vivo. Sequences encoding dominant negative forms of HDJ1, TPR2 and MLF also are included. Such dominant negative forms may inhibit interaction of the native endogenous protein with a signaling pathway thereby modulating the pathway.

Further included are double stranded RNA sequences from a HDJ1, TPR2 and MLF coding region. The use of double stranded RNA sequences (known as "RNAi") for inhibiting gene expression, for example, in insects and in other organisms is known in the art (Kennerdell et al., *Cell* 95:1017–1026 (1998); Fire et al., Nature, 391:806–811 (1998)). Such sequences can interfere with HDJ1, TPR2 and MLF activity or expression and be useful for increasing polyglutamine toxicity or sensitivity to polyglutamine toxicity, decreasing cell survival, increasing apoptosis, etc. An effective amount of double stranded RNA from the coding region of HDJ1, TPR2 or MLF, HDJ1, TPR2 and MLF antisense polynucleotides and polynucleotides encoding dominant negative forms of HDJ1, TPR2 and MLF can inhibit HDJ1, TPR2 and MLF function or expression and are therefore useful in the therapeutic and other methods of treating aberrant or undesirable cell survival, proliferation (e.g., cancer) or differentiation, as described herein. Such invention polynucleotides can be further contained within carriers or vectors suitable for passing through a cell membrane for cytoplasmic delivery, and can be modified so as to be nuclease resistant in order to enhance their stability or efficacy in the invention methods and compositions, for example.

Thus, in another embodiment, polynucleotides encoding HDJ1, TPR2 and MLF including the nucleotide sequence set forth in SEQ ID NO:2, SEQ ID NO:4, SEQ ID NO:6, and SEQ ID NO:8, as well as nucleic acid sequences complementary to the sequence (e.g., antisense polynucleotides) are provided. When a polynucleotide sequence is RNA, the deoxyribonucleotides A, G, C, and T of SEQ ID NO:2, SEQ ID NO:4, SEQ ID NO:6, and SEQ ID NO:8 are replaced by ribonucleotides A, G, C, and U, respectively.

It is understood that HDJ1, TPR2 and MLF homologs, including HDJ1, TPR2 and MLF homologs having polymorphisms as set forth herein, also are included and are useful in practicing the methods of the invention. Nucleic acid probes based on SEQ ID NO:2 and SEQ ID NO:4 can be used to identify such homologs, for example. Homologs are envisioned to be present in living organisms that reproduce sexually including animals, such as mammals.

As used herein, the term "polymorphism" refers to a naturally occurring or synthetically produced (e.g., EMS induced mutagenesis) nucleotide sequence difference that may or may not encode an altered amino acid sequence. Thus, polymorphisms can be silent such that a function or biological activity generally is comparable to unaltered polypeptide, or be detectable. For example, a polymorphism may inhibit or enhance/activate a HDJ1, TPR2 and MLF polypeptide function or biological activity (e.g., increase or decrease its suppression of polyglutamine toxicity).

Polynucleotides encoding portions of HDJ1, TPR2 and MLF polypeptide are included herein. Particular examples are nucleic acid sequences that encode HDJ1, TPR2 and MLF functional subsequences. As used herein, the term "functional polynucleotide" denotes a polynucleotide that encodes a functional polypeptide as described herein. Thus, the invention includes polynucleotides encoding a polypeptide having a function or biological activity of an amino acid sequence set forth in SEQ ID NO:1, SEQ ID NO:3, SEQ ID NO:5 and SEQ ID NO:7. Moreover, as polynucleotides having nonsense (stop) mutations in a nucleic acid sequence can still encode a functional subsequence of HDJ1, TPR2 and MLF polypeptides, such polynucleotides also are included.

Figure 12:
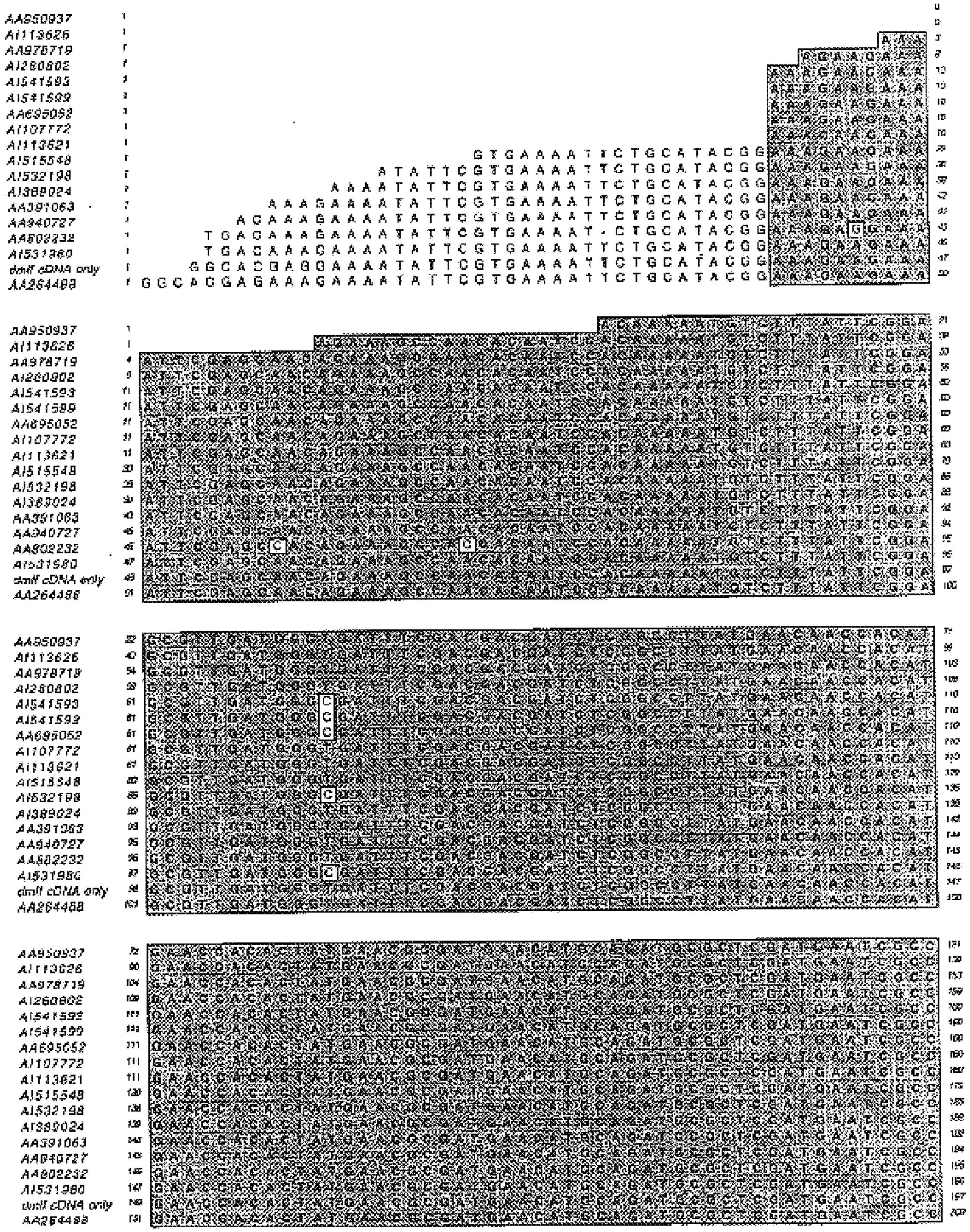
FIG. 12 shows a nucleic acid sequence alignment between Drosophila dMLF and several ESTs.
Figure 12:
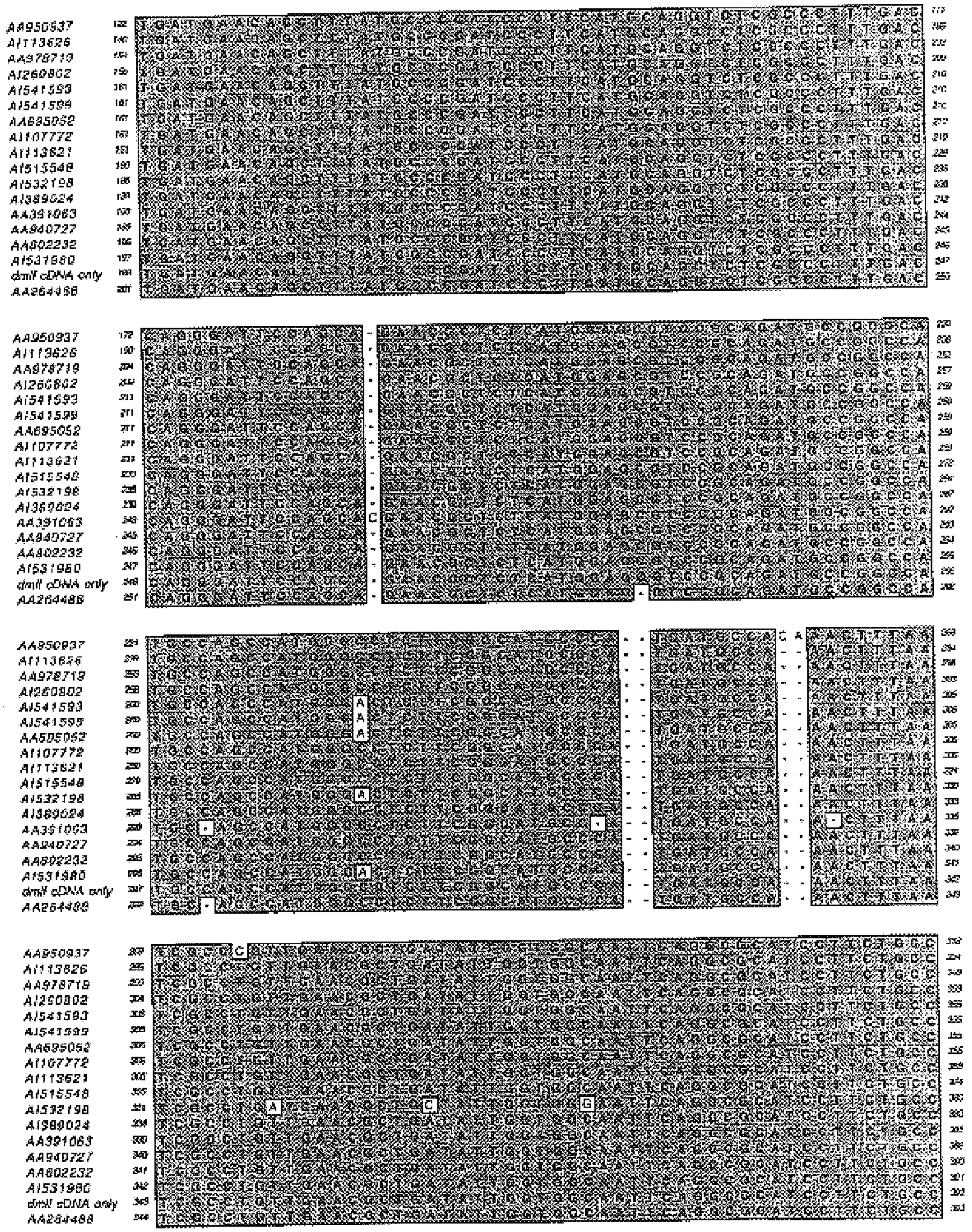
Figure 12:
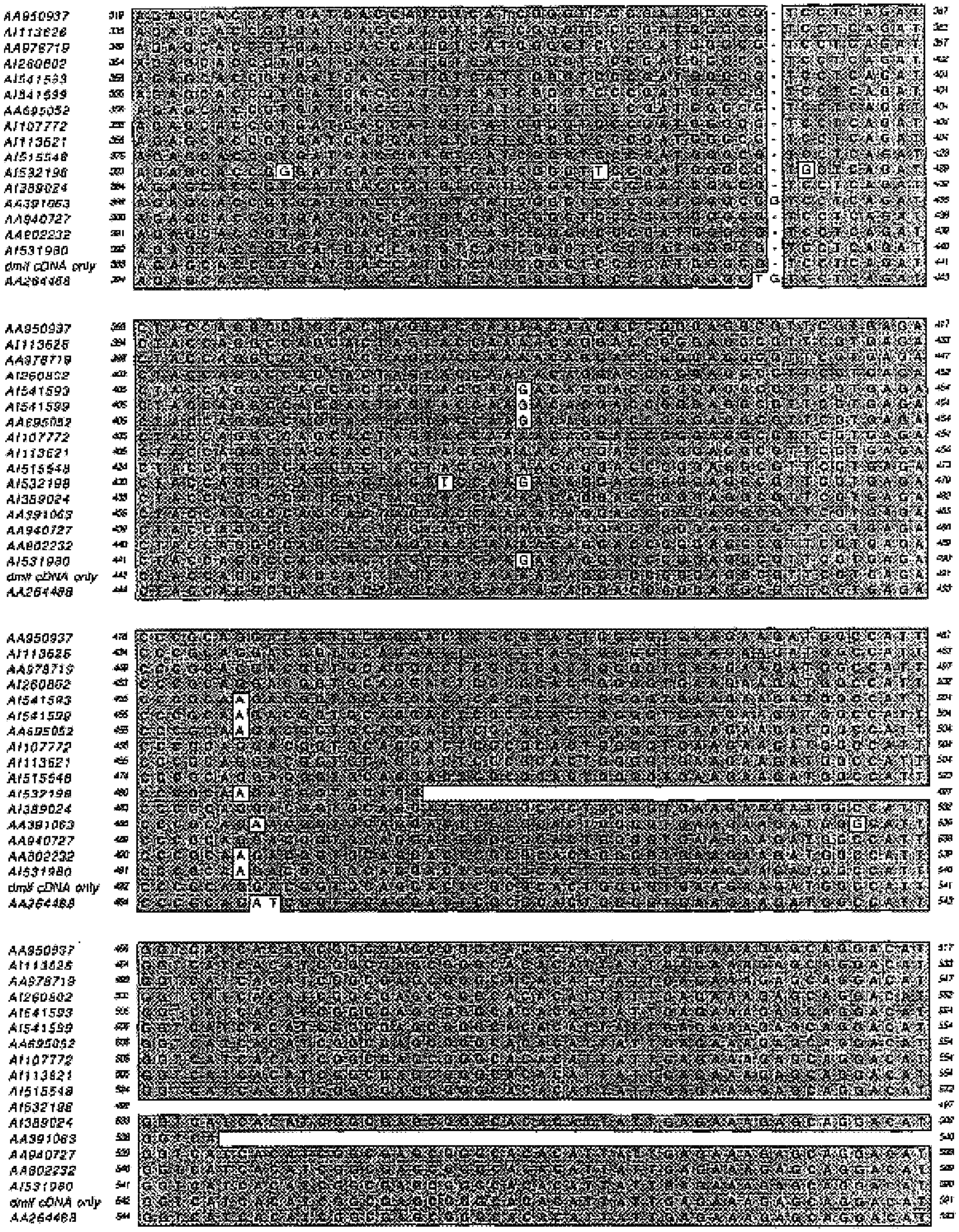
Figure 12:
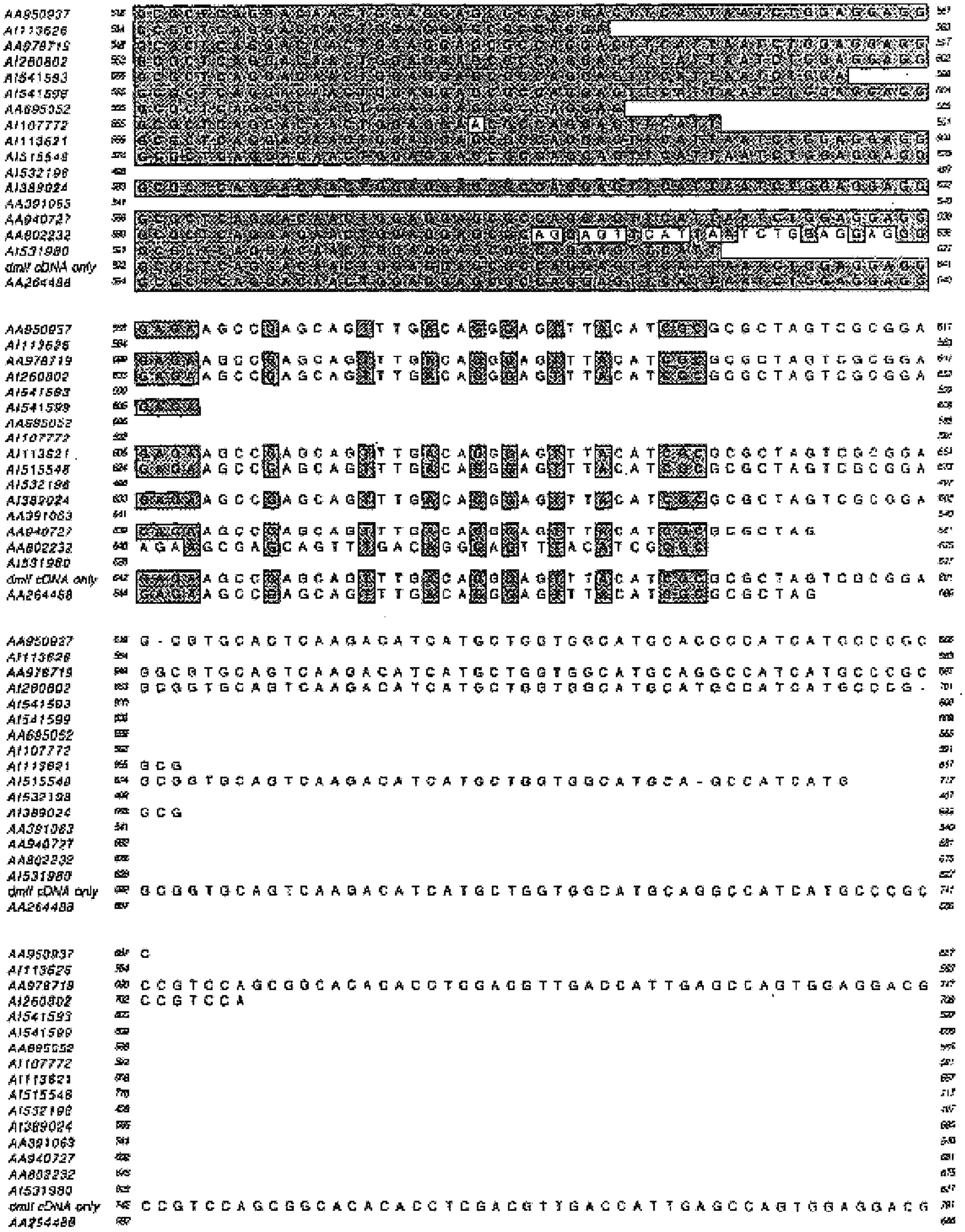

Additional polynucleotides included are fragments of the above-described nucleic acid sequences that are at least 15 bases in length, which is of sufficient length to permit a selective hybridization to a TPR2 and MLF nucleic acid set forth in SEQ ID NO:2 and SEQ ID NO;4, and a nucleic acid encoding an amino acid sequence set forth in SEQ ID NO:1 and 3 or functional subsequences thereof, provided that the polynucleotide fragments are distinct from the ESTs set forth in FIGS. 11 or 12. Thus, in another embodiment, fragments of SEQ ID NO:2 and SEQ ID NO:4; SEQ ID NO:2 and SEQ ID NO:4, where T can also be U; nucleic acid sequences complementary to SEQ ID NO:2 and SEQ ID NO:4 that are at least 15 bases in length; and nucleic acid sequences that selectively hybridize to DNA that encodes TPR2 and MLF polypeptide set forth in SEQ ID NO: 1 and SEQ ID NO:3, respectively, also are provided.

Polynucleotide fragments of at least 15 bases in length can be used to screen for TPR2 and MLF related genes in other organisms, such as mammals or insects, and are referred to herein as "probes." Invention probes additionally can have a "label" or "detectable moiety" linked thereto that provides a detection signal (e.g., radionuclides, fluorescent, chemi- or other luminescent moieties). If necessary, additional reagents can be used in combination with the detectable moieties to provide or enhance the detection signal. Such labels and detectable moieties also can be linked to invention TPR2 and MLF polypeptides, functional fragments, antibodies, and the compounds that modulate a polyglutamine toxicity or expression of a polynucleotide encoding TPR2 and MLF polypeptide disclosed herein.

Polynucleotide fragments also are useful for diagnostic purposes as under or aberrant expression or activity of TPR2 or MLF is likely to be associated with or contribute to polyglutamine toxicity, or protein aggregative, neurodegenerative or musculardegenerative disorders, prion diseases, or proliferative, developmental, viability, or behavioral disorders, etc. as set forth herein. Such polynucleotide fragments also are useful for detecting the presence or amount of a TPR2 or MLF transgene in a transgenic animal.

Thus, in accordance with the present invention, there are provided isolated polynucleotides that selectively hybridize to the polynucleotides described herein. In one embodiment, an isolated polynucleotide sequence hybridizes under stringent conditions to a Drosophila TPR2 (dTPR2) sequence set forth as SEQ. ID NO:2, with the proviso that the polynucleotide sequence is distinct from the EST sequences set forth in FIG. 11. In one aspect, the polynucleotide sequence comprises a polynucleotide having 20 or more contiguous nucleotides. In another aspect, the polynucleotide sequence comprises a polynucleotide having 50 or more contiguous nucleotides. In various additional aspects, the polynucleotide sequence comprises a polynucleotide having 60 or more, 70 or more, 80 or more, 100 or more, 120 or more, 140 or more, 160 or more contiguous nucleotides, up to the full length sequence.

In another embodiment, an isolated polynucleotide sequence hybridizes under stringent conditions to a Drosophila MLF (dMLF) sequence set forth as SEQ. ID NO:4, with the proviso that the polynucleotide sequence is distinct from the EST sequences set forth in FIG. 12. In one aspect, the polynucleotide sequence comprises a polynucleotide having 20 or more contiguous nucleotides. In another aspect, the polynucleotide sequence comprises a polynucleotide having 50 or more contiguous nucleotides. In various additional aspects, the polynucleotide sequence comprises a polynucleotide having 60 or more, 70 or more, 80 or more, 100 or more, 120 or more, 140 or more, 160 or more contiguous nucleotides, up to the full length sequence.

Hybridization refers to the binding between complementary nucleic acid sequences (e.g., sense/antisense). As used herein, the term "selective hybridization" refers to hybridization under moderately stringent or highly stringent conditions, which can distinguish TPR2 and MLF related nucleotide sequences from unrelated sequences (see e.g., the hybridization techniques described in Sambrook et al., 1989, supra). Screening procedures which rely on hybridization allow isolation of related nucleic acid sequences, such as a TPR2 and MLF homologs, orthologues, polymorphic sequences, etc. (e.g., cDNA or genomic DNA), from any organism.

In nucleic acid hybridization reactions, the conditions used in order to achieve a particular level of stringency will vary, depending on the nature of the nucleic acids being hybridized. For example, the length, degree of sequence complementarity, sequence composition (e.g., the GC v. AT content), and type (e.g., RNA v. DNA) of the hybridizing regions can be considered in selecting particular hybridization conditions. An additional consideration is whether one of the nucleic acids is immobilized, for example, on a filter.

As is understood by those skilled in the art, the Tm (melting temperature) refers to the temperature at which the binding between two sequences is no longer stable. For two sequences to form a stable hybrid, the temperature of the reaction must be less than the Tm for the particular hybridization conditions. In general, the stability of a nucleic acid hybrid decreases as the sodium ion decreases and the temperature of the hybridization reaction increases.

Typically, wash conditions are adjusted so as to attain the desired degree of stringency. Thus, hybridization stringency can be determined, for example, by washing at a particular condition, e.g., at low stringency conditions or high stringency conditions, or by using each of the conditions, e.g., for 10–15 minutes each, in the order listed below, repeating any or all of the steps listed. Optimal conditions for selective hybridization will vary depending on the particular hybridization reaction involved.

An example of a moderately stringent hybridization condition is as follows: 2×SSC/0.1% SDS at about 37° C. or 42° C. (hybridization conditions); 0.5×SSC/0.1% SDS at about room temperature (low stringency wash); 0.5×SSC/0.1% SDS at about 42° C. (moderate stringency wash). An example of a moderately-high stringent hybridization condition is as follows: 2×SSC/0.1% SDS at about 37° C. or 42° C. (hybridization conditions); 0.5×SSC/0.1% SDS at about room temperature (low stringency wash); 0.5×SSC/0.1% SDS at about 42° C. (moderate stringency wash); and 0.1×SSC/0.1% SDS at about 52° C. (moderately-high stringency wash). An example of high stringency hybridization conditions is as follows: 2×SSC/0.1% SDS at about room temperature (hybridization conditions); 0.5×SSC/0.1% SDS at about room temperature (low stringency wash); 0.5×SSC/0.1% SDS at about 42° C. (moderate stringency wash); and 0.1×SSC/0.1% SDS at about 65° C. (high stringency wash).

Homologs of HDJ1, TPR2 and MLF can be identified by sequence similarity. i.e., at least 50% sequence identity between nucleotide sequences, likely at least 60% sequence identity between nucleotide sequences, more likely at least 75% sequence identity between nucleotide sequences and most likely at least 80% sequence identity between nucleotide sequences. Highly homologous sequences will have at least 85%, 90%, 95% or more sequence identity. Sequence homology is calculated based on a reference sequence, which may be a region of a larger sequence, such as a conserved motif, coding region, flanking region, etc.

A reference sequence will usually be at least 18 nucleotides long, more usually at least 30 nucleotides long, and may extend to the complete sequence that is being compared. The extent of sequence identity between two sequences can be ascertained using various computer programs and mathematical algorithms known in the art. Such algorithms that calculate percent sequence identity (homology) generally account for sequence gaps and mismatches over the region of similarity. For example, a BLAST (e.g., BLAST 2.0) search algorithm (see, e.g., Altschul el al *J. Mol. Biol.* 215:403–10 (1990), which is publicly available through NCBI at http://www.ncbi.nlm.nih.gov) has exemplary search parameters as follows: Mismatch -2; gap open 5; gap extension 2. For polypeptide sequence comparisons, MacVector PPC 6.0.1 software program parameters for Drosophila dTPR2 and human TPR2 were Clustal W(1.4), Pairwise alignment mode: slow: Open Gap penalty 10.0: Extend gap penalty 0.1; similarity matrix blosum. For Drosophila dMLF and human MLF the program parameters were Clustal W(1.4), Pairwise alignment mode: slow: Open Gap penalty 1.0: Extend gap penalty 0.1; similarity matrix blosum. EST search parameters were BLASTN 2.0a19MP.

Thus, in one embodiment, a polynucleotide sequence of the invention comprises a sequence having 65% or more homology to a sequence set forth in SEQ ID NO:2, as determined using a BLAST search algorithm, provided that the polynucleotide sequence is distinct from the EST sequences set forth in FIG. 11. In another embodiment, a polynucleotide sequence of the invention comprises a sequence having 65% or more homology to a sequence set forth in SEQ ID NO:4, as determined using a BLAST search algorithm, provided that the polynucleotide sequence is distinct from the EST sequences set forth in FIG. 12. In various additional embodiments, a polynucleotide sequence of the invention can have at least 70%, 75%, 80%, 90%, or 95% sequence identity to a sequence set forth in SEQ ID NO:2 or SEQ ID NO:4.

Polynucleotides of the invention can be obtained using various standard cloning and chemical synthesis techniques. Purity of polynucleotides can be determined through sequencing, gel electrophoresis and the like. For example, nucleic acids can be isolated using hybridization as set forth herein or computer-based database screening techniques known in the art. Such techniques include, but are not limited to: (1) hybridization of genomic DNA or CDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Particular examples of such polynucleotide sequences having high homology to the sequences described herein are polymorphic sequences. Alterations in the sequence include but are not limited to intragenic mutations (e.g., point mutation, splice site and frameshift) and heterozygous or homozygous deletions. Termination signals or mutations that produce a stop codon leading to a terminated translation product may or may not retain a function or biological activity in vivo depending on the length of the terminated product, product stability, etc. Detection of sequences having altered nucleotides can be determined by standard methods known to those of skill in the art which include, for example, sequence analysis, Southern blot analysis, PCR based analyses (e.g., multiplex PCR, sequence tagged sites (STSs) and in situ hybridization).

Nucleotide probes, which correspond to a part of a TPR2 or MLF sequence encoding the protein, can be based upon TPR2 and MLF sequence, such as that set forth in SEQ ID NO:2 and SEQ ID NO:4, respectively. Alternatively, oligopeptide stretches of an amino acid sequence can be used to deduce the nucleic acid sequence based on the genetic code; however, as code degeneracy must be taken into account, a mixed addition reaction of a degenerate probe population can be performed. For such screening, hybridization is preferably performed on either single-stranded or denatured double-stranded nucleic acid. Alternatively, where at least two stretches of amino acid sequence of a polypeptide is known, polymerase chain reaction (PCR) of genomic DNA or CDNA using a mixed population of degenerate probes deduced from the two stretches of amino acid sequence, can be used to amplify a related polynucleotide sequence for subsequent cloning and characterization.

Another alternative for identifying similar or homologous nucleic acid sequences is to screen expressed DNA sequences. For example, among standard procedures for isolating DNA sequences of interest is by the formation of plasmid or phage-libraries. Thus, cDNA can be derived from reverse transcription of mRNA present in donor cells and cloned into an appropriate expression phage or plasmid. When used in combination with polymerase chain reaction (PCR) technology, rare expression products can be cloned and expressed. Lambda gt11 is one particular example of a phage suitable for expressing a cDNA encoding polypeptides or peptides having similar epitopes as HDJ1, TPR2 or MLF. Antibodies can be used to detect an expression product indicative of the presence of the corresponding cDNA, for example. As various types of libraries from a variety of different animals and cells are commercially available or can be produced from donor cells, tissue or whole organisms using well known methods, expression screening affords the capability of identifying homologs to HDJ1, TPR2 and MLF polypeptides from a variety of other sources.

An alteration in a TPR2 and MLF coding sequence can be, but is not limited to, a point mutation, nonsense mutation, missense mutation, splice site mutation, or a frameshift mutation. The alteration also can be a deletion of a segment of a nucleic acid encoding a TPR2 and MLF polypeptide such that a biological activity or function of the TPR2 and MLF polypeptide is removed or eliminated. Alternatively, an alteration can allow for expanded (e.g., in tissues/cells that do not normally express TPR2 and MLF) or for increased expression, for example, through the inactivation or deletion of an expression silencer.

An alteration in a TPR2 and MLF non-coding nucleic acid sequence (i.e., 5' and 3' non-coding flanking sequences and introns of a genomic sequence) can be, for example, a point mutation or deletion. A point mutation or deletion of a transcriptional control element conferring TPR2 and MLF expression can inhibit or eliminate TPR2 and MLF expression thereby increasing polyglutamine toxicity in an organism, for example. Another non-limiting example of an alteration is a deletion of a 3' flanking sequence that confers RNA stability. Point mutation or deletion of an intronic splice site is an additional example of a disrupted TPR2 and MLF gene. It is understood that alterations which disrupt TPR2 and MLF genes can be present simultaneously in coding and non-coding regions of a T?R2 and MLF nucleic acid sequence.

Another non-limiting example of a disrupted gene is a nucleic acid encoding a polypeptide into which another nucleic acid sequence has been inserted. An endogenous nucleic acid having such an insertion can eliminate expression of the endogenous gene.

dHDJ1, dTPR2 and dMLF polypeptides set forth as SEQ ID NO:1 and SEQ ID NO:3 when introduced into Drosophila, decrease polyglutamine toxicity. The mammalian homologues of these genes share structural features that likely account for this activity. Thus, invention dHDJ1, dTPR2 and dMLF polynucleotides and encoded polypeptides and functional subsequences, and the HDJ1, TPR2 and MLF mammalian homologues (e.g., SEQ ID NO:5 and SEQ ID NO:7), are useful in treating polyglutamine toxicity and related disorders in human subjects, as described herein.

Accordingly, the invention provides polynucleotides including an expression control element controlling expression of an operatively linked HDJ1, TPR2 or MLF nucleic acid. In one embodiment, the nucleic acid encodes a sequence set forth in SEQ ID NO: 1, SEQ ID NO:3, SEQ ID NO:5 or SEQ ID NO:7. In another embodiment, the nucleic acid encodes a functional subsequence of SEQ ID NO:1, SEQ ID NO:3, SEQ ID NO:5 or SEQ ID NO:7. In one aspect, a functional subsequence comprises a J domain (e.g., TPR2 amino acids 401 to 469). Such polynucleotides containing an expression control element controlling expression of a nucleic acid can be modified or altered as set forth herein, so long as the modified or altered polynucleotide has one or more functions or biological activities.

For expression in cells, invention polynucleotides, if desired, may be inserted into a vector. Accordingly, invention compositions and methods further include polynucleotide sequences inserted into a vector.

The term "vector" refers to a plasmid, virus or other vehicle known in the art that can be manipulated by insertion or incorporation of a polynucleotide. Such vectors can be used for genetic manipulation (i.e., "cloning vectors") or can be used to transcribe or translate the inserted polynucleotide (i e., "expression vectors"). A vector generally contains at least an origin of replication for propagation in a cell and a promoter. Control elements, including expression control elements as set forth herein, present within a vector are included to facilitate proper transcription and translation (e.g., splicing signal for introns, maintenance of the correct reading frame of the gene to permit in-frame translation of mRNA and, stop codons etc.).

By "promoter" is meant a minimal sequence sufficient to direct transcription. Although generally located 5' of the coding sequence, they can be located in introns or 3' of the coding sequence. Both constitutive and inducible promoters are included in the invention (see e.g., Bitter et al., *Methods in Enzymology*, 153:516–544 (1987)). Inducible promoters are activated by external signals or agents. Repressible promoters are inactivated by external signals or agents. Derepressible promoters are normally inactive in the presence of an external signal but are activated by removal of the external signal or agent. As discussed, also included are promoter elements sufficient to render gene expression controllable for specific cell-types, tissues or physiological conditions (e.g., heat shock, glucose starvation).

When cloning in bacterial systems, constitutive promoters such as T7 and the like, as well as inducible promoters such as pL of bacteriophage λ, plac, ptrp, ptac (ptrp-lac hybrid promoter) may be used. In yeast, a number of vectors containing constitutive or inducible promoters may be used (see e.g., *Current Protocols in Molecular Biology*, 2:13 (1988); Grant et al., *Methods in Enzymology*, 153:516–544 (1987); Glover, DNA Cloning, 11:3 (1986); Bitter, *Methods in Enzymology*, 152:673–684 (1987); and *The Molecular Biology of the Yeast Saccharomyces*, Eds. Strathem et al., Cold Spring Harbor Press, Vols. I and II (1982). A constitutive yeast promoter such as ADH or LEU2 or an inducible promoter such as GAL may be used (Rothstein, *DNA Cloning. A PracticalAprproach*, 11:3 (1986)). Alternatively, vectors that facilitate integration of foreign nucleic acid sequences into a yeast chromosome, via homologous recombination, for example, are known in the art and can be used. Yeast artificial chromosomes (YAC) are typically used when the inserted polynucleotides are too large for more conventional yeast expression vectors (e.g., greater than about 12 kb).

When cloning in mammalian cell systems, constitutive promoters such as SV40, RSV and the like or inducible promoters derived from the genome of mammalian cells (e.g., metallothionein promoter) or from mammalian viruses (e.g., the mouse mammary tumor virus long terminal repeat; the adenovirus late promoter) may be used. Promoters produced by recombinant DNA or synthetic techniques may also be used to provide for transcription of the nucleic acid sequences of the invention. Mammalian expression systems that utilize recombinant viruses or viral elements to direct expression may be engineered, if desired. For example, when using adenovirus expression vectors, the coding sequence may be ligated to an adenovirus transcription/translation control complex, e.g., the late promoter and tripartite leader sequence. Alternatively, the vaccinia virus 7.5K promoter may be used (see e.g., Mackett et al., *Proc. Natl. Acad. Sci. USA*, 79:7415–7419 (1982); Mackett et al., *J Virol.*, 49:857–864 (1984); and Panicali et al., *Proc. Natl. Acad. Sci. USA*, 79:4927–4931 (1982)).

Vectors based on bovine papilloma virus (BPV) have the ability to replicate as extrachromosomal elements (Sarver et al., *Mol Cell. Biol.*, 1:486 (1981)). Shortly after entry of an extrachromosomal vector into mouse cells, the vector replicates to about 100 to 200 copies per cell. Because transcription of the inserted CDNA does not require integration of the plasmid into the host's chromosome, a high level of expression occurs. These vectors can be used for stable expression by including a selectable marker in the plasmid, such as the neo gene, for example. Alternatively, the retroviral genome can be modified for use as a vector capable of introducing and directing the expression of the gene in host cells (Cone et al., *Proc. Nail. Acad. Sci. USA*, 81:6349–6353 (1984)). High-level expression may also be achieved using inducible promoters, including, but not limited to, the metallothionein IIA promoter and heat shock promoters.

Mammalian expression systems further include vectors specifically designed for in vivo applications. Such systems include adenoviral vectors (U.S. Pat. Nos. 5,700,470 and 5,731,172), adeno-associated vectors (U.S. Pat. Nos. 5,354,678, 5,604,090, 5,780,447), herpes simplex virus vectors (U.S. Pat. No. 5,501,979) and retroviral vectors (U.S. Pat. Nos. 5,624,820, 5,693,508 and 5,674,703 and WIPO publications W092/05266 and W092/14829). Bovine papilloma virus (BPV) has also been employed in gene therapy (U.S. Pat. No. 5,719,054). Such vectors also include CMV based vectors (U.S. Pat. No. 5,561,063). For targeting dividing neurons in vivo, genetic material and a growth factor may be administered for in vivo expression (U.S. Pat. No. 6,071,889). For targeting post-mitotic neurons in vivo (e.g., sympathetic, dopaminergic, or cortical), adenovirus vectors containing the nucleic acid can be administered for in vivo expression (U.S. Pat. No. 6,060,247). For targeting muscle in vivo, myoblasts can be transformed ex vivo and reintroduced into muscle tissue of a subject (U.S. Pat. No. 5,538,722). In addition to viral vectors suitable for expression in vivo, lipids for intracellular delivery of polypeptides (including antibodies) and polynucleotides also are contemplated (U.S. Pat. Nos. 5,459,127 and 5,827,703). Combinations of lipids and adeno-associated viral material also can be used for in vivo delivery (U.S. Pat. No. 5,834,441).

In accordance with the present invention, polynucleotide sequences encoding HDJ1, TPR2 and MLF polypeptide or functional subsequences may be inserted into an expression vector for expression in vitro (e.g., using in vitro transcription/translation kits, which are available commercially), or may be inserted into an expression vector that contains a promoter sequence which facilitates transcription in either prokaryotes or eukaryotes (e.g., an insect cell) by transfer of an appropriate nucleic acid into a suitable cell. A cell into which a vector can be propagated and its nucleic acid transcribed, or encoded polypeptide expressed, is referred to herein as a "host cell." The term also includes any progeny of the subject host cell. It is understood that all progeny may not be identical to the parental cell since there may be mutations that occur during replication. For example, although some progeny may contain mutations in the introduced vector, such progeny are nevertheless included when the term "host cell" is used.

Host cells include but are not limited to microorganisms such as bacteria, yeast, plant, insect and mammalian organisms. For example, bacteria transformed with recombinant bacteriophage nucleic acid, plasmid nucleic acid or cosmid nucleic acid expression vectors containing a HDJ1, TPR2 and MLF coding sequence; yeast transformed with recombinant expression vectors containing a HDJ1, TPR2 and MLF coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a RDJ1, TPR2 and MLF coding sequence; insect cell systems infected with recombinant virus expression vectors (e.g., baculovirus) containing a HDJ1, TPR2 and MLF coding sequence; or animal cell systems infected with recombinant virus expression vectors (e.g., retroviruses, adenovirus, vaccinia virus) containing a HDJ1, TPR2 and MLF coding sequence, or transformed animal cell systems engineered for stable expression.

For long-term expression in host cells, expression vectors that contain viral origins of replication, for example, can be transformed. Although not wishing to be bound or so limited by any particular theory, stable maintenance of expression vectors in mammalian cells is believed to occur by integration of the vector into a chromosome of the host cell. Optionally, the expression vector also can contain a nucleic acid encoding a selectable or identifiable marker conferring resistance to a selective pressure thereby allowing cells having the vector to be identified, grown and expanded. Alternatively, the selectable marker can be on a second vector that is cotransfected into a host cell with a first vector containing an invention polynucleotide.

A number of selection systems may be used to identify or select for transformed host cells, including, but not limited to the herpes simplex virus thymidine kinase gene (Wigler et al., *Cell,* 11:223 (1977)), hypoxanthine-guanine phosphoribosyltaansferase gene (Szybalska et al., *Proc. Natl. Acad. Sci. USA*, 48:2026 (1962)), and the adenine phosphoribosyltransferase (Lowy et al., *Cell*, 22:817 (1980)) genes can be employed in tk-, hgprt- or aprt- cells respectively. Additionally, antimetabolite resistance can be used as the basis of selection for dhfr, which confers resistance to methotrexate (Wigler et al., *Proc. Natl. Acad. Sci. USA*, 77:3567 (1980); O'Hare et al., *Proc. Natl. Acad Sci. USA* , 78:1527 (1981)); the gpt gene, which confers resistance to mycophenolic acid (Mulligan et al., *Proc. Natl. Acad. Sci. USA*, 78:2072 (1981); the neomycin gene, which confers resistance to the aminoglycoside G418 (Colberre-Garapin et al., *J. Mol. Biol*, 150:1 (1981)); and the hygromycin gene, which confers resistance to hygromycin (Santerre et al., *Gene*, 30:147 (1984)).

As used herein, the term "transformation" means a genetic change in a cell following incorporation of nucleic acid or polypeptide exogenous to the cell. Thus, a "transformed cell" is a cell into which (or a progeny of which) a nucleic acid or polypeptide molecule has been introduced by means of recombinant DNA techniques.

Transformation of a host cell with DNA may be carried out by conventional techniques known to those skilled in the art. For example, when the host cell is a eukaryote, methods of DNA transformation include, for example, calcium phosphate co-precipitates, conventional mechanical procedures such as microinjection, electroporation, insertion of a plasmid encased in liposomes, and viral vectors. Eukaryotic cells also can be cotransformed with DNA sequences with or without a selectable marker. Particularly useful eukaryotic host cells are cell lines in which polyglutamine toxicity can be assayed in vitro, or cell lines related to or obtained from in vivo tissues that have or can develop polyglutamine toxicity in vivo. When the host is prokaryotic (e.g., *E. coli*), competent cells which are capable of DNA uptake can be prepared from cells harvested after exponential growth phase and subsequently treated by the $CaCl_2$ method using procedures well known in the art. Transformation of prokaryotes also can be performed by protoplast fusion of the host cell.

Host cells also are useful in the various screening methods described herein. For example, compounds or transactivating protein factors that induce or stimulate expression of a target gene can be screened for by transforming host cells with a promoter or regulatory region of the target gene operatively linked to a reporter construct. Candidate target gene promoters and regulatory regions include, for example, dHDJ1, dTPR2 and dMLF, and their mammalian (e.g., human) homologues hHDJ1, hTPR2 and HMLF.

Figure 15:
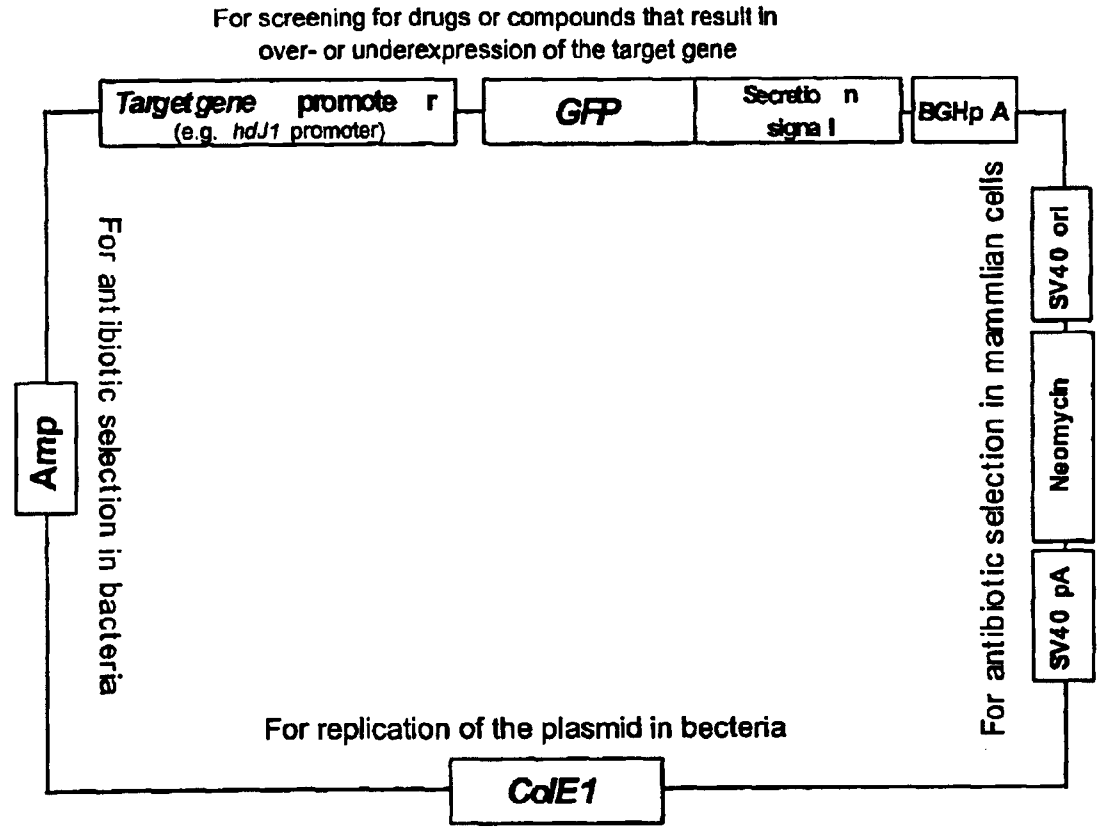
FIG. 15 is a drawing of a plasmid useful for drug screening.

Reporters such as a cDNA for green fluorescence protein (GFP), or others that directly or indirectly provide a signal (e.g., light) can be located 3' of the promoter. Since it would be advantageous to be able to screen a large number of compounds, to facilitate and accelerate the screening process, the sequence encoding a protein secretion signal, functional in the cell type used, is fused in-frame with the coding sequences for GFP (see, for example, FIG. 15). In creased expression of secreted GFP, or other suitable reporter, is used to identify compounds that may have a prophylactic or therapeutic value due to their ability to increase expression of the target gene. Transformed cell lines (e.g., neuron, retinal, muscle or mesoderm) can be cultured in one or more 96 well (or more) plates for large-scale screening, and various compounds and doses may be added to each of the wells. If a compound increases promoter activity, GFP is expressed in the cell and secreted into the culture medium. To detect fluorescence, appropriate wavelength of ultraviolet light is shone on each well of the plate in a plate reader and all plates are analyzed efficiently for compounds that increase promoter activity. Such compounds and transactivating factors are suitable candidates for use in the methods described herein.

Accordingly, in another embodiment, methods of identifying compounds and transactivating factors that modulate expression of genes that modulate polyglutamine toxicity are provided. In one embodiment, a method includes contacting an expression control element (e.g., promoter or other regulatory region) of such a gene with a test compound, and assaying for increased or decreased activity of an operatively linked reporter. In one aspect, a regulatory region comprises a polynucleotide sequence located 5' of a coding sequence for dHDJ1, dTPR2 or dMLF, as set forth in SEQ ID NO:9, SEQ ID NO:10 and SEQ ID NO:11, respectively (see, for example, FIGS. 16 to 18). In additional aspects, a regulatory region comprises a portion of a polynucleotide sequence located 5' of a coding sequence for DHDJ1, dTPR2 or dMLF, as set forth in SEQ ID NO:9, SEQ ID NO:10 and SEQ ID NO:11, wherein the sequence includes a polynucleotide sequence located 100 base-pairs, 250 base-pairs, 0.5Kb, 1.0 Kb, 2.0 Kb, 3.0 Kb, 4.0 Kb, 5.0 Kb or more 5' of the ATG start site of the coding sequence.

HDJ1, TPR2 and MLF polypeptides and functional subsequences can be used to generate additional reagents, such as antibodies. Thus, in accordance with the present invention, antibodies that bind to a dTPR2 and dMLF polypeptide, functional subsequences or to antigenic fragments thereof are provided. Antibody comprising polyclonal antibodies, pooled monoclonal antibodies with different epitopic specificities, and distinct monoclonal antibody preparations, also are provided. Such antibodies include those that distinguish dTPR2 and dMLF from their human homologues.

The term "antibody" includes intact molecules as well as fragments thereof, such as Fab, F(ab')2, and Fv which are capable of binding to an epitopic determinant present in a dTPR2 or dMLF polypeptide subsequence thereof. Other antibody fragments are included so long as the fragment retains the ability to selectively bind with its antigen.

Antibodies that bind to dTPR2 and dMLF polypeptides can be prepared using intact polypeptide or small peptide fragments thereof as the immunizing antigen. For example, as it may be desirable to produce antibodies that specifically bind to the amino- or carboxy-terminal domains or functional subsequences of dTPR2 and dMLF, amino- carboxy-terminal and functional subsequence fragments of dTPR2 and DMLF can be used as the immunizing antigen. The polypeptide or peptide used to immunize an animal which is derived from translated DNA or chemically synthesized can be conjugated to a carrier protein, if desired. Such commonly used carriers which are chemically coupled to the immunizing peptide include, for example, keyhole limpet hemocyanin (KLH), thyroglobulin, bovine serum albumin (BSA), and tetanus toxoid.

Monoclonal antibodies are made by methods well known to those skilled in the art and are also provided (Kohler et al., *Nature*, 256:495 (1975); and Harlow et al., "Antibodies: A Laboratory Manual", p 726, Cold Spring Harbor Pub. (1988)). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques which include, for example, affinity chromatography with Protein-A Sepharose, size-exclusion chromatography, and ion-exchange chromatography (see e.g., Coligan et al., *Current Protocols in Immunology* sections 2.7.1–2.7.12 and sections 2.9.1–2.9.3; and Barnes et al., "Methods in Molecular Biology," 10:79–104, Humana Press (1992)).

The preparation of polyclonal antibodies is well-known to those skilled in the art (see, e.g., Green et al., *Immunochemical Protocols*, pp 1–5, Manson, ed., Humana Press (1992); Harlow et al. (1988), supra; and Coligan et al. (1992), supra, section 2.4.1). Those of skill in the art will know of various techniques common in the immunology arts for purification and/or concentration of polyclonal and monoclonal antibodies (see e.g., Coligan et al., Unit 9, "Current Protocols in Immunology," Wiley Interscience (1994)).

Antibodies of the invention also can be derived from subhuman primate antibody. General techniques for raising therapeutically useful antibodies in baboons can be found, for example, in Goldenberg et al., International Patent Publication WO 91/11465, 1991, and Losman et al., *Int. J. Cancer*, 46:310 (1990). Alternatively, a useful anti-dTPR2 or DMLF antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl Acad. Sci. USA*, 86:3833 (1989). Techniques for producing humanized monoclonal antibodies are described, for example, by Jones et al., *Nature*, 321:522 (1986); Riechmann et al., *Nature*, 332:323 (1988); Verhoeyen et al., *Science*, 239:1534 (1988); Carteretal., Proc. Natl. Acad. Sci. USA, 89:4285 (1992); Sandhu, *Crit. Rev. Biotech.*, 12:437 (1992); and Singer et al., *J. Immunol.*, 150:2844 (1993).

Antibodies of the invention also may be derived from human antibody fragments isolated from a combinatorial immunoglobulin library (see e.g., Barbas et al., Methods: *A Companion to Methods in Enzymology*, 2:119 (1991); Winter et al., *Ann. Rev. Immunol*, 12:433 (1994)). Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described by Green et al., *Nature Genet.*, 7:13 (1994); Lonberg et at, *Nature*, 368:856 (1994); and Taylor et al., *Int. Immunol.*, 6:579 (1994).

Antibody fragments (e.g., Fab, F(ab')2, and Fv) of the present invention can be prepared by proteolytic hydrolysis of the antibody, for example, by pepsin or papain digestion of whole antibodies. In particular, antibody fragments produced by enzymatic cleavage with pepsin provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, (see also Nisonhoff et al., *Arch. Biochem. Biophys.*, 89:230 (1960); Porter, *Biochem. J*, 73:119 (1959); Edelman et al., *Methods in Enzymology*, 1:422 (1967); and Coligan et at at sections 2.8.1–2.8.10 and 2.10.1–2.10.4, supra). Alternatively, antibody fragments can be prepared by expression of a nucleic acid encoding an antibody fragment in *E. coli*, for example.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent, as described in Inbar et al. (*Proc. Natl Acad Sci. USA*, 69:2659 (1972)). Alternatively, the variable chains can be linked by an intermolecular disulfide bond or cross-linked by chemicals such as glutaraldehyde (e.g., Sandhu, 1992, supra,). Preferably, the Fv fragments comprise $V_H$ and $V_L$ chains connected by a peptide linker. These single-chain antigen binding proteins (sFv) are prepared by constructing a structural gene comprising nucleic acid sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sfvs are described, for example, by Whitlow et al., Methods: *A Companion to Methods in Enzymology* 2:97 (1991); Bird et a., *Science* 242:423–426 (1988); Ladner et al., U.S. Pat. No. 4,946,778; Pack et a., *Bio/Technology* 11:1271–77 (1993); and Sandhu (1992), supra.

Antibodies of the invention are useful for a variety of purposes including, for example, detecting an amount of HDJ1, TPR2 or MLF in a cell or tissue of a subject. Such methods comprise contacting a sample suspected of containing an invention polypeptide (in vitro or in viva; in a cell or organism) with an antibody under conditions that allow binding and, detecting the presence of the antibody bound to the query polypeptide thereby detecting the presence of the polypeptide. Such methods are useful for determining the amount of polypeptide produced in the transgenic animals, screening or therapeutic methods of the invention, for example. The presence of the polypeptide can be detected by methods well known in the art, for example, ELISA, immunohistochemical staining, flow cytometry, immunoprecipitation, etc.

Antibodies of the invention also are useful for purifying HDJ1, TPR2 and MLF polypeptides, functional subsequences and antigenic fragments thereof using standard immunopurification techniques known in the art.

Invention antibodies also are contemplated for use in detection assays for diagnostic purposes or for modulating a function or biological activity of a HDJ1, TPR2 and MLF polypeptide or functional subsequence. For example, an antibody that binds a MLF epitope at or near a region that confers a MLF polyglutamine decreasing toxicity can be used to modulate toxicity. An antibody or antibody fragment that binds to a polypeptide can therefore function as an antagonist or, alternatively, can function as an agonist if the antibody or antibody fragment mimics an activator that stimulates or enhances MLF activity. Invention antibodies that modulate an activity or function of a HDJ1, TPR2 and MLF polypeptide or subsequence are further contemplated as pharmaceutical compositions as described herein. A similar approach may be used with polypeptide fragments of HDJ1, TPR2 or MLF (e.g., dominant negative or agonistic forms) to inhibit or promote interactions with molecules that participate in the cell signaling pathways that modulate polyglutamine toxicity and related conditions.

The invention further provides methods for identifying genes, compounds and transactivating factors that modulate a function or biological activity of the genes that modulate polyglutamine toxicity. In one embodiment, a method of the invention includes breeding a first animal that exhibits modulated polyglutamine sequence toxicity due to expression or activity of a modulating genetic element, to a second animal having a marker sequence; screening progeny for increased or decreased polyglutamine toxicity; and identifying one or more genes in the progeny animal that modulates function or activity the genetic element that modulates polyglutamine toxicity.

In another embodiment, a method of the invention includes incubating components containing HDJ1, TPR2 and MLF polypeptide or subsequence thereof, or a cell or animal expressing HDJ1, TPR2 and MLF polypeptide or subsequence thereof, and a test compound, under conditions sufficient to allow the components to interact and, determining the effect of the test compound on HDJ1, TPR2 and MLF polypeptide activity or expression (e.g., polyglutamine toxicity).

In cells, proteins that bind HDJ1, TPR2 and MLF can be isolated, for example, by using antibody specific for HDJ1, TPR2 or MLF to immunoprecipitate HDJ1, TPR2 and MLF in association with binding protein from cells. Cells expressing HDJ1, TPR2 or MLF, or that are made to express HDJ1, TPR2 or MLF, can be metabolically labeled by adding an amino acid containing a radionuclide (e.g., methionine, cysteine) to the growth media The labeled cells are lysed, immunoprecipitated with HDJ1, TPR2 or MLF antibody under conditions sufficient to allow HDJ1-, TPR2- or MLF-protein binding and fractionated, for example, by SDS-PAGE, and isolated from the gel. The stringency of the immunoprecipitation conditions and/or optional wash conditions can be increased to distinguish specific from non-specific binding. Protein(s) that binds weakly to HDJ1, TPR2, or MLF can be isolated by subjecting cells to a chemical cross-linking agent prior to cell lysis or immunoprecipitation. Agents that selectively cross-link proteins in close proximity are known in the art and can be chosen in order to minimize non-specific cross-linking. If desired, the binding proteins so isolated can be identified using methods disclosed herein or known in the art. Such assays can also be performed in vitro, for example, HDJ1, TPR2, or MLF affinity columns can be generated to screen for potential HDJ1, TPR2, or MLF binding proteins. The protein can then be eluted and isolated using conventional methods.

As used herein, the term "incubating" refers to conditions that allow contact, binding or interaction, directly or indirectly, between HDJ1, TPR2 and MLF polypeptide or polynucleotides encoding same and the test compound. The term "contacting" includes in solution, in solid phase, in cells and in animals. As used herein, the term "binds" refers to an association, whether transient or stable, between a polypeptide and a second molecule. The term "bind" includes in solution, in solid phase in cells and in animals.

Incubations are performed at any suitable temperature, typically between 4 and 40° C. Incubation periods are selected for optimum activity, but may also be chosen to facilitate rapid high-throughput screening.

The invention therefore provides methods for isolating a protein that binds to HDJ1, TPR2 and MLF polypeptides or functional subsequences thereof. A method includes incubating at least one protein and a HDJ1, TPR2 or MU polypeptide or subsequence thereof under conditions sufficient to allow binding; separating bound HDJ1, TPR2 or MLF polypeptide subsequence thereof from unbound HDJ1, TPR2 or MLF polypeptide or subsequence thereof and, isolating the bound protein.

A compound that modulates HDJ1, TPR2 or MLF polypeptide activity or expression of a polynucleotide encoding HDJ1, TPR2 or MLF polypeptide includes "agonists," which are compounds that stimulate or activate an activity or expression and "antagonists," which are compounds that inhibit or interfere with an activity or expression. In this context, "modulate" further includes any enzymatic interaction wherein a compound stimulates or performs a biochemical modification of a HDJ1, TPR2 and MLF polypeptide. Thus, compounds that postranslationally alter HDJ1, TPR2 and MLF, such as to increase or decrease phosphorylation, ubquitination, glycosylation, proteolytic cleavage and the like are therefore included.

Compounds can function either directly or indirectly to modulate polypeptide activity or expression of a polypeptide encoding polynucleotide. For example, a competitive antagonist that binds HDJ1, TPR2 or MLF may directly prevent binding or participation in the signaling pathway that modulates polyglutamine toxicity. In contrast, a compound that functions indirectly may act through an intermediary molecule to achieve its agonist or antagonist affect on HDJ 1, TPR2 or MLF activity or expression.

Compounds that modulate activity or expression are identified by determining activity or polynucleotide expression in the presence and in the absence of a test compound. HDJ1, TPR2 and MLF biological activities or HDJ1, TPR2 and MLF expression, as disclosed herein, can be determined using cell free systems, in cells and in a whole organism. Compounds that modulate HDJ1, TPR2, and MLF expression can be identified by detecting expression of a reporter gene operatively linked to a HDJ1, TPR2, or MLF expression control element (e.g., functional analysis of a sequence in any of SEQ ID NOs:9, 10 or 11 or a human homologue). Such elements can be isolated and operatively linked to a reporter gene which provides a detection signal that reflects the amount of transcript or protein product produced. Compounds that modulate expression of a polynucleotide encoding HDJ1, TPR2 or MLF can therefore be identified by detecting expression of the reporter gene. A compound "stimulates" HDJ1, TPR2 or MLF expression if the detection signal provided by the reporter gene is increased as compared with the signal in the absence of the test compound. A compound "inhibits" HDJ1, TPR2 or MLF expression if the signal is decreased as compared with the signal in the absence of the test compound. For example, cells capable of expressing HDJ1, TPR2 and MLF that have an appropriate reporter gene can be treated with a test compound, and the detection signal produced in the presence and absence of the compound is determined.

Thus, the invention provides cell-based and in vitro methods to screen for novel binding proteins (e.g., transactivating factors) using the polynucleotides of the invention. In addition to the described cell based reporter assays, many other assays are available that screen for nucleic acid binding proteins and all can be adapted and used. A few illustrative examples include, for example, mobility shift DNA-binding assays, methylation and uracil interference assays, DNase and hydroxy radical footprinting analysis (in vitro or in vivo), fluorescence polarization, and UV crosslinking or chemical cross-linkers.

One technique for isolating co-associating proteins, including nucleic acid and DNA/RNA binding proteins, includes use of UV crosslinking or chemical cross-linkers, including cleavable cross-linkers dithiobis (succinimidylpropionate) and 3,3'-dithiobis (sulfosuccinimidyl- propionate); see, e.g., McLaughlin, *Am. J Hum. Genet.* 59:561–569 (1996); *Tang, Biochemistry* 35:8216–8225 (1996); Lingner, *Proc. Natl. Aca Sci. U.S.A.* 93:10712 (1996); and Chodosh, *Mol. Cell. Biol* 6:4723–4733(1986).

Mobility shift DNA-protein binding assay using nondenaturing polyacrylamide gel electrophoresis is an extremely rapid and sensitive method for detecting specific polypeptide binding to DNA (see, e.g., Chodosh (1986) supra, Carthew, *Cell* 43:439–448(1985); Trejo, *J. Biol. Chem.* 272:27411–27421 (1997); and Bayliss, *Nucleic Acids Res.* 25:3984–3990 (1997)). Interference assays and DNase and hydroxy radical footprinting can be used to identify specific residues in the nucleic acid protein-binding site, see, e.g., Bi, *J. Biol Chem.* 272:26562–26572(1997); Karaoglu, *Nucleic Acids Res.* 19:5293–5300 (1991). Fluorescence polarization is a powerful technique for characterizing macromolecular associations and can provide equilibrium determinations of protein-DNA and protein-protein interactions. This technique is particularly useful (and better suited than electrophoretic methods) to study low affinity protein-protein interactions, see, e.g., Lundblad, *Mol. Endocrinol.* 10:607–612 (1996).

Proteins identified in by these techniques can be further separated on the basis of their size, net surface charge, hydrophobicity and affinity for ligands. In addition, antibodies raised against such proteins can be conjugated to column matrices and the proteins immunopurified. All of these general methods are well known in the art (see e.g., Scopes, R. K., *Protein Purification: Principles and Practice*, 2nd ed., Springer Verlag, (1987)). Chromatographic techniques can be performed at any scale and using equipment from many different manufacturers (e.g., Pharmacia Biotech).

As described herein, MLF expression is likely to be linked to particular types of human cancers (e.g., myelodysplastic syndrome (MDS) and acute myeloid leukemia (AML)). Thus, compounds can be screened for their effect on activity or expression of MLF and such compounds are likely to be therapeutically useful in treating patients suffering from myelodysplastic syndrome (MDS) or acute myeloid leukemia (AML).

Transgenic flies that carry dMLF cDNA, DMLF cDNA as P-element chromosomal insert, UAS-containing P-elements inserted upstream of dmlf gene, or protein products of dMLF CDNA; are also useful for this purpose. Nuclear localization of a large portion of MLFin NPH-MLF fusion product appears required for its pro-apoptotic effect, and perhaps for its effect on cell proliferation. Therefore, to produce a similar phenotype, DMLF may be fused to a nuclear localization signal (dMLF-NLS) to allow the delivery of dMLF into the nucleus. A Drosophila model containing such an MLF chimera can exhibit a measurable phenotype such as early death or external tumor growth. Alternatively, dMLF can be fused to the fly homologue of nucleophosmin to generate a fusion protein similar to NPH-MLF and expressed in the animal. In any case, such dMLF chimeras can be expressed in various tissues and cells of the animal to determine its effect in different tissues and cells and to produce a suitable animal model for identifying genes and compounds that modulate MLF activity or expression.

Alternatively, over-expressing dMLF may produce a phenotype and such animals can be employed in the screen. As it is likely that dMLF is involved in a molecular cascade with several protein components, over-expression of dMLF will disrupt the normal stoichiometry between the various components of the pathway and produce a phenotype that can be used to identify modulatory genes or compounds as described herein. Subsequently, genetic partners of dMLF pathway are potential targets for therapeutic agents in treating patients with MDS, AML, and other forms of cancer related to MLF pathway.

Thus, compounds that regulate MLF activity or expression are likely to be useful as therapeutics for treating these and other cancers associated with MLF. Thus, in accordance with the invention, there are provided methods of identifying compounds that modulate MLF activity or expression as described herein for polyglutamine toxicity. Such an approach also is applicable to TPR2.

Chimeras comprising HDJ1, TPR2 or MLF, or subsequences, and a heterologous sequence from another protein (e.g., GAL4, VP16 DNA binding (DBD), activation domains (AD), and the like) also can be used to identify compounds that modulate a HDJ1, TPR2, or MLF activity in cells. Chimeras having particular HDJ1, TPR2 or MLF subsequences are useful for identifying genes or compounds that modulate activities conferred by the subsequence.

For example, to identify genes or compounds that modulate a HDJ1, TPR2 or MLF activity, a chimera comprising HDJ1, TPR2 or MLF, and a GAL4 DNA binding domain (GAL4DBD) can be expressed in cells. A library of polynucleotides linked to an activation domain also present in the cells allows a protein encoded by a polynucleotide of the library to interact with HDJ1, TPR2 or MLF. A sufficiently strong interaction between HDJ1, TPR2 or MLF and an interacting protein will activate transcription of the reporter gene driven by the GAL4 response element. Once identified, the assay can be extended further to identify compounds that modulate the interaction by adding a test compound and assaying for levels of reporter expression in the presence and absence of the test compound. Yeast and mammalian two-hybrid cell systems are well known in the art, are commercially available, and are therefore applicable in the methods for isolating and/or identifying binding proteins and those that modulate activity.

The signal provided by the reporter gene can be, for example, RNA, protein, an enzymatic activity, and the like. Thus, the signal can be detected by a variety of methods known in the art, including northern analysis, RNA dot blots, nuclear run-off assays, ELISA or RIA, Western blots, SDS-PAGE alone, or in combination with antibodies that immunoprecipitate the reporter gene product. Expressed products that provide an enzymatic activity or detection signal are preferred and include, for example,. -galactosidase, alkaline phosphatase, horseradish peroxidase, luciferase, green fluorescent protein, and chloramphenicol acetyl transferase. Cells contemplated for use in these methods include the cells describe herein, for example, insect cells, mammalian cells (e.g., CV-1, COS, HeLa and L-cells), yeast cells and bacteria.

The invention further includes heterologous functional domains that facilitate entry of a modulatory gene (e.g., HDJ1, TPR2, MLF) into a cell. One example of such a heterologous functional domain that facilitates entry into a cell is a ligand to a cell surface receptor. Additional heterologous domains that provide a cell targeting function or facilitate cellular entry also are known to those skilled in the art. Such domains include, for example, viral capsid proteins, retroviral envelope proteins, a natural or engineered viral protein with a desired cell tropism.

A heterologous functional domain also can decrease or increase the activity of the genes identified by the methods of the invention. To increase activity of a gene that increases polyglutamine toxicity, domains which exhibit apoptotic, cell cycle arrest or delay, cytotoxic or cytostatic activity can be included, for example, ligands or agonists to receptors that induce apoptosis. Fas ligands or anti-Fas antibodies are two specific examples of such apoptotic domains. Domains that exhibit cytotoxic or cytostatic activity include, for example, toxins and chemotherapeutic agents such as doxorubicin, methotrexate, vincristine, and cyclophospharide can be conjugated to a polypeptide. Other agents exist and are known to those skilled in the art and can be linked to enhancer genes to augment their cell toxicity. For example, genes required for cell proliferation or cell cycle progression can be inhibited by a heterologous antisense nucleic acid of that gene. Cell cycle arrest can be stimulated by a negative regulator of cell growth, for example, a growth suppressor gene such as Rb, p53, DPC, etc.

Heterologous functional domains also include regulatable moieties that modulate activity of a polypeptide identified by a method of the invention. When linked to a HDJ1, TPR2, MLF polypeptide, a modular domain can impart ligand-dependent activation or repression of its polyglutamine toxicity decreasing activity. Various different ligand-dependent transcription factors having inducible ligand-binding domains are known in the art are applicable in such chimeras.

A heterologous functional domain also can provide a variety of other useful functions known to those skilled in the art. For example, it can be a lipid-based agent to facilitate cell entry, or an agent that increases or decreases the stability of the HDJ1, TPR2, MLF polypeptide and subsequences thereof either intra- or extra-cellularly.

A heterologous functional domain also can provide an imaging and/or visualization function that is mediated by an isotopic, calorimetric, or fluorometric agent. Such an imaging function is useful for screening an expression library for interacting proteins, or for detecting or localizing apoptosis in vivo. As exemplified herein, a hemagluttinin tag is but one example of a tag (epitope tag) that can be used to detect or visualize the presence of the tagged protein in animal tissue sections. Additional examples include myc, Flag, GFP, T7, polyhistidine and DNA polymerase.

Polypeptides and polynucleotides also can contain multiple heterologous functional domains. For example, a gene that increases or decreases polyglutamine toxicity can be operatively linked to two or more identical or two or more different domains or moieties. An example of such a configuration would be a molecule containing two or more different domains, a cell targeting domain and a chemotherapeutic moiety, operatively linked to a gene that increases polyglutamine toxicity. The exact chemical nature and structural organization of such a molecule will be known to those skilled in the art and can be determined based on the particular application.

A heterologous functional domain can consist of a variety of different types of moieties ranging from small molecules to large macromolecules. Such moieties can be, for example, nucleic acid, polypeptide or peptide, carbohydrate, lipid, or small molecule compounds. Both natural and non-naturally occurring compounds and derivatives are similarly included.

Test compounds for use in the screening methods of the invention are found among biomolecules including, but not limited to: peptides, polypeptides, peptidomimetics, saccharides, fatty acids, steroids, purines, pyrimidines, derivatives, structural analogs or combinations thereof. Test compounds further include chemical compounds (e.g., small organic molecules having a molecular weight of more than 50 and less than 5,000 Daltons, such as hormones). Candidate organic compounds comprise functional groups necessary for structural interaction with proteins, particularly hydrogen bonding, and typically include at least anti amine, carbonyl, hydroxyl or carboxyl group, preferably at least two of the functional chemical groups. The candidate organic compounds often comprise cyclical carbon or heterocyclic structures and/or aromatic or polyaromatic structures substituted with one or more of the above functional groups. Known pharmacological compounds are candidates that may further be subjected to directed or random chemical modifications, such as acylation, alkylation, esterification, amidation, etc., to produce structural analogs.

Test compounds can additionally be contained in libraries, for example, synthetic or natural compounds in a combinatorial library; a library of insect hormones is but one particular example. Numerous libraries are commercially available or can be readily produced; means for random and directed synthesis of a wide variety of organic compounds and biomolecules, including expression of randomized oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

A variety of other compounds may be included in the screening method. These include agents like salts, neutral proteins, e.g., albumin, detergents, etc. that are used to facilitate optimal protein-protein binding or interactions and/or reduce nonspecific or background binding or interactions in vitro. For example, reagents that improve the efficiency of the assay, such as protease inhibitors, nuclease inhibitors, antimicrobial agents, etc., may be used.

Genetic elements and other compounds that decrease polyglutamine toxicity are useful in treating polyglutamine associated and polyglutamine related disorders characterized by cell degeneration, death, apoptosis, protein aggregation (in nucleus, cytoplasm in extracellular), misfolding, deficient or aberrant protein transport or degradation, etc., as set forth herein. Genetic elements and other compounds that increase polyglutamine toxicity are useful in treating cell proliferative disorders, or disorders associated with unsdesirable cell survival, cell growth or cell differentiation. For example, almost all cells express polypeptides that contain polyglutamine repeat sequences. Thus, by increasing cell sensitivity to polyglutamine repeat sequence toxicity, such polyglutamine repeat containing polypeptides may be rendered toxic. In this way, such cells would be rendered susceptible to polyglutamine toxicity by introducing a gene or contacting with a compound that increases polyglutamine toxicity. For example, a compound having an ability to decrease cell survival can be cell death or apoptosis inducer and can be useful in the therapeutic methods of the invention for treating cell proliferative disorders or disorders characterized by undesirable cell growth or survival.

Accordingly, as the invention provides animal models and screening methods useful for identifying classes of genes and compounds that increase and decrease toxicity the identified genes and compounds that increase or decrease cell survival, growth, proliferation, differentiation, apoptosis, development or viability, behavioral abnormalities, neuron excitability, protein aggregation, misfolding, transport, or degradation, the methods and identified genes and compounds have obvious therapeutic applications for identifying and treating disorders treatable by increasing or decreasing one or more of the aforementioned cellular or tissue effects.

Thus, the invention also provides genes and compounds that increase or decrease cell survival, growth, proliferation, differentiation, apoptosis, protein aggregation, protein misfolding, protein transport, protein degradation in a pharmaceutically acceptable carrier. In one embodiment, a composition of the invention includes a TPR2 polynucleotide and a pharmaceutically acceptable carrier. In another embodiment, a composition of the invention includes a TPR2 polypeptide and a pharmaceutically acceptable carrier. In yet another embodiment, a composition of the invention includes a MLF polynucleotide and a pharmaceutically acceptable carrier. In still another embodiment, a composition of the invention includes an MLF polypeptide and a pharmaceutically acceptable carrier. In particular aspects, TPR2 and MLF are mammalian, such as human, bovine, porcine, equine or ungulate sequence, or an insect (e.g., Drosophila) sequence. In additional aspects, the polynucleotide is operatively linked to an expression control element.

Polyglutamine related or polyglutamine like disorders are generally caused by pathological conditions characterized by protein aggregates (intracellular, in nucleus or cytoplasm, or extracellular), abnormal or enhanced cell degeneration, death or apoptosis, decrease cell survival, proliferation or differentiation, and the like can be treated by the genes and compounds of the invention and identified by the methods of the invention. Thus, the invention further provides methods of modulating polyglutamine toxicity or a polyglutamine like disorder in a cell. In one embodiment, a method of the invention includes contacting a cell with a gene or compound that modulates polyglutamine toxicity. In one aspect, the cell is in vitro. In another aspect, the cell is in vivo. In additional aspects, the cell is a neuron, retina, muscle or mesoderm cell.

In another embodiment, the cell is contacted with a J domain-containing gene. In one aspect, the gene is selected form HDJ1 or TPR2. In another aspect, the cell is a neural, retinal, muscle or mesoderm cell. In other aspects, the cell is contacted with a J domain gene, HDJ1, TPR2, or MLF gene antisense polynucleotide.

Polyglutamine disorders typically share features in common with other degenerative, cell death or apoptotic, decreased cell survival, growth or proliferation, and protein aggregative, folding, transport and degradative disorders. Such disorders are referred to herein as polyglutamine "related disorders," or polyglutamine "like disorders." The features frequently found to be in common among these disorders include cellular degeneration or atrophy, protein aggregation with or without protein accumulation in nucleus and/or cytoplasm of the cell, deficient or decreased protein folding or transport, increased cell death or apoptosis, decreased cell viability, growth or differentiation, and formation of intracellular or extracellular plaques. Accordingly, due to the common features that characterize such disorders, it is anticipated that the genes and other compounds that modulate polyglutaminc toxicity identified will also modulate cellular degeneration or atrophy, protein aggregation, aggregate accumulation in nucleus and/or cytoplasm of the cell, development or viability, behavioral abnormalities, neuron excitability, deficient or decreased protein folding or transport, increased cell death or apoptosis, decreased cell viability, growth or differentiation, or formation of intracellular or extracellular plaques, whether or not the particular conditions are due to expression of an expanded polyglutamine repeat sequence. Thus, genes or compounds that directly or indirectly modulate cellular degeneration or atrophy, development or viability, behavioral abnormalities, neuron excitability, protein aggregation, aggregate accumulation in nucleus and/or cytoplasm of the cell, protein folding or transport, cell death or apoptosis, cell viability, growth or differentiation, or formation of intracellular or extracellular plaques, whether or not the particular conditions are due to expression of an expanded polyglutamine repeat sequence, can therefore be identified using the methods of the invention. Accordingly, diseases characterized by apoptosis independent of polyglutamine sequence can be treated by using any of the described methods for treating polyglutamine toxicity.

Thus, the invention further provides methods of increasing cell survival. A method includes contacting a cell with an amount of a gene or compound that increases cell survival. In one embodiment, the cell is in vitro. In another embodiment, the cell is in vivo. In yet another embodiment, the cell is contacted with a gene or a polypeptide encoding the gene or compound that decreases polyglutamine toxicity. In still another embodiment, the cell exhibits polyglutamine toxicity.

In still another embodiment, the cell has or is at risk of degeneration, atrophy, protein aggregation with or without accumulation in nucleus and/or cytoplasm of the cell, deficient or decreased protein folding or transport, cell death or apoptosis, decreased cell viability, growth or differentiation, and developing intracellular or extracellular plaques. In one aspect, the gene comprises a J domain-containing gene. In another aspect, the gene is selected from HDJ1, TPR2, and MLF. In yet another aspect, the cell is a neural, retinal, muscle or mesoderm cell.

The invention additionally provides methods of decreasing cell death or apoptosis. A method includes contacting a cell with an amount of a gene or compound that decreases cell death or apoptosis. In one embodiment, the cell is in vitro. In another embodiment, the cell is in vivo. In yet another embodiment, the cell is contacted with a gene or a polypeptide encoding the gene or compound that decreases polyglutamine toxicity. In still another embodiment, the cell has or is at risk of degeneration, atrophy, protein aggregation with or without accumulation in nucleus and/or cytoplasm of the cell, deficient or decreased protein folding or transport, cell death or apoptosis, decreased cell viability, growth or differentiation, and developing intracellular or extracellular plaques. In still another embodiment, the cell exhibits polyglutamine toxicity. In one aspect, the gene comprises a J domain-containing gene. In another aspect, the gene is selected form HDJ1, TPR2 and MLF. In yet another aspect, the cell is a neural, retinal, muscle or mesoderm cell.

Methods of decreasing polyglutamine toxicity in a tissue or organ of a subject having or at risk polyglutamine toxicity also are provided. A method of the invention includes contacting the tissue or organ with an amount of a J domain containing polypeptide, a TPR2 or MLF polypeptide sequence, or a polynucleotide sequence encoding the J domain containing polypeptide, TPR2 or MLF polypeptide, to decrease polyglutamine toxicity in the tissue or organ of the subject. In one embodiment, the tissue is brain, eye, muscle or mesoderm.

Methods of decreasing the severity of a frontotemporal dementia, prion disease, polyglutamine disorder or protein aggregation disorder in a subject having or at risk of a frontotemporal dementia, prion disease, polyglutamine disorder or protein aggregation disorder also are provided. A method of the invention includes administering to the subject an amount of J domain containing polypeptide, a TPR2, or MLF polypeptide sequence, or a polynucleotide sequence encoding the J domain containing polypeptide, TPR2 or MLF polypeptide, to decease the severity of the frontotemporal dementia, prion disease, polyglutamine disorder or protein aggregation disorder in the subject. In one embodiment, the disorder is a neurological or muscle disorder. In another embodiment, the disorder impairs long term or short-term memory or coordination of the subject. In still another embodiment, the disorder is associated with polyglutamine toxicity.

In yet another embodiment, the disorder is characterized by the presence of protein aggregates, amyloid plaques, degeneration or atrophy in an affected tissue or organ. In still other embodiments, the disorder is selected from the group consisting of Alzheimer's disease, Parkinson's disease, Creutzfeldt-Jacob's disease (CJD), bovine spongiform encephalopathy, Huntington's disease (HD), Machado-Joseph disease (MJD), Spinocerebellar ataxias (SCA), dentatorubropallidoluysian atophy (DRPLA), Kennedy's disease, stroke and head trauma. The severity of such disorders can be decreased by decreasing cell death or by decreasing protein aggregation, for example.

In additional embodiments, the methods of the invention include treating the various disorders or conditions herein by prophylactic administration.

Apoptosis participates in the maintenance of tissue homeostasis in a number of physiological processes such as embryonic development, hematopoietic cell regulation, and normal cell turnover. Dysfunction, or loss of regulated apoptosis, can lead to a variety of pathological disease states. For example, the loss of apoptosis can lead to the pathological accumulation of self-reactive lymphocytes, hyperproliferative cells, such as neoplastic or tumor cells, virally infected cells and cells that contribute to fibrotic conditions. Inappropriate activation of apoptosis also can contribute to a variety of pathological disease states, including, for example, acquired immunodeficiency syndrome (AIDS), neurodegenerative and musculardegenerative diseases, and ischemic injury. Treatments designed to modulate the apoptotic pathways in these and other pathological conditions can alter the progression of many of these diseases.

The invention therefore also provides methods of identifying genes or compounds that modulate apoptosis or cell death. Such genes and compounds include those useful for treating neoplastic, malignant, autoimmune, or fibrotic pathological conditions. A method of the invention included is essentially as set forth for the methods for identifying modulators of polyglutamine toxicity.

As the invention chimeric polypeptides, polynucleotides and antibodies will be administered to subjects, including humans, the present invention also provides pharmaceutical formulations comprising invention polypeptides, polynucleotides and antibodies. The compositions administered to a subject will likely be in a "pharmaceutically acceptable" or "physiologically acceptable" formulation. As used herein, the terms "pharmaceutically acceptable" and "physiologically acceptable" refer to biologically compatible carriers, diluents, excipients and the like that can be administered to a subject, preferably without excessive adverse side effects (e.g., nausea, headaches, etc.). Such preparations for administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present, such as antimicrobial, anti-oxidants, chelating agents, and inert gases, for example. Various pharmaceutical formulations appropriate for administration to a subject are known in the art are applicable in the methods of the invention (e.g., *Remington's Pharmaceutical Sciences*, 18th ed., Mack Publishing Co., Easton, Pa. (1990); The Merck Index, 12th ed., Merck Publishing Group, Whitehouse, N.J. (1996)).

Pharmaceutically acceptable formulations further include compositions where the duration of action or delivery of an administered composition is controlled. Such formulations include particles or a polymeric substance such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. The rate of release of the composition may be controlled by altering the concentration or composition of the macromolecules. For example, it is possible to entrap a polynucleotide or polypeptide in microcapsules prepared by coacervation techniques or by interfacial polymerization, for a example, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, beads, and lipid-based systems including oil-in-water emulsions, micelles, mixed micelles, and liposomes.

The compositions administered by a method of the invention can be administered parenterally by injection, by gradual perfusion over time, or by bolus administration (for example, or by microfabricated implantable device. The composition can be administered intracranially, intravenously, intramuscularly, intraperitoneally, subcutaneously, intracavity, via inhalation, transdermally, or intravascularly. The compositions can be administered in multiple doses or at multiple sites in the same or in different amounts. The composition can be administered to a subject at the site of the pathology (e.g., the brain, muscle, etc.). For the treatment of a neoplastic or undesirable cell growth or proliferative disorder, the composition can be administered by direct injection into a solid tumor mass or into a region of fibrosis. The active ingredient can enter the tissue by passive diffusion or, alternatively, by a delivery vehicle (e.g., a lipid-based vessicle is one example of a delivery vehicle).

The "effective amount" will be sufficient to decrease, prevent, or ameliorate polyglutamine toxicity, a polyglutamine related disorder, or any of the biological or pathophysiological features that characterize such disorders as described herein or known in the art. The doses sufficient to provide an "effective amount" for treating, decreasing or improving polyglutamine toxicity will be sufficient to ameliorate or improve one or all of the symptoms of the condition, although preventing a progression or worsening of the condition is a satisfactory outcome for many conditions. The concentration of the aforementioned compositions required to be effective will depend on the organism targeted and the formulation of the composition and the ameliorative effect desired (i.e., increased or decreased toxicity). For example, an effective amount of a composition is that amount sufficient to cause a reduction in polyglutamine toxicity, as determined using any of the parameters described herein (e.g., decreased cell degeneration, death or apoptosis, increased cell survival, proliferation, differentiation, viability or development, decreased behavioral abnormality, decreased protein aggregation, increased protein transport or folding, etc.). As the various cellular, biological, morphological, phenotypical and behavioral effects of polyglutamine toxicity are disclosed herein, or otherwise known in the art, the effect of a gene or compound on each of these elements individually, or in any combination, can be conveniently determined in order to ascertain an effective amount. Introduction of the invention compositions into a sufficient number of diseased cells of the subject can inhibit or decrease toxicity or improve any of these parameters thereby altering the course of the pathology.

Thus, for treating Alzheimer's disease, Parkinson's disease, Creutzfeldt-Jacob's disease (CJD), bovine spongiform encephalopathy, Huntington's disease (HD), Machado-Joseph disease (MJD), Spinocerebellar ataxias (SCA), dentatorubropallidoluysian atophy (DRPLA), Kennedy's disease, stroke and head trauma, for example, treatment can be initiated at an early or mid-level progressive stage. An inhibition, delay or decreased worsening of the condition is a satisfactory clinical outcome. Doses sufficient to treat cell proliferative disorders, or conditions characterized by abnormal or undesirable cell survival, proliferation or differentiation will be sufficient to delay proliferation or differentiation, for example, by arresting or delaying progression through the cell cycle. Again, an inhibition or delay of cell growth or proliferation, or preventing a worsening of the condition (for example, by slowing growth of a tumor, by slowing metastasis of the tumor) is considered a satisfactory clinical outcome. An effective amount can readily be determined by those skilled in the art (see for example, Ansel et al., "Pharmaceutical Drug Delivery Systems," 5th ed. (Lea and Febiger ( 1990), Gennaro ed.)).

In accordance with the present invention, there are provided kits containing the compositions of the invention. In one embodiment, a kit of the invention contains one or more J domain containing, HDJ1, TPR2, or MLF polypeptides, functional subsequences thereof, antibodies that specifically bind to the polypeptides, or J domain, HDJ1, TPR2, and MLF encoding polynucleotides, and a label or packaging insert in suitable packaging material. In one embodiment, the label or insert includes instructions for treating a disorder as described herein by administering J domain containing, HDJ1, TPR2, or MLF polypeptides, or J domain, HDJ1, TPR2, and MLF encoding polynucleotides. In one aspect, the kit contains a human TPR2 or MLF encoding polynucleotide operatively linked to an expression control element in a pharmaceutically acceptable carrier, and a label or insert with instructions for treating polyglutamine toxicity or a polyglutamine related disorder, as described herein.

In another embodiment, the label or insert includes instructions for detecting TPR2 or MLF in a biological sample (e.g., neural tissue, eye tissue, muscle or mesoderm) having or suspected of having or developing polyglutamine toxicity or a polyglutamine related disorder, as described herein.

In yet another embodiment, the kit contains a transgenic animal of the invention. In one aspect, the transgenic animal comprises a Drosophila that includes a polyglutamine repeat sequence encoded by a plurality of CAGs and at least one CAA that exhibits polyglutamine toxicity, and a label or insert including instructions for maintaining the animal. In one aspect, the kit additionally contains instructions for identifying modulators of polyglutamine toxicity.

As used herein, the term "packaging material" refers to a physical structure housing the components of the kit, such as invention polypeptides, antibodies, polynucleotides and animals. The packaging material can maintain the components sterilely, and can be made of material commonly used for such purposes (e.g., paper, corrugated fiber, glass, plastic, foil, etc.). The label or packaging insert can indicate that the kit is to be used in a method of the invention, for example.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents, other references, GenBank citations and ATCC citations mentioned herein are incorporated by reference in their entirety. In case of conflict, the present specification, including definitions, will control.

Other features and advantages of the invention will be apparent from the following detailed description, and from the claims. The invention is further described in the following examples, which do not limit the scope of the invention (s) described in the claims.

EXAMPLE 1

This example describes various materials and methods used in the studies.

Production of Transgenic Flies

Flies were maintained on cornmeal/yeast/agar at 25° C. and 70% humidity. Transgenic constructs were prepared for microinjection as follows: 13.5 $\mu$g transgenic vector, 4.5 $\mu$g transposase vector, 0.1M sodium phosphate buffer (pH 7.8), 5 mM potassium chloride, in 50 $\mu$l aqueous solution. Using Transjector 5246 and Femtotips II (Eppendorf), the transgenic constructs were microinjected into 5–30 min. old, fertilized $w^{1118}$ fly eggs. Several transgenic lines for each were established. Since the expression of the UAS transgenes requires activation by a GAL4-expressing driver, these lines had no obvious phenotypes and were easily maintained.

Sections and Antibody Fluorescent Labeling

Fly heads were placed in OCT 4583 embedding medium (Sakura Finetek) and horizontal sections were prepared with Tissue-Tek 11 using Leica knives and transferred onto Superfrost/Plus microscope slides (Fisher Scientific). Slides were dried on a 50° C. hot plate for 30 sec and sections were fixed in Mirsky's fixative (National Diagnostics) for 30 min. at room temperature. After washing 3 times within 10 min. using PBS/fTween20 (0.1%), sections were blocked in a PBS/bovine serum albumin fraction V (1%) (Sigma) solution and incubated with 1 $\mu$g/ml of primary polyclonal antibody (Y- 11, Santa Cruz Biotechnology, Inc.) in the solution for 2 hrs. at room temperature. The sections were washed 3 times, 5-min each, with PBS/Tween20 (0.1%), then incubated with 4 $\mu$/ml of FITC-labeled secondary anti-rabbit antibody (Jackson ImmunoResearch Laboratories) in the solution for 1 hr at room temperature. The sections were washed for 5-min with PBS/Tween20 (0.1%), covered with DAPI for 1 min., and washed 3 times (I5-min. each) with PBS/Tween20 (0.1%). Finally, the sections were mounted in 0.1 mg/ml phenyl diamine (PDA)/0.5 $\mu$g/ml 4'–6' diamino-2-phenylindole (DAPI)/90% glycerol mounting solution. The immunofluorescence-labeled sections were photographed on a Zeiss axioplan microscope with an MC100 camera, using Kodak 100 ASA color films.

Scanning Electron and Light Microscopy

Adult flies, 1–6 hours old, were anaesthetized by ether for 1–2 min. and attached by their backs to stubs with adhesive, placed in the vacuum chamber of ETEC scanning electron microscope, and photographed within 10 min. For light microscopy, adult flies, 1–6 hours old, were etherized for 2–3 min., placed on their side on the white strip of RITE-ON micro slides (Gold Seal Products) and photographed by Leica MZFLIII dissecting microscope, illuminated by two sets of optic fiber illuminators (Ehrenreich Photo Optical Industries or Cole Parmer Instrument Company), using Fuji 1600 ASA Super HG color film. Prints were scanned on Lacie Silverscanner III with Adobe Photoshop 5.0 at 300 dpi and processed on graphics software Canvas 5.0.3.

Identification of Genes Modulating Polyeutamine by Plasmid Rescue

Plasmid rescue (Pirrotta (1986); Pirrotta, *Cloning Drosophila Genes: A Practical Approach*, pp 83–110, IRL Press, Oxford, Washington, D.C., ed. D. B. Roberts (1986)) was done with the following modification: from an established line, genomic DNA was isolated by QIAamp Tissue kit (Qiagen) and digested with 6 restriction enzymes: BfrI, BglI, EcoRI, HincII, SacI, and SacII in 100$\mu$l reaction volume overnight. Digested fragments were purified by QIAprep Spin Miniprep kit (Qiagen), circularized by ligation in 50 $\mu$l reaction and transformed by electroporation of 1.5 III of ligation reaction into the DH10B (Gibco/BRL) strain of *E. coli*. Colonies carrying the P-element were selected by plating transformed bacteria on media with Kanamycin. DNA was isolated from positive colonies and the approximate size of the insert (flanking genomic DNA) determined by AvaI restriction enzyme digestion. Inserts of sufficient size were sequenced by automated sequencing and the results were compared with known DNA or protein sequences in the database by Berkeley Drosophila Genome Project (BDGP) BLAST server (BLASTN) and The Baylor College of Medicine Search Launcher (BLASTP+ BEAUTY). Protein alignments were performed by MacVector PPC 6.0.1 application software. Program parameters for Drosophila dTPR2 and human TPR2 were Clustal W(1.4), Pairwise alignment mode: slow: Open Gap penalty 10.0: Extend gap penalty 0.1; similarity matrix blosum. For Drosophila DMLF and human MLF the program parameters were Clustal W( 1.4), Pairwise alignment mode: slow: Open Gap penalty 1.0: Extend gap penalty 0.1; similarity matrix blosum. EST search parameters were BLASTN 2.0a19MP.

Cloning of Supressor Genes

The cDNA containing the coding region of dHDJ1 was removed from GH26396 (contained in the plasmid pOT2a, obtained from Research Genetics, Inc.) by complete digestion of 2.5 $\mu$g of plasmid DNA, in NEB #2 restriction enzyme buffer and 0.1 mg/ml BSA (New England Biolabs), with 20 u HindIII for 3 hrs at 37° C. to fragment pOT2a backbone, followed by partial digestion with 1, 2 or 4 u of PstI and XhoI for 10 min. at 37° C., and enzyme inactivation at 65° C. for 10 min. The reactions were run on 1% agarose gel and a 1816-bp fragment was isolated and purified by QLAquick gel extraction kit (Qiagen). This fragment, which contains 106 bp PstI/EcoRI fragment of pOT2a, 11 bp upstream of the reported 5'UTR, the 5'UTR, dHDJ1 ORF, 406 bp of the 579 bp reported 3'UTR, and a 23-bp-long poly(A), was ligated into the transgenic vector pINDY6 PstI/XhoI site.

For cloning dTPR2, the Pst1/XhoI fragment containing 106 bp PstI/EcoRI fragment of pOT2a, the 365-bp 5'UTR, the 1527-bp dTPR2 ORF, the 328-bp 3'-UTR, and a 20-bp-long poly(A) was removed from GH09432 (within pOT2a) and ligated into the transgenic vector pINDY6 PstI/XhoI site.

For cloning dMLF cDNA, the PstI/XhoI fragment of GH20101 in pOT2a plasmid (Research Genetics, Inc.) containing dMLF orf and its 5' and 3' UTR was removed and ligated into the transgenic vector pINDY6 PstI/XhoI site.

EXAMPLE 2

This example describes the construction of polyglutamine repeat sequence expression vectors and *Drosophila melanogaster* that express variously sized polyglutamine repeat sequences. This example also describes the generation of P-element insertion flies used for screening for genetic elements that modulate polyglutamine toxicity.

Polyglutamine sequences encoded by short (20), intermediate (63) and expanded (127) CAG tracts interspersed with CAA were synthesized using a modified version of a polymerase chain reaction (PCR) method (Kazemi-Esfaijani et al., *Hum. Mol. Genet.*, 4:523–527 (1995)). Briefly, the fly prospero gene, in the p139cACI plasmid (Robertson et al., *Genetics*, 118:461–470 (1988)), was used as a template because it has a polyglutamine encoding tract of 20 repeats. The primers used for PCR to amplify two fragments were: ProsBamHI3229F (5'-ATG CGC GGA TCC CAG CAG CTG GAG CAG AAC GAG GCC-3') with ProsAflIIR (5' phosphorylated) (5'-ATT GCT GTT GCC GCC GTT CTT AAG CTG TTG TTG TTG CTG TTG TTG-3') and ProsBstBIF (5'-ACC GGA GGC CCA CCG TCA TTC GAA CAG CAG CAG CAA CAG-3') with Pros3650R (5'-GCT GCG TGC GGA TTG AAG AAC GGC-3'). The reaction mixture contained 100ng p139cAC1 template, 50 pmol of each primer, 1X cloned Pfu buffer (Stratagene), 0.2 mM dNTP, 5% glycerol, 5% dimethyl sulfoxide (DMSO), and 1.25 unit cloned Pfu DNA polymerase (Stratagene) in a total volume of 62 μl aqueous solution, overlaid with mineral oil. PCR was performed with a Stratagene Robocycler Gradient 96 in 200-μl thin-walled tube strips. The thermal cycling parameters were denaturation at 95° C. for 3 min., for one cycle, followed by 35 cycles of denaturation at 95° C. for 30 sec., annealing at 65° C.–80° C. for 1 min., extension at 75° C. for 1 min., and finally, extension at 75° C. for 10 min.

The PCR products were digested with BamHI (5'fragment) or BstXI (3' fragment) and ligated (T4 DNA ligase, Gibco/BRL) into p139cACI digested with BamHI/BstXI. After cloning and amplifying this construct in XL1 Blue strain of *E. coli* (Stratagene), the sequence between the two polyCAG tracts was removed by digestion with BstBI and AflII (or BfrI), blunt-ended with Mung bean nuclease (New England Biolabs) followed by ligation and transformation into XL1 Blue. To synthesize polyglutamine of 63 repeats, this procedure was repeated twice, an additional time (3X) for 127 repeats, an additional time for 190 (4×) and an additional time (5×) for 223 repeats.

To produce the hemagglutinin (HA) tagged polyglutamine sequence driven by a yeast upstream activating sequence (UAS), UAS-20QHA, UAS-63QHA and UAS-127QHA, the polyglutamine encoding and flanking nucleotide sequences were PCR-amplified as above with primers 5'Gln2F (5'-CGG AAT TCG CCG CCA CCA TGG GAG GCC CAC CGT CAA CCC CCC AGC AG-3') and 3'GlnR (5'-ATT GCT GTT GCC GCC GTT ACT AGT CTG TTG CTG CTG CTG TTG-3'). The PCR product was digested with EcoRI and SpeI and, by using a PstI-EcoRI adaptor, inserted in-frame with a hemagglutinin tag DNA sequence into PstI/SpeI digested pINDY6 transgenic vector (a pUC 19 backbone containing a miniwhite gene, an ampicillin-resistance gene, and 5 tandem upstream activating sequences (UAS), followed by a minimal hsp70 promoter, a polyclonal site, a SV40 polyA signal, and 5' and 3' P-elements). The resulting plasmids express the polyglutamine repeat flanked by 8 amino acids on the N-terminal side and 13 amino acids on the C-terminal side (MGGPPSTPQ$_n$TSRTYPYDVPDYA; FIG. 1B). FIG. 2 shows a schematic of P-element constructs having variously sized HA-tagged polyglutamine repeat sequences.

Several transgenic lines for each polyglutamine repeat sequence were established following microinjection of fertilized w$^{1118}$ fly eggs with the transgenic vector. Since expression of the UAS polyglutamine sequence transgenes requires activation by a GAL4-expressing driver, these fly lines had no obvious phenotypes.

To activate expression of the polyglutamine repeat sequences in transgenic flies, genetic crosses between the transgenic polyglutamine flies and flies expressing yeast GAL4 transcription factor were produced. Yeast GAL4 was regulated by an eye-specific promoter GMR (GLASS multiple repeats) (Spradling et al., *Science*, 218:341–347 (1982); and Pirrotta, *Cloning Drosophila Genes: A Practical Approach*, pp 83–110, IRL Press, Oxford, Washington, D.C., ed. D. B. Roberts (1986)) cloned upstream of the GAL4 cDNA. GMR is active in all retinal cells, from the time of their differentiation throughout adulthood. In a separate set of studies, a neuron-specific driver ApplGAL4 was used to express polyglutamine r e peat sequences in the fly nervous system (Torroja et a an, *Current Biology*, 9:489–492 (1999)).

EXAMPLE 3

This example describes histological and pathophysiological characteristics of polyglutaiine toxicity in Drosophila melanogaster. This example also describes screening for genetic elements that modulate polyglutamine toxicity, and the isolation of flies that contain genetic elements which suppress and enhance polyglutamine toxicity.

Figure 4:
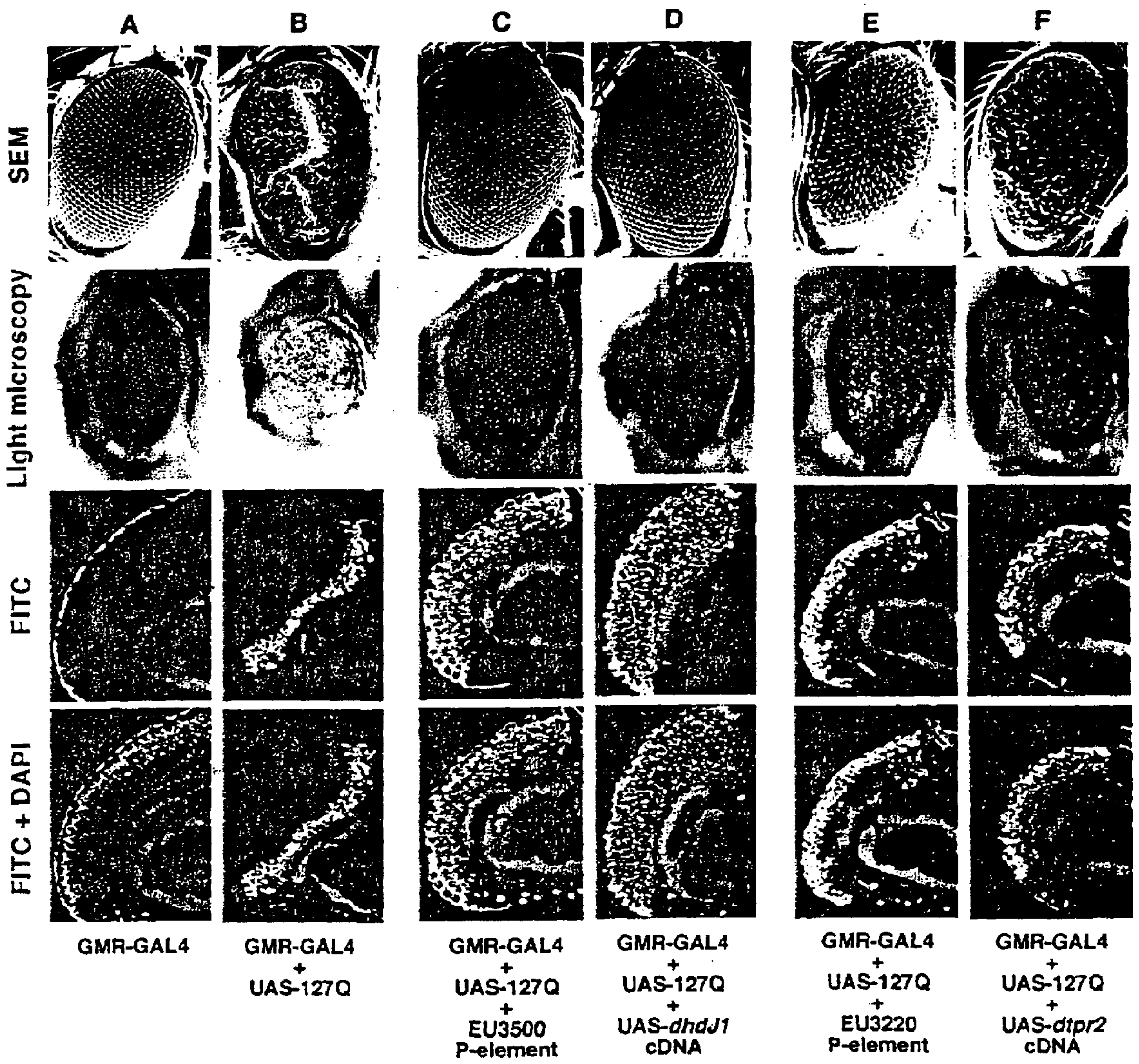
FIG. 4 shows structural and histological changes that occur after expressing 127Q in the eye and suppression of the toxic effect by EU3500 P-element, dHDJ1 CDNA, EU3220 P-element, and dTPR2 cDNA. (A) Control expressing GAL4 regulated by GMR in the absence of 127Q; (B) flies expressing 127Q peptide driven by GMR-GAL4; (C) suppressor P-element insertion EU3500 restores external eye structure and pigmentation despite presence of polyglutamine aggregates; (D) confirmation of suppression in flies carrying a transgenic insertion of dHDJ1 cDNA, corresponding to the gene downstream of the EU3500 P-element insertion; (E) suppressor P-element insertion EU3220 improves external eye structure and pigmentation; (F) confirmation of suppression in flies carrying a transgenic insertion of dTPR2 cDNA, corresponding to the gene downstream of the EU3220 P-element insertion. SEM=Scanning electron microscopy. FITC=Frozen eye sections labeled with Ab to the HA tag on 127Q peptide (green). FITC+ DAPI=Double exposure with DAPI to stain nuclei (blue).
Figure 5:
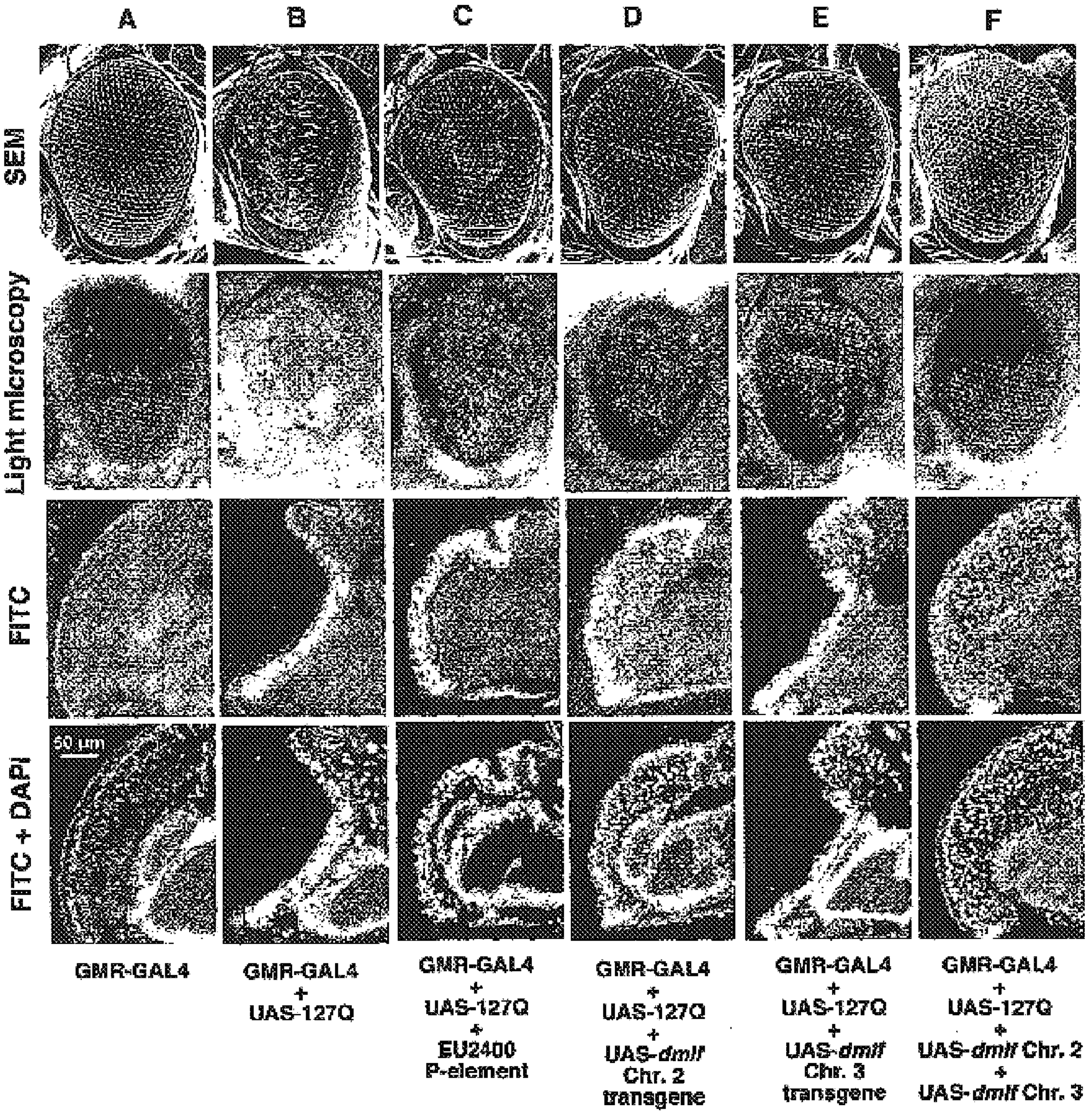
FIG. 5 shows structural and histological changes that occur after expressing 127Q in the eye and suppression of the toxic effect by dMLF. (A) Control in the absence of 127Q, expressing GAL4 regulated by GMR, the eye-specific enhancer/promoter; (B) flies expressing 127Q peptide driven by GMR-GAL4; (C) suppressor P-clement insertion EU2490 partially restores external eye structure and pigmentation; (D and E) flies carrying a transgenic insertion of dMLF cDNA, corresponding to the gene downstream of the EU2490 P-element insertion, either on chromosome 2 or on chromosome 3, as indicated, confirm the identity of the suppressor gene; (F) double dosage of dMLF expression, achieved by combining both the chromosome 2 and chromosome 3 transgenes. Abbreviations are as above.

Flies with a heterongous insertion of nMR-GAL4 alone had fully developed eyes (FIG. 4A and 5A). When combined with chromosome carrying UAS and a short length of polyglutamine (20Q), eye development was normal for external structure and pigmentation. Using an anti-HA antibody, immunohistological examination of head cryosections of one-day-old flies carrying GAL4 alone, or GALA plus 20Q, revealed no polyglutamine aggregates. In contrast, flies expressing the 127 polyglutamine repeat sequence had severely collapsed eyes lacking pigmentation, and, in sections, anti-HA antibody revealed abundant polyglutamine aggregates in the eye (FIG. 4B and 5B). The 127 polyglutamine repeat sequence expressing flies were subsequently used to screen for genetic factors that modulate polyglutamine toxicity.

To screen for genes that modulate toxicity of 127Q, flies having random P-element transpositions were de novo generated using the fly stock carrying the P[ry$^+$, Δ2-3](99B) transposase (Robertson et al., *Genetics* 118:461–70 (1988)) and an X-linked EP insert (EP55; Rorth, *Proc. Natl. Acad Sci. USA* 93:12418–22 (1996)) (FIG. 3). EP P-elements contained fourteen UAS sequences in tandem to enhance expression of nearby gene(s), followed by the hsp70 heat shock minimal promoter (pEP plasmid) (Rorth, *Proc. Natl. Acad Sci. USA* 93:12418–22 (1996)). The mutant fly lines were generated by mobilizing the X-linked P-element in the EP55 strain, and isolating those with new insertions on chromosomes 2 and 3. In detail, homozygous EP55 virgin females were crossed with males homozygous for a defective transposon, expressing the transposase. The F1 male progeny were crossed with virgin w1118 females (w/w). The F2 Male progeny that had coloured eyes and lacked the transposon's genetic markers were selected, as they contain a new stable P-element insertion on an autosomal chromosome.

The P-elements containing14 tandem UAS elements, which, in the presence of GAL4, drive the expression of downstream genomic sequences (Rorth, *Proc Natl Acad Sci USA*, 93:12418–12422 (1996)). Hence, if there is a locus downstream of a P-element insertion that codes for a modifier gene, it will be activated and cause a change in the eye phenotype. Once a modulator was found, a single male was crossed to female (CyO;TM3)/Xa. The resulting male progeny were crossed to w1118 flies to separate the P-elements. This resulted in colored-eye progeny that carry a balancer for one chromosome and a P-element on another. Males from such progeny were tested for suppression or enhancement of activity by crossing to female w;GMR/CyO;127Q/127Q. The lines were established by crossing the latter males to (Cyo;TM3)/Xa, and by crossing the resulting flies carrying CyO and TM3 balancers. The lines that produced the expected effects were selected for further amplification and plasmid rescue.

Seven thousand randomly generated P-element insertion strains were crossed with GMR-GAL4/UAS-127Q flies, and the F1 progeny were assessed for either suppression or enhancement of the eye phenotype. Among the 7000 P-element insertion strains screened, 30 suppressor and 29 enhancer lines were identified that either suppressed or enhanced the polyglutamine-dependent eye degeneration of GMR-GAL4/UAS- 127Q flies.

EXAMPLE 4

This example describes characterization of several flies that contain a genetic element which suppresses polyglutamine toxicity. This example also describes the identification of dHDJ1, dTPR2 and DMLF that confer suppression of polyglutamine toxicity.

Characterization and Identification of dHDJ1

Of the 30 suppressor lines, EU3500 was selected for further studies. As shown by the scanning electron microscopy, the structural integrity of the eye of GMR-GAL4/UAS-127Q flies was dramatically improved in the presence of suppressor EU3500 (FIG. 4C). The eyes in flies carrying EU3500 retained their globular structure, and had a more uniform arrangement of bristles and pigmentation.

Internal eye structure was examined in horizontal cryostat sections of the heads. In unsuppressed GMR-GAL4/UAS-127Q flies, immunolabeling of the HA-tagged polyglutamine peptides showed fluorescent aggregates. In contrast, although N's appeared to be the same in the presence of the EU3500 suppressor, the retinal structure was significantly improved (FIG. 4C). Thus, the EU3500 suppressor was able to ameliorate the polyglutamine toxicity that occurred in the eye.

Figure 6:
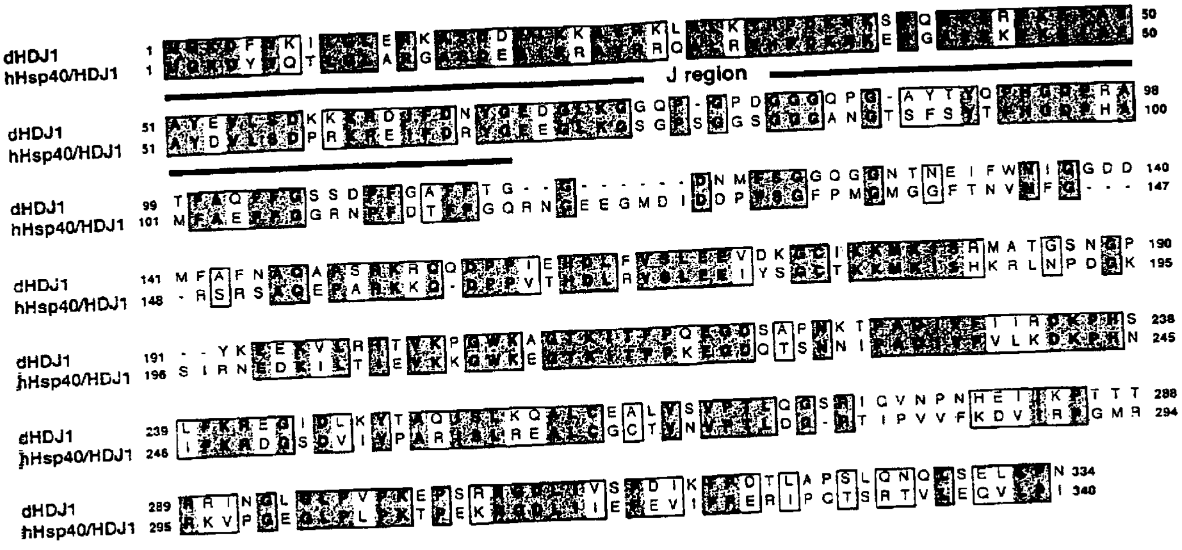
FIG. 6 shows a sequence alignment between Drosophila HDJ1 (DHDJ1) and human HDJ1 (hHsp40/HDJ1). Overall amino acid sequence homology is 54% identical (dark gray) and 72% similar (light gray). J region homology (bold underlining) is 74% identical (dark gray) and 88% similar (light gray).

Plasmid rescue of the EU3500 suppressor P-element and its flanking genomic DNA and sequence analysis with a BDGP BLAST search identified an EST that matched the genomic sequences starting 98 bp downstream of the P-clement. This EST corresponded to at least 3 independent cDNA clones with different lengths of 3'UTR. The GH26396 clone (BDGP and Research Genetics, Inc.), a 1711 base pair cDNA sequence which encodes dHDJ1, a predicted protein of 334-amino-acid and molecular weight of 37 kDa, with an amino-terminal J domain and homologous to human Hsp40/HDJ1 was tested (54% identity and 72% similarity using the parameters described above; FIG. 6) (submitted directly to NCBI by Lee et al. (1995); Palter, K. et al. (1998); http://www.ncbi.nlm.nih.gov/entrez/query.fcgi).

In order to verify that the gene(s) immediately 3' to EU3500 was responsible for the observed suppression of polyglutamine toxicity, the corresponding cDNA, GH26396, containing the coding sequences for dHDJ1, was placed in the transgenic vector pINDY6 (with UAS mediated expression) and microinjected into early stage fly embryos. In brief, the cDNA containing the coding region of dHDJ1 was removed from GH26396 (contained in the plasmid pOT2a, obtained from Research Genetics, Inc.) by complete digestion of 2.5 μg of plasmid DNA, in NEB #2 restriction enzyme buffer and 0.1 mg/ml BSA (New England Biolabs), with 20 u HindIII for 3 hrs at 37° C. to fragment pOT2a backbone, followed by partial digestion with 1, 2 or 4 u of PstI and XhoI for 10 min. at 37° C., and enzyme inactivation at 65° C. for 10 min. The reactions were run on 1% agarose gel and a 1816-bp-fragment was isolated and purified by QIAquick gel extraction kit (Qiagen). This fragment, which contains 106 bp PstI/EcoRI fragment of pOT2, 11 bp upstream of the reported 5'UTR, the 5'UTR, droJ1 ORF, 406 bp of the 579 bp reported 3'UTR, and a 23-bp-long poly(A), was ligated into the transgenic vector pINDY6 PstI/XhoI site.

At least 3 independent transgenic lines carrying a heterozygous insertion of UAS-dHDJ1 together with GMR-GAL4/UAS-127Q closely reproduced the results of SEM, light microscopy, and immunofluorescence microscopy of cryostat sections observed for EU3500 P-element insertion (a representative line shown; FIG. 4D). This result indicates that the suppression of polyglutamine-dependent degeneration of the eye by the P-element insertion and its transgenic counterparts were due to increased levels of dHDJ1. Upon closer examination of the retinas, labeled with DAPI for staining of the nuclei and Y-11 anti-HA antibody/FITC for labeling 127Q peptides, in transgenic dHDJ1 flies expressing 127Q, cytoplasmic inclusions as well as nuclear ones were evident (FIG. 4D).

Characterization and Identification of dTPR2

A second suppressor line, EU3220, was studied further. Although the improvement in eye morphology was less than EU3500, scanning electron microscopy revealed that this suppressor also significantly improved eye structure and pigmentation (FIG. 4E). In cryostat head sections, as with EU3500, EU 3220 improved retinal structure, although the effect was slightly weaker and the number of aggregates did not appear to change.

Plasmid rescue of the EU3220 suppressor P-element and its flanking genomic DNA and sequence analysis with a BDGP BLAST search identified an EST that matched the genomic sequences starting 293 base pairs downstream of the P-element. The corresponding cDNA clone, GH09432 was sequenced. The P-element insertion was 649 bp 5' of the open reading frame (ORF) of a 2239-bp cDNA, corresponding to a predicted protein of 508 amino acids and molecular weight of 58 kDa, containing seven tertatricopeptide repeats and a C-terminal J domain. A protein database search revealed high homology (46% identity and 67% similarity using the parameters described above; FIG. 7) between this and the human tetratricopeptide repeat protein 2 (TPR2). The identified drosophila sequences was therefore designated dTPR2 (FIG. 9).

At least 3 independent transgenic lines carrying a heterozygous insertion of UAS-dTPR2 together with GMR-GAL4/UAS-127Q confirmed that suppression by the EU3200 P-element and its transgenic counterpart were due to increased expression of dTPR2 (FIG. 4F). This data indicates the EU3220 suppressor was also able to ameliorate the polyglutamine toxicity that occurred in the eye.

Characterization and Identification of dMLF

Figure 8:
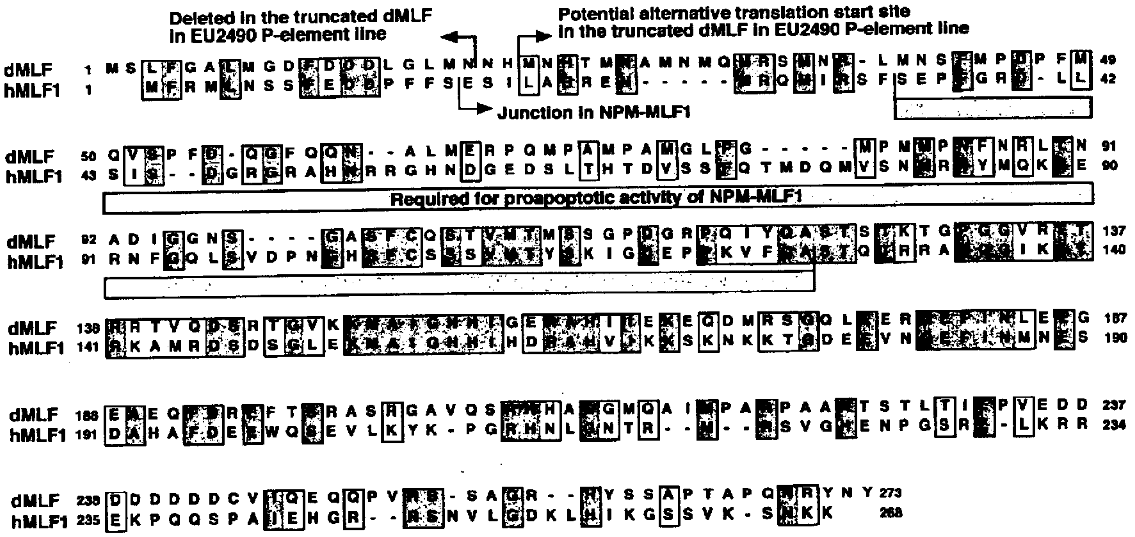
FIG. 8 shows a sequence alignment between *Drophila myeloid* leukemia factor 1 (dMLF) and its human homologue (dMLF). Overall amino acid sequence homology is 32% identical and 49% similar, denoted as above. The region absent from the full dMLF protein in the EU2490 P-element flies (MSLF . . . GLMN) which exhibit suppression of polyglutamine toxicity is indicated by an arrow pointing to the left. The portion of hMLF included in the chimeric NPM-MLF created by the (3:5)(q25. 1, q34) chromosomal translocation (Yoneda-Kato et al., *Oncogene*, 12:265–275 (1996)) is indicated by an arrow pointing to the right. The segment of hMLF in NPM-MLF required for its proapoptotic activity (Yoneda-Kato et al., *Oncogene*, 18:3716–3724 (1999)) is indicated by a gray bar.
Figure 11A:
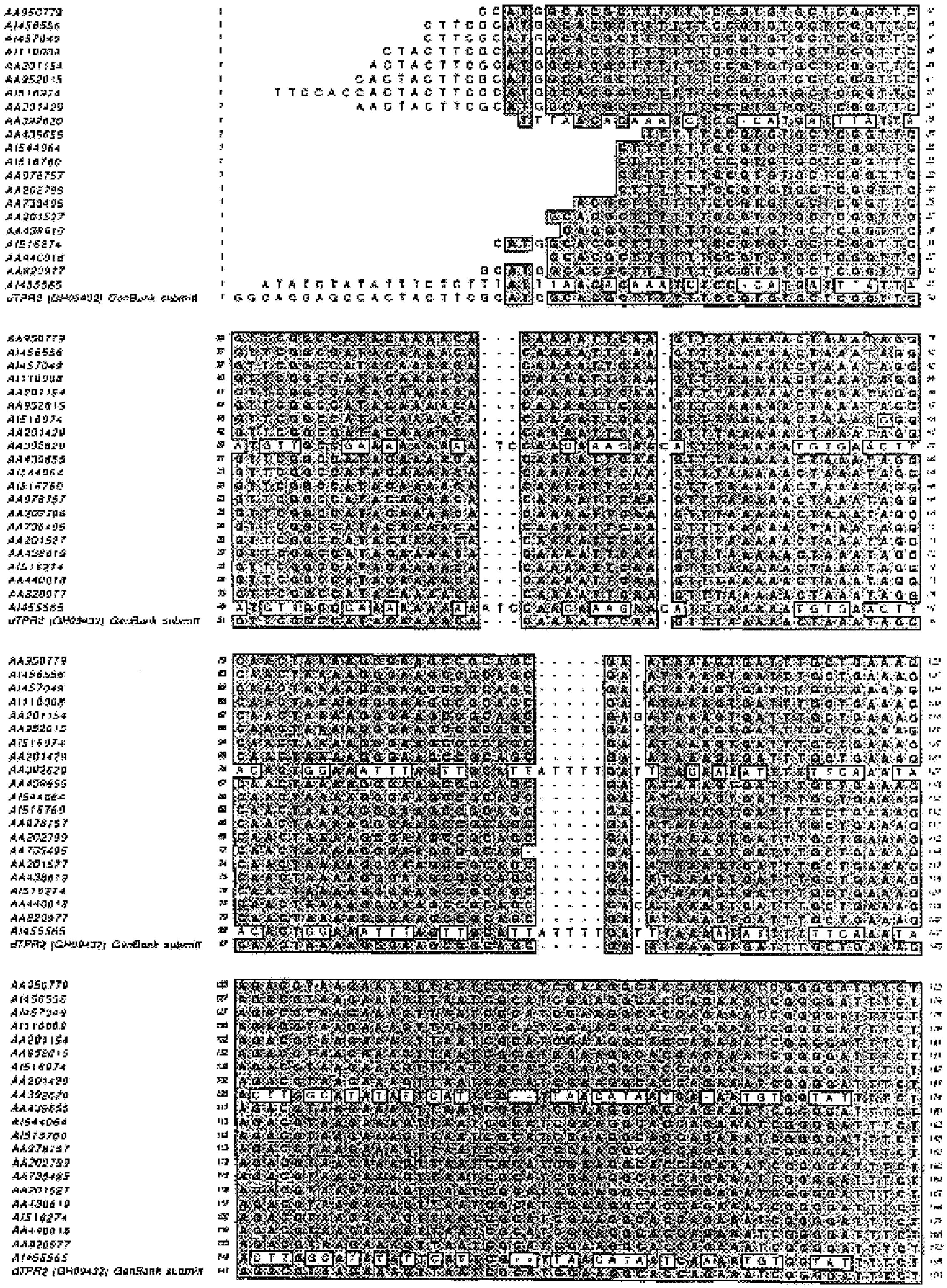
FIG. 11 shows a nucleic acid sequence alignment between Drosophila d1?R2 and several ESTs.
Figure 11A:
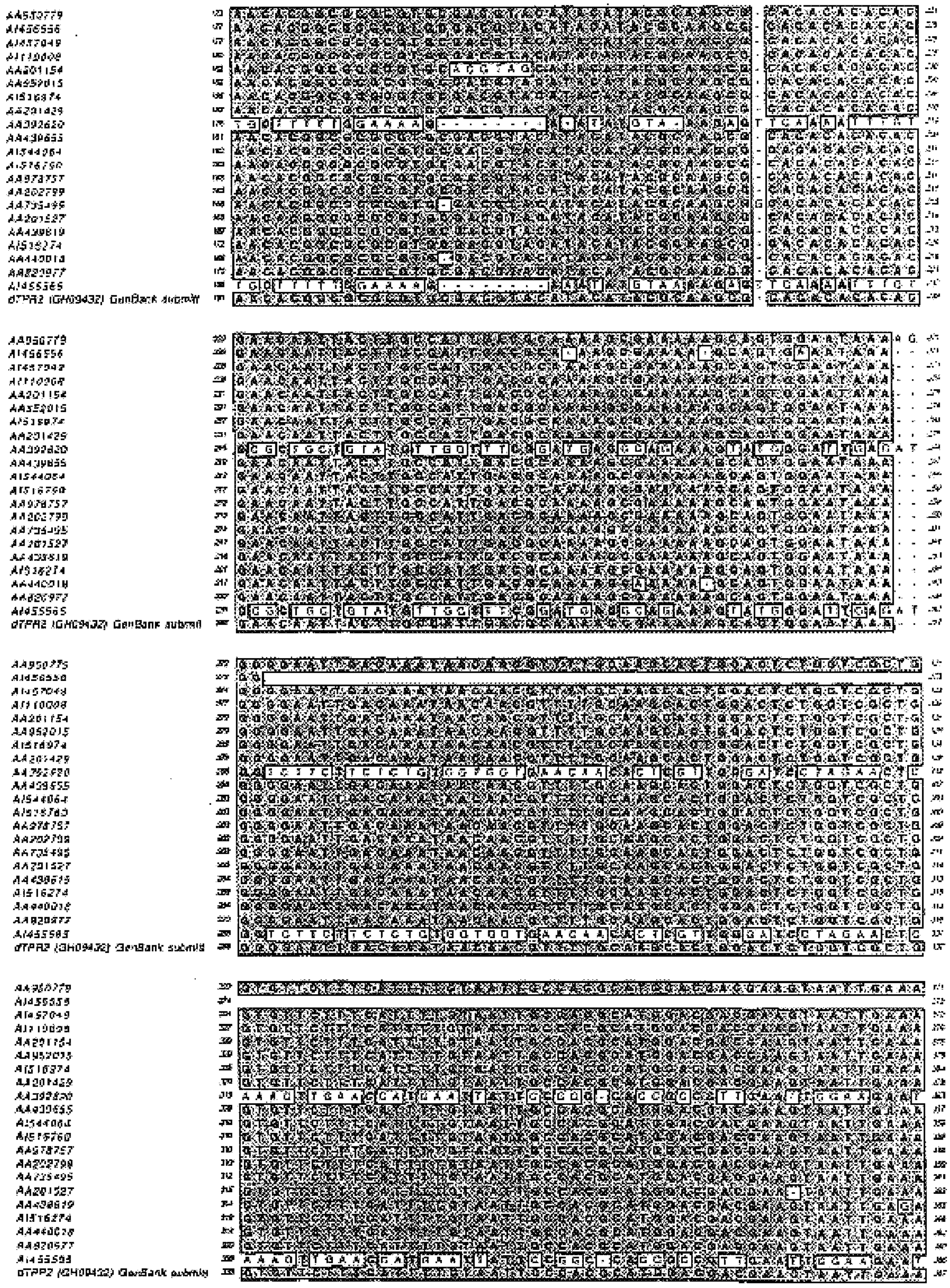
Figure 11A:
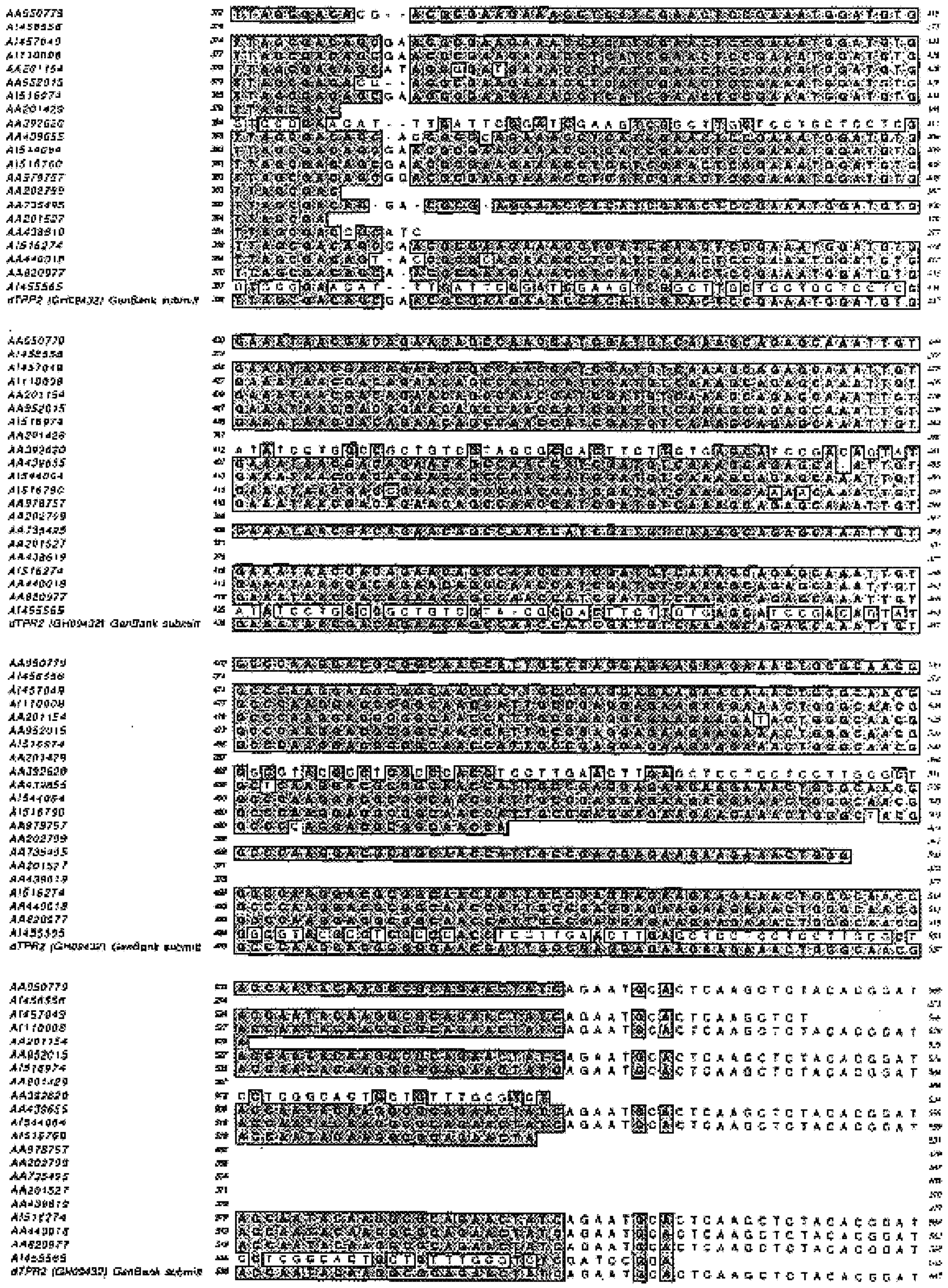
Figure 11B:
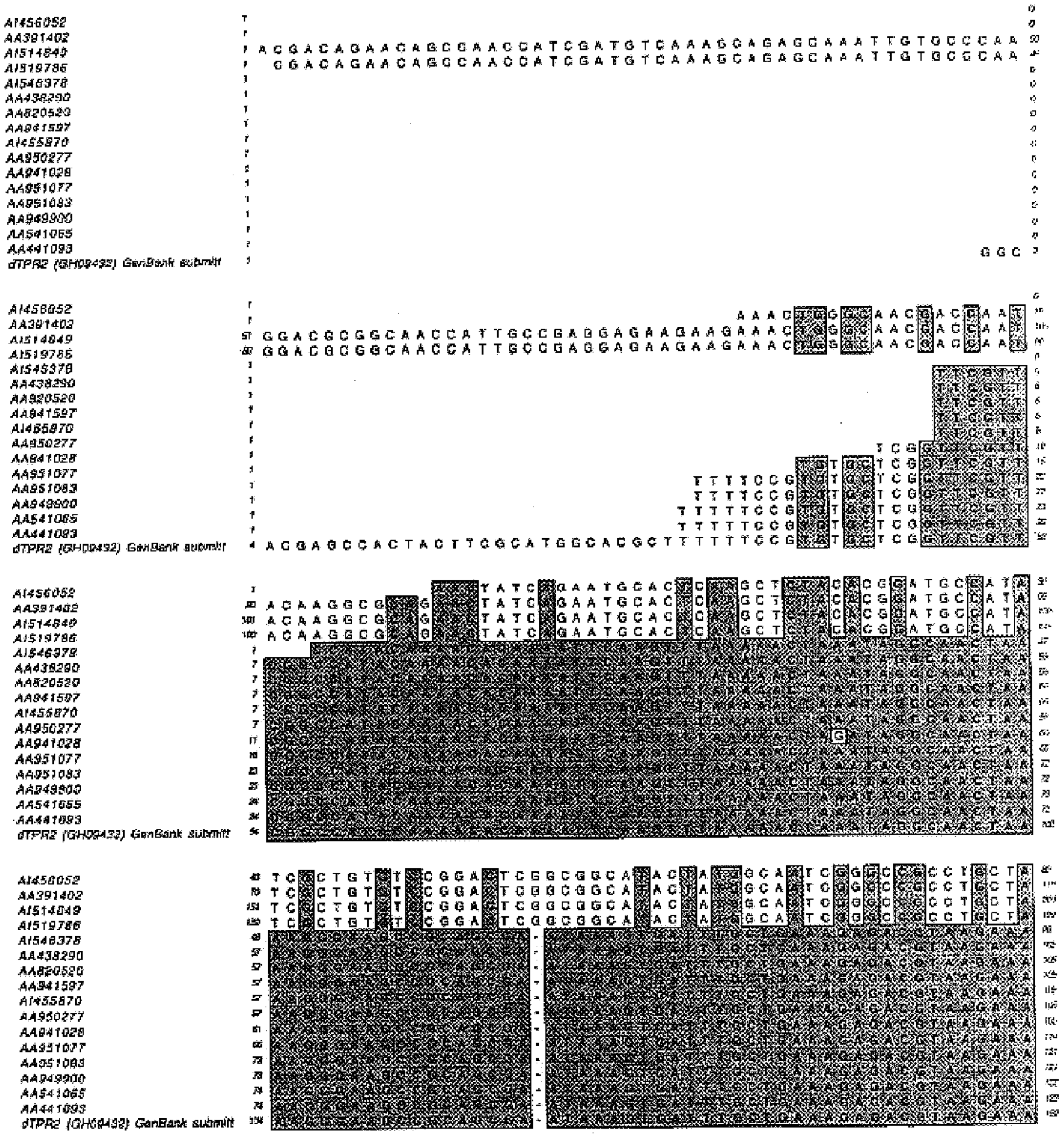
Figure 11B:
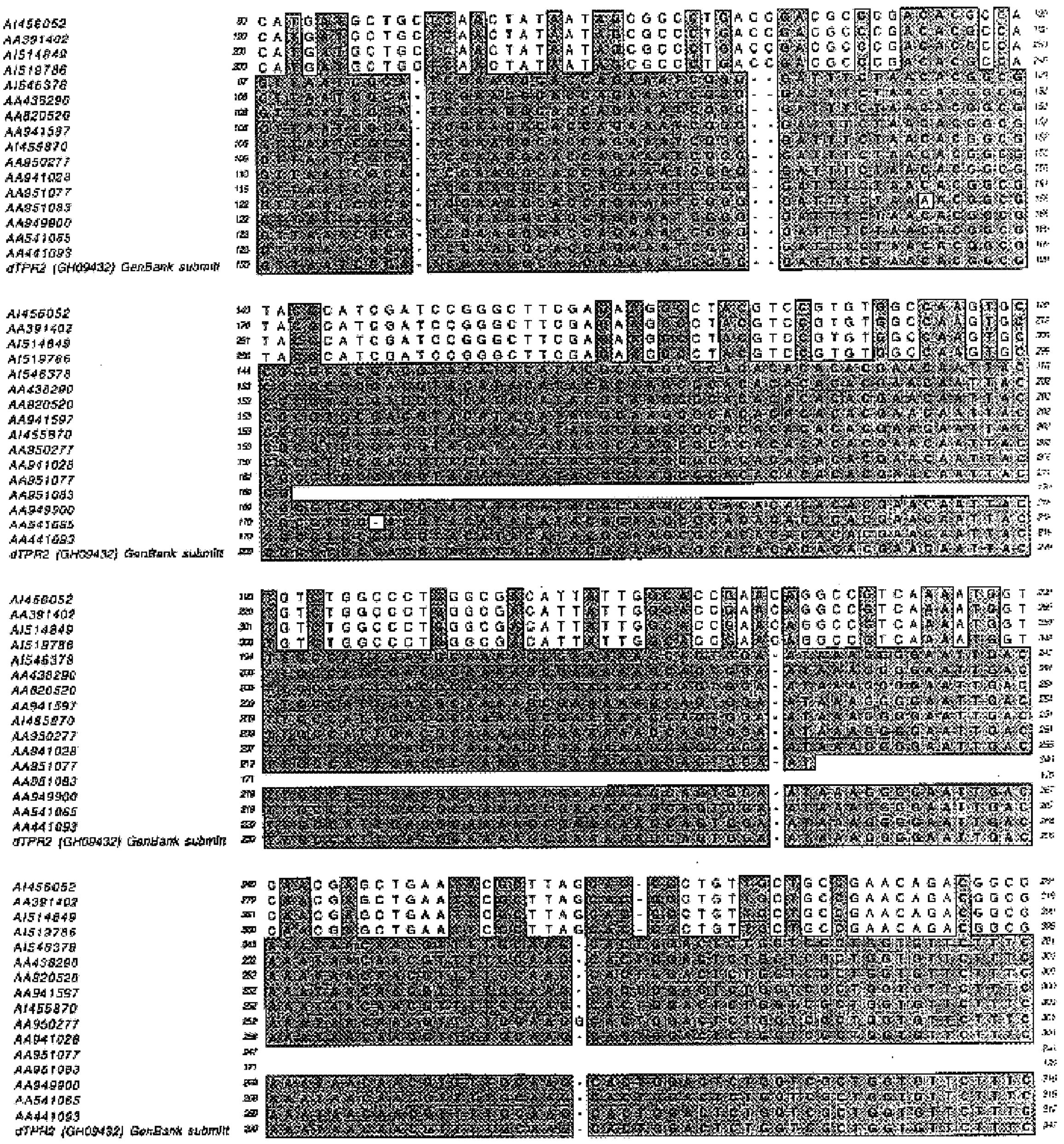
Figure 11B:
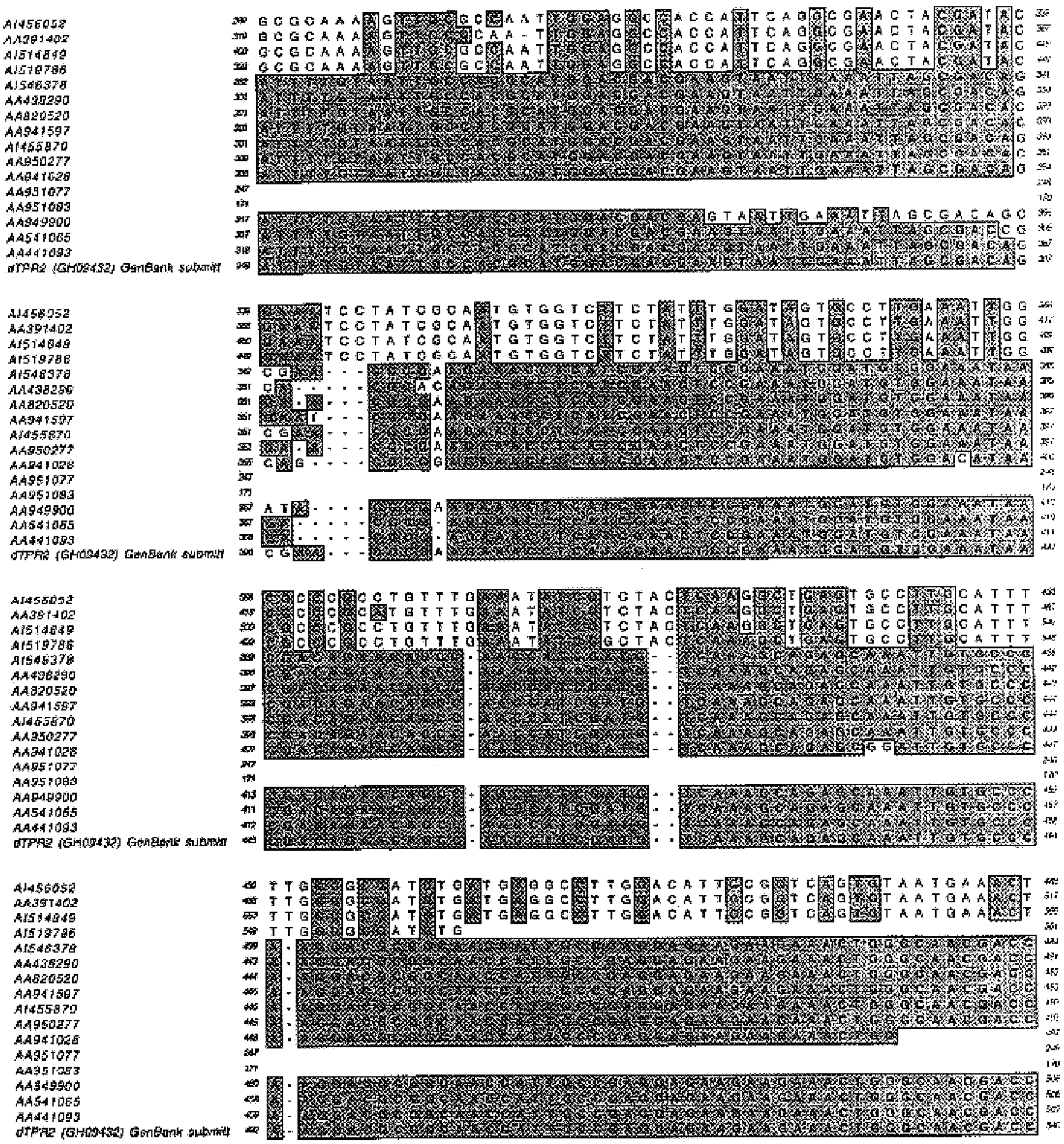
Figure 11B:
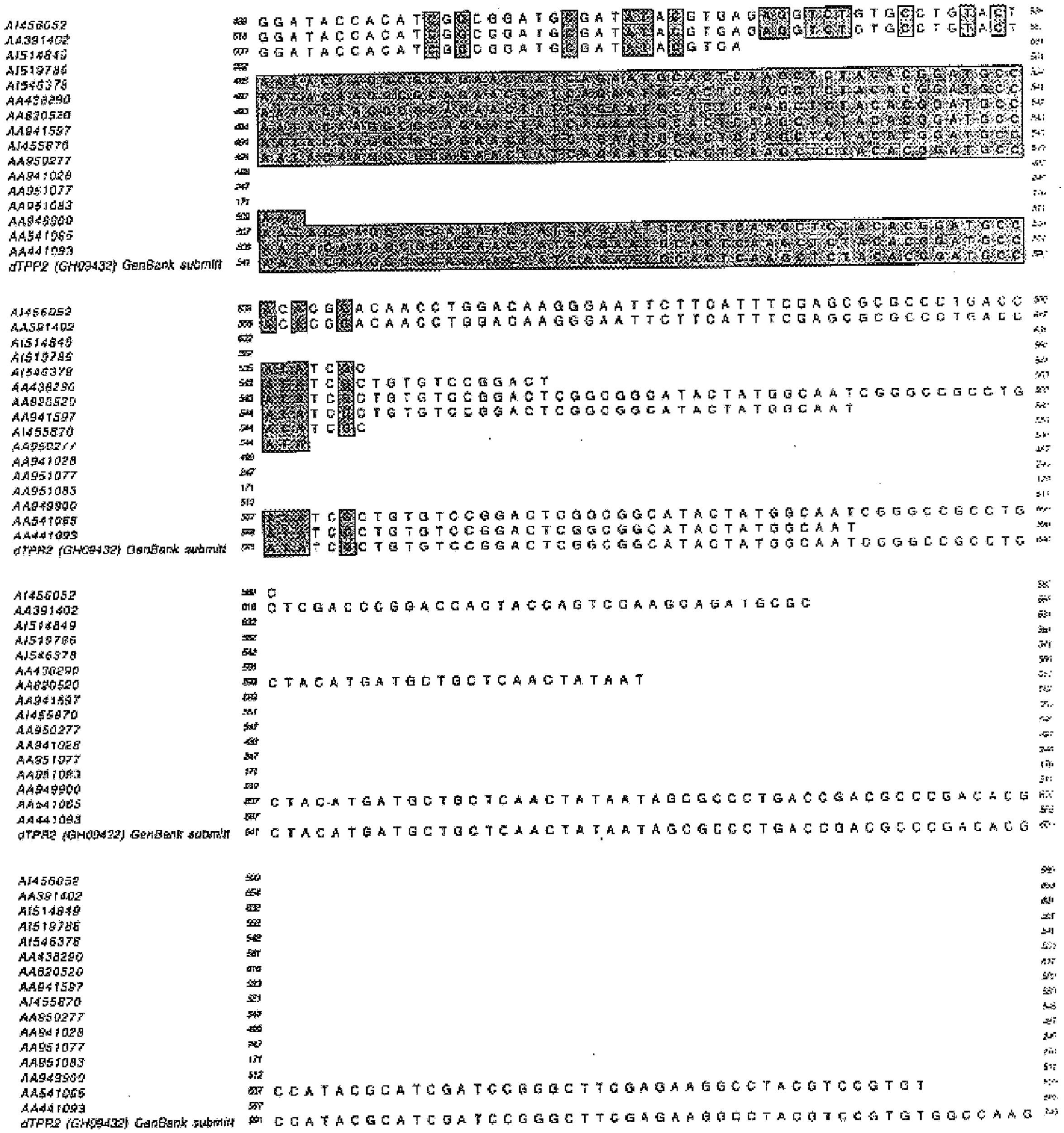

A third suppressor line, EU2490 (the $2490^{th}$ P-element insertion tested), dramatically counteracts the external eye and pigmentation defect caused by 127Q (FIG. 5C). A lesser internal improvement was seen in cryosections. P-element rescue was performed and the DNA flanking the 3' end of the P-element was sequenced (Pirrotta, *Cloning Drosophila Genes: A Practical Approach*, IRL Press, Oxford, Washington D.C., ed. D. B. Roberts, pp 83–110 (1986)). A BLAST search of the Berkeley Drosophila Genome Project (BDGP) server identified several ESTs with corresponding cDNA clones. A stretch of approximately 220 bp of the genomic DNA, beginning at 385 bp downstream of the EU2490 P-element insertion site, was 97% identical to the DNA sequence beginning 54 bp downstream of a predicted ATG start site of an open reading frame (ORF). This ORF has been found in a cDNA clone, GH20101, from an adult head library. The ORF is 822 bp long and lies within a 1753-bp cDNA insert with 82 bp 5'UTR, 849 bp 3'UTR, and an 18-base polyA tail. The predicted translation product of the ORF is a 273-amino-acid protein with a molecular weight of 30 kDa. Surprisingly, it is homologous to a human myeloid leukemia factor (MLF) (Yoneda-Kato et al:, *Oncogene*, 12:265–275 (1996)), with 32% identity and 49% similarity (FIG. 8). Therefore, this gene is denoted as *Drophila myeloid* leukemia factor, dMLF (FIG. 10).

To confirm that the expression of dMLF is responsible for the suppression effect, the cDNA insert in GH20101 was placed in the same kind of P-element vector as UAS-127Q, and transgenic lines established. Three independently established lines, each carrying a heterozygous autosomal insertion of UASMLF in the presence of GMR-GAL4/UAS-127Q, reproduced the improvement in external eye structure and pigmentation to an even greater extent than did the original P-element insertion (FIG. 5D and 5E). The internal eye structure was only slightly improved; however higher doses of the suppressor gene almost completely restored both external and internal eye structures to normal (FIG. 5F). Three different transgenic lines were established, each carrying UAS-dMLF transgenic insertions on both the second and third chromosomes, and all exhibited greater improvements in eye structure. Nevertheless, as with the two previous suppressor genes described above, fluorescent aggregates indicating the presence of polyglutamine nuclear inclusions were present in the eye. Thus, the suppressors do not appear to prevent aggregation of polyglutamine repeat sequence. Rather, they appear to enhance the ability of the cells to resist their toxic effect. This suggests that the suppressor genes identified act a later point along the pathway that results in cellular toxicity.

The protective effect of dMLF on polyglutamine toxicity in Drosophila neuronal tissues was ascertained. In brief, a neuron-specific driver, Appl, was used to drive expression of the GAL4 protein (Appl-GAL4); Appi is derived from the promoter region of the amyloid precursor protein-like gene, the Drosophila homologue of human amyloid precursor protein (APP) (Torroja et al., *Current Biology*, 9:489–492 (1999)). Appl is expressed exclusively in post-mitotic neurons of the central and peripheral nervous system, from mid to late stages of embryogenesis onward (Martinmorris et al., *Development*, 110:185–195 (1990)).

Transgenic flies carrying only Appl-GAL4 developed normally. The same was true for three independent UAS-20Q insertions in the presence of Appl-GAL4. UAS-63Q, a UAS driven construct encoding a polyglutamine repeat sequence 63 residues in length however, had a strong toxic effect. In four transgenic lines tested three were pre-adult lethal; only one gave rise to adults which were exclusively female. Since the Appl-GAL4 transgene was on the X chromosome, dosage compensation may have produced higher expression in males, resulting in the increased lethality. Three UAS-127Q lines were all pre-adult lethal in the presence of Appl-GAL4. Therefore, 63Q females were studied for suppression of toxicity by dMLF, using survival of adults versus age as a criterion.

The flies with Appl-GAL4 alone remained vital throughout the 20-day observation period; no polyglutamine aggregates were detected, as determined by anti-HA fluorescent staining, in brain or thoracic ganglion sections of the nervous system. In contrast, flies carrying Appl-GALA and a heterozygous insertion of UAS-63Q began to die by day 12 and almost all flies were dead by day 20. Shortly before death, the flies became progressively lethargic, unable to climb the walls of the plastic vial; these were also counted as dead.

Cryosections of oneday-old adult Appl-GAL4/UAS-63Q flies revealed aggregates in the neuronal cell bodies of the cortices surrounding the neuropils of the brain and the thoracic ganglion. The fluorescent aggregates appeared to be almost exclusively localized to neuronal cell bodies, as evident by co-localization of the nuclear stain with staining by DAPI, and the absence of anti-HA stain in synaptic neuropil region. In plastic sections stained with toluidine blue, no signs of gross neuronal degeneration were observed, even in the last surviving flies at 20 days. Death may therefore be due to dysfunction of the neurons associated with polyglutamine repeat sequence expression.

Expression of dMLF with 63Q increased fly survival. At day 20, 60% of flies expressing dMLF with 63Q remained alive. Therefore, dMLF can protect against polyglutamine toxicity in neuronal tissues, as well as in the eye. These results also demonstrate that the eye can be used as a convenient morphological substitute in screening for suppression of polyglutamine toxicity in neuronal tissues.

EXAMPLE 5

This example describes several structural features characteristic of the dHDJ1, dTPR2 and dMLF that are likely to be important for the ability to decrease polyglutamine toxicity.

Both dHDJ1 and dTPR2 are implicated in protein chaperone function. For example, each has a J domain (FIG. 6 and 7), a stretch of approximately 70 amino acids present in J proteins that stimulates ATPase activity of Hsp70(Marsh et al., *Hum. Mol Genet*., 9:13–25 (2000)) which results in closure of its peptide-binding pocket, trapping protein substrates (Kazemi-Esfaijani et al., *Science*, 287:1837–1840 (2000)). J proteins also independently bind other proteins having secondary and tertiary structure (Ellis et al., *Development*, 119:855–865 (1993)).

Direct evidence for the role of heat shock proteins, particularly J proteins, in preventing protein aggregation has been provided in vitro by showing that a five-fold molar excess of *E. coli* DnaJ completely suppresses aggregation of a substrate protein (bovine mitochondrial rhodanese) (Freeman, *Cell*, 87:651–660 (1996)). J proteins may also play a role in the proteasome degradation pathway, since the J domain of the simian virus 40 (SV40) large T antigen (TAg) was required for proteasome-dependent degradation of p130 (related to retinoblastoma tumor suppressor protein, pRB) in human osteosarcoma cell line U-2 OS (Torroja et al., *Current Biology*, 9:489–492 (1999)). In fact, the J domains of human HDJ2 (also known as DNAJ2) or HSJ1 could substitute for the J domain in SV40 TAg, and substitution of a glutamine for a conserved histidine in the J domains could abolish that effect.

Drosophila TPR2 may also act as a suppressor in another way due to the presence of multiple TPR domains (FIG. 7). TPR domains are made of 3 to 16 degenerate repeats of a 34-amino-acid stretch, each of which forms a pair of anti-parallel α helices (Rorth, *Proc Natl Acad Sci USA*, 93:12418–12422 (1996)). Multiple tandem TPR units assemble into right-handed superhelical structures that are suited for protein-protein interfaces. They are found in proteins involved in various functions, including protein import, neurogensis, stress response, and chaperone action (Warrick et al., *Cell*, 93:939–949 (1998); and Pirrotta, *Cloning Drosophila Genes: A Practical Approach*, IRL Press, Oxford, Washington D.C., ed. D. B. Roberts, pp 83–110 (1986)). The human TPR2 was isolated from a HeLa cell cDNA library in a two-hybrid screen, using as "bait" a 271 -amnino-acid fragment of GTPase-activating protein-related domain (GRD) of neurofibromin, the neurofibromatosis type 1 (NF1) gene product (Warrick et al., (1998), supra). Neurofibromin stimulates the GTPase-activity of p2l Ras and converts it from the active form (Ras-GTP) to its inactive form (Ras-GDP) (Yoneda-Kato et al., *Oncogene*, 12:265–275 (1996)). Conceivably, overexpression of dTPR2 in the fly eye inhibits the Drosophila homologue of neurofibromin (dNF1) (Martinmorris et al., *Development*, 110:1 85–195 (1990)), by masking its GRD. This would increase the activity of Ras-GTP, which is known to inhibit the proapoptotic head involution defective (HID) protein Yoneda-Kato et al., *Oncogene*, 18:3716–3724 (1999)), and enhance the survival of eye cells.

In cultured cells transfected with full-length ataxin-1, or the androgen receptor, each having expanded polyglutamines, co-expression of HDJ2/HSDJ resulted in 40–50% reduction in the number of cells containing aggregates (Ross et al., *Blood*, 91:4419–4426 (1998); and Sorensen et al., *Cancer*, 86:1342–1346 (1999)). Surprisingly, similar to the effect of HSPA1L, the EU3500 or EU3220 P-elements, or expression of their transgenic counterparts, inhibited deterioration of the eye structure, yet the formation of aggregates did not appear to be suppressed. Since the GMR promoter acts early in eye development, it is possible that dHDJ1 and dTPR2 act at that early stage of differentiation, by binding to 127Q, maintaining a non-toxic milieu, thus permitting eye development to proceed more normally. Alternatively, these suppressor proteins, rather than directly interacting with 127Q peptide, may reduce its toxicity by a downstream effect.

The mechanism of protection against polyglutamine toxicity by dMLF may relate to the role of its human counterpart in cell survival and proliferation. In this regard, human MLF gene was first identified as a portion of a chimeric product including the nucleolar transport protein, nucleophosmin (NPM), in the chromosomal translocation t(3:5)(q25.1, q34) associated with myelodysplastic syndrome (MDS) and acute myeloid leukemia (AML) (Yoneda-Kato et al., *Oncogene*, 12:265–275 (1996)). In stable transfections of NIH3T3 mouse fibroblast cells with MLF cDNA, MLF Ab stained the cytoplasm, whereas the NPM-MLF chimeric product was exclusively nuclear and nucleolar (Yoneda-Kato et al., *Oncogene*, 18:3716–3724 (1999)). Neither MLF nor NPM alone had any detectable effect, but NPM-MLF induced apoptosis. The region necessary for apoptotic activity was narrowed down to a 92-amino acid stretch in MLF (FIG. 8) (Yoneda-Kato et al. (1999), supra. Therefore, it is likely that the corresponding region of dMLF has a similar function.

When the anti-apoptotic protein Bc1–2 was expressed in the presence of NPM-MLF, the cells, instead of undergoing apoptosis, entered a proliferative phase. The induction of apoptosis resembles the anemia resulting from the cellular dysplasia in MDS patients, and the proliferative condition is reminiscent of the transformation of MDS to AML. Therefore, dMLF may protect against polyglutamine toxicity through its function as a component of cell survival signaling pathways. Accordingly, a fly genetic system that exhibits a dMLF phenotype, such as abnormal cell proliferation or a tumor, can be used to identify genes or other factors that have therapeutic value in treating myelodysplastic syndrome and acute myeloid leukemia in humans.

Another finding relating polyglutamine disease to cancer is the chromosomal translocation t(5;7)(q33; q11.2) observed in a patient suffering from chronic myelomonocytic leukemia (CMML), another form of MDS/AML (Ross et al., *Blood*, 91:44194426 (1998). The putative chimeric product is made of Huntingtin-interacting protein 1 (HIP1) and platelet-derived growth factor P receptor. HIP 1 was found in a yeast two-hybrid assay, using the $NH_2$-terminal portion of Huntingtin (encoded by the Huntington's disease gene, HD). Based on cell fractionation analyses and its similarity to Sla2p, a membrane-associated protein in yeast, HIP1 appears to be involved in maintaining the integrity of the cell membrane (Kalchman et al., Nat. Genet, 16:44–53 (1997); Sittler. et al., *Mol Cell*, 2:427–436 (1998)). A lower incidence of cancer has been reported among individuals with Huntington's disease Sorensen et al., *Cancer*, 86:1342–1346 (1999)). Therefore, the molecular pathways that give rise to Huntington's disease may be beneficial in preventing or treating cancer, and vice versa.

Discovery of dHDJ1, dTPR2 and dMLF as suppressors of polyglutamine toxicity underscores the fact that this fly system identifies genes effective in preventing one or more cellular or molecular aspects of polyglutamine diseases, without any knowledge of their function. The sequence of the Drosophila genome was recently compiled (Adams et al., *Science*, 287:2185–2195 (2000)), and about 68% of known human cancer-associated proteins analyzed appear to have Drosophila homologues (Rubin et al., *Science*, 287:22042215 (2000)). However, dMLF was not among those listed. This may have been due to stringent criteria for homology, including a requirement for sharing a known protein domain, whereas MLF and dMLF both lack such domains.

Although the invention has been described with reference to the presently preferred embodiments, it should be understood that various modifications can be made without departing from the spirit of the invention. Accordingly, the invention is limited only by the following claims.

What is claimed is:

1. A transgenic *D. melanogaster* comprising a transgene containing a plurality of CAG's and at least one CAA sequence encoding a polyglutamine repeat sequence operably linked to a constitutive, regulatable, or tissue specific expression control element, wherein the tissue specific expression control element is selected from the group consisting of Appl, rhodopsin 1 promoter, and GLASS transcription factor element, and wherein the transgene produces polyglutamine toxicity in the transgenic *D. melanogaster.*

2. The *D. melanogaster* of claim 1, wherein the number of CAG's to CAA's is in ratio of between about 1:1 and 2:1.

3. The *D. melanogaster* of claim 1, wherein the number of CAG's to CAA's is in ratio of between about 2:1 and 5:1.

4. The *D. melanogaster* of claim 1, wherein the number of CAG's to CAA's is in ratio of between about 5:1 and 10:1.

5. The *D. melanogaster* of claim 1, wherein the number of CAG's to CAA's is in ratio of between about 10:1 and 50:1.

6. The *D. melanogaster* of claim 1, wherein the tissue specific expression control element confers neural, retinal, muscle or mesoderm cell expression.

7. The *D. melanogaster* of claim 1, wherein the polyglutamine sequence is between about 50 and 100 amino acids in length.

8. The *D. melanogaster* of claim 1, wherein the polyglutamine sequence is between about 100 and 200 amino acids in length.

9. The *D. melanogaster* of claim 1, wherein the polyglutamine sequence is between about 50 and 200 amino acids in length.

10. The *D. melanogaster* of claim, 1, wherein the polyglutamine sequence further comprises a tag.

11. The *D. melanogaster* of claim 1, wherein the Drosophila further comprises a marker sequence inserted into its genomic DNA, wherein the marker is located adjacent to a gene selected from the group consisting of a HDJ1 gene, a TPR2 gene, and a MLF gene in the Drosophila, and wherein the marker sequence comprises an inducible upstream activating sequence, a minimal promoter sequence and 5' and 3' transposon elements containing terminal inverted repeats.

12. The *D. melanogaster* of claim 11, wherein the gene is HDJ1.

13. The *D. melanogaster* of claim 11, wherein the gene is TPR2.

14. The *D. melanogaster* of claim 11, wherein the marker sequence is adjacent to an MLF gene.

15. A method of producing a transgenic *D. melanogaster* characterized by polyglutamine toxicity comprising:

(a) transforming a *D. melanogaster* embryo or fertilized egg with a transgene comprising a plurality of CAA and CAG sequences encoding a polyglutamine sequence operably linked to a constitutive, regulatable, or tissue specific expression control element, wherein the tissue specific expression control element is selected from the group consisting of AppI, rhodopsin 1 promoter, and GLASS transcription factor element and (b) selecting a *D. melanogaster* that exhibits polyglutamine toxicity.

* * * * *

SEQUENCE LISTING

<160> NUMBER OF SEQ ID NOS: 69

<210> SEQ ID NO 1
<211> LENGTH: 508
<212> TYPE: PRT
<213> ORGANISM: Human

<400> SEQUENCE: 1

```
Met Asp Asp Glu Val Ile Glu Ile Ser Asp Ser Glu Arg Glu Glu Thr
 1               5                  10                  15

Ser Ser Asn Ser Glu Met Asp Val Glu Ile Thr Thr Glu Gln Pro Thr
            20                  25                  30

Ile Asp Val Lys Ala Glu Gln Ile Val Pro Lys Asp Ala Ala Thr Ile
        35                  40                  45

Ala Glu Glu Lys Lys Lys Leu Gly Asn Asp Gln Tyr Lys Ala Gln Asn
    50                  55                  60

Tyr Gln Asn Ala Leu Lys Leu Tyr Thr Asp Ala Ile Ser Leu Cys Pro
65                  70                  75                  80

Asp Ser Ala Ala Tyr Tyr Gly Asn Arg Ala Ala Cys Tyr Met Met Leu
                85                  90                  95

Leu Asn Tyr Asn Ser Ala Leu Thr Asp Ala Arg His Ala Ile Arg Ile
            100                 105                 110

Asp Pro Gly Phe Glu Lys Ala Tyr Val Arg Val Ala Lys Cys Cys Leu
        115                 120                 125

Ala Leu Gly Asp Ile Ile Gly Thr Glu Gln Ala Val Lys Met Val Asn
    130                 135                 140

Glu Leu Asn Ser Leu Ser Thr Ala Val Ala Ala Glu Gln Thr Ala Ala
145                 150                 155                 160

Gln Lys Leu Arg Gln Leu Glu Ala Thr Ile Gln Ala Asn Tyr Asp Thr
                165                 170                 175

Lys Ser Tyr Arg Asn Val Val Phe Tyr Leu Asp Ser Ala Leu Lys Leu
            180                 185                 190

Ala Pro Ala Cys Leu Lys Tyr Arg Leu Leu Lys Ala Glu Cys Leu Ala
        195                 200                 205

Phe Leu Gly Arg Cys Asp Glu Ala Leu Asp Ile Ala Val Ser Val Met
    210                 215                 220

Lys Leu Asp Thr Thr Ser Ala Asp Ala Ile Tyr Val Arg Gly Leu Cys
225                 230                 235                 240

Leu Tyr Tyr Thr Asp Asn Leu Asp Lys Gly Ile Leu His Phe Glu Arg
                245                 250                 255

Ala Leu Thr Leu Asp Pro Asp His Tyr Lys Ser Lys Gln Met Arg Ser
            260                 265                 270

Lys Cys Lys Gln Leu Lys Glu Met Lys Glu Asn Gly Asn Met Leu Phe
        275                 280                 285

Lys Ser Gly Arg Tyr Arg Glu Ala His Val Ile Tyr Thr Asp Ala Leu
    290                 295                 300

Lys Ile Asp Glu His Asn Lys Asp Ile Asn Ser Lys Leu Leu Tyr Asn
305                 310                 315                 320

Arg Ala Leu Val Asn Thr Arg Ile Gly Asn Leu Arg Glu Ala Val Ala
                325                 330                 335

Asp Cys Asn Arg Val Leu Glu Leu Asn Ser Gln Tyr Leu Lys Ala Leu
            340                 345                 350

Leu Leu Arg Ala Arg Cys Tyr Asn Asp Leu Glu Lys Phe Glu Glu Ser
```

-continued

```
        355                 360                 365

Val Ala Asp Tyr Glu Thr Ala Leu Gln Leu Glu Lys Thr Pro Glu Ile
    370                 375                 380

Lys Arg Met Leu Arg Glu Ala Lys Phe Ala Leu Lys Lys Ser Lys Arg
385                 390                 395                 400

Lys Asp Tyr Tyr Lys Ile Leu Gly Ile Gly Arg Asn Ala Ser Asp Asp
                405                 410                 415

Glu Ile Lys Lys Ala Tyr Arg Lys Lys Ala Leu Val His His Pro Asp
            420                 425                 430

Arg His Ala Asn Ser Ser Ala Glu Glu Arg Lys Glu Glu Glu Leu Lys
        435                 440                 445

Phe Lys Glu Val Gly Glu Ala Tyr Ala Ile Leu Ser Asp Ala His Lys
    450                 455                 460

Lys Ser Arg Tyr Asp Ser Gly Gln Asp Ile Glu Glu Gln Glu Gln Ala
465                 470                 475                 480

Asp Phe Asp Pro Asn Gln Met Phe Arg Thr Phe Phe Gln Phe Asn Gly
                485                 490                 495

Gly Gly Arg Asn Asn Ser Ser Phe Asn Phe Glu Phe
            500                 505


<210> SEQ ID NO 2
<211> LENGTH: 2239
<212> TYPE: DNA
<213> ORGANISM: Drosophila

<400> SEQUENCE: 2

ggcacgagcc actacttcgc atggcacgct tttttccgtg tgctcggttc gttcggccat     60

acaaaacaca aaattcaagt ttaaaaacta aataggcaac taaaagggaa gccgcagcga    120

ataaagtgat ttgctgaaag agacgtaaga aagttaatcg catcgaaggc accagaaatc    180

ggggatttct aacacggcgc gcgtgcgacg tacatacata cgcaagcgca cacacacacg    240

aacaattact tgccattgac gcaaaagcga aaaagcagtg gaataaaggg gaattgacaa    300

ataacaacgt tttgcaagca ctggactctg gtcgctggtg ttctttcatt ttgtaattgc    360

cacgcatgga cgacgaagta attgaaatta gcgacagcga acgcgaagaa acctcatcga    420

actccgaaat ggatgtggaa ataacgacag aacagccaac catcgatgtc aaagcagagc    480

aaattgtgcc caaggacgcg gcaaccattg ccgaggagaa gaagaaactg ggcaacgacc    540

aatacaaggc gcagaactat cagaatgcac tcaagctcta cacggatgcc atatcgctgt    600

gtccggactc ggcggcatac tatggcaatc gggccgcctg ctacatgatg ctgctcaact    660

ataatagcgc cctgaccgac gcccgacacg ccatacgcat cgatccgggc ttcgagaagg    720

cctacgtccg tgtggccaag tgctgtctgg ccctgggcga cattattggc accgaacagg    780

ccgtcaaaat ggtcaacgag ctgaattcgc ttagcacggc tgttgctgcc gaacagacgg    840

cggcgcaaaa gttgcgccaa ttggaggcca ccattcaggc gaactacgat acgaaatcct    900

atcgcaatgt ggtcttctat ttggatagtg ccttgaaatt ggcgcccgcc tgtttgaaat    960

atcgtctact caaggctgag tgccttgcat tttggggcg atgtgatgag gccttggaca   1020

ttgcggtcag tgtaatgaaa ctggatacca catcggcgga tgcgatatac gtgagaggtc   1080

tgtgcctgta ctacacggac aacctggaca agggaattct tcatttcgag cgcgccctga   1140

ccctcgaccc ggaccactac aagtccaagc agatgcgcag caaatgcaag cagctcaagg   1200

agatgaagga gaacggcaat atgctattca agtcgggtcg gtatcgcgag gcacacgtta   1260
```

-continued

```
tctacacgga cgccctgaag atcgatgaac acaacaagga tatcaattcg aaattgcttt   1320

acaatcgggc tttggtcaac acgcgtattg gcaatttgcg agaggccgtg gccgattgca   1380

atcgagtgct ggagctgaat agtcagtatc tgaaggctct gttgctgcga gcgcgctgct   1440

acaatgatct ggagaagttc gaggagtcgg tggcggacta tgagacggcg ctgcagctgg   1500

agaagacgcc ggagattaag cgaatgctgc gcgaggccaa gtttgcgttg aagaagtcga   1560

agcgaaagga ctactacaag atcctgggca ttggacgcaa tgcgtccgac gacgagatca   1620

agaaggcgta tcgcaaaaag gcgctggtac atcatccgga tcgacacgca aacagcagtg   1680

ccgaggagcg caaggaggag gagctcaagt tcaaggaggt gggcgaggcg tacgccatac   1740

tgtcggatgc tcacaagaag tcgcgctacg acagcggcca ggatatcgag gagcaggagc   1800

aagccgactt cgatccgaat caaatgttcc gcacattctt ccaattcaac ggcggtggcc   1860

ggaataattc atcgttcaac tttgagttct aggatcccaa cgagtgttgt tcaccaccac   1920

agagaagaag accatctcaa tcccatactt tctgcctcat ccgaaaccaa catacagcag   1980

cgcacaaatt ttgaactctt ttacatattt cttttccaaa aagcaagaaa ataccacatt   2040

ttgattatgt taacgaatga atatatgcca agttatttga aaaaatattc taaatcaaaa   2100

taatgcaact aaatttccag tgtaagttca catttttaaa tgttctttct tggatttttt   2160

tttcggcaac attaataaat catgggagat ttgtgttaaa taaacagaaa tatacatata   2220

aaaaaaaaaa aaaaaaaaa                                                 2239
```

<210> SEQ ID NO 3
<211> LENGTH: 273
<212> TYPE: PRT
<213> ORGANISM: Drosophila

<400> SEQUENCE: 3

```
Met Ser Leu Phe Gly Ala Leu Met Gly Asp Phe Asp Asp Asp Leu Gly
 1               5                  10                  15

Leu Met Asn Asn His Met Asn His Thr Met Asn Ala Met Asn Met Gln
            20                  25                  30

Met Arg Ser Met Asn Arg Leu Met Asn Ser Phe Met Pro Asp Pro Phe
        35                  40                  45

Met Gln Val Ser Pro Phe Asp Gln Gly Phe Gln Gln Asn Ala Leu Met
    50                  55                  60

Glu Arg Pro Gln Met Pro Ala Met Pro Ala Met Gly Leu Phe Gly Met
65                  70                  75                  80

Pro Met Met Pro Asn Phe Asn Arg Leu Leu Asn Ala Asp Ile Gly Gly
                85                  90                  95

Asn Ser Gly Ala Ser Phe Cys Gln Ser Thr Val Met Thr Met Ser Ser
            100                 105                 110

Gly Pro Asp Gly Arg Pro Gln Ile Tyr Gln Ala Ser Thr Ser Thr Lys
        115                 120                 125

Thr Gly Pro Gly Gly Val Arg Glu Thr Arg Arg Thr Val Gln Asp Ser
    130                 135                 140

Arg Thr Gly Val Lys Lys Met Ala Ile Gly His His Ile Gly Glu Arg
145                 150                 155                 160

Ala His Ile Ile Glu Lys Glu Gln Asp Met Arg Ser Gly Gln Leu Glu
                165                 170                 175

Glu Arg Gln Glu Phe Ile Asn Leu Glu Glu Gly Glu Ala Glu Gln Phe
            180                 185                 190

Asp Arg Glu Phe Thr Ser Arg Ala Ser Arg Gly Ala Val Gln Ser Arg
```

-continued

```
        195                 200                 205

His His Ala Gly Gly Met Gln Ala Ile Met Pro Ala Arg Pro Ala Ala
    210                 215                 220

His Thr Ser Thr Leu Thr Ile Glu Pro Val Glu Asp Asp Asp Asp Asp
225                 230                 235                 240

Asp Asp Asp Cys Val Ile Gln Glu Gln Gln Pro Val Arg Ser Ser Ala
                245                 250                 255

Gly Arg His Tyr Ser Ser Ala Pro Thr Ala Pro Gln Asn Arg Tyr Asn
            260                 265                 270

Tyr


<210> SEQ ID NO 4
<211> LENGTH: 1753
<212> TYPE: DNA
<213> ORGANISM: Drosophila

<400> SEQUENCE: 4

ggcacgagga aaatattcgt gaaaattctg catacggaaa gaagaaaatt cgagcaacag     60

aaagccaaca caatccacaa aaatgtcttt attcggagcg ttgatgggtg atttcgacga    120

cgatctcggc cttatgaaca accacatgaa ccacactatg aacgcgatga acatgcagat    180

gcgctcgatg aatcgcctga tgaacagctt tatgcccgat cccttcatgc aggtctcgcc    240

ctttgaccag ggattccagc agaacgctct catggagcgt ccgcagatgc cggccatgcc    300

agccatgggc ctcttcggca tgcccatgat gccaaacttt aatcgcctgt tgaacgctga    360

tattggtggc aattcaggcg catccttctg ccagagcacc gtgatgacca tgtcatcggg    420

tcccgatggg cgtcctcaga tctaccaggc cagcactagt accaaaacag gaccgggagg    480

cgttcgtgag acccgcagga cggtgcagga ctcgcgcact ggggtgaaga agatggccat    540

tggtcatcac atcggcgagc gggcacacat tattgagaaa gagcaggaca tgcgctcagg    600

acaactggag gagcgccagg agttcattaa tctggaggag ggagaagccg agcagtttga    660

cagggagttt acatcgcgcg ctagtcgcgg agcggtgcag tcaagacatc atgctggtgg    720

catgcaggcc atcatgcccg cccgtccagc ggcacacacc tcgacgttga ccattgagcc    780

agtggaggac gacgacgacg atgatgatga ctgtgtaatc caggagcagc aaccggttcg    840

ctcctccgcg ggccgccatt attccagtgc gccaacggca ccgcagaaca gatataatta    900

ctaaatctaa agtcaataca gtatatttta ctaactatcc gataaaacag aaacagaatt    960

gcatactata aatttctgct aattacattc ccaactgcgt tcaaacgaaa cgaatatcga   1020

atcgaaatca tagaatgcac agagcagcat acatccacat ccctatgccg ccaatccgag   1080

gcgccaacaa cgtgccgtaa aacattttca cacggaggac gaagcggcca gctcctacaa   1140

ggcggtcaag cgcggcaaga agaagtagta gaaacgtgat catctgtatg ccaacatctt   1200

ccgcatcgca cactcaaaaa cactaggaag caaagcgttg ggttctgttc catagcagga   1260

aaaccaattc aaatattttt taacaaacac aattctttac cagttctgtc ttatcctgcg   1320

tgagtcgacc agaatgcaac actaaaaaat gtacaacttc aagatgctat tgatgtgcac   1380

gcaggataca gaacaacttg cttaaattta cttaaaacaa atgtgactat tcaacgccga   1440

aatcattaca acacacactc tcagacctaa tcgaaaaatt caatgaaagt aatggaatat   1500

atatgaaatc gtaattataa gtttgaatta tttgattaat tctcaagttt ttagattttg   1560

ttagccacta agctttaaat tatggatgcc agttagcgtg caaatgaaca caattgattt   1620

gaaggctccg aacgatagaa aacaacaatt accaattccc caaatacatg taattcgtaa   1680
```

-continued ggcctaagta aatgttaacg tgaatttaat taaatggtaa ttacattata atagtaaaaa 1740
aaaaaaaaaa aaa 1753

<210> SEQ ID NO 5
<211> LENGTH: 484
<212> TYPE: PRT
<213> ORGANISM: Human

<400> SEQUENCE: 5

```
Met Ala Ala Thr Glu Pro Glu Leu Leu Asp Asp Gln Glu Ala Lys Arg
 1               5                  10                  15

Glu Ala Glu Thr Phe Lys Glu Gln Gly Asn Ala Tyr Tyr Ala Lys Lys
            20                  25                  30

Asp Tyr Asn Glu Ala Tyr Asn Tyr Tyr Thr Lys Ala Ile Asp Met Cys
        35                  40                  45

Pro Lys Asn Ala Ser Tyr Tyr Gly Asn Arg Ala Ala Thr Leu Met Met
    50                  55                  60

Leu Gly Arg Phe Arg Glu Ala Leu Gly Asp Ala Gln Gln Ser Val Arg
65                  70                  75                  80

Leu Asp Asp Ser Phe Val Arg Gly His Leu Arg Glu Gly Lys Cys His
                85                  90                  95

Leu Ser Leu Gly Asn Ala Met Ala Ala Cys Arg Ser Phe Gln Arg Ala
            100                 105                 110

Leu Glu Leu Asp His Lys Asn Ala Gln Ala Gln Gln Glu Phe Lys Asn
        115                 120                 125

Ala Asn Ala Val Met Glu Tyr Glu Lys Ile Ala Glu Thr Asp Phe Glu
    130                 135                 140

Lys Arg Asp Phe Arg Lys Val Val Phe Cys Met Asp Arg Ala Leu Glu
145                 150                 155                 160

Phe Ala Pro Ala Cys His Arg Phe Lys Ile Leu Lys Ala Glu Cys Leu
                165                 170                 175

Ala Met Leu Gly Arg Tyr Pro Glu Ala Gln Ser Val Ala Ser Asp Ile
            180                 185                 190

Leu Arg Met Asp Ser Thr Asn Ala Asp Ala Leu Tyr Val Arg Gly Leu
        195                 200                 205

Cys Leu Tyr Tyr Glu Asp Cys Ile Glu Lys Ala Val Gln Phe Phe Val
    210                 215                 220

Gln Ala Leu Arg Met Ala Pro Asp His Glu Lys Ala Cys Ile Ala Cys
225                 230                 235                 240

Arg Asn Ala Lys Ala Leu Lys Ala Lys Lys Glu Asp Gly Asn Lys Ala
                245                 250                 255

Phe Lys Glu Gly Asn Tyr Lys Leu Ala Tyr Glu Leu Tyr Thr Glu Ala
            260                 265                 270

Leu Gly Ile Asp Pro Asn Asn Ile Lys Thr Asn Ala Lys Leu Tyr Cys
        275                 280                 285

Asn Arg Gly Thr Val Asn Ser Lys Leu Arg Lys Leu Asp Asp Ala Ile
    290                 295                 300

Glu Asp Cys Thr Asn Ala Val Lys Leu Asp Asp Thr Tyr Ile Lys Ala
305                 310                 315                 320

Tyr Leu Arg Arg Ala Gln Cys Tyr Met Asp Thr Glu Gln Tyr Glu Glu
                325                 330                 335

Ala Val Arg Asp Tyr Glu Lys Val Tyr Gln Thr Glu Lys Thr Lys Glu
            340                 345                 350
```

-continued

```
His Lys Gln Leu Leu Lys Asn Ala Gln Leu Glu Leu Lys Lys Ser Lys
        355                 360                 365

Arg Lys Asp Tyr Tyr Lys Ile Leu Gly Val Asp Lys Asn Ala Ser Glu
    370                 375                 380

Asp Glu Ile Lys Lys Ala Tyr Arg Lys Arg Ala Leu Met His His Pro
385                 390                 395                 400

Asp Arg His Ser Gly Ala Ser Ala Glu Val Gln Lys Glu Glu Glu Lys
                405                 410                 415

Lys Phe Lys Glu Val Gly Glu Ala Phe Thr Ile Leu Ser Asp Pro Lys
            420                 425                 430

Lys Lys Thr Arg Tyr Asp Ser Gly Gln Asp Leu Asp Glu Glu Gly Met
        435                 440                 445

Asn Met Gly Asp Phe Asp Pro Asn Asn Ile Phe Lys Ala Phe Phe Gly
    450                 455                 460

Gly Pro Gly Gly Phe Ser Phe Glu Ala Ser Gly Pro Gly Asn Phe Phe
465                 470                 475                 480

Phe Gln Phe Gly


<210> SEQ ID NO 6
<211> LENGTH: 1756
<212> TYPE: DNA
<213> ORGANISM: Human

<400> SEQUENCE: 6

cggctgccgc ggagtgcgat gtggtaatgg cggcgaccga gccggagctg ctcgacgacc     60

aagaggcgaa gagggaagca gagactttca aggaacaagg aaatgcatac tatgccaaga    120

aagattacaa tgaagcttat aattattata caaaagccat agatatgtgt cctaaaaatg    180

ctagctatta tggtaatcga gcagccacct tgatgatgct tggaaggttc cgggaagctc    240

ttggagatgc acaacagtca gtgaggttgg atgacagttt tgtccgggga catctacgag    300

agggcaagtg ccacctctct ctggggaatg ccatggcagc atgtcgcagc ttccagagag    360

ccctagaact ggatcataaa aatgctcagg cacaacaaga gttcaagaat gctaatgcag    420

tcatggaata tgagaaaata gcagaaacag attttgagaa gcgagatttt cggaaggttg    480

ttttctgcat ggaccgtgcc ctagaatttg cccctgcctg ccatcgcttc aaaatcctca    540

aggcagaatg tttagcaatg ctgggtcgtt atccggaagc acagtctgtg gctagtgaca    600

ttctacgaat ggattccacc aatgcagatg ctctgtatgt acgaggtctt tgcctttatt    660

acgaagattg tattgagaag gcagttcagt ttttcgtaca ggctctcagg atggctcctg    720

accacgagaa ggcctgcatt gcctgcagaa atgccaaagc actcaaagca aagaaagaag    780

atgggaataa agcatttaag gaaggaaatt acaaactagc atatgaactg tacacagaag    840

ccctggggat agaccccaac aatataaaaa caaatgctaa actctactgt aatcggggta    900

cggttaattc caagcttagg aaactagatg atgcaataga agactgcaca aatgcagtga    960

agcttgatga cacttacata aaagcctact tgagaagagc tcagtgttac atggacacag   1020

aacagtatga agaagcagta cgagactatg aaaaagtata ccagacagag aaaacaaaag   1080

aacacaaaca gctcctaaaa aatgcgcagc tggaactgaa gaagagtaag aggaaagatt   1140

actacaagat tctaggagtg gacaagaatg cctctgagga cgagatcaag aaagcttatc   1200

ggaaacgggc cttgatgcac catccagatc ggcatagtgg agccagtgct gaggttcaga   1260

aggaggagga gaagaagttc aaggaagttg gagaggcctt tactatcctc tctgatccca   1320

agaaaaagac tcgctatgac agtggacagg acctagatga ggagggcatg aatatgggtg   1380
```

-continued

```
attttgatcc aaacaatatc ttcaaggcat tctttggcgg tcctggcggc ttcagctttg   1440

aagcatctgg tccagggaat ttcttttttc aatttggcta atgaagggca accacccaga   1500

acccagaaaa tgcagattca ctcagtttaa tcttgaatgt ggaaacagtt cacctcctcc   1560

cttcatcacg tctccgtgtg cttagagcag tttcgttttc tcagttggat gccctgtgtc   1620

tctgtgagtg gggtggagca aagggaacca atgccgaaga ccgagggcag gggagggagg   1680

cgggggtgga cagggaggca gcttgtgaat ttttgtttta ctgtttaact ttattaaaaa   1740

agaaaaaaaa aaaaaa                                                   1756


<210> SEQ ID NO 7
<211> LENGTH: 268
<212> TYPE: PRT
<213> ORGANISM: Human

<400> SEQUENCE: 7

Met Phe Arg Met Leu Asn Ser Ser Phe Glu Asp Asp Pro Phe Phe Ser
 1               5                  10                  15

Glu Ser Ile Leu Ala His Arg Glu Asn Met Arg Gln Met Ile Arg Ser
            20                  25                  30

Phe Ser Glu Pro Phe Gly Arg Asp Leu Leu Ser Ile Ser Asp Gly Arg
        35                  40                  45

Gly Arg Ala His Asn Arg Arg Gly His Asn Asp Gly Glu Asp Ser Leu
    50                  55                  60

Thr His Thr Asp Val Ser Ser Phe Gln Thr Met Asp Gln Met Val Ser
65                  70                  75                  80

Asn Met Arg Asn Tyr Met Gln Lys Leu Glu Arg Asn Phe Gly Gln Leu
                85                  90                  95

Ser Val Asp Pro Asn Gly His Ser Phe Cys Ser Ser Ser Val Met Thr
            100                 105                 110

Tyr Ser Lys Ile Gly Asp Glu Pro Pro Lys Val Phe Gln Ala Ser Thr
        115                 120                 125

Gln Thr Arg Arg Ala Pro Gly Gly Ile Lys Glu Thr Arg Lys Ala Met
    130                 135                 140

Arg Asp Ser Asp Ser Gly Leu Glu Lys Met Ala Ile Gly His His Ile
145                 150                 155                 160

His Asp Arg Ala His Val Ile Lys Lys Ser Lys Asn Lys Lys Thr Gly
                165                 170                 175

Asp Glu Glu Val Asn Gln Glu Phe Ile Asn Met Asn Glu Ser Asp Ala
            180                 185                 190

His Ala Phe Asp Glu Glu Trp Gln Ser Glu Val Leu Lys Tyr Lys Pro
        195                 200                 205

Gly Arg His Asn Leu Gly Asn Thr Arg Met Arg Ser Val Gly His Glu
    210                 215                 220

Asn Pro Gly Ser Arg Glu Leu Lys Arg Arg Glu Lys Pro Gln Gln Ser
225                 230                 235                 240

Pro Ala Ile Glu His Gly Arg Arg Ser Asn Val Leu Gly Asp Lys Leu
                245                 250                 255

His Ile Lys Gly Ser Ser Val Lys Ser Asn Lys Lys
            260                 265


<210> SEQ ID NO 8
<211> LENGTH: 1116
<212> TYPE: DNA
<213> ORGANISM: Human
```

-continued

<400> SEQUENCE: 8
gttatgtgtt cccgtccgta ctggaggcta gctcttgtcg cggccgcggc gagttaacat 60
cgtttttcca atctgtccgc ggctgccgcc acccaagaca gagccagaat gttcaggatg 120
ctgaacagca gttttgagga tgaccccttc ttctctgagt ccattcttgc acaccgagaa 180
aatatgcgac agatgataag aagtttttct gaacccttg gaagagactt gctcagtatc 240
tctgatggta gagggagagc tcataatcgt agaggacata atgatggtga agattctttg 300
actcatacag atgtcagctc tttccagacc atggaccaaa tggtgtcaaa tatgagaaac 360
tatatgcaga aattagaaag aaacttcggt caactttcag tggatccaaa tggacattca 420
ttttgttctt cctcagttat gacttattcc aaaataggag atgaaccgcc aaaggttttt 480
caggcctcaa ctcaaactcg tcgagctcca ggaggaataa aggaaaccag gaaagcaatg 540
agagattctg acagtggact agaaaaaatg gctattggtc atcatatcca tgaccgagct 600
catgtcatta aaaagtcaaa gaacaagaag actggagatg aagaggtcaa ccaggagttc 660
atcaatatga atgaaagcga tgctcatgct tttgatgagg agtggcaaag tgaggttttg 720
aagtacaaac caggacgaca caatctagga aacactagaa tgagaagtgt tggccatgag 780
aatcctggct cccgagaact taaaagaagg gagaaacctc aacaaagtcc agccattgaa 840
catggaagga gatcaaatgt tttgggggac aaactccaca tcaaaggctc atctgtgaaa 900
agcaacaaaa aataaatagc catgcatttg atttgtttag ttttgattgt tttaacagtt 960
agtaatggtg ctgggtaata agcataagac caatctcttg ctgttaaatc agttctgtcc 1020
ttggcaactt tcttctgata tctgaatgtt catgaaggtc ctagctttat attgtccctc 1080
ttttaggaat aaaattttga ttttcaacaa aaaaaa 1116

<210> SEQ ID NO 9
<211> LENGTH: 24333
<212> TYPE: DNA
<213> ORGANISM: Drosophila

<400> SEQUENCE: 9
ttacggttta tttactatta ctctagttaa tcaaataaac tgtataattc ctggcttgta 60
caataatttt gctaacacgc cgatgcgttc gatctttttt tttaccgctc tccgtcgtat 120
tcatcatggt acatattaca tccaacatac tttatttttt ttgggttatt aacattggca 180
atatcgctgc tcgccgccgt tcggttatgc tctataaata aaagggggc gccgctaaaa 240
ttataataaa attttcatgg gtcctaaatc tagtctcgaa atctatgtac aaagtttgct 300
tgcatgctgg ttaggcatag gttcttaacg tattattggg ttgctttatt tccattctgc 360
gcagttgtgc agcctgttta gtgtttgcct ttacggggtt aacatttttt aaaaatgaaa 420
cattagagcg gtaaccttgt tgtctgatta ttggcgtcat taaagcggta tcgccagcac 480
gcgattgatg caaggatacc gattcaatga aataaaaacg aattcagcca aacacaatct 540
ttcatttctt tttttttatc gtacttaatg atagccttag tttctaatgg gactgtgtgc 600
ttcggtgaag gttggggatg attttgggag gcaacaatta tgttctagct tatagcttac 660
agtcctacgc ctactcctat ttctaatatg ttcatcatca gcagttaaaa aacgtttaca 720
aaactcatgc gaaattgaaa tccaataaca aatgcacacg ccgcagtcgc atcggcgtca 780
tctctttctc ctgaccctcg cctatccgca tccagttagg tttgctgctg ctgctgcgcc 840
gacggttgtc gccgactgaa gccaccgccg gcggacagat gtcgttgcag ggctcgctgc 900

-continued

```
tgctggaact tggcgctgcc tggtcctccg aagcggttga acttgaactt gttgcgctgc    960
tggaagttct ggcgatagtt ctgattgtag aatcgcggaa atcctccacc tccgccgttc   1020
ttgttccagc gcttctggcc ctcgtactcc tggaatggat tgtacccggg cgtgctgttg   1080
ctggcattgt ttcccttagc cgaaccggac ttcaccttcc gctgacgtcc acgatccatc   1140
tcgttctctt cgtcgtcgtc gatgtcccgc tgccgctgct cacgcgcatc caccagtagc   1200
tacggaaaac agaatatcaa gcattaggct agagttcgga ccttgtgaat ggggaggctt   1260
ggctggctgg ctgacgcatg cgctagttaa tggagcttat gcagatgagt acggtcgctc   1320
gcgaacaagc actgggaata tgcacattgt attcgaaatg ggtgagtggc ttacggttca   1380
cggttcactg taacaggtta tcaggcaaaa cggtaacggc acaacggttg aatttatggc   1440
gtatcaggcg gttgaaatga aagaaacaac gtgccggcca gcagtcaaat cataagcttc   1500
attgcacggg aaaacggatg cggagtcatc gggtgaatta cctaggctcc ggtgcagtca   1560
ctctctcccg caatgacttt tgcaactctc tctacacttt tcacgctcgc tgaacggagg   1620
acgcgttgtg gtgaccgccc ggttgggaac ggataccagc aacgcagcca tcacagacta   1680
ttcggggtaa tcgtattatt tgtatttgtt ttgtgtggta tgtgcttagt ggggaaaaag   1740
aagaagcgtc gcctctgccg ccgacgcttc tacctcctac cggccgtccg tgagacgatc   1800
cggatcgggt gcgtcagcgg tcgtgtctgt taccgccact gcaattacga ccacatcttt   1860
actgtcactg ccactagtca ctgccgcgtc gactgcaacc gagccctcga cgatatcgct   1920
gccttccaca ctgccgtgac cagctatccg tttcgcacaa accaactcaa aagtctaaat   1980
gaatggggat aatgtggaaa caaatgcaaa ttacaaacaa gttcgtttag taaatcaact   2040
caatcgaatt gcattttatg caacagctaa gcgaacgaca tagaaaacaa aaaagaagac   2100
caaagagcca gttaaataat aaagaattag ttaaacccgc aaaaagagaa ccaatttatg   2160
tacattttca tcgtattaag cccgcaactt gttatttttg aagcacagac ccaaagaaag   2220
tgttaaccat gcatagattt agtatctacg ttagtgacat ggtcacaagg gatagataag   2280
cgcttcaagg tgaatgcctc tctaaactca cctccttttc gagctccgcg ggcttgccat   2340
tccaactgag cacgggggag ccgtatccac gatacgattg cttcagcagc tcattgatgg   2400
tgctcccatt cgaggtggca ttgctctggt agccattgcc caccccttggc tgctggtgcg   2460
acttgagcgc actgccgttg agcaactttt ggcgcttggc gcctggcgtt gcgggcgagt   2520
ccgtggaggg cttgctactc gagaagggat tgcgatggtt cttgttcggc gtcggaattt   2580
tcaccggcga tccctccacc accacgacgt caacatcatc ttcgatggca tcgacctcat   2640
cgttacgcgt aactttccag atacccgttt tcgatttgat gaccgctggc gagggtggcg   2700
tctttggcga tggtggtgct ttgctttgag actgtgattg cttctgtggg tgccagccat   2760
tcgttagctg aatgctgggc tcctcctcat cgtcgtcctc atcactgtct gcggactttt   2820
ttaggctctt gaatatctcg tctatggcat cagtcttttg tttgctgttg ttaacgtgaa   2880
ccgatgacga ggctgagccg ttggtgtggc tgccattggt cttactgtga ccattggtct   2940
ggccagactc ttggtccgac tcgctagaat cctccccact tggacgcttg cggggattcg   3000
gtagaggcgc ctcctcctcc tcagatgctg attcgtaggg cacaagactt ttcagtggcg   3060
ttttgacggg agtctttact tgaatcttta caggagactt tgccttaggc tccgtatgat   3120
tctccgtcat attgggcatg ctcggtagct gggctgtcgt tggtctgggc ttcatctcat   3180
cctcgatgtc ttcatcatcc gaggaaattg gcagatattg ttgctggttt attgatttat   3240
ggttgctgct gctgttgctg cttggggagg aacttttgtt accatttgca gtgggagctg   3300
```

-continued

```
aagtagcttc gcctttagcg tgagcgccaa ccagtggagg cttcgcagtg tcctgaaact   3360
ttccggtacc cagctggagt ccgttctgtg gactttgctg gttttgttgc ttgaactgga   3420
tggcggtttt ctgggcattt ccattagtgt aaccgtttgc tccacccgcc ggcagttgag   3480
gaccaatgaa acgcgttggt gaaggcgaag acacagtcgc cgccggcact ggcgttgtgc   3540
tgtgtccgtt ggtcaaacgc actccattgg gcctgttggc cgccggactg gcagcctgtg   3600
agaggtccag ttcgaaaaac attatatagg catttgtgtt gcacacactg tgcattgcga   3660
ttggccgcac gtagctgtcg tcgaagttgt aaaagctgcc cgtatccgtg gagccaatgg   3720
ccgtgtagtg accgcagtgc tgggacgccc ccaagtgagt gaccatcgac accaggcgat   3780
aggtgagcgg ttgagcctga gctgcttgtg aacgggctgc gtatttgctc aaatctatgc   3840
gtgacttgaa ggaaatctgc ttggtcagtt tgttgccgat catggagaat cgcttcagct   3900
gtatacaaag cgtgattggg gcacgctcca aagagaattg ctttgtggca gatacctgca   3960
agcgatacgt ttaaataaaa tgaactacag aacaaaggtc acaaagacct accttcttct   4020
tgcatccctc gcacttgtag cccatatcct ctagccgttc gcgagaaaag tgtccctcga   4080
aagcatcctc caaggagtct gccttgcgga tgtcgagcaa cagatcctgg aagtgctgaa   4140
acgtaatgga cacatggttg cagctcagac agcgcacctc gctgcgcaga tagccgccaa   4200
agatctgtcc cagcggcgtg gtctccttaa ccaactgatc cagctctttg tagttacgaa   4260
accgcatcaa atacgcccgc tccatggcct cgaccaggaa gcgcaggaac tcgtgcgcat   4320
cctcttggcg accaacgacc atgtgtttgc agatctgctt tagcttcgag tagatgagga   4380
agggtctgac ggccgactga ttgctttggg tggccaaaag tgttttggtc atggcgcaaa   4440
tgatgcaacc gctgccaggt tcggccacat tgcagtcagc cagatgcgcc tgctccgaaa   4500
cgagccaatt ggccagggcg ggtatgtgca ggagcgcctg aagcgttgag ttgaggtagc   4560
aggtgttgcc cacattgatc atgcccgtgc ccacctgcca tttgcgctcc gactgcttcc   4620
agccaatgcg tatgttctcc cgcggataga ggaccctctt cggcttgggc agctcattgg   4680
gattgcttgt cggatgctga tgattgtggt ggttgatgtg gtgcgactga ttgttcgggt   4740
gctccgcttg cttgcgggcg ccgttattgt ctgcaaaggt aaagaggacg gtagacagtt   4800
taagcacgtg ccacaggaga aggcagcagg gagacaggaa cagcttgtag agcagccaca   4860
gggcgaaccc gtccaccatt atcacagtca taatgcattt attggaagaa ttcccttctg   4920
cagattaagt cacttgatcc gcgctgctat gaaatataaa taaaacgagc agtgctcgct   4980
gtggaaactg ctgacacaca atcgcgcttc catcacctgt tcgcagtgtt ggaaagggta   5040
cacatttgtt gtacctaggc accggactgt gcagcattaa gatagctatt ctattgaaca   5100
aagaaacttg aacacaaagt atacgccgaa aaaaatttcc agtactagat tttgaaatac   5160
aattctttga acatcgttac agaatgtgat atcaccagat tttatctgaa aatattttca   5220
cagcatcgta atttcatatg taccctgaat atgtatcttg cagttttgtt tgggaaagtg   5280
taccaatcga ggtacttatc ctggtacaca tatctcagat attacccagc actattgtat   5340
ctttgataac agctagcgtg tgagcgggat ggcgactggc agaagaagaa atttaaactg   5400
ataacagcaa gcgaatgaga gggatggcga gtggtgaagc agtccaagtg tctgctgccg   5460
acgaatacag tggtctcgtt ctggcgtagg gggttggggc ggcagtgttg ccaactgaat   5520
ttttggcgcg acctaacagt ggttgttgta ggcccaatgc tcccccct tt tattgtcttt   5580
gtaactgtgt tcgaggcatt gaccaggcca aaaaaaagaa aagaaaagaa aagtcgaaac   5640
```

-continued

```
atcgtgtaac agctcctggt gctgagcttt gtgtccactt cctgctctgt gtgaatcact   5700
tctgcgagtc tggcctttgt ttgtgctctt tttatcacgc aaaagcagat tgcggcgcat   5760
ttaccgcatc taaaaaaata aagcaaagcc aataaaagca ccgctggggc tggccatgtg   5820
cgggggaaag agacggaact acggagggga gccctcgtgc tttttgtctt tttttccttc   5880
tttcatttgc cgctggaaat acagcacgtt tttttccgcc acaacttctg tgaatcagaa   5940
gtttggaaga ggcggctctg ttgttgctgc tgctgctgtc acttttccag cttactcttt   6000
acggcgttgt acttgttttg ctttttccgc gtattccttt gcattctgtt tacacgtaca   6060
ccacccaaaa acgccgtcac acacggacac acacgcacgc actcacatac agaagcgcct   6120
aaaaagtaca ggtatgctgc gctgccgacg tcgactgcac tgccgacaaa atgcaggcgg   6180
agcaataaaa aaaatatgtt tgcggaaaaa catcacacgt gatttgtgga gggatattcc   6240
caaaagattt ggcaaaaaca aacgggacga tacataaata catttaagta tatatacatc   6300
ttatatatat aatatgaaga tatagcacat ggaaaattgc gcaaaaaattg ccacacaaag  6360
aagaaacaca gacgaaggcg cagacggaaa aagccacttt tgcaagcaac ttttggattt   6420
tacattttgt tgtatcttta cacagtgtac tcaccatgtc catttgcgcc cacaagtttg   6480
cctgtattgt ttttgccact aaagccattg atggcgcctg gatttcccgg cttgatgaca   6540
atatatttgg acttgaggtt ctccagcacc gattcgtggt agttgggcac ctcctcgtat   6600
tcgattttgg ccatcaggat gcgtttggca ttggccacga tgtgattttg caggctgccg   6660
ttggtgtcct cgccgctctt ggcctggtca gtcgacgagc cggcggagga gttgccgcca   6720
agggattcgc gcagcgctgc gttgacgaca ttcgccgttt cgcatacggc catcgaaacg   6780
ggcatggcga tgctccggct ggggatttgc ggtggaattt tgaacgggtg tgaggggcgt   6840
ggtgtggcgt gtgttggtgg ttttcgccac ccagttagct aatgcacatg ggcgtgcgat   6900
ccaaagcaga tactagagat ccttctgcac agcccacacg tccttcaaaa ctctcctact   6960
gctctacgct cacttttctc ctcgcccctc tctcgaacac ttcttgtttc acacaccgac   7020
tgcgacaccg acacacgcac actaacgcac tcgggagcac tcttcttttt ctggcttttt   7080
cgcgctgcga tctcgatctg ttggcctact gagcattacg attaagaaac gttcgctcac   7140
aaattgatct gtttcaattt cgtgcgcggc caggcatttt agaacgaaaa gtctgctttc   7200
gaaaataatg gcaattcctt ccctcgtgtt tcttccgact gcggattctc ttttcgcttc   7260
attttcgtca tttggggatg ccaactcgcg agtggccaag tgacgcgata ggcctctcga   7320
aatgtcctaa agcatttcac gatatttaca aaaatgtatt tcgatgtttt cttaacaata   7380
aaaaattggt ttaaatttaa taagacattt gttaccttga atatgtaagc aatatcttat   7440
tgaaaggctt gcagcgacat tttttattta tgcctactat tcaagttata aatttaattt   7500
ttataacggt atttttacac cttatcagca catatcgata agtgtgattg ggaacgacaa   7560
cccatcggca caatgttgat gcaattgttg agctagcctt cataattagt cgcaatcaat   7620
cgagcagaat ggcttcatcc acaggtctcc tggtggtgtc caacatcaag caccttggca   7680
aatccctgcg agccatcgag aagtacgtga attcactgta catccaccta aatgtggcgg   7740
ggtcaacgtc cacgacgtca ccagttccac cgcctccggt ttggggtcgt ctaatctcgc   7800
agctgtacgc caacagcagc agctatgtgg gcaagcagtt ggaccttcgc gtccttgtct   7860
ctcccctacg accaggtgcc aatggatccc tgaagttgcg ccagcccgtc gacctaatct   7920
tctcggatgc acatcatccg gagctgtgcg acaggcttcg cgcggatctt aacatcagca   7980
agccaacaat cttcctggat gactcggtca tctcggattt aagtgcccag caggatgaca   8040
```

-continued

```
cccagccgcc taaggtgtat ccctcggttg tcctgggcgg aacattcgat cgcatccatc   8100
tgggacacaa gatattcctc acccaggctg tactgcgcac ctgcaagcgt ttggttgtgg   8160
gcgtaaccac ctccgccatg acgaagggta agacgggcat gaattggcaa aataaaacgc   8220
ttatcttaac gaccattctt atcgctgtct gcaggaaaga cgctgccgga cttgattttg   8280
cccgtggaag agcgcatcgc ccggctaagg gagttcctgg tggacataga tgatacgctg   8340
cagtacgaaa ttgtgcccat cgatgatccc tttggtccca cgcaagtgga tcctgacctg   8400
gacatgattg tggtcagtgc ggagacgttg cgaggagggc agaaggtcaa cgaggtacgc   8460
tccgctaagc aactgcgcga gctggagatc tttgtgattg acattgttga aagcaacgtg   8520
catgatggca tccacgagac caaggtcagc tcgagtaaca cacgcatcga tctgctggga   8580
acccgctgga gaaggccgga gccacgacca cagctcccgc cgcgccctta cattattgga   8640
ctcactggcg gcatcgcatc tggcaagagc aagatgggcg agagattggc caacatgggc   8700
gcccacgtga tcgactgcga taaggtggcg cacgatgttt acgaacctgg tcagttgtgc   8760
tacacccgaa ttgtgcagca cttcggacag ggtattgttt cagacgatgg tcgcatcgat   8820
cggtccaagc tgggaccctt ggtgtttgcc gatcccaagc agttgcaagc actcaacggc   8880
attgtctggc cggaacttat tgcggaggtt aacaggcggc tggatgcact gcgttcccag   8940
gcggacgtgc cgcgtgtggt ggtcctggag gcagcggtgc tgctgcgagc gggctgggag   9000
accaattgcc atgaggtgtg gtccatgatt gtgccaccgg atgaggctgt gcggcggatt   9060
attgagcgca acaagttgag cgaagtggag gcccaaaagc gactggccag tcaggtgccc   9120
aattctgaga tcgtggccaa gtcgcatgtg atattcagtt cgcaatggga tcacgaattc   9180
acccagaaac aggcggagcg tgcgtggaaa atgcttacca aggaactgga ctcttaccag   9240
agcagccttt aacccgatgg atatttagat tatcttgttg atccttattt tgtatgattt   9300
tttatgcatt tgttgtatat tgtttagttg taagtccaaa gttgaaaaga aatgctggga   9360
cgtcattggg gaaaaacgct gaaaatttca atggaacctt agtggctctc gcccttcttg   9420
ccagccactc gcttgaagtc gttcatcttg gtggtcatga tgggggaacc gatgaagccg   9480
atataatcaa tctgcgtcac atcgccacct gactgattgt tcttcacgaa gatttggatg   9540
ttttgcacat tctggaactt gacgtagcgc agattcacgg gcactccact ctccagctcc   9600
ttctgagcca ggctgcaaaa tggattgaac agtgagaaga gctaagcagc catagagaag   9660
gcaatagcta ccttagatcc tgcacactgt tcatggactc ggccatgtca aagtcaatcg   9720
tgcggggctg gttaatgaac agcttcacat ccttgggacc caggtgcgaa ggtgccttga   9780
acttcaaaga gtggatcttc acagcctgat taaaggtgat ggacaggatg agctgctcat   9840
cgcaatcgga ctgcaggtag ccaccggcgg aggccagggc gtgctttaag ttgtggtcat   9900
cagcttcgtt gaggcactcg cactcctgct tcgaaataaa tgtattcagt tccatctgta   9960
agaaggatta gggattattt ttggaacatt tccaaatact gcactatatt accaatccct  10020
gcccgtaatc ctcgcccccc tcctcgccac cggatgtacc gatgtgctcc tggatcttgg  10080
cctcgagccc attgacgtcc gcaccctgga cgcgatcgat cttggtcctg ttcctgtaga  10140
agatgaatgt tggcatggcc gaaacgccct gtccagcagc cgtgtcctgg cacttgtcca  10200
catccacttt caggaagatg gcctttgggt actttgttgg aaacgtctcg aagatgggcg  10260
caatccgctt gcagggacca caccacgaag ctgtgaagtc caccacaacc aattgaatgc  10320
ccgcttgggc caactccgcc tggaagtggg actcgtcgtt gatcacgcgc acggacatgg  10380
```

-continued

```
tgataggatt aggtttctat taattgagct tttgtttcgg cagccgaatt ggatttaagc  10440
aagtaaatgt tattattaac gttcaatgca aattttttt gttaaagatg acttgtaata  10500
tgcatttagt ccaaattcgt gctaagaaaa ataccgaatg cggtattcca caagcggtca  10560
cactgtgatg gtatcgatat ttcgagctct ttgacttcct atttttagag ggaccattta  10620
tgtgtaatag aaaaaaaccg aaacttaata tttaaacttt tattgaaata ttagtggatt  10680
acaatatgta aaactatgaa atattctcat ttgatatagc tcaaagtgtt atttaaaatt  10740
cattcagtgt ttacgactag caatctacgc tttcacgctc atcttaagct taccgcccat  10800
ttgccagggt tgtcaaggcg aatgagcggt cccaccatac acgccactgg aactttcgat  10860
acctgcgctg cgcctggcca cacgttcatt acctcgtggt gtttcagtcg gtcgcatttt  10920
cattaagtcg ccattttaaa attattagag tcaagtacaa tggcagatgt ggaaaaggag  10980
cccgagaaga ccatcgccga ggatttggtg gtgaccaagt ataagttggc cggcgaaatc  11040
gtcaacagtg agtattcctt ggccggaaac agcgaacgct ggccgattcc tggagtcgct  11100
gctacgtggc gcttacacaa tgcaccgaat gccgctttcc cttgtgcgcc acgcgttggt  11160
taatctgcct atttctggac tctgtctgct cgtttaattt tagaaaccct caaggcggta  11220
attggactct gcgtggttga tgcctccgtc cgggagatct gcacccaggg cgacaatcag  11280
ctcaccgagg agaccggcaa agtaagtggt ggccacctgg cggtcattcg cgccaatttc  11340
atgtccaatg attaagactt acacctttga gggtttcccg atggcgagcc atgtgctgtg  11400
cgggctgggg atcacctcgt ggtcgccagg cgcacgcggg gactccaatg ctccacgtgc  11460
ccggcttgtg tgctctccaa aaggtcccga ggatttacag attatgagat ctgaggacac  11520
accgcgcact atcattgata tatagtacaa cgaacaagca atctaatgct tttatcgatc  11580
tttcacaaac aggtatacaa aaaggagaaa gacctgaaga agggcattgc ctttcccacc  11640
tgtctgtccg tcaacaactg tgtctgccac ttctcgccag ccaaaaacga tgctgactac  11700
acgttaaagg ccggtgatgt ggtcaaaatg taagttgaac ctcctattcc acatataccg  11760
ccactaaata cgtaacattt cttttctaca gcgatctggg tgcccacatt gatggtttca  11820
ttgccgtggc cgctcacaca attgtggtag gcgctgctgc ggatcagaag atcagtggtc  11880
gccaggccga tgtcatcctc gccgcctact gggctgtcca ggctgcctta cgtctgctca  11940
agtccggcgc caatgtgagt cctcccttac ttctaggtaa tcctccgtta atccctgcaa  12000
gaaacggatt gtctgccgcg attctccagc gactgaacat ctcaacactt gcaaagatca  12060
gctgtggcag ctggtaattg ccctggccta ttattcagga ctggaggctt cttgtcagtt  12120
gtccacaagg ttatttcttc tgcaggcaac ggattgactg cgctcaaact ctgacacaga  12180
tcagctcaac acctgcggat agaaactgtg tcaatttcgt gaactgaaca agttcattcc  12240
atagaagtgt tcggtcttta aatttgtcca catctccagt ttatagatat gtcggaattg  12300
taatctgcag gcaacggatt gtctgctgcc ttaactcgtg gctcagcaca gctcaacgtc  12360
tgcagagatc aacagtgtcg atttcgtgaa ctgaacaagt ttagatactt gaaatgttcg  12420
gtctttaaag ttgtccacaa tcgcaatgat aatgccgatc agttattgtt attttgcgtt  12480
atctatagta tactatgata tttgattaag attagtcaaa gggaattgga atgttttctt  12540
tatctctgct ttgaactatt tccattttat ttcatactta atatttatgt ttcaattctg  12600
tatccttaca gaactactcc ctcaccgatg cagtgcaaca aatcagcgag tcgtataagt  12660
gcaagcccat tgagggcatg ctcagtcacg agctgaagca gttcaaaatt gacggcgaga  12720
agacgatcat acagaacccc agcgaggcgc agcgcaagga gcatgagaag tgcaccttcg  12780
```

-continued aaacgtacga ggtgtatgcc atcgatgtta tcgtcagtac cggcgaagga gtggttagta 12840
atccatcaat agacactaca tctccactaa tttgttcgat gattaaaaac acgcgcttga 12900
ggctgacttt gctggaatgc ggtgtttgtt gcgagagtga cttgtttgct cggcgttttt 12960
ttatactaaa atgcggcacg tgcagacacc aagttccggc tggctgttgt ccgaagattg 13020
caagattatg agatctgaga acgccaaatt taagctggat cctggatcat cgcagccaga 13080
gcattattgc taacattatt cgtattcgtt gcagggacgc gaaaaggaca ccaaggtctc 13140
aatttacaag aagtctgagg agaactacat gctcaagatg aaggcgtccc gtgctctgct 13200
ggcagaggtg aaaaccaagt acggaaacat gccattcaac atccgcagct tcgaggagga 13260
gaccaaggcc cgcatgggag ttgttgagtg cgtcggccac aagatgattg agcccttcca 13320
agtgctgtac gagaagccat gtaagtgtga tgcatattat tattaatcct attccctatt 13380
atgcgagttg gcagaactta attccggacc tggtacacct tcgggtgcta agtgcggcca 13440
gacattttgc cagaacaaat tccaggcatt gtcgtcttca gcagttgcct cagtgtggcc 13500
tctgtctgaa catggcactg tcacaatcgt atccaatcta ttaacctgtt ttcttatact 13560
tattaaagtt aatttagaga ctaaactagt ttgagcaacc tttataaagt tcgaatttta 13620
gccggaagta atagcaaagt taaacaatcc ttttccttat cttgcattac agccgagatt 13680
gtggcgcagt ttaagcacac ggttctgctc atgcctaacg gcgtcaactt ggtcaccggc 13740
atcccattcg aggcggagaa ctatgtgagc gagtacagtg ttgcgcagga ggagctcaag 13800
gtaagctgca acaatttcct tgtattcacg atgcgtactc aatgaaatct caacttttg 13860
cagactctgc tcgcgcagcc tttgggtcct gtgaagggca agggtaaggg caagaaggca 13920
acagctgggg cggcgacaaa ggtggaaacg gcgccggccg tggagaccaa ggcatagacc 13980
agcccgctga tgatgatccg caccgccaag ccatcaacgg aaacacaatg tgaacaattg 14040
cgctgcccaa cgctgcgctc cacagatttt tactatcgaa ttcgttgcgt attagaggac 14100
ccttttgaca acagaacagg acagaagaga agacggcaac aatttgagga tacatttccc 14160
cagaaatcct ccatccatca acaaggcggg cggtcggtcg gtcccgcgcc aactttacct 14220
ctttatttcc tttactataa gctgccttcg tttatcggtc tgttcaacat catcgcaacg 14280
aaaaagcaaa gcaagaactg tcatcaaatt gtaacaattt taacgctaaa tgatcttaaa 14340
atataattca agtgaaacgt tattaacgct gcgtagtagg tattaaataa aattaacatt 14400
ttctataaaa cagccgataa atgccaaacg atttttcatt tatttacttt ccgctggcgc 14460
ccaattttaa ttcgatttcg atacgcttct cattctaata aatgcacttg cgagttgtgt 14520
ttattttata cgtttaattt agttttgatg ttcacattca cattatacaa tttgtaattt 14580
agatttcttg ccttttgtta ttttaaattt tacagtctca tctttgaact cttgtattac 14640
gaaagttgca agaataactt cgttatgtta aacgtcactt agtgctgtgc tcacttggcc 14700
accccagttg tccatcccag atccaatccc aacaagacca gaccaattcg atgccgtata 14760
cggcgacttt gcccaactcg ctgacctctt cccttgcgtc aaacaaaata aagaacaaca 14820
aaaaacgcaa ttgctgcgga tgaagtatag aaaacacgag cagcacttgc agacgacaaa 14880
gatatgtggc cggtgatcaa aagaggatct gggatttaat ggtctgccgt cgcttacata 14940
catggtttgg tgtacttttt ttttttttgt tatgatcgcc gcgactgttt tctactcgcc 15000
agactaatta ttgacatgca cgtccatcgg tgcggaggcg gtcacgttgc tcgacttctc 15060
cggagagtcc aggtaaatct tcaaggcacg ttcccggcgc tgcgcatacc gcgtggtgga 15120

-continued

```
cacgcagccc acccgatcca gtcgtgcctt ctccctggcg ttcatcaggc gtcgctcctc  15180
cagcgtcagc tctcgcgcag gtaccgtcct atctctgttg aattcattgg ttagtctagg  15240
aactgaactg ccacttgctc cacgcttact tgtacaggta gatgtttcct gtctgtgtgc  15300
tattaagcgg atatttgtcc agggtggtgg gcacggagta ccaactgctg gactcgttaa  15360
cacttaacgc tgatatgctt gtgcagggga agttgctgtt caactgcaga gaagaccaat  15420
tagatcaata tacacagtag aacgcaattt tacgaacctt catatagctc agtttgtcta  15480
ttgggatgtc gctgatctgt gataatgaaa gtctgatttc gctgtcctct gcagaagata  15540
cgagttcgat ttactgctta cagggcaata tacagattta acttacggtc caaagtgatt  15600
tcttggaact ttccaaactc cagtttagcc ggacaccacc gtcttacaaa taaagtcaga  15660
gaatcgtcct tgggctgcgg gtccacttcc tcctcgcact cttgcacaat gaactgaaat  15720
ggtgtgatat aaaatccaag ttaagttttt ttctcatcac agagacaggg gaacccacct  15780
ccgctgcgat gctggagcgc atgtcgcagt agagcgtttc atcgtcggac agaattttga  15840
tgggaatacg tccgcccttc agccagatgc gacagttttg cacagacagt gtggcgtact  15900
tggcgtctat gcgatgcagc ttggccacca gttccttctt ggcctgctcc gccgtggtgt  15960
tggcattgta gacccactcg catacgcaag gcagtttgga cgtctcgtta tcaatgtccg  16020
ccagtcgcag gaagtgaatc ttggccttga actcgtccgg ctccagcgtc ttacccaact  16080
ccaccgtcag tgtttcgcct tctatgagat gtaccaacga gttgttctgg ttgttcgaca  16140
gattattatc gtgtttccgc tgcagtttaa agtgggcggc gggcacttgg atcagctgct  16200
cgatgtgttt cttaaaggcc cccattcgca tgtgtgtgcc caccagcagc ttataggcac  16260
gcgtgggctt acgcagctga gcctcttcgt cggactggtg accagaactg gaaccggtgc  16320
caaccacatc cacgcactcg acctttgtgg cgtagaagaa gtggttggtg ctggtgggca  16380
ggagcagcgg atccaccaca tcggccgccg cataactgcc gtttccattg cagtaggcat  16440
gaacgcgcat catggcatcg tgtgaggctg cttcgtcctc cggactagac agctgcggcg  16500
agtgactggt ggaactgact tggctgtcgc ctccaccgcg atgtgccatg ttgtccgtct  16560
ccaccagagt tcggtctccg tcgctcagac tactgtcctc cgagttggac tcgtggccgt  16620
ggctgggact gggttgtgac atgggttcca ctagatctcg cttgtagcgc ctccaatcgt  16680
agtcgttgct ggatgacatg tgaccaggtg ccacgccatt catcattgca gcatccacaa  16740
catcaccccc gctggcgcac tgaaaggaca gccaaaaatt aaccttagtt ataaacccaa  16800
cagctgtata acctacctcg actgactcaa cggtgggcac accgagcatc tcaagggtcg  16860
cggcatccgt gttgggtacg ttcaagtaga agtatgttat ggacttaaac tgggtgttgg  16920
ccatgttctg gagatgttgc agggcctccg gcgtcggatg cggatcgtag gacacgaaag  16980
ccttcggcac cgtggcgcgc accgtggcga gtaggaactg ctgctcgcta atgtgcaaac  17040
ggagggcgat cgagcggcga aggacgtcgc tggcttcccg ctcccgcgct gctgagtaaa  17100
ccaggaaggg accgtccatc gccatggtcg atagatctac cttaaacaca taccaagtaa  17160
tgccgttcgg cggatagacc tcaaactctt ggtcctcggc ccggtactcc agcaggaagt  17220
cgagactgta gttctgcgcc gcgcgcagtt cggtcaaagc tgggtctgtg caactctcca  17280
gggactgaat aatcgtgtcc atcgaggagt tgtaagccac caaacgacag cgggaaagcg  17340
gcgcgaattg ttccacattc aacatctcat aggccgacat gaggaccaag ttgatgttga  17400
aactctgcga tacgtacact ctggtaatct tcatcttctt cagggaggga ttatagaagt  17460
agacgcgcgg cttgtacaaa tccggaagag ccaagtccgt aaccgtgata tgcctgccca  17520
```

-continued ggcgggacac gcgcgtctcc tcctccgagt gcagctttgg tagcagcgtt ttgatgtgct 17580
caggaaagtc ggccaccttg gcgactagct cgtttctttt ggcatccacc tgccggtaca 17640
tcaacatgta tgcattggtg ctggaggtgt aggcactgga gtagtagctc ccgttgggtc 17700
cgccaaacga acgttggatg tcctcttggg tgatctatgg atagatagtc gttcaatatt 17760
ttctcaagtt atgaatgtgt tgcgaaaacc tacactagtc acgttctgat cgttaaaaca 17820
gaaccactcg ttgttgtcga agtccttaat ataagcatag tagtgtccgc ccgaagcgct 17880
gcctgaatga atcatgatgg cgaacagttc gtagagatac ggaccggatc cttgcttggc 17940
gctcttgctg gtgctgctgc tcatgtcgat gccttcatcc tcgtcgttca gatcgttttc 18000
gtgctgacta gagctcgctg tggtcaccac gccgctgctc aaattatcgt cctccatggc 18060
ggatccacta tccgccgtgc tgcaatcgtc cacggtgccg ttgagctgag agttttgctc 18120
accgctgttt ccacttcggt taatgaacgt gttcaggttg agcgtctgag ggaaggtcac 18180
tctgaaatag agggcgagca tggaattaaa tgcttatgga ttatggcaaa gagactaacc 18240
tgtcgtttaa tttgatgcgg tgcatggtct ggtagtcaaa gtcaaagcgt ttaaggtgca 18300
gcgtgaggat gtagggaaag gacttaaagt gcagtccctt gtgggcgtcg cattttttct 18360
tgcacttctc gcacagatac tggttattgc catcgagtgt ttcgggctga acgaaggcac 18420
gcagagcttc ctcgatgctg ccgtatgcgg agctgcttcc aaagggcctc acagggagcg 18480
ggatatctag aaaggtgtcc tcgcgcgtct tctcggtatt gcactccaaa cacttgacat 18540
aatcattcat cttgccctcg tacagattag agatgagatt tgcctgctta gtgttcttga 18600
atttgtgctc cagagcgtcg aacataactc ggcacagttc ctggatatcg tgctgctgcc 18660
atgcctccgt cgagtcccac ccaaagctgc gagtcaggtc tgtggtttct accgccgctt 18720
tgggcgaggt ctgcaagttg aggaagagct tttgcagttg gtatggtatg ttcttggcct 18780
cgttgtcatt gtcgaactcc cagcggtaca gagcatttct gaactcgggt gtcataaaga 18840
gtgcctgcag caagctgttt agatagcagg tcatggcttg gttgaccaaa ccaacatatc 18900
ccctgggacc caagctcgcc tgccttgcct ctgcctcagt ttctgtggtg gccgaggaca 18960
cgaagtccgc acccgttgtg ttgactctct gccatgctcg caactcatcg cctccatact 19020
tgcgacgata gaagtttgac agagccgggt acgtaccatc gtctgttcca attgtggatg 19080
ggtctgtcac tccggtcaca ccctcgacgt ccgagtcacc ggtcggagct ccgtaatcgt 19140
atccaggtcc cagcattgtc ggactagcag atgctccgag tgccaggtcg tcatccgaca 19200
attgttcagc atctgagatg aaaagatctg aaggagcatc gtccaccggt gagattaggt 19260
ttctaccttg tggatacagc tgcagttgct cagagagctg ttgcttgctc agggtgtcta 19320
ctggttcgca gtccaactct ttgatgggtg atgacggctt gattggactc agcaactcta 19380
aagtcggctt agaagtgacc ttggccgttt tcttggccac aggactctcc gaagaagtgt 19440
ttttagagtt tatctctgta gacagctcgg gacattcttc agggctagcc ctgggagctt 19500
tttccgaacc gggcttggag atctttgctg cagtcgtctt gatcttggaa gtcttttcgg 19560
gacttgattc cgaactgatg ctggtcttag ccaaagagtc ctcactcgtc gtcttggcct 19620
tgcttggaga ggaagatccc gaagctggct tctttttcgt tttctcacca actacgcgtt 19680
tcttcttctc gccggtggca ggactcttgg ccttctcgcc gtccgacttc ataacctttt 19740
tgactaccac tcttttaatg ggtaactcaa agcgtttggt cacgtcacca tcccaactgc 19800
cggagggcag caggatcaag tgattcttca gctggggctc aaaaccagcc acttcgtaca 19860

-continued

```
tcagctgaga ttccagggca ttcagattga cctaaagtaa aggggaattc aattagcggt  19920
ttattagaac ctcaagatgt gcagatattt ttaccagatc cttgttatcg tgtggctgca  19980
gcaacagctc gaacttttcg tacgagaact gcgtgccaat aaggtcaatc acgcgtttca  20040
ccgtgaagtg ggagcggacc actacgttga tcttcttttg ctccgagccg ggtgtctggt  20100
caaagaccga gacggtgcac tgctcgctct ccttgtccgt catgtccagc ccgcggaata  20160
atcaagtgat ggtggagaaa accctgcaaa aagattgtag gcgaaacgtt ggctttactt  20220
atgaattttg tctggagttt tctttttatt ttttttttatt tctttatttt agaattaaaa  20280
aggtgacacg acacctttga cgttttcggc ggggccaagt tcctggacat gacgatgctt  20340
cttggcccat agtaaataag gaagagatgc ccagccccaa attactgcga aatcttcttg  20400
ttttcgaccc cattcgcgaa taaagcggca gaaaccaaga agattccgtc ccacctcccg  20460
cagccgcaga tattgacgtg ctccgggttt gcttttcgcg ccttatttgt acgggccagc  20520
accagttgcc gtatacatat atatatatat atatagatag atatacacat atagcacgta  20580
cacccaatcg agcatcgact gcccccccgaa atcgacgtcg tgactaacgc gcaggggaat  20640
ttcgtaaaca accggccatc agagttgcct ccggaggatg ctacgggaat tattatttgc  20700
ctccaatgga ctaccaacgt catcatcatc atcatgacca tagctatcac catcgggcgt  20760
accgaatgca taaatttcag tgcaaatgtc gctccatgtt tcagctggct tcctttgtgg  20820
ctccccgcaa gactctgtaa cggaagtggt ggctattata cgaacgaata tctggcgcct  20880
tcaattcggc agtgcgcata ttgcaagtgg acggtggaca tatccatatg tacaaattaa  20940
tacttatcgg acatcagcgt gaacactgcg aattattcta gaaacatttg tagaattcga  21000
aagatttaag gaaagcagat gctgaatatt aggcgaaaag cgattgaact actctataat  21060
atgcagtcaa aaatatcatc gattcgcctg tcaattaatt gtatctaaaa ttatactttt  21120
cgaatgtcta ttttggcaat aatctttagt gattcgtact gctcagcatt taattgagtg  21180
tcgcaagcaa ttggggccgg ggtatttgca atgtttttcc aattctctgc accgaaataa  21240
ccacaaaaaa gacagccagt cagccaagat attttgggtc tcctccgaat ggaggatgca  21300
catccacgat gtgcgatgtg aatgcgctgc aattgggcgt tcaaacacat gttggatggt  21360
ccaaacacaa accgcattgc ccggcaaggg agcgagtgag atggggatcc aaaaatgcta  21420
atacacgtcg gccagcacaa aatcaaaata agaaacccat gctgctaaaa ataaaaactg  21480
gcggcggcga cacaacgaca catcggagcg gtcggaaaaa gcacacaggc gagtggagga  21540
gcaagatata agacagcttt gggagcgtct tgaatacgcg tatatctggc tatttgtgaa  21600
tgcgaaggtt tttgagaaat tcagagaagc gcacagactg ttcgaatacg tctatcctat  21660
acatcagaat ggtcaggcac tttcaacaca ttggccccat ccatcccact caatatttac  21720
atgatgacga tgatcttttg gtcaatgttt gtgttggtcg ggtattacag aaaccgatat  21780
cgcgagttat ctatgccata tacacgatcc aatgggggga cggcgggagg ggcaacagtc  21840
atgctcgcat atatttgtgc tatttttgaa ctatttcggt actgcgaaat ctatgtgatc  21900
tacaaaaacc atgagatgtc tgagatatga ctgctgagtg ccggaaattg taggattctc  21960
gattcccgat catataatgc attctcgaac agaaaatctc cattacgaaa tgctttctat  22020
tcttaggcgt cgcacaactt taattggagc ttccaatgtt gtgtgaataa gtgtgtatat  22080
atccgtggtc tatatatgca acggattttg gtgagtttta ccgtctgtgt cggaactgag  22140
tgtgccgaaa tctttccgaa ctagaagacc gcaccgtcaa cgcacggcat agttcacgcg  22200
tgtactggcc gcttaggatg ccgatgccga ttccgattgc gatccgaaga tacaccaccc  22260
```

-continued

```
gatctggcgc ccgatctttg gcgaagcgag ctacgtgtta agttctcggc gtgatgtact  22320
ataacaatga gaaacagttt acttatctgg cttacacttc aataggaaaa caatactttt  22380
atatagcttc tataacttcg gggtgcgata agaacatgaa tacagataca cggattgcaa  22440
cagtacccaa gccacttgtt ttaaacaaat aacaggataa tggggagtaa tgtaagctat  22500
tgactgggtt acaatcaggg gtctgataac aatcaaacat tgtccagttg ccttttgcga  22560
atatcaatga ccactcacga gttgcaactg ataacgatta tcgccgcaca atgcagtggg  22620
tgggtatttc actgggggga acttttgggt ccctagaacc cagacggatt actcaatgaa  22680
tataggcgat atgtttgggt ttacagcgaa agtgctatta atgtcgaccg tatgctctct  22740
tcgatgtgcc agctctctat ttgcgggaat gaatgactat ttttatgggt ctgccgtcgc  22800
tgctacaatg ctgcattgct gcagtgggac atcctttgaa caggcgccat gccaaaggat  22860
attctttgtg gaaggggggg ggggggcaag ggttaagggt cacattcgtt tgcgcaatac  22920
ttccagcgat ggggcggtga acggtgggcg gggcgatcgg tcaaggcttc gactgtggaa  22980
cgtgacacgc atatgtcggc cggagtttgg cccaaaaagt ggccccaatg gttgtccttc  23040
gcgctggcaa ttagtcccta gcaaggcgcg tccatatttt gcaaaaattc gtggggcgcc  23100
ttgttttctt ctctctgtat gtgtgcatgt gtgtgtacct ccgtctcact cacctcaagt  23160
gtgtgtgtgt gtatgaaaat actgcggtat acggctgcgt ttgtgtgtga gtgtgggttt  23220
cggctctact ctcccgatga tcctgctcct ccggtcctaa tcccggcctg ctcggctgct  23280
cctgcgtcct gactgcgcta gaaattcgct taaaacgagc ctcgacgggt catttttaca  23340
attgtttttt gttgttccgt tcggctgttt taccagacgt gctcgttccg gtgtgactgc  23400
ccgccgctga ctgtaaaata ctaaacgcat tgcagctgtg gcaatgccca agtcttggtc  23460
ttacggtcac actggcaaag tttaaaaatt tatttatttc aactttcagt tacttttcgt  23520
tggcttgaat attacactaa gaattcaatt tgacacttgc aatttataca ttgtatatta  23580
taatatatta tatgtattat attttatatc atataaagat atttatatct attgatcttt  23640
tgattataag ctctttggtt gaacaatata agtgcaactt tctccatcac cttcctatct  23700
ttttacaata tgcttacctc gtcaatacgt tttttctatt tcaaatattt caatatttca  23760
aagaaatatt ttgtttattt ttctgtgtgt ttttaagcaa tctgacccct gtagaagaat  23820
cccttataat attaacaaat gtatcctcaa aatagatcga tctctatctt cgcagactta  23880
cacgaaacat tccagaaccg atagttttat gcgatatatg agatttaagg agtactttcc  23940
gcatttcgcc atcacagtca cgctttcctt ggcatttgca atcaaataag cgctaataat  24000
aatcgtaaaa gcataagaag catataaaga agagtcaccg ccaaaagcat gcacaaatat  24060
atataaatgg ggagcgattt aaaaacagtg cactgtgttt aaaacatcga cagctatcgg  24120
ttagcatatc gatattgaca ttcgcagtca aacgttttcg agatacaacc ctaaaatccg  24180
agaagcatcc agaaatttcg acgtagacga gggcgaacct ataaaatgag gttgacgcac  24240
gaatcccgct cattattaaa caaaattttg aagagaaaga aactctgaag tagggtgtgt  24300
ttttagtgcg caagccacat ttggtggata aag                               24333
```

<210> SEQ ID NO 10
<211> LENGTH: 13015
<212> TYPE: DNA
<213> ORGANISM: Drosophila

<400> SEQUENCE: 10

-continued

```
agacaaagac agcgctgact tcagtcgact ttcgtattca ttgttaaatg acatgcaaat     60
gtacgaatga catggcattc gccaaagggt tttgaaaggg gggccagatc caaagggcag    120
gtctcaggga aatgtttcca ggctaattgt gggttttacg ccctgtactt ctccaaatga    180
tcaagtacgt catttaatgg aagccactga caattggaat cgtaaattat acagcacaaa    240
ctagatttgt ttgagtgctc tcaatgtagg ctaatattag atttctgcgc tgaattaaaa    300
ttattgtaat acgtattata atgcatttgt acccaaattt gacagactta agcagttctc    360
taacataatt ggcatcattg gcaaagagaa ataatattaa attggcagca ttgccagaaa    420
aaactcttct cctaaatttt gcttgattga atgttgtagt tgagaatgtt gtaaaatagt    480
gttagtattg taacacacga catttttcaa atatttaaat gaaaatcaca tggtaattag    540
caattttggg tggccttctt tcctccccaa gccaaagcca tataatttca gccagctact    600
tgcgatttcc cccatgacca acaacaacag ccccatatgt gcagtgcatt aatgcagatt    660
tcttggcaat tgtttttgca tactttgttt tttcctcact cacttcaatt tcaattggcg    720
tgctaataac tcatttagtt cgcaacaaaa aaacaaaaaa cgaacagcgg gccacaaaaa    780
atgtagctac aaacatggca caccaacaat ggattggatg gctaaccaag atcgccccca    840
cttccctttc catcaattgc gaatatatcg catctcatga tgctgagaga atactcgtac    900
tcaactatgc cgactttata tgaacactgt gtgcagtttt gttttaggct ttgtaattat    960
tataaaaata aattgaacta ttgttgcctc atttagattg aacagtgagg cagccacaat   1020
gttgcttttg ttattcggat acactcaatt aagctgaatt tgcaaaatgc aaatggcccg   1080
tatgaaactc acacctcgaa aatcatagac tcgaattatt ttagaaattt aatataatta   1140
tattttgttt tcttcttttt ttttggtttg gttttttttt tttttttgtt ttttgtttcc   1200
ttgcaacact tttccgcctc tcattttgac agcccgagga gttcggttgg ttcagttgat   1260
ctcttgattg tcagtcagtc atttgtgatt agacattcga cagtcgccgc tattgttgga   1320
tggcataaat tatagtctgt ctcaacaaca aagcgctgca tatgaaatcc acataataaa   1380
tcaatgtgct gtcgtaattt gtgttaagtt atttgtaatc aatttgaatt ctcgccgtac   1440
ctccccaccc ccctcggttg gtgagattta tgggaatatt ttattcattt tgctattttg   1500
gttaaatggc tttttggggt tttcccgaat ataagtttaa aattaacgcg gcaataggct   1560
taagatcatg taatattata tattgcccgt aaacaaatgc tttctacttt cattatcatg   1620
agtgttttaa aactccacga ctgctctaaa ctttaatctt taaatatttt tgtacccttt   1680
gaagaactaa ccacttagca aatccctcct attatttcct caaactcttg cacttatcga   1740
actcgcttcc tttccccgcc atcttcactc gaacaaattt aacaacaaat taaactgaaa   1800
tgcagtcaaa tcaatcgctg acttttcaat tcgtttttcc ttctttttcg gcccaacatt   1860
ttccacttgg cccgagcgtt ttgcatagtc catggcttcg attggatcgg ctcggatcgg   1920
ttggtaagtc ttcggcggag tatggcttta gtccaattta gtggaaaggt gtgcccacca   1980
gctcggtcac aacacgttgc tgtggctcat tggagtttcg cctttgcctc gctggctttt   2040
gagccgtttg gtcggtgccg cttaaacgcc gttttagcca agttaggtga aaaatgccaa   2100
gggagtgagg agtggagacc gaactgtcaa ctgtgatcaa aatcaattgt ttgccatttg   2160
ccaaaccaaa ttgactgagc caagtcagtg cgagtcacac aaaaatgctg acaaaattat   2220
accataaccc atgaaatgtc agtgtcaata atttttgtaa ttatgagagc attgagcttg   2280
agtacataaa aaaaaagtta tatatttaaa aaaatcatta ttttagttgg ctgccattgg   2340
agaagccccc aaaaaaggca aacaaatata ataaaaaatt attgcaacgt aagttttgat   2400
```

-continued

```
ttgaacaaaa ggcgtataca attggatgag ctcaagagtg ttttagagtg aaaatgtgag   2460
gatcattgtt cgcaaccaac taacagaggt tcgtctctaa catttttcaa aaaaattaca   2520
taacttttaa atttgatttc agtttatttg taagtgagaa gcctattttc taaccataaa   2580
ttctgcacgt taagagtatt tcctttcata tcgtatctac aaaaatcaat ccaacacacc   2640
tgtttcatct accgttaaca ccgttaagcc ccgccccatt ttcttatcga aaatatagcc   2700
ctttttcacg ctctatttat agcattcaca ttctttcttt ttttttgcac tttttagctg   2760
gcatatcctt tcgacttccg ccattcgagg ctcgcccaat ttccgtttcg agtttaatta   2820
atttaataaa caaattcttt tcgctctaaa aactctcaag tgtatcgata cgatgcgttt   2880
ctttttttcc ttcgttaaat aaataataac caaaaaaaaa aaaaaccaaa aagtaggagg   2940
agaaaagtta ttgccatagt ttttttatta tacttgtgtg tttacctttc tggtggcttg   3000
atcgataggc atctgcaatt aaaaagagaa gaagaagaga caagtgaggc aaaattgtta   3060
aacgttttgt gtaagcttta atacgaaaaa caagtactgc aacataacgg aaggaaacac   3120
ggcttaaatt cggggcacaa atgctgaaag ggaagttttt cattgacggg ttcgttctga   3180
cggacttgca ttttggcggg caagcgggtg tgaaaatgca cacgccccga gaaccccccct  3240
ttccaccccc cctggacccc tttatccagc ccactggcca aaaacaattt gtaattatcc   3300
acagagagcg ctgccttcag cggtttcgca tttccccttt cgctcgctct cccaacttgt   3360
ttcaatttag cgcaaaactt tttcaaccta ataataggtt taaccgcatt tttaaccgtt   3420
cctcatgttc ggtccggttc ggttttcaaa accgggaatc gtacttagac tgggtctcct   3480
tatttctgtt ctggctctct gtacaacttt tcattgagaa aaatgtaact agtttttcat   3540
agcaacggaa tacaatttaa tccaataatc caatagttta atccaataca aatgatatta   3600
ctaccatttc tattttcgtt aatttcgatt tgacttattt ggctggattt acttttcaaa   3660
atatatgtta tcaataagac acaaacctta cttttctagc tattaacata gtttaaaaaa   3720
aaaaaaaaac taataaaaat tacgtgaatc taaattttta aacccgatat ccaagaagat   3780
ctcaattttt gcctgtgtac tcagttctct gaacaaagcg catgtgcact ttggagcaca   3840
ctccatacat gtggctcagc ccttttccat aattaactag atggttttcc atcgacttca   3900
ttgtggtcag cggccagttc aacccgttct tcactgcaac cgagaactgt aaacacaaaa   3960
accccaggac tctacattgg cttaaaaaaa taagaacaga acagaaccaa aaccaaaaaa   4020
agaagggata ttgaaataca aggttgtaat cgtttcgact gttgatgtct caatgcatgg   4080
gcagttcagt tagtaaatgt ttttcaaaat ctttcaggca ggagatgttt aaatatccat   4140
gaaatatttg gatctcctgg ggatcaatcg gaatattagc ctttaattgt gttgatcttt   4200
taagcctttt tgtatctaat ctaagccatt cgatctaatc acaatttata aatatctgca   4260
tatttctgta taagtctgca tcatttgacg taactcttta agtcttttgg cttaagttgc   4320
aactataagg aagtatttat tttagagaca caaatatttc agtcgccttc atttgaacaa   4380
atcggcgaaa attggctagc tcgccaaact ttctgtaacc aaggacaatg gttttatttt   4440
aaaccattaa aaactttaga cccactagct cctagatccc cctcaaaaga tttaaaaaaa   4500
aaaaacacga tacccatttc tactgaactt cgtttttgct tgtcgttttt tccactcgaa   4560
cggaaatgag ctgacagcgc accgcacacg tcgattgcag aaaaacatcg gataaaacag   4620
gaggaaaagt tgtgcaaggt ggaaaactgt tttaccaact attgttagag gcgttcaaaa   4680
gaattacgca gctttcggtt agttagcaag gggtcaccgg ggagcgttac gtttgcattg   4740
```

-continued

```
cgtatttccg ctaaatgtca tcggaaaagg caaacggcga aatgcgaaac gaaagttttt   4800
tgattgcccg tgttaatcga tatcgatgca caaactattt gcattgcaac cgttgcaaga   4860
atatgcaaga agttgggggc ggccgcggca gggggtggaa gttgagtgcg taagttggct   4920
aaagcggaaa caggaaatga gaaaattttg cagagcaaac cccgaactgg aaatgcaact   4980
aactgggcac atgcactttg cgaaatcatt ggatagcgtt aagaaattta ttttaaaatt   5040
gtaactaaca tttaatcgta ttcaaaagca attaaatccc aatccaattc ttatataaaa   5100
tccttacaag attattctat ttactgtaaa tctaagcaaa aactcccttt gcaaaatatt   5160
cgcctgcaca gcacagatca gtgaaataat caaatgaagt cttgaaataa cgaaaaaccc   5220
ccaattgcgt gtggaactgc ccccaatgct tttgcttcgg tttcgtacct ggccgtggtg   5280
cagtccctgt agaggatgtc gaagtccttg cagcagagca acttgcagcg attgacgccc   5340
ggctggatgg cgcccaagcc gcgtaatatg cgcacctgtt ccacattgca gacgagcggt   5400
acgatgtcaa ggcgctttag tttggtataa accgtatgca gaccgccgac caagtgcttc   5460
aggaagagct cgaaggcctg cggcaggcag agcatcgttt cgttgctaat tatgaatgcg   5520
gcgaccttct gaccccggta ctccaccagc ttgcactcat tggcactggg atccgaggtg   5580
gagatcggcg gcggtgagtt gtacgacctt ggcggcacat ggtgatgggc ggcggccatc   5640
agttccaagg gggaggcatg gtgcatcatc tgcagggagt tgaggagccc cagcgaatgg   5700
ggcggcagtc catggggcat tctgggcggt aggcccgtcg gcagtccgtt gcccgatggc   5760
attccatgtg gcgggggcct gagctgatgg tgttgctgct gctgctgttg ctgctgctgt   5820
tgttgctgct gttgctgcat ctgctgcatc atggagtggt tgagggagct caccggactg   5880
acggcactgg gatggcgact tggtgaactg gccggtgagc aactggatcc tcgtcctgtg   5940
tgcgagctcc gtccatttgg acgatcctcg ttggctccac gcgaactgtt gctaccgtcg   6000
cgtccattgt gctgctgctg ttgctgctgg gctgctgcgg ctgccgctgc tgcggctgcc   6060
tgctgctgct gctggtgatg catcaacatg gcggtggtgt tcatattgcc cgcggctctt   6120
tcaataccac tattaatatt gttatttatt gcgcccgctt tattgttgtt attttcactc   6180
tgttcacttg tcacagaatc catacttcat catggccgac acttttgttt atttactttt   6240
taatcgattc gttaatttga cgttttttct atcgtgacaa aaatttgaca caaagtaagg   6300
gagaaataga aaatagatgg tgagaggaag ataaataatt aatgaactct taattcattt   6360
ttaattattt attaggcttc tatatgcaaa ttctaagtga gcgtgtctcg tatattccta   6420
tccgcttatt attggcttta catttttaat acttctgtaa gttttataac atcaaattta   6480
aatgcagacc ttcaaaaaat ttacaaacga tttaggattt gtattaggct cagctatgct   6540
cctatttatt aaaatctatt tttgagccag tttagttagt tatatggtag ctacaagttt   6600
atattgctaa atattttttg taaattaata tcctaacaaa cattttactt acaaagaaat   6660
atagagaact aacagaaaat agaaaagttt cctttcagac atttaaagtc cgattatctt   6720
ctaatacccc ccataaataa tcctttatca acagaactat tgctttgcaa actttgcttt   6780
aattaagttt tgggaaaaac aaggcaatga agctaatttg gatccttact gccaatttgc   6840
ataaatatac ctattgtcag ctttatttga ataattcgat atagaacata gatttacctt   6900
taaggaggtc taaaagtaat ttataaactc aacatcactg acacaagaca ctcgcgcact   6960
ttgctttttg aatttcgctg tgaaatatat actctgaata tttcaagtta tttattccga   7020
ttgcccgctt gtgttaatcg agttcgaata accgttttcg tactggaatt ttggaaaccg   7080
gagctgtgtc cgttttcgag taccgtaccg acggattgtc actcagagat tgagagatgg   7140
```

-continued

```
cagctactcc gctgcgacgg cgacggtggc gtcgctgcct ctgcttcttc gccttcgact   7200
ggttcctctt ccccctctcg ttcggagaaa tcaacgaaac gaattgcatt cgaatgggaa   7260
tcgactgaga gcgagacggc gcgaggcgac gactgcgagt gagcgagtga gcgggcgcta   7320
acgagtgcta tttttttagc ccacccacac acacgtacgt acgtacgtac acacgaagcg   7380
ctaccgttat gtactgagag aaatgcgcgc gcaaaagttt tattgcatta ccttctcttg   7440
cgaatgacaa attcgtaatg aaaggcgagt ttcaattcga ttcctttcgg attttcgtgg   7500
cagcgacgcc ggcagcgcgg tcggccgaga cgagtgtgct tgtatgtgtg tgtctgtgcc   7560
tgtgagagcg agctggtgta tctgtatctg cgattgtgca aaaccagaat acgaatacga   7620
gtacgaatac gaatgtctgt tgcccgtcca cgtctcgcat tacaccaata ccaggccaaa   7680
aaggggagtg gtatgtgcga ttgatcggtg tgtttgcatc tgtgtatatt tctgtgtgca   7740
accccgaaaa tacaatgaca aacgtaatcg ctctctctct cttgcattcg ttttatttat   7800
tttttcaatt cgtttgtgcg tgttgtgttc ttcaaatcct cccgctctct ctctttggaa   7860
aaaaaaacgt ttttcatttc aatttcattt cgtttcagtc tgagccctct ctctcacacc   7920
atctcgccat ctctgtcgca cgctcaggtg ggctgcaacc aataaacacg agcgagcgag   7980
aaagcagcat atttgcatag ccagtcgtac atgtttgcgc tctcgctcgc ccccatgggc   8040
gacgccttat ataaacaaat gacaattgtt ttggcatttt gtgttgcaaa gtaaattata   8100
ataaatgcat tgccagagaa gaaaagtaaa aaaaaatagc tttacttcga gtttgcgcag   8160
ctgtctttga caaaaagcat tttaatttca attaaaagta aatgacaaac tttcaacgaa   8220
ttatactttt cggggcagtg ttgctatctc tttccgtccc aagctttgat tttttttgtc   8280
aaccgttttc cgtttcccat tcgtttccat tcgagtcccg tttatttgta tttctttttg   8340
tgttgctgat tcggaggaga gcagcactat ggcagggcat ctttcttcca cttacacata   8400
ttgcgataat ggggtttttt ttcgcctgag gggcgttcgt ttttcgggtt cttataaata   8460
gcattgctta taaattctgg catcgcacct ttgccacctc tatatgttta tgtacaatgt   8520
atctgagagc tcggtcattt ttctattatt tgtcttcgtt tcgccttctg cgattcttct   8580
ccataacgat tgccattccg tcgccgaacc aatcgcattc cgttctctcc atttgagagt   8640
tccatgtaca tatttctttc tatatgggaa tggaatacgt ctttatgtat tgtgtttgca   8700
catgacgtat gaatttttct tgttcgtttc gtttggggct tttcttttgt ggatttcctc   8760
acccactgtc ttttaggtga cagcaaccat ttaatattaa attgattgca aatgtggatt   8820
tccaacagct tttagaaaat attttcgggc tttaaagaag aatttaaaac acaataatta   8880
ttgtaatgta aatattttat ttttacatcg gtttgtttca ttaaaaaata gttataagat   8940
tatattagat atgaaaatta atatgtaacg ctactttttt tctaaactgt gacattttag   9000
gctatttttt cttttaccat ttccttatgt catatgaatt tcatttaatt atgacatata   9060
catgaatcgc tggctttaaa ttcgaataag tacattaaat ttaccaaaaa tgacatgcag   9120
aattaaaaag tattcattca aacaaatttg ttttcccccc ataaatggac aacaaaaagg   9180
tactgcctct atcatccaag tgtcaaaata tgtcatagca accaactatc gtcagtaaga   9240
aatgagttct acaacatgca actttttcat ggtgtcgcaa ctgtgggcgg gaagtttgat   9300
ttttcgcaac aaacagctcg ctttgaactc tggtttttct ctttaataaa tgcaactgat   9360
ctaactatta agtaaaattg tatttttat taaccacaag caagcgcaaa gatgagttta   9420
tattctaaaa aaaaggaggg tgattaattt ctattagttt ggattacaaa tttggactag   9480
```

-continued

```
gagtcaattt gaaagtcgtt atatcaataa tacttctgga ctttgaagcg acagttactg   9540
ttccataact tcggattatc agctttgcct tcaccacata tatagagtat tctctggatg   9600
tgtcgagatt tgtattttta aacgacgact ggatggcaaa agttcagtgc gctcgcagct   9660
attatgtgga ttatctgcct cttgctggtg ccccttgtgg cggccagttc caatacaaga   9720
cttctaaatg gcatcctaag tcatgtggac aaggaagcca atccctgtga gaactactac   9780
aaccacgcct gcggccagta caacatgcgt cacatcgacg acaccttctt cgacattata   9840
caaatgctgg atcaccaggt taaccagaac ttggtgaaac taatggacga gctggaaatg   9900
agttctcaat tgccggactt taatgtatct agtgtagatg gcaaggtcct tcgttactac   9960
cttagttgtc gtggagcgcc gcggaatatg gatagtttaa gccagtatct gaaagtgatt  10020
tcccccggcg aaggactcac atggcctcaa ttcattccgg acggtagttc ttggccccag  10080
gagaatttca aatggctcaa ggcactggct catctgcatc gctacggtct aactaacgtg  10140
ttttttaacc ttgaagtcgt gtcaaaccca cgaaatgcca gcgagtacat ggtagaatta  10200
aatacaccca cttttggaga agaatctcaa ctgccgaaca gttttattga aattctatcc  10260
gttctctata tcataaaggt tccttccagt gaaatcatta ctctggcgcg aaaaatgcga  10320
acgcttgaat tgttgcttaa aacgatgatc aatccgatcg acacactgaa taatagatac  10380
attagtatcc gcgattttca gatggaaacc ggtcacaact ggcagcgttt ctttgagatt  10440
ttaataggct ccagcgcagc cccagaactc caagtgttgg tgcgcaattt taggtacttt  10500
accgccctta aggaactaat ggacaaacag gatgctcggc tggtggccag ctacataatg  10560
acccgatttg caatatttct attggatgaa accatgggtg gcagagaatc cacggagtgt  10620
gtgtcacagg tgcgccgcaa catgaatttg gctgcaaaca tgctctataa ggaacgattt  10680
ttcgaagact ccactttcag tgccaatatc ctggaaatta aggacatttt cgagaaacta  10740
cgccatcagt ttctgctgca agtcgatcaa aatcatctag agttgactgc tttgcagatg  10800
aaatttttcg ttcgaaaggc agaggcaatt gagatcaacg ttgtgaatct tccaaaaacc  10860
gatgatcttc gccatttcat cggccagtac taccaagact tgcagtttcc cactggcgag  10920
ctggattacc atcaggagca cctcaaggtg ctgcagtttc gcacccaaaa gatgttggcc  10980
caatccagca aagggcactc agaggagcag aatattttga cttacaggag ccaagcggcg  11040
ccattgcctc cacctcgtac tatgtgatgc gccccaatgt gattattgtc ccccttgggc  11100
tactgcaaga gccattcttt cagctggaaa gcgaagatgt cttcaaatac agcctgatgg  11160
gatatattat ggcacatcac ttgataagcg cctttgccac cgagggcatt acaattggca  11220
gcgatggaaa cgatcaatca tttagatcgc atcgtttcga agaagcagtc agttgcttgt  11280
cacgcaattc agagaacatc gatgaaagca tgggcgatat tgctggttta gaactggcct  11340
attttactta tgctaagatg gccaagaatc gaaaccgttt ggatttcacc catttgccac  11400
cggagcagat attcttccta aatgttggcc agttcttctg cggcaatagc gatatgttgg  11460
ttcagtacaa ggaagatcaa gtgcgtttac agcgagctat tgaagggttt gagccatttg  11520
acaaggcttt tgggtgctac cgcaataagc ctaagcacga gaagtgtcgt ttatagtgaa  11580
taccttgtac atatgcttag aaatacatat tttttgataa caataataca agacaatcgt  11640
gttaaattat aaaagtgtta caatcacatc cattctgttc ttttaaaatt agttttaaac  11700
taacaatagt caataggcta agatagttaa atgatcatca ttcgaataaa caacgttcaa  11760
gattgactct tcaatgtcat gcacctgcaa gattaccatt tattataaat taaaaaaaca  11820
cacaaagtta tacgtgtgtt acttacatgc attacattcg ggcctggcca tccacttaat  11880
```

-continued

```
atactgagat gtagcggtct ttgatttgcg ggatctctta tggattttag aacattgtta  11940
actttgctga caaagtaaat tcaactttta acgacttgtg gtgtgtgcgg cccgatgaaa  12000
tgtcttaaaa tacaaattaa atacaattca aatataattc agacgtcaaa aggtttaaag  12060
ttaaaatata ttttaccttt tagtgttatt tatacgtatg agccttgaaa acacagttga  12120
atatcaaacg gatttttgtt accaacagat tccaacagat tctccaactt tcgtttttttg  12180
attgcctatt cactcgaaga tctatttcca gtactatgat cctccatagt agagtcagct  12240
caggatcttg tgataatccg caagcaattc gacaaagaat tcgtcggcca gaacaaaatt  12300
tattaaatca ttgtagtcat tctcaggatc tctcttaact ggcaatccgt aataacgtat  12360
ttcattatct ccaaaataca gtcggaattc agattaaatt tgccgtttcc gtcctttttt  12420
ataaatatac atacaaatat actaagcaat agactgaaat gaattctaga atttgaggaa  12480
actaattatg tacctttatg aatacttttc cttacttgta ctaatcaaac taatttttaa  12540
cagatttttc atgccgaatg attacaatct tatttggatg atttgataga gcttaggaat  12600
aatggtttta attttggatt aaagagttgc gattaagaaa cgaagatatt atctagtttt  12660
tgaagaacac agggtacttt aaatttcgca cgcggaacgt caaaacaaga agaagttttc  12720
atcaacactg aatttccgct tggtaatcag ctgataagcg tgctcacgat agccgagttc  12780
acatccaaca gatgtttccc ttagcagggt ttcagaccca aatgatgatt tatcttattt  12840
tgattaagct ccaacacgca ttgctttgca taattcaggt attattaggc tgcttaatat  12900
acaatccact tatattgttg tgtccatgag gaacatcgac acgtgaggat aaaaatattt  12960
atttatcgat atatttttac tcttgagcct tttgcacacc cctagttgtg ttcca       13015
```

<210> SEQ ID NO 11
<211> LENGTH: 8374
<212> TYPE: DNA
<213> ORGANISM: Drosophila

<400> SEQUENCE: 11

```
gcctgattgt tttccacttt gcagcagagg agccgggaag gagcggtaga ggcgcaccca     60
gtgtatccgg caaaggcaag tcaccccagg tgcgttccat gcccagctct ccgctgcctc    120
agcgatccgc tacgccgacg cggctgatga gccaacgtgt ccgtgaggcg gccgagcgtc    180
ttgcccaaca gcacacggtg gccagtgctc agcggcattt gggcaatggg agaggcactg    240
gcactggcaa tggaaatggc aatagcaata gtaatggcaa tggtaatggg aacaccgcgg    300
agacgaatcg cgaatcacgc gcgcgacgtc tcatcaaccg attcaatagc gaaacgcagc    360
atatcacgtc ctagtttaag tcggttaaat gccgacgagc ataactttat tacagataaa    420
gcagatatag cattgtttaa gtaaaaaata tatatatata ccccagagaa actttacgaa    480
acactcgaat atgaatgcga ctgcggatca gcatcccacc cacccacaca cacacgtcta    540
cccactcaca gtaggatata tgtatgtatg tctgcattca agcggatgca ctccctccgt    600
tcagagggaa ctgtacttag gctagaggaa gctaagtgtt taaattattg tatcgattta    660
tatacatatt taccatacta attaaagtta atgtaacgaa aacgcaggat cagtaatctt    720
atttagttca atggtaatca atgtgcgatt agcggatgat cgcgctcctt gagtcgcacc    780
cacagtccgc cggaggctct cagcgtaatc cggaaggtgg ccgcaatggt tgtctttccg    840
gttacaggaa gcagctggta gctacgcagc aggcgcgaca ctatggtctt gatctccatg    900
atggcgaatc gattgccaat gcaatatctc ggtccagcgc tgaagggtaa aaaggcgtag    960
```

-continued ggatgacggt tctcggagtt ctcgggcgaa aatcgctccg gctggaactt ttccggatcg 1020
ggataaatgt gggcaagacg atgggtggca taggggcaaa tgaaaacgtt gctgccggcg 1080
ggcaatgtgt gctttgccag gcgaacctct tcgcccagtt tacgagcaat aagcgggaca 1140
ctgggataca gacgcagtgc ctccttgatg cacatctcca tgtaacgcat ctcgtgcaga 1200
tccgtcatcg tgggagctct attactgtcc tcgaatatgg tcgccagctc caggacacag 1260
cgatcctggc actcgggatt ctgtgtcagc agaaagagag tgaaagccac ggcggcaccc 1320
accgaatcct ggccagccag cataaaggta caggcctcgt tgacgatatc ctcctcggtg 1380
aagtcccgat tgctctcgga gatctcgatc atgtggtcga gcagacactt tcgctcgcta 1440
ttgccattat tattgttctg gatttggcga cgtctctgga tcattttgcg tgtgaagtca 1500
ttgaggcgct tcttctggtt aagctcatcg ttggccatct tggtccagtg gtagatcccg 1560
tccagcagca gccagggttg cgtaaaccgc gcgggcatca tgatcttgcc ctggcggaac 1620
ggcgagtcct ccatcatggc cacatcctga cctcttttct tgatcggcac acccaaaacg 1680
gcctctgcaa gtcgttcagg gattaagtga gaaattatag cttgctaatc ccctagagac 1740
tcaccattta gtatgtccag tacacagttg ttcacgtact tggcaatatt tatctccgtt 1800
cccacggctt cggcatccag attctcgtac aacgattgcg aggcatccac aaaggtgtcg 1860
atgaacttct ccagcagatt gtgatgaaac gctggctgga tgagccgtcg atgattgctc 1920
cacttggaac cactgctggt tatcagccca tcacccagga aattgtgcat cagtcggtag 1980
aagaagacct tgttggtgtg cttcttcgag gagagtatca cctgcagatc ctccggctcc 2040
aggacagcaa agaagggaaa gagcagcacc cagatccgca ccagagatcc atatagatcg 2100
aaggccttgc cggcacatct gcgcatcact gtgaaatggg attcaattta acttaaaagg 2160
tatctttcac gaaaaggttt cttcaaggat cttacagtcc ttatccgtga ccagcatgca 2220
gttgcccaga aatggcagcg atggcggacc cgtgagtctc agcgagagga gaaccgatct 2280
caagtacgtg ttcagggtgg cgtagaatgt gtagatgctc aggctgatca ccaggaggat 2340
cagaatggag catagctcca aattggtggt gcgctccagc tgtgggggcg aaagcaaacg 2400
taaatgcatt gggtcaagtc gcgtggataa ttgcccgctt aggtcaatat ttggtttgct 2460
atcgagaacg ccgagctctt gaacgcactt catcagctac gcactgcgct cactggagtc 2520
taattaactg aggaatcttg gagcacttag gcattcgaac ttggatgcga gcacttgccc 2580
ttgccgcgtg tcgcaagttt tcggcaaaca cacgttatcg taatcgcaac gaaagtataa 2640
gttatgtatc taactgcggt gtgaattgct tgggccaaca tggcgtatgg gcgatgctat 2700
aagtacgtgt gtgtgtatcc ataagatcga ttaaagcacc acaccgttca tgtgtacgtg 2760
ttgctttgct ttggtttttt tttctttatt tttgggccat tcgcgtcgat gtttcgtggt 2820
gcaacaggtt acacgatgag cacaaaacat gacaaatgat gatgatcacc ggacaaaaat 2880
ccagggacag ccttttgttg cccacacttc ccacacctgt cgtcgcccca caccettgca 2940 ccactaaccc cccccccccc cccaaaaaaa aaccccttg tttggttctg gacgagagtg 3000
agagccccaa caccattagc caaatgcgat tggtttcagg gccaagtgaa accaccggtt 3060
ggttaactga ctcagatctc aatgattaat ttattacgga caaggaatcg gcaaacgatc 3120
gcagttggtc atcataaagt ttatccaaaa atctaggtgg cattccattt agtgggaact 3180
tcttaccatc agttcgtagt aagctaagtt aaagagtaaa ataataggcg cttttaatcc 3240
tcctcagcca cctcatcctc gtagccctcg ggcagggcat tcacctcggc attgtgaaac 3300
aaactgcgat tgccatctcc ccatgggaat cgtttggtcc gccgcctcag gtactcgtac 3360

-continued ttggcgaacg gctcccgctc cacgtgcttg tgtccggtga aggcgtttgc ggcgcacagg 3420
acgatggccg gtagggccag caggaaggtg acacgcttcc acagaccagc ggtattggcg 3480
ggcatattgc ccataagccg gatatcaaag atcggcatgt atctgcacaa taactcgact 3540
tattctgatg cctggctgga tggctaagct agcttgaatt tgaatactac gtactgtagc 3600
gatttgaatc tgatccgtaa cacccacgcc tgctgcccga aactattgtc gcaattagga 3660
actctcaagg ggatccgagc cagcgccaca aggtccaaca acccgcgtat ctttgtttaa 3720
tcagcccaat atttgaccag aaaccgctga agcgtccaga aggcttgcgc tccgctccaa 3780
gcggctactt ctattttttt tcctcttcat cgaatatttc tttcttagtt tcgaatgctt 3840
cttttttttt ttgggcacgg catatccatc cccatccagg ctgcgaggtg tgcagaaccc 3900
gcgccgtgtt tgctcgccaa ttggcacctg gccactaata gatatacatc atgattattt 3960
cccactaatt ccataagtta tcataatggt cttcctaaac gagaggctgc ttgtcgaggc 4020
actaagaccg cccaaaatct aacgatccat tgagattgcg gttaaaaatg attcaaatgc 4080
aagcgaagtt actaaaattt gtgagagtat atctagttga aaacttgaac ttgaaaatgt 4140
ggttttcata aaattatcca aattgatggg tgtgaattaa aattaaatta aaaacttgca 4200
cttgaatact caaaattcat tgctcaattc attgatagat aaatgatgat taaataataa 4260
gttataaacc tagatcattt cactttagta ttggtaatga aatttaggtt tatatatcct 4320
cactcttctt aaagtaatgt aaatatttgt tatcctttag gaaatacacc ttattaaaat 4380
aattatttta aattctatta aaattctttt aaaaaacaga aacgtaatag ccaccatttt 4440
acattttact taaacgtttt tccttttctt ttttaaactt tagctgtgag taatcctttt 4500
tattcataac gaattgcgtt taaatatttt tatattttct tcactcacca ctttttccac 4560
aaacatttta gtcacgtatt tgtattccct tgatatagtc aatatatttt gtttttatct 4620
ttaatagctt cacacaaaag tccttgccac aagcactgtc caaatccaca catacaccaa 4680
gttagttagc tccacttcga tttgggatat atccgtattg tgatcttatt ggccagagtc 4740
acatccggcg actgatgagc tacgagtgcg ggacctccgc cggttagcgt ctatttataa 4800
ccgatttggc ccgatcaagc tcggcttgaa cgccgccgaa aatgatgtac gtgctagcta 4860
agtcgttgga gtccccggat acccgaatcc ccgtatcacc gaatcaccaa atcgccgagt 4920
cgccgcgtat ccgctagatg cccgagtgta tcgagtatag gtagtaattg ccaactagtc 4980
ggcactcgaa gtgctaagta gctagaagtg gatatggtgc tggatgctgg atgcccctgc 5040
caagtggcat ggcaatcaat tatccgtttg gtgcttgttt gatgtatccc tcctccgcca 5100
ccgcccacgc tatccacctc ctccatggaa tggcagaccc tttgggttgc cagtggcact 5160
caacgatctg agcggtggga acgaggggga agtcagctag aaatcttcag acgcgtgcca 5220
gtggatcgaa ctttgagcgg atattcaaat ggcgcagacg gacctcttca cgttgttgat 5280
tacatcaatc atttatgttt acagtgtagt cgtcggatct ttgcacattc acatactgtt 5340
gcttttaacg tcatcataaa ttctacaaaa tatattcggg atttatttcc gcgaaatttt 5400
aacctttgct aatcttcaat tgtttactga acacaaacga attacgtttc ttattcattc 5460
attcatcatt cagtattcct agatgtgttt agtcagttaa gatcgtttga gttataggtt 5520
tagaaatctt ggaaattcaa tagcgcattg gttactgatt aagagttatt atcagtaaga 5580
atattattag taattattat tatgccaatc agaccgatta gactaccact tcttgtactt 5640
ttgctgcgag ttctcgtgca ccaccgatta atatggtaaa taaatctcag cctgcttttc 5700

-continued caacaccact tatctgaaga cacgattcca tggagcacat ggagattgag attacagcca 5760
tcgactagac gccttcgtca ttcgggacga ttaaagttca gtggcaaatg aaatagagtc 5820
gatcgatgac tcaacggatc gctttgctga taatccccat ttgtgttctc cttagctggc 5880
cagttgactt tttggtcagt tgactttctg gccagttggc tttctggcca tttgggtctt 5940
tagaagacca ccgcccagtt tataatggat ataaaacgaa ttgagctgca agtcgtataa 6000
actttacgat atcatagcag aagtttatga aaatccaaaa taccaatcat ggatgatcgc 6060
taaattcgcc attttggtga taagtgataa gctggctact ccagccctat ataagagacc 6120
taaatcgaac cacactttaa gtttaaccat gtcgctacgt ttgggtttgt ttcttttggc 6180
tgcacttggt gtggtaattc tcacggattc cgcctccata agcacccaca ttgttggtgg 6240
cgatcaggcg gacatcgctg actttccgta ccaggtgtcc gttcgcctgg agacctacat 6300
gctgctccac atctgcggtg gtagcatcta tgcaccacgg gtcgtcatca ccgccgccca 6360
ctgcatcaag ggacgctatg cctcgtacat ccggatcgtg gctggtcaga actcgattgc 6420
cgatctggag gagcagggtg ttaaggtcag caaactgatc ccccatgccg gctacaataa 6480
gaaaacgtat gtgaatgata tcggtttgat catcactcgc gagccattgg agtactcagc 6540
cctggtgcaa cccattgctg tggccctgga ggcaccgccg tcgggtgccc aggccgttgt 6600
aagtggttgg ggcaagcggg ctgaagatga tgaagctctg cccgccatgc tgcgcgccgt 6660
tgagctgcag atcatcgaga agagcacctg cggtgcccag tatctgacca aggactacac 6720
ggtgaccgat gagatgctct gcgccggcta tctggagggc ggcaaggaca cctgcaacgg 6780
cgattccggt ggacccttgg ccgtggacgg agtcctggtg ggtgtggtgt cctggggcgt 6840
gggttgcggc agggaaggat tcccgggtgt ctacaccagc gtcaattccc atatcgattg 6900
gatcgaagag caggcggagg cgtatctcta aaaatgtgga tagcttcaca agcacaacgc 6960
gaacaaataa atcgaacaaa ttattatttt accacaataa taaatatgaa atgagcattt 7020
agaaaacatg gtttataata tatttacaaa ttaatatacg gtgtttaact cttcatttca 7080
actggttttc ctaatcaaaa accttttta tctgaccatt acattggaat ctataagcca 7140
ttctcgacga tttatataaa aataaaatta ttacccaatt ggcataggtg aaggcaattt 7200
atcttgagga agggaaaaag tacaatgtaa ctaaccataa attttatact ttacaaaatc 7260
gtttgattgc atcattttag aataactcaa tgcagaaatt aaaattataa aatatgtaaa 7320
tgtggcttga agtatcatta ttatttattt gtgacattta tatttgactt gatgcaatca 7380
aataatatcc acaatattag aaatttaccg tttgcagata gtttaacgta ttcgagtaag 7440
attacatttg tttaaatctt aaaaatttaa aataattagg aagattttgt ttttaaatat 7500
taacggcttc tggtattttt tagagctagt atatactttc gtggtagacg tcgctggtat 7560
ttaagccagt aagattcagc cacactgaca aagaaaatat tcgtgaaaat tctgcatacg 7620
gaaagaagaa aattcgagca acagaaagcc aacacaatcc acaaaaatgt ctttattcgg 7680
agcgttgatg ggtgatttcg acgacgatct cggccttatg aagtaagtac caaatggcgc 7740
aaaaaaaaac taaataaatg cggctcgccc cgcagaagcc ccatatattt ccatacgtgt 7800
gcagctaacg aagccctctt ggggcgtgga aaaacagcca aataatcgca aaacaaggtg 7860
taaatcatta attggcccat aggcacacaa ttaggccaat taaacatatt tacgtgccca 7920
aaaattagca ataaatagcg tgccaaaatt aacagtaacc atcggagtgt gcgtgtgtgt 7980
gtgtgcgcag catgcgtgaa gtgaagacgt aataatcgat aatttgaatc gagcgaccgc 8040
agggaaatgg aattggggaa aatgcactag caggcgttat ttcaaaggtt tcgccctgtc 8100

-continued

```
actgggactt ttgataaggc ccaaccgcaa agtgacccat gtaaaggcag gctatcagac   8160

cctattttat gtatatacgt aggctacgct gcctttatca ctatactgcg atatttggcc   8220

acaagtcatt tagtttggct ttgtttaaaa cttaatttcg gctcagttta aaatgaaaca   8280

aaaacgtaaa agcaaatcaa accgttcaca aatggagctc cagtaactcg cacatcagtc   8340

aagtatcact aagttactca tctttcgttt gcag                                8374


<210> SEQ ID NO 12
<211> LENGTH: 165
<212> TYPE: DNA
<213> ORGANISM: Artificial Sequence
<220> FEATURE:
<223> OTHER INFORMATION: Synthetic DNA

<400> SEQUENCE: 12

ctgcaggcca gcgtcctgat aagtgaattc gccgccacca tgggaggccc accgtcaacc     60

ccccagcagc agcaacagca gcagcaacag caacagcagc agcaacaaca gcagcagcaa    120

cagactagtc gtacgtatcc ctatgacgtg cccgactatg cgtag                    165


<210> SEQ ID NO 13
<211> LENGTH: 486
<212> TYPE: DNA
<213> ORGANISM: Artificial Sequence
<220> FEATURE:
<223> OTHER INFORMATION: Synthetic DNA

<400> SEQUENCE: 13

ctgcaggcca gcgtcctgat aagtgaattc gccgccacca tgggaggccc accgtcaacc     60

ccccagcagc agcaacagca gcagcaacag caacagcagc agcaacaaca gcagcagcaa    120

cagcaacagc agcagcaaca acagcagcag caacagcaac agcagcagca acagcagcag    180

caacagcaac agcagcagca acaacagcag cagcaacagc aacagcagca gcaacaacag    240

caacaacaac agcaacagca gcagcaacag cagcagcaac agcaacagca gcagcaacaa    300

cagcagcagc aacagcaaca gcagcagcaa caacagcagc agcaacagca acagcagcag    360

caacagcagc agcaacagca acagcagcag caacaacagc agctgcaaca gcaacagcag    420

cagcaacaac agcagcagca acagactagt cgtacgtatc cctatgacgt gcccgactat    480

gcgtag                                                               486


<210> SEQ ID NO 14
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 14

Met Gly Gly Pro Pro Ser Thr Pro Thr Ser Arg Thr Tyr Pro Tyr Asp
 1               5                  10                  15

Val Pro Asp Tyr Ala
            20


<210> SEQ ID NO 15
<211> LENGTH: 148
<212> TYPE: PRT
<213> ORGANISM: Artificial Sequence
<220> FEATURE:
<223> OTHER INFORMATION: Synthetic Polypeptide
```

-continued

<400> SEQUENCE: 15

```
Met Gly Gly Pro Pro Ser Thr Pro Gln Gln Gln Gln Gln Gln Gln Gln
 1               5                  10                  15

Gln Gln Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Gln Gln Gln Gln Gln Gln Gln Gln Gln Gln Gln
                85                  90                  95

Gln Gln Gln Gln Gln Gln Gln Gln Gln Gln Gln Gln Gln Gln Gln Gln
            100                 105                 110

Gln Gln Gln Gln Gln Gln Gln Gln Gln Gln Gln Gln Gln Gln Gln Gln
        115                 120                 125

Gln Gln Gln Gln Gln Gln Gln Thr Ser Arg Thr Tyr Pro Tyr Asp Val
    130                 135                 140

Pro Asp Tyr Ala
145
```

<210> SEQ ID NO 16
<211> LENGTH: 582
<212> TYPE: DNA
<213> ORGANISM: Drosophila
<220> FEATURE:
<221> NAME/KEY: misc_feature
<222> LOCATION: (1)...(582)
<223> OTHER INFORMATION: n = A,T,C or G

<400> SEQUENCE: 16

```
gcatggcacg ctttttccg tgtgctcggt tcgttcggcc atacaaaaca caaaattcaa      60

gtttaaaaac taaataggca actaaaaggg aagccgcagc gaataaagtg atttgctgaa    120

agagacgtaa gaaagttaat cgcatcgaag gcaccagaaa tcggggattt ctaacacggc    180

gcgcgtgcga cgtacataca tacgcaagcg cacacacaca cgaacaatta cttgccattg    240

acgcaaaagc gaaaaagcag tggaataaaa gggggaattg acaaataaca acgttttgca    300

agcactggac tctggtcgct ggtgttcttt cattttgtaa ttgccacgca tggacgacga    360

agtaattgaa attagcgaca cgnnacgcga agaaacctca tcgaactccg aaatggatgt    420

ggaaataacg acagaacagc caaccatcga tgtcaaagca gagcaaattg tgcccaagga    480

cgcggcaacc attgccgagg agaagaagaa actgggcaac gaccaataca aggcgcagaa    540

ctatcagaat gcactcaagc tctacacgga tgccatatcg ct                        582
```

<210> SEQ ID NO 17
<211> LENGTH: 274
<212> TYPE: DNA
<213> ORGANISM: Drosophila
<220> FEATURE:
<221> NAME/KEY: misc_feature
<222> LOCATION: (1)...(274)
<223> OTHER INFORMATION: n = A,T,C or G

<400> SEQUENCE: 17

```
cttcgcatgg cacgcttttt tccgtgtgct cggttcgttc ggccatacaa aacacaaaat      60

tcaagtttaa aaactaaata ggcaactaaa agggaagccg cagcgaataa agtgatttgc    120
```

-continued

```
tgaaagagac gtaagaaagt taatcgcatc gaaggcacca gaaatcgggg atttctaaca    180

cggcgcgcgt gcgacgtaca tacatacgca agcgcacaca cacacgaaca attacttgcc    240

attgacgcan aagcgaaaag cagtgaaata aagg                                274
```

<210> SEQ ID NO 18
<211> LENGTH: 565
<212> TYPE: DNA
<213> ORGANISM: Drosophila

<400> SEQUENCE: 18

```
cttcgcatgg cacgcttttt tccgtgtgct cggttcgttc ggccatacaa aacacaaaat     60

tcaagtttaa aaactaaata ggcaactaaa agggaagccg cagcgaataa agtgatttgc    120

tgaaagagac gtaagaaagt taatcgcatc gaaggcacca gaaatcgggg atttctaaca    180

cggcgcgcgt gcgacgtaca tacatacgca agcgcacaca cacacgaaca attacttgcc    240

attgacgcaa aagcgaaaaa gcagtggaat aaaggggaat tgacaaataa caacgttttg    300

caagcactgg actctggtcg ctggtgttct ttcattttgt aattgccacg catggacgac    360

gaagtaattg aaattagcga cagcgaacgc gaagaaacct catcgaactc cgaaatggat    420

gtggaaataa cgacagaaca gccaaccatc gatgtcaaag cagagcaaat tgtgcccaag    480

gacgcggcaa ccattgccga ggagaagaag aaactgggca acgaccaata caaggcgcag    540

aactatcaga atgcactcaa gctct                                          565
```

<210> SEQ ID NO 19
<211> LENGTH: 679
<212> TYPE: DNA
<213> ORGANISM: Drosophila
<220> FEATURE:
<221> NAME/KEY: misc_feature
<222> LOCATION: (1)...(679)
<223> OTHER INFORMATION: n = A,T,C or G

<400> SEQUENCE: 19

```
ctacttcgca tggcacgctt ttttccgtgt gctcggttcg ttcggccata caaaacacaa     60

aattcaagtt taaaaactaa ataggcaact aaaagggaag ccgcagcgaa taaagtgatt    120

tgctgaaaga gacgtaagaa agttaatcgc atcgaaggca ccagaaatcg gggatttcta    180

acacggcgcg cgtgcgacgt acatacatac gcaagcgcac acacacacga acaattactt    240

gccattgacg caaaagcgaa aaagcagtgg aataaagggg aattgacaaa taacaacgtt    300

ttgcaagcac tggactctgg tcgctggtgt tctttcattt tgtaattgcc acgcatggac    360

gacgaagtaa ttgaaattag cgacagcgaa cgcgaagaaa cctcatcgaa ctccgaaatg    420

gatgtggaaa taacgacaga acagccaacc atcgatgtca aagcagagca aattgtgccc    480

aaggacgcgg caaccattgc cgaggagaag aagaaactgg gcaacgacca atacaaggcg    540

cagaactatc agaatgcact caagctctac acggatgcca tatcgctgtg tccggactcg    600

gcggcatact atggcaatcg ggccgnctgc tacatgatgc tgctcaacta taatagcgcc    660

ctgaccgacg cccgacacg                                                 679
```

<210> SEQ ID NO 20
<211> LENGTH: 529
<212> TYPE: DNA
<213> ORGANISM: Drosophila

<400> SEQUENCE: 20

-continued

```
actacttcgc atggcacgct tttttccgtg tgctcggttc gttcggccat acaaaacaca     60

aaattcaagt ttaaaaacta aataggcaac taaaagggaa gccgcagcga gataaagtga    120

tttgctgaaa gagacgtaag aaagttaatc gcatcgaagg caccagaaat cggggatttc    180

taacacggcg cgcgtgcacg tagcatacat acgcaagcgc acacacacac gaacaattac    240

ttgccattga cgcaaaagcg aaaaagcagt ggaataaagg ggaattgaca aataacaacg    300

ttttgcaagc actggactct ggtcgctggt gttctttcat tttgtaattg ccacgcatgg    360

acgacgaagt aattgaaatt agcgacagca tacgggatga aacctcatcg aactccgaaa    420

tggatgtgga aataacgaca gaacagccaa ccatcgatgt caaagcagag caaattgtgc    480

ccaaggacgc ggcaaccatt gccgaggaga agaagatact gggcaacga                529
```

```
<210> SEQ ID NO 21
<211> LENGTH: 783
<212> TYPE: DNA
<213> ORGANISM: Drosophila
<220> FEATURE:
<221> NAME/KEY: misc_feature
<222> LOCATION: (1)...(783)
<223> OTHER INFORMATION: n = A,T,C or G

<400> SEQUENCE: 21

cactacttcg catggcacgc ttttttccgt gtgctcggtt cgttcggcca tacaaaacac     60

aaaattcaag tttaaaaact aaataggcaa ctaaaaggga agccgcagcg aataaagtga    120

tttgctgaaa gagacgtaag aaagttaatc gcatcgaagg caccagaaat cggggatttc    180

taacacggcg cgcgtgcgac gtacatacat acgcaagcgc acacacacac gaacaattac    240

ttgccattga cgcaaaagcg aaaaagcagt ggaataaagg ggaattgaca aataacaacg    300

ttttgcaagc actggactct ggtcgctggt gttctttcat tttgtaattg ccacgcatgg    360

acgacgaagt aattgaaatt agcgacacgn acgcgaagaa acctcatcga actccgaaat    420

ggatgtggaa ataacgacag aacagccaac catcgatgtc aaagcagagc aaattgtgcc    480

caaggacgcg gcaaccattg ccgaggagaa gaagaaactg ggcaacgacc aatacaaggc    540

gcagaactat cagaatgcac tcaagctcta cacggatgcc atatcgctgt gtccggactc    600

ggcggcatac tatggcaatc gggccgcctg ctacatgatg ctgctcaact ataatagcgc    660

cctgaccgac gcccgacacg ccatacgcat cgatccgggc ttcgagaagg cctacgtccg    720

tgtggccaag tgctgtctgg ccctgggcga cattattggc ccgaacaggc cgtcaaaatg    780

gtt                                                                  783
```

```
<210> SEQ ID NO 22
<211> LENGTH: 677
<212> TYPE: DNA
<213> ORGANISM: Drosophila

<400> SEQUENCE: 22

ttccaccact acttcgcatg gcacgctttt ttccgtgtgc tcggttcgtt cggccataca     60

aaacacaaaa ttcaagttta aaaactaaat gggcaactaa aagggaagcc gcagcgaata    120

aagtgatttg ctgaaagaga cgtaagaaag ttaatcgcat cgaaggcacc agaaatcggg    180

gatttctaac acggcgcgcg tgcgacgtac atacatacgc aagcgcacac acacacgaac    240

aattacttgc cattgacgca aaagcgaaaa agcagtggaa taaaggggaa ttgacaaata    300

acaacgtttt gcaagcactg gactctggtc gctggtgttc tttcattttg taattgccac    360

gcatggacga cgaagtaatt gaaattagcg acagcgaacg cgaagaaacc tcatcgaact    420
```

-continued

```
ccgaaatgga tgtggaaata acgacagaac agccaaccat cgatgtcaaa gcagagcaaa    480

ttgtgcccaa ggacgcggca accattgccg aggagaagaa gaaactgggc aacgaccaat    540

acaaggcgca gaactatcag aatgcactca agctctacac ggatgccata tcgctgtgtc    600

cggactcggc ggcatactat ggcaatcggg ccgcctgcta catgatgctg ctcaactata    660

atagcgccct gaccgac                                                   677
```

<210> SEQ ID NO 23
<211> LENGTH: 386
<212> TYPE: DNA
<213> ORGANISM: Drosophila

<400> SEQUENCE: 23

```
aactacttcg catggcacgc ttttttccgt gtgctcggtt cgttcggcca tacaaaacac     60

aaaattcaag tttaaaaact aaataggcaa ctaaaaggga agccgcagcg aataaagtga    120

tttgctgaaa gagacgtaag aaagttaatc gcatcgaagg caccagaaat cggggatttc    180

taacacggcg cgcgtgcgac gtacatacat acgcaagcgc acacacacac gaacaattac    240

ttgccattga cgcaaaagcg aaaaagcagt ggaataaagg ggaattgaca aataacaacg    300

ttttgcaagc actggactct ggtcgctggt gttctttcat tttgtaattg ccacgcatgg    360

acgacgaagt aattgaaatt agcgac                                         386
```

<210> SEQ ID NO 24
<211> LENGTH: 537
<212> TYPE: DNA
<213> ORGANISM: Drosophila
<220> FEATURE:
<221> NAME/KEY: misc_feature
<222> LOCATION: (1)...(537)
<223> OTHER INFORMATION: n = A,T,C or G

<400> SEQUENCE: 24

```
tttaacacaa atctcccatg atttattaat gttgccgaaa aaaaaatcca agaaagaaca     60

tttaaaaatg tgaacttaca ctggaaattt agttgcatta ttttgattta gaatattttt    120

tcaaataact tggcatatat tcattcgtta acataatcan aatgtggtat tttcttgctt    180

tttggaaaag anatatgtan aagagttcaa aatttgtgcg ctgctgtatg ttggtttcgg    240

atgaggcaga aagtatggga ttgagatggt cttcttctct gtggtggtga acaacactcg    300

ttgggatcct agaactcaaa gttgaacgat gaattattcc ggccaccgcc gttgaattgg    360

aagaatgtgc ggaacatttg attcggatcg aagtcggctt gctcctgctc ctcgatatcc    420

tggccgctgt cgtagcgcga cttcttgtga gcatccgaca gtatggcgta cgcctcgccc    480

acctccttga acttgagctc ctcctccttg cgctcctcgg cactgctgtt tgcgtgt       537
```

<210> SEQ ID NO 25
<211> LENGTH: 570
<212> TYPE: DNA
<213> ORGANISM: Drosophila
<220> FEATURE:
<221> NAME/KEY: misc_feature
<222> LOCATION: (1)...(570)
<223> OTHER INFORMATION: n = A,T,C or G

<400> SEQUENCE: 25

```
tttttccgtg tgctcggttc gttcggccat acaaaacaca aaattcaagt ttaaaaacta     60

aataggcaac taaaagggaa gccgcagcga ataaagtgat ttgctgaaag agacgtaaga    120
```

-continued

```
aagttaatcg catcgaaggc accagaaatc ggggatttct aacacggcgc gcgtgcgacg    180

tacatacata cgcaagcgca cacacacacg aacaattact tgccattgac gcaaaagcga    240

aaaagcagtg gaataaaggg gaattgacaa ataacaacgt tttgcaagca ctggactctg    300

gtcgctggtg ttctttcatt ttgtaattgc cacgcatgga cgacgaagta attgaaatta    360

gcgacagcac cgcgcagaaa cctcatcgaa ctccgaaatg gatgtggaaa taacgacaga    420

acagccaacc atcgatgtca aagcagagca nattgtgctc aaggacgcgg caaccattgc    480

cgaggagaag aagaaactgg gcaacgacca atacaaggcg cagaactatc agaatgcact    540

caagctctac acggatgcca tatcgctgtg                                     570
```

<210> SEQ ID NO 26
<211> LENGTH: 688
<212> TYPE: DNA
<213> ORGANISM: Drosophila

<400> SEQUENCE: 26

```
ctttttttccg tgtgctcggt tcgttcggcc atacaaaaca caaaattcaa gtttaaaaac     60

taaataggca actaaaaggg aagccgcagc gaataaagtg atttgctgaa agagacgtaa    120

gaaagttaat cgcatcgaag gcaccagaaa tcggggattt ctaacacggc gcgcgtgcga    180

cgtacataca tacgcaagcg cacacacaca cgaacaatta cttgccattg acgcaaaagc    240

gaaaaagcag tggaataaag gggaattgac aaataacaac gttttgcaag cactggactc    300

tggtcgctgg tgttctttca ttttgtaatt gccacgcatg gacgacgaag taattgaaat    360

tagcgacagc gaacgcgaag aaacctcatc gaactccgaa atggatgtgg aaataacgac    420

agaacagcca accatcgatg tcaaagcaga gcaaattgtg cccaaggacg cggcaaccat    480

tgccgaggag aagaagaaac tggcaacga ccaatacaag gcgcagaact atcagaatgc    540

actcaagctc tacacggatg ccatatcgct gtgtccggac tcggcggcat actatggcaa    600

tcgggccgcc tgctacatga tgctgctcaa ctataatagc gccctgaccg acgcccgaca    660

cgccatacgc atcgatccgg gcttcgag                                       688
```

<210> SEQ ID NO 27
<211> LENGTH: 531
<212> TYPE: DNA
<213> ORGANISM: Drosophila

<400> SEQUENCE: 27

```
ctttttttccg tgtgctcggt tcgttcggcc atacaaaaca caaaattcaa gtttaaaaac     60

taaataggca actaaaaggg aagccgcagc gaataaagtg atttgctgaa agagacgtaa    120

gaaagttaat cgcatcgaag gcaccagaaa tcggggattt ctaacacggc gcgcgtgcga    180

cgtacataca tacgcaagcg cacacacaca cgaacaatta cttgccattg acgcaaaagc    240

gaaaaagcag tggaataaag gggaattgac aaataacaac gttttgcaag cactggactc    300

tggtcgctgg tgttctttca ttttgtaatt gccacgcatg gacgacgaag taattgaaat    360

tagcgacagc gaacgcgaag aaacctcatc gaactccgaa atggatgtgg aaataacgac    420

cgaacagcca accatcgatg tcaaagcaaa acaaattgtg cccaaggacg cggcaaccat    480

tgccgaggag aagaagaaac tgggctacga ccaatacaag gcgcagaact a             531
```

<210> SEQ ID NO 28
<211> LENGTH: 479
<212> TYPE: DNA
<213> ORGANISM: Drosophila

<400> SEQUENCE: 28

```
cttttttccg tgtgctcggt tcgttcggcc atacaaaaca caaaattcaa gtttaaaaac      60
taaataggca actaaaaggg aagccgcagc gaataaagtg atttgctgaa agagacgtaa     120
gaaagttaat cgcatcgaag gcaccagaaa tcggggattt ctaacacggc gcgcgtgcga     180
cgtacataca tacgcaagcg cacacacaca cgaacaatta cttgccattg acgcaaaagc     240
gaaaaagcag tggaataaag gggaattgac aaataacaac gttttgcaag cactggactc     300
tggtcgctgg tgttctttca ttttgtaatt gccacgcatg gacgacgaag taattgaaat     360
tagcgacagc ggacgcgaag aaacctcatc gaactccgaa atggatgtgg aaataacgac     420
agaacagcca accatcgatg tcaaagcaga gcaaattgtg ccccaggacg cggcaacca     479
```

<210> SEQ ID NO 29
<211> LENGTH: 367
<212> TYPE: DNA
<213> ORGANISM: Drosophila

<400> SEQUENCE: 29

```
cttttttccg tgtgctcggt tcgttcggcc atacaaaaca caaaattcaa gtttaaaaac      60
taaataggca actaaaaggg aagccgcagc gaataaagtg atttgctgaa agagacgtaa     120
gaaagttaat cgcatcgaag gcaccagaaa tcggggattt ctaacacggc gcgcgtgcga     180
cgtacataca tacgcaagcg cacacacaca cgaacaatta cttgccattg acgcaaaagc     240
gaaaaagcag tggaataaag gggaattgac aaataacaac gttttgcaag cactggactc     300
tggtcgctgg tgttctttca ttttgtaatt gccacgcatg gacgacgaag taattgaaat     360
tagcgac                                                               367
```

<210> SEQ ID NO 30
<211> LENGTH: 506
<212> TYPE: DNA
<213> ORGANISM: Drosophila
<220> FEATURE:
<221> NAME/KEY: misc_feature
<222> LOCATION: (1)...(506)
<223> OTHER INFORMATION: n = A,T,C or G

<400> SEQUENCE: 30

```
acgcttttttt ccgtgtgctc ggttcgttcg gccatacaaa acacaaaatt caagtttaaa      60
aactaaatag gcaactaaaa gggaagccgc agganataaa gtgatttgct gaaagagacg     120
taagaaagtt aatcgcatcg aaggcaccag aaatcgggga tttctaacac ggcgcgcgtg     180
gacgtacata catacgcaag cggcacacac acacgaacaa ttacttgcca ttgacgcaaa     240
agcgaaaaag cagtggaata aaggggaatt gacaaataac aacgttttgc aagcactgga     300
ctctggtcgc tggtgttctt tcattttgta attgccacgc atggacgacg aagtaattga     360
aattagcgac aggancgcgn agaaacctca tcgaactccg aaatggatgt ggaaataacg     420
acagaacagc caaccatcga tgtcaaagca gagcaaattg tgcccaagga cgcggcaacc     480
attgccgagg agaagaagaa actggg                                          506
```

<210> SEQ ID NO 31
<211> LENGTH: 370
<212> TYPE: DNA
<213> ORGANISM: Drosophila

<400> SEQUENCE: 31

-continued

```
gcacgctttt ttccgtgtgc tcggttcgtt cggccataca aaacacaaaa ttcaagttta     60

aaaactaaat aggcaactaa aagggaagcc gcagcgaata aagtgatttg ctgaaagaga    120

cgtaagaaag ttaatcgcat cgaaggcacc agaaatcggg gatttctaac acggcgcgcg    180

tgcgacgtac atacatacgc aagcgcacac acacacgaac aattacttgc cattgacgca    240

aaagcgaaaa agcagtggaa taaaggggaa ttgacaaata acaacgtttt gcaagcactg    300

gactctggtc gctggtgttc tttcattttg taattgccac gcatggacga cgaataattg    360

aaattagcga                                                           370
```

<210> SEQ ID NO 32
<211> LENGTH: 377
<212> TYPE: DNA
<213> ORGANISM: Drosophila

<400> SEQUENCE: 32

```
cacgcttttt tccgtgtgct cggttcgttc ggccatacaa aacacaaaat tcaagtttaa     60

aaactaaata ggcaactaaa agggaagccg cagcgaataa agtgatttgc tgaaagagac    120

gtaagaaagt taatcgcatc gaaggcacca gaaatcgggg atttctaaca cggcgcgcgt    180

gcgacgtaca tacatacgca agcgcacaca cacacgaaca attacttgcc attgacgcaa    240

aagcgaaaaa gcagtggaat aaaggggaat tgacaaataa caacgttttg caagcactgg    300

actctggtcg ctggtgttct ttcattttgt aattgccacg catggacgac gaagtaattg    360

agattagcga ccgcatc                                                   377
```

<210> SEQ ID NO 33
<211> LENGTH: 691
<212> TYPE: DNA
<213> ORGANISM: Drosophila

<400> SEQUENCE: 33

```
catggcacgc tttttttccgt gtgctcggtt cgttcggcca tacaaaacac aaaattcaag     60

tttaaaaact aaataggcaa ctaaaaggga agccgcagcg aataaagtga tttgctgaaa    120

gagacgtaag aaagttaatc gcatcgaagg caccagaaat cggggatttc taacacggcg    180

cgcgtgcgac gtacatacat acgcaagcgc acacacacac gaacaattac ttgccattga    240

cgcaaaagcg aaaaagcagt ggaataaagg ggaattgaca aataacaacg ttttgcaagc    300

actggactct ggtcgctggt gttctttcat tttgtaattg ccacgcatgg acgacgaagt    360

aattgaaatt agcgacagcg aacgcgaaga aacctcatcg aactccgaaa tggatgtgga    420

aataacgaca gaacagccaa ccatcgatgt caaagcagag caaattgtgc ccaaggacgc    480

ggcaaccatt gccgaggaga agaagaaact gggcaacgac caatacaagg cgcagaacta    540

tcagaatgca ctcaagctct acacggatgc catatcgctg tgtccggact cggcggcata    600

ctatggcaat cgggccgcct gctacatgat gctgctcaac tataatagcg ccctgaccga    660

cgcccgacac gccatacgca tcgatccggg c                                   691
```

<210> SEQ ID NO 34
<211> LENGTH: 635
<212> TYPE: DNA
<213> ORGANISM: Drosophila

<400> SEQUENCE: 34

```
gcacgctttt ttccgtgtgc tcggttcgtt cggccataca aaacacaaaa ttcaagttta     60

aaaactaaat aggcaactaa aagggaagcc gcagcgacat aaagtgattt gctgaaagag    120
```

-continued

```
acgtaagaaa gttaatcgca tcgaaggcac cagaaatcgg ggatttctaa cacggcgcgc    180

gtggacgtac atacatacgc aagcgcacac acacacgaac aattacttgc cattgacgca    240

aaagcaaaaa gcagtggaat aaaggggaat tgacaaataa caacgttttg caagcactgg    300

actctggtcg ctggtgttct ttcattttgt aattgccacg catggacgac gaagtaattg    360

aaattagcga cagtaccgcg cagaaacctc atcgaactcc gaaatggatg tggaaataac    420

gacagaacag ccaaccatcg atgtcaaagc agagcaaatt gtgcccaagg acgcggcaac    480

cattgccgag gagaagaaga aactgggcaa cgaccaatac aaggcgcaga actatcagaa    540

tgcactcaag ctctacacgg atgccatatc gctgtgtccg gactcggcgg catactatgg    600

caatcgggcc gcctgctaca tgatgctgct caact                                 635
```

```
<210> SEQ ID NO 35
<211> LENGTH: 589
<212> TYPE: DNA
<213> ORGANISM: Drosophila
<220> FEATURE:
<221> NAME/KEY: misc_feature
<222> LOCATION: (1)...(589)
<223> OTHER INFORMATION: n = A,T,C or G

<400> SEQUENCE: 35

gcatggcacg ctttttttccg tgtgctcggt tcgttcggcc atacaaaaca caaaattcaa     60

gtttaaaaac taaataggca actaaaaggg aagccgcagc gaataaagtg atttgctgaa    120

agagacgtaa gaaagttaat cgcatcgaag gcaccagaaa tcggggattt ctaacacggc    180

gcgcgtgcga cgtacataca tacgcaagcg cacacacaca cgaacaatta cttgccattg    240

acgcaaaagc gaaaaagcag tggaataaag gggaattgac aaataacaac gttttgcaag    300

cactggactc tggtcgctgg tgttctttca ttttgtaatt gccacgcatg gacgacgaag    360

taattgaaat tagcgacagc anacgcgaag aaacctcatc gaactccgaa atggatgtgg    420

aaataacgac agaacagcca accatcgatg tcaaagcaga gcaaattgtg cccaaggacg    480

cggcaaccat tgccgaggag aagaagaaac tgggcaacga ccaatacaag gcgcagaact    540

atcagaatgc actcaagctc tacacggatg ccatatcgct gtgtccgga                 589
```

```
<210> SEQ ID NO 36
<211> LENGTH: 566
<212> TYPE: DNA
<213> ORGANISM: Drosophila
<220> FEATURE:
<221> NAME/KEY: misc_feature
<222> LOCATION: (1)...(566)
<223> OTHER INFORMATION: n = A,T,C or G

<400> SEQUENCE: 36

atatgtatat ttctgtttat ttaacacaaa tctcccatga tttattaatg ttgccgaaaa     60

aaaaaatcca agaaagaaca tttaaaaatg tgaacttaca ctggaaattt agttgcatta    120

ttttgattta aaatattttt tcaaataact tggcatatat tcattcgtta acataatcaa    180

aatgtggtat tttcttgctt tttggaaaag aaatatgtaa aagagttcaa aatttgtgcg    240

ctgctgtatg ttggtttcgg atgaggcaga aagtatggga ttgagatggt cttcttctct    300

gtggtggtga acaacactcg ttgggatcct agaactcaaa gttgaacgat gaattattcc    360

ggccaccgcc gttgaattgg aagaatgtgc ggaacatttg attcggatcg aagtcggctt    420

gctcctgctc ctcgatatcc tggccgctgt cgtancgcga cttcttgtga gcatccgaca    480
```

-continued

```
gtatggcgta cgcctcgccc acctccttga acttgagctc ctcctccttg cgctcctcgg    540

cactgctgtt tgcgtgtcga tccgga                                          566


<210> SEQ ID NO 37
<211> LENGTH: 589
<212> TYPE: DNA
<213> ORGANISM: Drosophila

<400> SEQUENCE: 37

aactatcaga atgcactcaa gctctacacg gatgccatat cgctgtgtcc ggactcggcg     60

gcatactatg gcaatcgggc cgcctgctac atgatgctgc tcaactataa tagcgccctg    120

accgacgccc gacacgccat acgcatcgat ccgggcttcg agaaggccta cgtccgtgtg    180

gccaagtgct gtctggccct gggcgacatt attggcaccg aacaggccgt caaaatggtc    240

aacgagctga attcgcttag cacggctgtt gctgccgaac agacggcggc gcaaaagttg    300

cgccaattgg aggccaccat tcaggcgaac tacgatacga aatcctatcg caatgtggtc    360

ttctatttgg atagtgcctt gaaattggcg cccgcctgtt tgaaatatcg tctactcaag    420

gctgagtgcc ttgcattttt ggggcgatgt gatgaggcct tggacattgc ggtcagtgta    480

atgaaactgg ataccacatc ggcggatgcg atatacgtga gaggtctgtg cctgtactac    540

acggacaacc tggacaaggg aattcttcat ttcgagcgcg ccctgaccc                589


<210> SEQ ID NO 38
<211> LENGTH: 654
<212> TYPE: DNA
<213> ORGANISM: Drosophila
<220> FEATURE:
<221> NAME/KEY: misc_feature
<222> LOCATION: (1)...(654)
<223> OTHER INFORMATION: n = A,T,C or G

<400> SEQUENCE: 38

aaactgggca acgaccaata caaggcgcag aactatcaga atgcactcaa gctctacacg     60

gatgccatat cgctgtgtcc ggactcggcg gcatactatg gcaatcgggc cgcctgctac    120

atgatgctgc tcaactataa tagcgccctg accgacgccc gacacgccat acgcatcgat    180

ccgggcttcg agaaggccta cgtccgtgtg gccaagtgct gtctggccct gggcgacatt    240

attggcaccg aacaggccgt caaaatggtc aacgagctga attcgcttag cacggctgtt    300

gctgccgaac agacggcggc gcaaaagttg cccaanttgg aggccaccat tcaggcgaac    360

tacgatacga aatcctatcg caatgtggtc ttctatttgg atagtgcctt gaaattggcg    420

cccgcatgtt tgaaatatcg tctactcaag gctgagtgcc ttgcattttt ggggcgatgt    480

gatgaggcct tggacattgc ggtcagtgta atgaaactgg ataccacatc ggcggatgcg    540

atatacgtga gaggtctgtg cctgtactac acggacaacc tggacaaggg aattcttcat    600

ttcgagcgcg ccctgaccct cgacccggac cactaccagt ccaagcagat gcgc          654


<210> SEQ ID NO 39
<211> LENGTH: 631
<212> TYPE: DNA
<213> ORGANISM: Drosophila

<400> SEQUENCE: 39

acgacagaac agccaaccat cgatgtcaaa gcagagcaaa ttgtgcccaa ggacgcggca     60

accattgccg aggagaagaa gaaactgggc aacgaccaat acaaggcgca gaactatcag    120

aatgcactca agctctacac ggatgccata tcgctgtgtc cggactcggc ggcatactat    180
```

-continued

```
ggcaatcggg ccgcctgcta catgatgctg ctcaactata atagcgccct gaccgacgcc    240

cgacacgcca tacgcatcga tccgggcttc gagaaggcct acgtccgtgt ggccaagtgc    300

tgtctggccc tgggcgacat tattggcacc gaacaggccg tcaaaatggt caacgagctg    360

aattcgctta gcacggctgt tgctgccgaa cagacggcgg cgcaaaagtt gcgccaattg    420

gaggccacca ttcaggcgaa ctacgatacg aaatcctatc gcaatgtggt cttctatttg    480

gatagtgcct tgaaattggc gcccgcctgt ttgaaatatc gtctactcaa ggctgagtgc    540

cttgcatttt tggggcgatg tgatgaggcc ttggacattg cggtcagtgt aatgaaactg    600

gataccacat cggcggatgc gatatacgtg a                                   631
```

```
<210> SEQ ID NO 40
<211> LENGTH: 562
<212> TYPE: DNA
<213> ORGANISM: Drosophila

<400> SEQUENCE: 40

acgacagaac agccaaccat cgatgtcaaa gcagagcaaa ttgtgcccaa ggacgcggca     60

accattgccg aggagaagaa gaaactgggc aacgaccaat acaaggcgca gaactatcag    120

aatgcactca agctctacac ggatgccata tcgctgtgtc cggactcggc ggcatactat    180

ggcaatcggg ccgcctgcta catgatgctg ctcaactata atagcgccct gaccgacgcc    240

cgacacgcca tacgcatcga tccgggcttc gagaaggcct acgtccgtgt ggccaagtgc    300

tgtctggccc tgggcgacat tattggcacc gaacaggccg tcaaaatggt caacgagctg    360

aattcgctta gcacggctgt tgctgccgaa cagacggcgg cgcaaaagtt gcgccaattg    420

gaggccacca ttcaggcgaa ctacgatacg aaatcctatc gcaatgtggt cttctatttg    480

gatagtgcct tgaaattggc gcccgcctgt ttgaaatatc ggctactcaa agctgagtgc    540

cttgcatttt tggggcgatg tg                                             562
```

```
<210> SEQ ID NO 41
<211> LENGTH: 541
<212> TYPE: DNA
<213> ORGANISM: Drosophila

<400> SEQUENCE: 41

ccatacaaaa cacaaaattc aagtttaaaa actaaatagg caactaaaag ggaagccgca     60

gcgaataaag tgatttgctg aaagagacgt aagaaagtta atcgcatcga aggcaccaga    120

aatcggggat ttctaacacg gcgcgcgtgc gacgtacata catacgcaag cgcacacaca    180

cacgaacaat tacttgccat tgacgcaaaa gcgaaaaagc agtggaataa aggggaattg    240

acaaataaca acgttttgca agcactggac tctggtcgct ggtgttcttt cattttgtaa    300

ttgccacgca tggacgacga agtaattgaa attagcgaca gcgaacgcga agaaacctca    360

tcgaactccg aaatggatgt ggaaataacg acagaacagc caaccatcga tgtcaaagca    420

gagcaaattg tgcccaagga cgcggcaacc attgccgagg agaagaagaa actgggcaac    480

gaccaataca aggcgcagaa ctatcagaat gcactcaagc tctacacgga tgccatatcg    540

c                                                                    541
```

```
<210> SEQ ID NO 42
<211> LENGTH: 561
<212> TYPE: DNA
<213> ORGANISM: Drosophila
<220> FEATURE:
```

-continued

<221> NAME/KEY: misc_feature
<222> LOCATION: (1)...(561)
<223> OTHER INFORMATION: n = A,T,C or G

<400> SEQUENCE: 42
ttcgttcggc catacaaaac acaaaattca agtttaaaaa ctaaataggc aactaaaagg 60
gaagccgcag cgaataaagt gatttgctga aagagacgta agaaagttaa tcgcatcgaa 120
ggcaccagaa atcggggatt tctaacacgg cgcgcgtgcg acgtacatac atacgcaagc 180
gcacacacac acgaacaatt acttgccatt gacgcaaaag cgaaaaagca gtggaataaa 240
ggggaattga caaataacaa cgttttgcaa gcactggact ctggtcgctg gtgttctttc 300
attttgtaat tgccacgcat ggacgacgaa gtaattgaaa ttagcgacag cancgcacag 360
aaacctcatc gaactccgaa atggatgtgg aaataacgac agaacagcca accatcgatg 420
tcaaagcaga gcaaattgtg cccaaggacg cggcaaccat tgccgaggag aagaagaaac 480
tgggcaacga ccaatacaag gcgcagaact atcagaatgc actcaagctc tacacggatg 540
ccatatcgct gtgtccggac t 561

<210> SEQ ID NO 43
<211> LENGTH: 618
<212> TYPE: DNA
<213> ORGANISM: Drosophila
<220> FEATURE:
<221> NAME/KEY: misc_feature
<222> LOCATION: (1)...(618)
<223> OTHER INFORMATION: n = A,T,C or G

<400> SEQUENCE: 43
ttcgttcggc catacaaaac acaaaattca agtttaaaaa ctaaataggc aactaaaagg 60
gaagccgcag cgaataaagt gatttgctga aagagacgta agaaagttaa tcgcatcgaa 120
ggcaccagaa atcggggatt tctaacacgg cgcgcgtgcg acgtacatac atacgcaagc 180
gcacacacac acgaacaatt acttgccatt gacgcaaaag cgaaaaagca gtggaataaa 240
ggggaattga caaataacaa cgttttgcaa gcactggact ctggtcgctg gtgttctttc 300
attttgtaat tgccacgcat ggacgacgaa gtaattgaaa ttagcgacac ganacgcgaa 360
gaaacctcat cgaactccga aatggatgtg gaaataacga cagaacagcc aaccatcgat 420
gtcaaagcag agcaaattgt gcccaaggac gcggcaacca ttgccgagga gaagaagaaa 480
ctgggcaacg accaatacaa ggcgcagaac tatcagaatg cactcaagct ctacacggat 540
gccatatcgc tgtgtccgga ctcggcggca tactatggca atcgggccgc ctgctacatg 600
atgctgctca actataat 618

<210> SEQ ID NO 44
<211> LENGTH: 582
<212> TYPE: DNA
<213> ORGANISM: Drosophila

<400> SEQUENCE: 44
ttcgttcggc catacaaaac acaaaattca agtttaaaaa ctaaataggc aactaaaagg 60
gaagccgcag cgaataaagt gatttgctga aagagacgta agaaagttaa tcgcatcgaa 120
ggcaccagaa atcggggatt tctaacacgg cgcgcgtgcg acgtacatac atacgcaagc 180
gcacacacac acgaacaatt acttgccatt gacgcaaaag cgaaaaagca gtggaataaa 240
ggggaattga caaataacaa cgttttgcaa gcactggact ctggtcgctg gtgttctttc 300
attttgtaat tgccacgcat ggacgacgaa gtaattgaaa ttagcgacac gaatcgcgaa 360

-continued

```
gaaacctcat cgaactccga aatggatgtg gaaataacga cagaacagcc aaccatcgat    420

gtcaaagcag agcaaattgt gcccaaggac gcggcaacca ttgccgagga gaagaagaaa    480

ctgggcaacg accaatacaa ggcgcagaac tatcagaatg cactcaagct ctacacggat    540

gccatatcgc tgtgtccgga ctcggcggca tactatggca at                       582


<210> SEQ ID NO 45
<211> LENGTH: 550
<212> TYPE: DNA
<213> ORGANISM: Drosophila

<400> SEQUENCE: 45

ttcgttcggc catacaaaac acaaaattca agtttaaaaa ctaaataggc aactaaaagg     60

gaagccgcag cgaataaagt gatttgctga aagagacgta agaaagttaa tcgcatcgaa    120

ggcaccagaa atcggggatt tctaacacgg cgcgcgtgcg acgtacatac atacgcaagc    180

gcacacacac acgaacaatt acttgccatt gacgcaaaag cgaaaaagca gtggaataaa    240

ggggaattga caaataacaa cgttttgcaa gcactggact ctggtcgctg gtgttctttc    300

attttgtaat tgccacgcat ggacgacgaa gtaattgaaa ttagcgacag cgaacgcgaa    360

gaaacctcat cgaactccga aatggatgtg gaaataacga cagaacagcc aaccatcgat    420

gtcaaagcag agcaaattgt gcccaaggac gcggcaacca ttgccgagga gaagaagaaa    480

ctgggcaacg accaatacaa ggcgcagaac tatcagaatg cactcaagct ctacacggat    540

gccatatcgc                                                           550


<210> SEQ ID NO 46
<211> LENGTH: 547
<212> TYPE: DNA
<213> ORGANISM: Drosophila
<220> FEATURE:
<221> NAME/KEY: misc_feature
<222> LOCATION: (1)...(547)
<223> OTHER INFORMATION: n = A,T,C or G

<400> SEQUENCE: 46

ttcgttcggc catacaaaac acaaaattca agtttaaaaa ctaaataggc aactaaaagg     60

gaagccgcag cgaataaagt gatttgctga aagagacgta agaaagttaa tcgcatcgaa    120

ggcaccagaa atcggggatt tctaacacgg cgcgcgtgcg acgtacatac atacgcaagc    180

gcacacacac acgaacaatt acttgccatt gacgcaaaag cgaaaaagca gtggaataaa    240

ggggaattga caaataacaa cgttttgcaa ggcactggac tctggtcgct ggtgttcttt    300

cattttgtaa ttgccacgca tggacgacga agtaattgaa attagcgaca cganacgcga    360

agaaacctca tcgaactccg aaatggatgt ggaaataacg acagaacagc caaccatcga    420

tgtcaaagca gagcaaattg tgcccaagga cgcggcaacc attgccgagg agaagaagaa    480

actgggcaac gaccaataca aggcgcagaa ctatcagaat gcactcaagc tctacacgga    540

tgccata                                                              547


<210> SEQ ID NO 47
<211> LENGTH: 487
<212> TYPE: DNA
<213> ORGANISM: Drosophila

<400> SEQUENCE: 47

tcggttcgtt cggccataca aaacacaaaa ttcaagttta aaaactagat aggcaactaa     60
```

-continued aagggaagcc gcagcgaata aagtgatttg ctgaaagaga cgtaagaaag ttaatcgcat 120
cgaaggcacc agaaatcggg gatttctaac acggcgcgcg tgcgacgtac atacatacgc 180
aagcgcacac acacacgaac aattacttgc cattgacgca aaagcgaaaa agcagtggaa 240
taaaggggaa ttgacaaata acaacgtttt gcaagcactg gactctggtc gctggtgttc 300
tttcattttg taattgccac gcatggacga cgaagtaatt gaaattagcg acagcagcgc 360
ggagaaacct catcgaactc cgaaatggat gtggacataa cgacagaaca gccaaccatc 420
gatgtcaaag cagagcggat tgtgcccaag gacgcggcaa ccattgccga ggagaagaag 480
aaactgg 487

<210> SEQ ID NO 48
<211> LENGTH: 246
<212> TYPE: DNA
<213> ORGANISM: Drosophila

<400> SEQUENCE: 48
tgtgctcggt tcgttcggcc atacaaaaca caaaattcaa gtttaaaaac taaataggca 60
actaaaaggg aagccgcagc gaataaagtg atttgctgaa agagacgtaa gaaagttaat 120
cgcatcgaag gcaccagaaa tcggggattt ctaacacggc gcgcgtgcga cgtacataca 180
tacgcaagcg cacacacaca cgaacaatta cttgccattg acgcaaaagc gaaaaagcag 240
tggaat 246

<210> SEQ ID NO 49
<211> LENGTH: 170
<212> TYPE: DNA
<213> ORGANISM: Drosophila

<400> SEQUENCE: 49
ttttccgtgt gctcggttcg ttcggccata caaaacacaa aattcaagtt taaaaactaa 60
ataggcaact aaaagggaag ccgcagcgaa taaagtgatt tgctgaaaga gacgtaagaa 120
agttaatcgc atcgaaggca ccagaaatcg gggatttcta aacggcgcg 170

<210> SEQ ID NO 50
<211> LENGTH: 511
<212> TYPE: DNA
<213> ORGANISM: Drosophila

<400> SEQUENCE: 50
ttttccgtgt gctcggttcg ttcggccata caaaacacaa aattcaagtt taaaaactaa 60
ataggcaact aaaagggaag ccgcagcgaa taaagtgatt tgctgaaaga gacgtaagaa 120
agttaatcgc atcgaaggca ccagaaatcg gggatttcta acacggcgcg cgtgcgacgt 180
acatacatac gcaagcgcac acacacacga acaattactt gccattgacg caaaagcgaa 240
aaagcagtgg aataaagggg aattgacaaa taacaacgtt ttgcaagcac tggactctgg 300
tcgctggtgt tctttcattt tgtaattgcc acgcatggac gacgagtaat tgaaattagc 360
gacagcatac gcgaagaaac ctcatcgaac tccgaaatgg atgtggaaat aacgacagaa 420
cagccaacca tcgatgtcaa agcagagcaa attgtgccca aggacgcggc aaccattgcc 480
gaggagaaga agaaactggg caacgaccaa t 511

<210> SEQ ID NO 51
<211> LENGTH: 702
<212> TYPE: DNA
<213> ORGANISM: Drosophila

-continued

<220> FEATURE:
<221> NAME/KEY: misc_feature
<222> LOCATION: (1)...(702)
<223> OTHER INFORMATION: n = A,T,C or G

<400> SEQUENCE: 51

```
tttttccgtg tgctcggttc gttcggccat acaaaacaca aaattcaagt ttaaaaacta     60

aataggcaac taaaagggaa gccgcagcga nataaagtga tttgctgaaa gagacgtaag    120

aaagttaatc gcatcgaagg caccagaaat cggggatttc taacacggcg cgcgtgcacg    180

tacatacata cgcaagcgca cacacacacg aacaattact tgccattgac gcaaaagcga    240

aaaagcagtg gaataaaggg gaattgacaa ataacaacgt tttgcaagca ctggactctg    300

gtcgctggtg ttctttcatt ttgtaattgc cacgcatgga cgacgaagta attgaaatta    360

gcgaccggan cgcgnagaaa cctcatcgaa ctccgaaatg gatgtggaaa taacgacaga    420

acagccaacc atcgatgtca aagcagagca aattgtgccc aaggacgcgg caaccattgc    480

cgaggagaag aagaaactgg gcaacgacca atacaaggcg cagaactatc agaatgcact    540

caagctctac acggatgcca tatcgctgtg tccggactcg gcggcatact atggcaatcg    600

ggccgcctgc tacatgatgc tgctcaacta taatagcgcc ctgaccgacg cccgacacgc    660

catacgcatc gatccgggct tcgagaaggc ctacgtccgt gt                       702
```

<210> SEQ ID NO 52
<211> LENGTH: 598
<212> TYPE: DNA
<213> ORGANISM: Drosophila
<220> FEATURE:
<221> NAME/KEY: misc_feature
<222> LOCATION: (1)...(598)
<223> OTHER INFORMATION: n = A,T,C or G

<400> SEQUENCE: 52

```
tttttccgtg tgctcggttc gttcggccat acaaaacaca aaattcaagt ttaaaaacta     60

aataggcaac taaaagggaa gccgcagcga ataaagtgat ttgctgaaag agacgtaaga    120

aagttaatcg catcgaaggc accagaaatc ggggatttct aacacggcgc gcgtgcgacg    180

tacatacata cgcaagcgca cacacacacg aacaattact tgccattgac gcaaaagcga    240

aaaagcagtg gaataaaggg gaattgacaa ataacaacgt tttgcaagca ctggactctg    300

gtcgctggtg ttctttcatt ttgtaattgc cacgcatgga cgacgaagta attgaaatta    360

gcgacaggan cgcgnagaaa cctcatcgaa ctccgaaatg gatgtggaaa taacgacaga    420

acagccaacc atcgatgtca aagcagagca aattgtgccc aaggacgcgg caaccattgc    480

cgaggagaag aagaaactgg gcaacgacca atacaaggcg cagaactatc agaatgcact    540

caagctctac acggatgcca tatcgctgtg tccggactcg gcggcatact atggcaat      598
```

<210> SEQ ID NO 53
<211> LENGTH: 669
<212> TYPE: DNA
<213> ORGANISM: Drosophila
<220> FEATURE:
<221> NAME/KEY: misc_feature
<222> LOCATION: (1)...(669)
<223> OTHER INFORMATION: n = A,T,C or G

<400> SEQUENCE: 53

```
acaaaaatgt ctttattcgg agcgttgatg ggtgatttcg acgacgatct cggccttatg     60

aacaaccaca tgaaccacac tatgaacgcg atgaacatgc agatgcgctc gatgaatcgc    120
```

-continued

```
ctgatgaaca gctttatgcc cgatcccttc atgcaggtct cgccctttga ccagggattc    180

cagcagaacg ctctcatgga gcgtccgcag atgccggcca tgccagccat gggcctcttc    240

ggcatgccca nntgatgcca caaactttaa tcgcccgttg aacgctgata ttggtggcaa    300

ttcaggcgca tccttctgcc agagcaccgt gatgaccatg tcatcgggtc ccgatgggcg    360

tcctcagatc taccaggcca gcactagtac caaaacagga ccgggaggcg ttcgtgagac    420

ccgcaggacg gtgcaggact cgcgcactgg ggtgaagaag atggccattg gtcatcacat    480

cggcgagcgg gcacacatta ttgagaaaga gcaggacatg cgctcaggac aactggagga    540

gcgccaggag ttcattaatc tggaggaggg agaagccgag cagtttgaca gggagtttac    600

atcgcgcgct agtcgcggag cgtgcagtca agacatcatg ctggtggcat gcaggccatc    660

atgcccgcc                                                            669
```

<210> SEQ ID NO 54
<211> LENGTH: 563
<212> TYPE: DNA
<213> ORGANISM: Drosophila

<400> SEQUENCE: 54

```
agaaagccaa cacaatccac aaaaatgtct ttattcggag cgttgatggg tgatttcgac     60

gacgatctcg gccttatgaa caaccacatg aaccacacta tgaacgcgat gaacatgcag    120

atgcgctcga tgaatcgcct gatgaacagc tttatgcccg atcccttcat gcaggtctcg    180

ccctttgacc agggattcca gcagaacgct ctcatggagc gtccgcagat gccggccatg    240

ccagccatgg gcctcttcgg catgcccatg atgccaaact ttaatcgcct gttgaacgct    300

gatattggtg gcaattcagg cgcatccttc tgccagagca ccgtgatgac catgtcatcg    360

ggtcccgatg ggcgtcctca gatctaccag gccagcacta gtaccaaaac aggaccggga    420

ggcgttcgtg agacccgcag gacggtgcag gactcgcgca ctggggtgaa gaagatggcc    480

attggtcatc acatcggcga gcgggcacac attattgaga aagagcagga catgcgctca    540

ggacaactgg aggagcgcca gga                                            563
```

<210> SEQ ID NO 55
<211> LENGTH: 763
<212> TYPE: DNA
<213> ORGANISM: Drosophila

<400> SEQUENCE: 55

```
aaaattcgag caacagaaag ccaacacaat ccacaaaaat gtctttattc ggagcgttga     60

tgggtgattt cgacgacgat ctcggcctta tgaacaacca catgaaccac actatgaacg    120

cgatgaacat gcagatgcgc tcgatgaatc gcctgatgaa cagctttatg cccgatccct    180

tcatgcaggt ctcgcccttt gaccagggat tccagcagaa cgctctcatg gagcgtccgc    240

agatgccggc catgccagcc atgggcctct tcggcatgcc catgatgcca aactttaatc    300

gcctgttgaa cgctgatatt ggtggcaatt caggcgcatc cttctgccag agcaccgtga    360

tgaccatgtc atcgggtccc gatgggcgtc ctcagatcta ccaggccagc actagtacca    420

aaacaggacc gggaggcgtt cgtgagaccc gcaggacggt gcaggactcg cgcactgggg    480

tgaagaagat ggccattggt catcacatcg gcgagcgggc acacattatt gagaaagagc    540

aggacatgcg ctcaggacaa ctggaggagc gccaggagtt cattaatctg gaggagggag    600

aagccgagca gtttgacagg gagtttacat cgcgcgctag tcgcggaggc gtgcagtcaa    660

gacatcatgc tggtggcatg caggccatca tgcccgcccg tccagcggca cacacctcga    720
```

-continued

```
cgttgaccat tgagccagtg gaggacgacg acgacgatga tgc                    763


<210> SEQ ID NO 56
<211> LENGTH: 709
<212> TYPE: DNA
<213> ORGANISM: Drosophila
<220> FEATURE:
<221> NAME/KEY: misc_feature
<222> LOCATION: (1)...(709)
<223> OTHER INFORMATION: n = A,T,C or G

<400> SEQUENCE: 56

agaagaaaat tcgagcaaca gaaagccaac acaatccaca aaaatgtctt tattcggagc     60

gttgatgggt gatttcgacg acgatctcgg ccttatgaac aaccacatga accacactat    120

gaacgcgatg aacatgcaga tgcgctcgat gaatcgcctg atgaacagct ttatgcccga    180

tcccttcatg caggtctcgc cctttgacca gggattccag cagaacgctc tcatggagcg    240

tccgcagatg ccggccatgc cagccatggg cctcttcggc atgcccatga tgccaaactt    300

taatcgcctg ttgaacgctg atattggtgg caattcaggc gcatccttct gccagagcac    360

cgtgatgacc atgtcatcgg gtcccgatgg gcgtcctcag atctaccagg ccagcactag    420

taccaaaaca ggaccgggag gcgttcgtga gacccgcagg acggtgcagg actcgcgcac    480

tggggtgaag aagatggcca ttggtcatca catcggcgag cgggcacaca ttattgagaa    540

agagcaggac atgcgctcag gacaactgga ggagcgccag gagttcatta atctggagga    600

gggagaagcc gagcagtttg acagggagtt tacatcgcgc gctagtcgcg gagcggtgca    660

gtcaagacat catgctggtg gcatgcatgc catcatgccc gnccgtcca                709


<210> SEQ ID NO 57
<211> LENGTH: 599
<212> TYPE: DNA
<213> ORGANISM: Drosophila

<400> SEQUENCE: 57

aaagaagaaa attcgagcaa cagaaagcca acacaatcca caaaaatgtc tttattcgga     60

gcgttgatgg gcgatttcga cgacgatctc ggccttatga acaaccacat gaaccacact    120

atgaacgcga tgaacatgca gatgcgctcg atgaatcgcc tgatgaacag ctttatgccc    180

gatcccttca tgcaggtctc gccctttgac cagggattcc agcagaacgc tctcatggag    240

cgtccgcaga tgccggccat gccagccatg ggactcttcg gcatgcccat gatgccaaac    300

tttaatcgcc tgttgaacgc tgatattggt ggcaattcag gcgcatcctt ctgccagagc    360

accgtgatga ccatgtcatc gggtcccgat gggcgtcctc agatctacca ggccagcact    420

agtaccaaga caggaccggg aggcgttcgt gagacccgca agacggtgca ggactcgcgc    480

actggggtga agaagatggc cattggtcat cacatcggcg agcgggcaca cattattgag    540

aaagagcagg acatgcgctc aggacaactg gaggagcgcc aggagttcat taatctgga     599


<210> SEQ ID NO 58
<211> LENGTH: 608
<212> TYPE: DNA
<213> ORGANISM: Drosophila

<400> SEQUENCE: 58

aaagaagaaa attcgagcaa cagaaagcca acacaatcca caaaaatgtc tttattcgga     60

gcgttgatgg gcgatttcga cgacgatctc ggccttatga acaaccacat gaaccacact    120
```

-continued

```
atgaacgcga tgaacatgca gatgcgctcg atgaatcgcc tgatgaacag ctttatgccc    180

gatcccttca tgcaggtctc gccctttgac cagggattcc agcagaacgc tctcatggag    240

cgtccgcaga tgccggccat gccagccatg ggactcttcg gcatgcccat gatgccaaac    300

tttaatcgcc tgttgaacgc tgatattggt ggcaattcag gcgcatcctt ctgccagagc    360

accgtgatga ccatgtcatc gggtcccgat gggcgtcctc agatctacca ggccagcact    420

agtaccaaga caggaccggg aggcgttcgt gagacccgca agacggtgca ggactcgcgc    480

actggggtga agaagatggc cattggtcat cacatcggcg agcgggcaca cattattgag    540

aaagagcagg acatgcgctc aggacaactg gaggagcgcc aggagttcat taatctggag    600

gagggaga                                                             608
```

<210> SEQ ID NO 59
<211> LENGTH: 585
<212> TYPE: DNA
<213> ORGANISM: Drosophila

<400> SEQUENCE: 59

```
aaagaagaaa attcgagcaa cagaaagcca acacaatcca caaaaatgtc tttattcgga     60

gcgttgatgg gcgatttcga cgacgatctc ggccttatga acaaccacat gaaccacact    120

atgaacgcga tgaacatgca gatgcgctcg atgaatcgcc tgatgaacag ctttatgccc    180

gatcccttca tgcaggtctc gccctttgac cagggattcc agcagaacgc tctcatggag    240

cgtccgcaga tgccggccat gccagccatg ggactcttcg gcatgcccat gatgccaaac    300

tttaatcgcc tgttgaacgc tgatattggt ggcaattcag gcgcatcctt ctgccagagc    360

accgtgatga ccatgtcatc gggtcccgat gggcgtcctc agatctacca ggccagcact    420

agtaccaaga caggaccggg aggcgttcgt gagacccgca agacggtgca ggactcgcgc    480

actggggtga agaagatggc cattggtcat cacatcggcg agcgggcaca cattattgag    540

aaagagcagg acatgcgctc aggacaactg gaggagcgcc aggag                    585
```

<210> SEQ ID NO 60
<211> LENGTH: 591
<212> TYPE: DNA
<213> ORGANISM: Drosophila

<400> SEQUENCE: 60

```
aaagaagaaa attcgagcaa cagaaagcca acacaatcca caaaaatgtc tttattcgga     60

gcgttgatgg gtgatttcga cgacgatctc ggccttatga acaaccacat gaaccacact    120

atgaacgcga tgaacatgca gatgcgctcg atgaatcgcc tgatgaacag ctttatgccc    180

gatcccttca tgcaggtctc gccctttgac cagggattcc agcagaacgc tctcatggag    240

cgtccgcaga tgccggccat gccagccatg ggcctcttcg gcatgcccat gatgccaaac    300

tttaatcgcc tgttgaacgc tgatattggt ggcaattcag gcgcatcctt ctgccagagc    360

accgtgatga ccatgtcatc gggtcccgat gggcgtcctc agatctacca ggccagcact    420

agtaccaaaa caggaccggg aggcgttcgt gagacccgca ggacggtgca ggactcgcgc    480

actggggtga agaagatggc cattggtcat cacatcggcg agcgggcaca cattattgag    540

aaagagcagg acatgcgctc aggacaactg gaggaacgcc aggagttcat t             591
```

<210> SEQ ID NO 61
<211> LENGTH: 657
<212> TYPE: DNA
<213> ORGANISM: Drosophila

-continued

<400> SEQUENCE: 61

```
aaagaagaaa attcgagcaa cagaaagcca acacaatcca caaaaatgtc tttattcgga     60
gcgttgatgg gtgatttcga cgacgatctc ggccttatga acaaccacat gaaccacact    120
atgaacgcga tgaacatgca gatgcgctcg atgaatcgcc tgatgaacag ctttatgccc    180
gatcccttca tgcaggtctc gccctttgac cagggattcc agcagaacgc tctcatggag    240
cgtccgcaga tgccggccat gccagccatg ggcctcttcg gcatgcccat gatgccaaac    300
tttaatcgcc tgttgaacgc tgatattggt ggcaattcag gcgcatcctt ctgccagagc    360
accgtgatga ccatgtcatc gggtcccgat gggcgtcctc agatctacca ggccagcact    420
agtaccaaaa caggaccggg aggcgttcgt gagacccgca ggacggtgca ggactcgcgc    480
actggggtga agaagatggc cattggtcat cacatcggcg agcgggcaca cattattgag    540
aaagagcagg acatgcgctc aggacaactg gaggagcgcc aggagttcat taatctggag    600
gagggagaag ccgagcagtt tgacagggag tttacatcgc gcgctagtcg cggagcg       657
```

<210> SEQ ID NO 62
<211> LENGTH: 718
<212> TYPE: DNA
<213> ORGANISM: Drosophila
<220> FEATURE:
<221> NAME/KEY: misc_feature
<222> LOCATION: (1)...(718)
<223> OTHER INFORMATION: n = A,T,C or G

<400> SEQUENCE: 62

```
gtgaaaattc tgcatacgga aagaagaaaa ttcgagcaac agaaagccaa cacaatccac     60
aaaaatgtct ttattcggag cgttgatggg tgatttcgac gacgatctcg gccttatgaa    120
caaccacatg aaccacacta tgaacgcgat gaacatgcag atgcgctcga tgaatcgcct    180
gatgaacagc tttatgcccg atcccttcat gcaggtctcg ccctttgacc agggattcca    240
gcagaacgct ctcatggagc gtccgcagat gccggccatg ccagccatgg gcctcttcgg    300
catgcccatg atgccaaact ttaatcgcct gttgaacgct gatattggtg gcaattcagg    360
cgcatccttc tgccagagca ccgtgatgac catgtcatcg ggtcccgatg ggcgtcctca    420
gatctaccag gccagcacta gtaccaaaac aggaccggga ggcgttcgtg agacccgcag    480
gacggtgcag gactcgcgca ctggggtgaa gaagatggcc attggtcatc acatcggcga    540
gcgggcacac attattgaga aagagcagga catgcgctca ggacaactgg aggagcgcca    600
ggagttcatt aatctggagg agggagaagc cgagcagttt gacagggagt ttacatcgcg    660
cgctagtcgc ggagcggtgc agtcaagaca tcatgctggt ggcatgcang ccatcatg      718
```

<210> SEQ ID NO 63
<211> LENGTH: 497
<212> TYPE: DNA
<213> ORGANISM: Drosophila

<400> SEQUENCE: 63

```
atattcgtga aaattctgca tacggaaaga agaaaattcg agcaacagaa agccaacaca     60
atccacaaaa atgtctttat tcggagcgtt gatgggcgat ttcgacgacg atctcggcct    120
tatgaacaac cacatgaacc acactatgaa cgcgatgaac atgcagatgc gctcgatgaa    180
tcgcctgatg aacagcttta tgcccgatcc cttcatgcag gtctcgccct ttgaccaggg    240
attccagcag aacgctctca tggagcgtcc gcagatgccg gccatgccag ccatgggact    300
```

-continued

```
cttcggcatg cccatgatgc caaactttaa tcgcctgatg aacgctgcta ttggtgggaa    360

ttcaggcgca tccttctgcc agagcaccgg gatgaccatg tcatcgggtt ccgatgggcg    420

tgctcagatc taccaggcca gcactagttc caagacagga ccgggaggcg ttcgtgagac    480

ccgcaagacg gtgcagg                                                   497
```

<210> SEQ ID NO 64
<211> LENGTH: 685
<212> TYPE: DNA
<213> ORGANISM: Drosophila

<400> SEQUENCE: 64

```
aaaatattcg tgaaaattct gcatacggaa agaagaaaat tcgagcaaca gaaagccaac     60

acaatccaca aaaatgtctt tattcggagc gttgatgggt gatttcgacg acgatctcgg    120

ccttatgaac aaccacatga accacactat gaacgcgatg aacatgcaga tgcgctcgat    180

gaatcgcctg atgaacagct ttatgcccga tcccttcatg caggtctcgc cctttgacca    240

gggattccag cagaacgctc tcatggagcg tccgcagatg ccggccatgc cagccatggg    300

cctcttcggc atgcccatga tgccaaactt taatcgcctg ttgaacgctg atattggtgg    360

caattcaggc gcatccttct gccagagcac cgtgatgacc atgtcatcgg gtcccgatgg    420

gcgtcctcag atctaccagg ccagcactag taccaaaaca ggaccgggag gcgttcgtga    480

gacccgcagg acggtgcagg actcgcgcac tggggtgaag aagatggcca ttggtcatca    540

catcggcgag cgggcacaca ttattgagaa agagcaggac atgcgctcag gacaactgga    600

ggagcgccag gagttcatta atctggagga gggagaagcc gagcagtttg acagggagtt    660

tacatcgcgc gctagtcgcg gagcg                                          685
```

<210> SEQ ID NO 65
<211> LENGTH: 540
<212> TYPE: DNA
<213> ORGANISM: Drosophila

<400> SEQUENCE: 65

```
aaagaaaata ttcgtgaaaa ttctgcatac ggaaagaaga aaattcgagc aacagaaagc     60

caacacaatc cacaaaaatg tctttattcg gagcgttgat gggtgatttc gacgacgatc    120

tcggccttat gaacaaccac atgaaccaca ctatgaacgc gatgaacatg cagatgcgct    180

cgatgaatcg cctgatgaac agctttatgc ccgatccctt catgcaggtc tcgccctttg    240

accagggatt ccagcacgaa cgctctcatg gagcgtccgc agatgccggc catgcagcca    300

tgggcctctt cggcatgcca tgatgccaac tttaatcgcc tgttgaacgc tgatattggt    360

ggcaattcag gcgcatcctt ctgccagagc accgtgatga ccatgtcatc gggtcccgat    420

gggcggtcct cagatctacc aggccagcac tagtaccaaa acaggaccgg gaggcgttcg    480

tgagacccgc agaacggtgc aggactcgcg cactggggtg aagaagatgg gcattggtca    540
```

<210> SEQ ID NO 66
<211> LENGTH: 681
<212> TYPE: DNA
<213> ORGANISM: Drosophila

<400> SEQUENCE: 66

```
acaaagaaaa tattcgtgaa aattctgcat acggaaagaa gaaaattcga gcaacagaaa     60

gccaacacaa tccacaaaaa tgtctttatt cggagcgttg atgggtgatt tcgacgacga    120

tctcggcctt atgaacaacc acatgaacca cactatgaac gcgatgaaca tgcagatgcg    180
```

-continued

```
ctcgatgaat cgcctgatga acagctttat gcccgatccc ttcatgcagg tctcgccctt    240

tgaccaggga ttccagcaga acgctctcat ggagcgtccg cagatgccgg ccatgccagc    300

catgggcctc ttcggcatgc ccatgatgcc aaactttaat cgcctgttga acgctgatat    360

tggtggcaat tcaggcgcat ccttctgcca gagcaccgtg atgaccatgt catcgggtcc    420

cgatgggcgt cctcagatct accaggccag cactagtacc aaaacaggac cgggaggcgt    480

tcgtgagacc cgcaggacgg tgcaggactc gcgcactggg gtgaagaaga tggccattgg    540

tcatcacatc ggcgagcggg cacacattat tgagaaagag caggacatgc gctcaggaca    600

actggaggag cgccaggagt tcattaatct ggaggaggga gaagccgagc agtttgacag    660

ggagtttaca tcgcgcgcta g                                               681
```

<210> SEQ ID NO 67
<211> LENGTH: 675
<212> TYPE: DNA
<213> ORGANISM: Drosophila

<400> SEQUENCE: 67

```
tgacaaagaa aatattcgtg aaaatctgca tacggaaaga ggaaaattcg agccacagaa     60

agccaccaca atccacaaaa atgtctttat tcggagcgtt gatgggtgat ttcgacgacg    120

atctcggcct tatgaacaac cacatgaacc acactatgaa cgcgatgaac atgcagatgc    180

gctcgatgaa tcgcctgatg aacagcttta tgcccgatcc cttcatgcag gtctcgccct    240

ttgaccaggg attccagcag aacgctctca tggagcgtcc gcagatgccg gccatgccag    300

ccatgggcct cttcggcatg cccatgatgc caaactttaa tcgcctgttg aacgctgata    360

ttggtggcaa ttcaggcgca tccttctgcc agagcaccgt gatgaccatg tcatcgggtc    420

ccgatgggcg tcctcagatc taccaggcca gcactagtac caaaacagga ccgggaggcg    480

ttcgtgagac ccgcaagacg gtgcaggact cgcgcactgg ggtgaagaag atggccattg    540

gtcatcacat cggcgagcgg gcacacatta ttgagaaaga gcaggacatg cgctcaggac    600

aactggagga gcgcaggagt tcattaatct ggaggaggga gaagcgagca gtttgacagg    660

gagtttacat cgcgc                                                      675
```

<210> SEQ ID NO 68
<211> LENGTH: 627
<212> TYPE: DNA
<213> ORGANISM: Drosophila

<400> SEQUENCE: 68

```
tgacaaagaa aatattcgtg aaaattctgc atacggaaag aagaaaattc gagcaacaga     60

aagccaacac aatccacaaa aatgtcttta ttcggagcgt tgatgggcga tttcgacgac    120

gatctcggcc ttatgaacaa ccacatgaac cacactatga acgcgatgaa catgcagatg    180

cgctcgatga atcgcctgat gaacagcttt atgcccgatc ccttcatgca ggtctcgccc    240

tttgaccagg gattccagca gaacgctctc atggagcgtc cgcagatgcc ggccatgcca    300

gccatgggac tcttcggcat gcccatgatg ccaaacttta atcgcctgtt gaacgctgat    360

attggtggca attcaggcgc atccttctgc cagagcaccg tgatgaccat gtcatcgggt    420

cccgatgggc gtcctcagat ctaccaggcc agcactagta ccaagacagg accgggaggc    480

gttcgtgaga cccgcaagac ggtgcaggac tcgcgcactg ggtgaagaa gatggccatt    540

ggtcatcaca tcggcgagcg ggcacacatt attgagaaag agcaggacat gcgctcagga    600
```

-continued

```
caactggagg agcgccagga gttcatt                                        627


<210> SEQ ID NO 69
<211> LENGTH: 686
<212> TYPE: DNA
<213> ORGANISM: Drosophila

<400> SEQUENCE: 69

ggcacgagaa agaaaatatt cgtgaaaatt ctgcatacgg aaagaagaaa attcgagcaa     60

cagaaagcca acacaatcca caaaaatgtc tttattcgga gcgttgatgg gtgatttcga    120

cgacgatctc ggccttatga acaaccacat gaaccacact atgaacgcga tgaacatgca    180

gatgcgctcg atgaatcgcc tgatgaacag ctttatgccc gatcccttca tgcaggtctc    240

gccctttgac cagggattcc agcagaacgc tctcatggag gtccgcagat gccggccatg    300

cagccatggg cctcttcggc atgcccatga tgccaaactt taatcgcctg ttgaacgctg    360

atattggtgg caattcaggc gcatccttct gccagagcac cgtgatgacc atgtcatcgg    420

gtcccgatgg gctgtcctca gatctaccag gccagcacta gtaccaaaac aggaccggga    480

ggcgttcgtg agacccgcag atcggtgcag gactcgcgca ctggggtgaa gaagatggcc    540

attggtcatc acatcggcga gcgggcacac attattgaga aagagcagga catgcgctca    600

ggacaactgg aggagcgcca ggagttcatt aatctggagg agggagaagc cgagcagttt    660

gacagggagt ttacatcgcg cgctag                                         686
```